United States Patent
Spangenberg

(10) Patent No.: US 9,994,577 B2
(45) Date of Patent: Jun. 12, 2018

(54) AZEPANYL-DERIVATIVES AND PHARMACEUTICAL COMPOSITIONS COMPRISING THE SAME WITH ANTIPARASITIC ACTIVITY

(71) Applicant: Merck Patent GmbH, Darmstadt (DE)

(72) Inventor: Thomas Spangenberg, Geneva (CH)

(73) Assignee: MERCK PATENT GMBH, Darmstadt (DE)

( * ) Notice: Subject to any disclaimer, the term of this patent is extended or adjusted under 35 U.S.C. 154(b) by 0 days. days.

(21) Appl. No.: 15/323,215

(22) PCT Filed: Jul. 6, 2015

(86) PCT No.: PCT/EP2015/001368
§ 371 (c)(1),
(2) Date: Dec. 30, 2016

(87) PCT Pub. No.: WO2016/000827
PCT Pub. Date: Jan. 7, 2016

(65) Prior Publication Data
US 2017/0137428 A1 May 18, 2017

(30) Foreign Application Priority Data
Jul. 4, 2014 (EP) ..................................... 14002292

(51) Int. Cl.
| | | |
|---|---|---|
| C07D 403/04 | (2006.01) | |
| C07D 413/04 | (2006.01) | |
| C07D 417/04 | (2006.01) | |
| C07D 487/04 | (2006.01) | |
| A61K 31/55 | (2006.01) | |
| A61P 33/06 | (2006.01) | |
| C07D 471/04 | (2006.01) | |

(52) U.S. Cl.
CPC ............ *C07D 487/04* (2013.01); *A61K 31/55* (2013.01); *C07D 403/04* (2013.01); *C07D 413/04* (2013.01); *C07D 417/04* (2013.01); *C07D 471/04* (2013.01)

(58) Field of Classification Search
CPC .. C07D 403/04; C07D 413/04; C07D 417/04; C07D 471/04; C07D 487/04; A61K 31/55
USPC ...................... 540/544; 514/217.11
See application file for complete search history.

(56) References Cited

U.S. PATENT DOCUMENTS

2013/0040977 A1    2/2013   McKnight et al.

FOREIGN PATENT DOCUMENTS

| WO | WO 01/29028 A1 | 4/2001 |
| WO | WO 02/060867 A2 | 8/2002 |
| WO | WO 2005/074971 A1 | 8/2005 |
| WO | WO 2007/062399 A2 | 5/2007 |
| WO | WO 2010/010027 A1 | 1/2010 |
| WO | WO 2014/108168 A1 | 7/2014 |

OTHER PUBLICATIONS

Singh S.B., Bioorganic & Medicinal Chemistry Letters 24 (2014) 3683-3689.*
Wilson D.N.,Critical Reviews in Biochemistry and Molecular Biology, 2009;44(6): 393-433.*
Maguire B.A., Microbiology and Molecular Biology Reviews, Mar. 2009, p. 22-35.*
Rehm et al.,Clinical Infectious Diseases 2010; 51 (2):176-182.*
Freshney et al.,Culture of Animal Cells, A Manual of Basic Technique, Alan R. Liss, Inc., 1983, New York, p. 4.*
Dermer et al., Bio/Technology, 1994, 12:320.*
Bassetti et al. Annals of Clinical Microbiology and Antimicrobials 2013, 12:22, pp. 1-15.*
Shaffer Yale Journal of Biology and Medicine 86 (2013), pp. 261-270.*
Theuretzbacher et al. Current Opinion in Pharmacology, 2011,11: 429-432.*
Kint et al. Trends in Microbiology, Dec. 2012, vol. 20, No. 12, 577-585.*
Becker D.E. Anesth Prog 60:111-123, 2013.*
Babic et al., Drug Resistance Updates 9, 142-156, 2006.*
Paterson et al., Clinical Microbiological reviews 18(40, 657-686, 2005.*

(Continued)

*Primary Examiner* — Venkataraman Balasubramanian
(74) *Attorney, Agent, or Firm* — Grüneberg and Myers PLLC

(57) ABSTRACT

The present invention provides compounds of Formula (i). Furthermore, pharmaceutical compositions are provided comprising at least one compound of Formula (i), for the treatment of parasitic diseases including malaria, as well as neurodegenerative diseases.

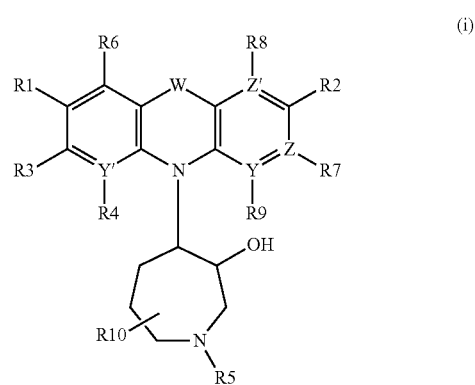

30 Claims, No Drawings

(56) References Cited

OTHER PUBLICATIONS

International Search Report dated Aug. 25, 2015 in PCT/EP2015/001368 filed Jul. 6, 2015.
Jerome Molette, et al., "Identification and Optimization of an Aminoalcohol-Carbazole Series with Antimalarial Properties" ACS Medicinal Chemistry Letters, vol. 4, XP055189170, 2013, pp. 1037-1041.
Rogerio Amino, et al. "Quantitative imaging of *Plasmodium* transmission from mosquito to mammal", Nature Publishing Group, vol. 12, No. 2, 2006, pp. 220-224.
Inigo Angulo-Barturen, et al. "A Murine Model of *falciparum*-Malaria by In Vivo Selection of Competent Strains in Non-Myelodepleted Mice Engrafted with Human Erythrocytes", PLoS ONE, vol. 3, No. 5, 2008, pp. 1-14.
L.H. Bannister, et al. °A Brief Illustrated Guide to the ultrastructure of *Plasmodium falciparum* Asexual Blood Stages°, Parasitology Today, vol. 16, No. 10, 2000, pp. 427-433.
Robin B. Bedford, et al. "Intramolecular direct arylation in the synthesis of fluorinated carbazoles", Tetrahedron, vol. 64, 2008, pp. 6038-6050.
Ian A Clark, et al. °Human malarial disease: a consequence of inflammatory cytokine release°, Malaria Journal, vol. 5, No. 85, 2006, pp. 1-32.
Vadim A. Davankov, et al. "Analytical Chiral Separation Methods", International Union of Pure and Applied Chemistry, vol. 69, No. 7, 1997, pp. 1469-1474.
Robert E. Desjardins, et al. "Quantitative Assessment of Antimalarial Activity In Vitro by a Semiautomated Microdilution Technique", Antimicrobial Agents and Chemotherapy, vol. 16, No. 6, 1979, pp. 710-718.
Xavier C. Ding, et al. "A framework for assessing the risk of resistance for anti-malarials in development", Malaria Journal, vol. 11, No. 292, 2012, pp. 1-11.
Celia R.S. Garcia, et al. "Tertian and Quartan Fevers: Temporal Regulation in Malarial Infection", Journal of Biological Rhythms, vol. 16, No. 5, 2001, pp. 436-443.
Anil Ghosh, et al. "The Journey of the Malaria Parasite in the Mosquito: Hopes for the New Century", Parasitology Today, vol. 16, No. 5, 2000, pp. 196-201.
Peter G.M. Wuts, et al. "Greene's Protective Groups in Organic Synthesis", Wiley-Interscience, vol. 4, 2007, pp. v-vii, ix-xxviii (with four cover pages).
Timo Heikkila, et al. "Design and Synthesis of Potent Inhibitors of the Malaria Parasite Dihydroorotate Dehydrogenase", Journal of Medicinal Chemistry, vol. 50, No. 2, 2007, pp. 186-191.
Richard Idro, et al. "Pathogenesis, clinical features, and neurological outcome of cerebral malaria", Lancet Neurology, vol. 4, 2005, pp. 827-840.
Philip J. Kocienski, "Protecting Groups", Thieme, vol. 1, 1994, pp. XII-XVI (with cover page).
Ngampong Kongkathip, et al. "Constituents and Bioactivities of *Clausena excavata*", Heterocycles, vol. 79, 2009, pp. 121-144.
Michael Korsinczky, et al. "Mutations in *Plasmodium falciparum* Cytochrome b That Are Associated with Atovaquone Resistance Are Located at a Putative Drug-Binding Site", Antimicrobial Agents and Chemotherapy, vol. 44, No. 8, 2000, pp. 2100-2108.
Ellen S. Martinsen, et al. "A three-genome phylogeny of malaria parasites (*Plasmodium* and closely related genera): Evolution of life-history traits and host switches", Molecular Phylogenetics and Evolution, vol. 47, 2008, pp. 261-273.
William H. Porter, "Resolution of chiral drugs", International Union of Pure and Applied Chemistry, vol. 63, No. 8, 1991, pp. 1119-1122.
Rodney W. Rickards, et al. "Calothrixins A and B, Novel Pentacyclic Metabolites from *Calothrix* Cyanobacteria with Potent Activity against Malaria Parasites and Human Cancer Cells", Tetrahedron, vol. 55, 1999, pp. 13513-13520.
Louis Schofield, et al. "Immunological Processes in Malaria Pathogenesis", Nature Publishing Group, vol. 5, 2005, pp. 722-735.
Marianne E. Sinka, et al. "A global map of dominant malaria vectors", Parasites & Vectors, vol. 5, No. 69, 2012, pp. 1-11.
Mary M. Stevenson, et al. "Innate Immunity to Malaria", Nature Publishing Group, vol. 4, 2004, pp. 169-180.
Praveen Tyle, "Iontophoretic Devices for Drug Delivery", Pharmaceutical Research, vol. 3, No. 6, 1986, pp. 318-326.
Nicholas J. White, et al. "Malaria", Lancet, vol. 383, 2014, pp. 723-735.
Nicholas J. White, "Determinants of relapse periodicity in *Plasmodium vivax* malaria", Malaria Journal, vol. 10, No. 297, 2011, pp. 1-35 (with cover page).
"World Malaria Report 2013", World Health Organization, 2013, 178 pp.
Written Opinion of the International Searching Authority dated Aug. 25, 2015 in PCT/EP2015/001368 filed Jul. 6, 2015.

* cited by examiner

AZEPANYL-DERIVATIVES AND PHARMACEUTICAL COMPOSITIONS COMPRISING THE SAME WITH ANTIPARASITIC ACTIVITY

FIELD OF THE INVENTION

The present invention pertains to the production and pharmaceutical use of antiparasitic compounds. More particularly, the present invention provides compounds of formula (i), their use in the treatment of parasitic diseases such as malaria and cerebral malaria.

BACKGROUND

Malaria constitutes one of the most devastating global health problems in human history. Infection with malarial parasites affects more than 207 million people annually, killing ~627,000 children. (World Malaria Report 2013). More than 85% of malaria cases and 90% of malaria deaths occur in sub-Saharan Africa, mainly in young children (ie, those younger than 5 years).

Malaria is a protozoan disease, caused by *Plasmodium* species, which are transmitted by *Anopheles* mosquitoes. There are more than 400 anopheline species known to date, however, only around 25 are good vectors for the transmittal of the disease (Sinka M E, et al. Parasit Vectors 2012; 5: 69). About 200 *Plasmodium* species are known (cf. Martinsen et al. Mol Phylogenet Evol. 2008 April; 47(1):261-73), out of which only five species of the genus cause all malarial infections in human beings. Most cases are caused by either *Plasmodium falciparum or Plasmodium vivax*, but human infections can also be caused by *Plasmodium ovale, Plasmodium malariae*, and, in parts of southeast Asia, the monkey malaria *Plasmodium knowlesi*. Almost all deaths are caused by *P. falciparum* malaria. Malaria in pregnancy, which is caused by both *P. falciparum* and *P. vivax* causes indirect mortality from abortion and intrauterine growth retardation, which increases infant mortality (White et al., (2014) Lancet; 383: 723-35).

The pathogenesis of malaria is multifactorial, and serious sequalae can result from three primary pathophysiological events: (i) red blood cell destruction; (ii) adhesion of infected erythrocytes to the capillary veins; and (iii) an excessive pro-inflammatory response. Excessive pro-inflammatory response is responsible for sepsis-like signs and symptoms such as rigors, headache, chills, spiking fever, sweating, vasodilatation and hypoglycemia. (Clark et al. Malaria Journal 5 (2006); Stevenson et al. Nat. Rev. Immunol. 4:169-180 (2004); Schofield et al. Nature Reviews Immunology 5:722-735 (2005)). Cerebral malaria is a severe neurological complication of malarial infection and is a major cause of acute non-traumatic encephalopathy in tropical countries. (Idro et al. Lancet Neurol. 4: 827-840 (2005)).

The life cycle of *P. falciparum* begins with inoculation of motile sporozoites into the dermis of a human by an anopheline mosquito. Sporozoites then travel to the liver, where the sporozoites invade hepatocytes and then multiply. After about a week, the liver schizonts burst, releasing a large number of merozoites into the bloodstream. The merozoites in turn invade erythrocytes and begin the asexual cycle of *P. falciparum*. Once inside the erythrocyte the merozoites develop inside parasitophorous vacuoles, undergoing several biochemical and morphological changes that can be identified by three stages known as ring, trophozoite and schizont. Following proliferation in the erythrocytes, the infected erythrocytes rupture and release merozoites allowing the continuity of the intraerythrocytic cycle (Bannister et al. (2000) Parasitol Today 16: 427-433).

The illness starts when total asexual parasite numbers in the circulation reach roughly 100 million. Some parasites develop into sexual forms (gametocytes). Gametocytes are taken up by a feeding anopheline mosquito and reproduce sexually, forming an ookinete and then an oocyst in the mosquito gut. The oocyst bursts and liberates sporozoites, which migrate to the salivary glands to await inoculation at the next blood feed. Typically, the entire cycle roughly takes about 1 month.

Recently, it was proven that the sporozoites injected first cross through the dermis and only a few of them migrate into the capillary vessels, while others migrate into lymph vessels and give rise to exoerythrocytic forms, which were unknown until recently. The exoerythrocytic forms may have an important influence on host immunological system (Amino R, et al. (2006) Nat Med 12: 220-224).

In the bloodstream some parasites develop into gametocytes, which are the infectious form of *P. falciparum* for its vector mosquito in which the sexual cycle occurs. Once in the mosquito the gametocytes mature in the mosquito bowel, a process which is also referred to as gametogenesis. Maturation is followed by fertilization with the union of male and female gametes originating in the formation of a zygote. The zygotes then migrate and adhere to the bowel epithelium, where they develop into an oocyst. Upon rupture of an oocyst, sporozoites are released which then migrate to the salivary gland of the mosquito and are released during mosquito feeding (Ghosh A, et al. (2000) Parasitol Today 16: 196-201).

Besides the great variety of parasite forms in the host and vector mosquito, a noticeable feature of the life cycle of several species of *Plasmodium* is its synchronization and periodicity. Such distinguished periodicity in formation of gametocytes, the sexual forms of parasite, have been observed since the beginning of last century, and all research done with several species of *Plasmodium* show the existence of a gametocyte production peak at night, every 24 hours, usually at the same time of mosquito feeding. In this way, the circadian rhythm of the gametocytes is likely to be an important adaptation for maintenance of parasite sexual cycle in the vector mosquito (Garcia C R S. et al. (2001) J Biol Rhythms 16: 436-443). Until now the signal responsible for the induction of gametocytes formation in the vertebrate host bloodstream remains elusive.

The high degree of synchronization of intraerythrocytic asexual forms results in recurring fever attacks and shivers, always in periods of time multiple of 24 hours, coinciding with a practically simultaneously release of billion of merozoites into the bloodstream. Blood-stage infection can persist for months or years or for decades in cases of *P. malariae* infections when untreated. In tropical regions, *P. vivax* relapses typically every 3-4 weeks, or every 6-8 weeks after treatment when individuals are treated with slow eliminating drugs which suppress the first relapse. In temperate areas, *P. vivax* can remain latent for 8-10 months between primary infection and first relapse (White N J., Malar J 2011; 10: e297; White N J et al., (2014) Lancet; 383: 723-35). In children, recurrent *P. falciparum* and *P. vivax* malaria have pronounced adverse effects as they interfere with growth, development, and schooling.

Malaria infections also have a strong impact on the shape of the human genome: The geographic distributions of sickle cell disease, haemoglobins C and E, ovalocytosis, thalassaemias, and glucose-6-phosphate dehydrogenase (G6PD)

deficiency are roughly similar to that of malaria before the introduction of control measures, which suggests that these disorders confer a survival advantage in the presence of malaria. In the case of haemoglobin S [HbS], the heterozygote is protected against malaria, whereas the homozygote gets sickle cell disease. The adaptive genomic changes, which provide protective mechanisms against Malaria include decreased parasite growth at low oxygen tensions (haemoglobin AS [HbAS], reduced cytoadherence (haemoglobins AC [HbAC] and CC [HbCC], HbAS), reduced invasion (ovalocytosis), reduced parasite densities (G6PD defi ciency), and reduced multiplication at high densities (haemoglobin AE [HbAE]) (White N J et al., (2014) Lancet; 383: 723-35).

The primary objective in the treatment of Malaria is to ensure the rapid and complete elimination of the *Plasmodium* parasite from the patient's blood in order to prevent progression of uncomplicated malaria to severe disease or death, and to prevent chronic infection that leads to malaria-related anaemia. Furthermore, from a public health perspective, it is important to reduce transmission of the infection to others by means of treatment, by reducing the infectious reservoir, and to prevent the emergence and spread of resistance to antimalarial medicines.

The World Health Organization (WHO) recommends artemisinin-based combination therapies (ACTs) for the treatment of uncomplicated malaria caused by the *P. falciparum* parasite. By combining two active compounds with different mechanisms of action, ACTs are the most effective antimalarial medicines available today. The WHO currently recommends five ACTs for use against *P. falciparum* malaria. The choice of the respective ACT is based on the results of therapeutic efficacy studies against local strains of *P. falciparum* malaria.

In the treatment of *P. falciparum* malaria, artemisinin and its derivatives should not be used as oral monotherapy, as this promotes the development of artemisinin resistance in the parasite. Moreover, fixed-dose formulations, which combine two different active compounds co-formulated in one tablet are strongly preferred and recommended over co-blistered, co-packaged or loose tablet combinations, since they facilitate adherence to treatment and reduce the potential use of the individual components of co-blistered medicines as monotherapy. A treatment regimen of *P. falciparum* in children and adults typically comprises the administration of artesunate 2.4 mg/kg by intravenous or intramuscular injection, followed by 2.4 mg/kg at 12 h and 24 h with continued injections once daily if necessary. Where injectable treatment cannot be given, patients with severe malaria should immediately receive treatment with intrarectal artesunate and should be referred to an appropriate facility for full parenteral treatment.

The occurrence of malaria drug resistance is a major problem in the tropical and subtropical world, which is a phenomenon common to all anti-infective agents that can be defined as a genetically encoded reduction in efficacy of a drug. Anti-malarial drugs are amongst the most commonly used drugs worldwide. Historically, the administration of these drugs has been relatively unsupervised, which in combination with their frequency of use has led to the successive demise of drugs used first line treatments, such as chloroquine, proguanil, pyrimethamine, sulphadoxie-pyrimethamine and mefloquine. These drugs have become unable to produce a 90% clinical response in many areas where they have been intensively deployed (Ding et al. (2012) Malaria Journal 11:292).

Some anti-malarial medicines are more prone to resistance than others, e.g. resistant strains to chloroquine took decades to emerge, while for other drugs, such as atovaquone, which is an electron chain inhibitor, resistance emerged almost in parallel with its first clinical use. Studies have shown that the differences to build up a drug resistance has a molecular basis: chloroquine resistance requires several mutations in the transporter pfcrt (chloroquine resistance transporter), while resistance to atovaquone only requires a single point mutation in the mitochondrially-encoded cytochrome bcl pfcytb (cytochrome b) (Korsinczky M. et al., Antimicrob Agents Chemother (2000) 44:2100-2108). The emergence of resistance and its spread are influenced by several factors. Among them is the level of immunity against the malaria parasite in the population, e.g. in low or unstable transmission areas, drug resistance propagates rapidly. This is due to minimal immunity in a population, thus parasite infections lead to acute symptomatic disease which is most likely treated. Therefore, drug resistance is likely to propagate rapidly due to high drug pressure on existing parasites in these areas. In areas with a high level of disease immunity, the spread of drug resistance is restricted. Here, the requirement for treatment is reduced, due to fewer clinical symptoms in this population.

To date the development of resistance to arteminsinin has been relatively slow. This is partly due to the recommendation of the WHO that only fixed-dose combinations of arteminsinin derivatives with other anti-malarials should be used. However, the first signs of a reduction of the anti-parasitic activity of arteminsinins are emerging in Cambodia and Thailand, manifesting in a decrease in parasite clearance time.

Various anti-malarial drugs have been pursued to overcome malarial resistance and to provide novel and effective treatment options: Natural carbazol alkaloids have been used for the treatment of malaria in folklore medicine (Heterocycles, Vol 79, 2009, pages 121-144).

Calothrixins A and B have potential antimalarial effect (Tetrahedron 55 (1999) 13513-13520). Carbazol derivatives have been synthesized to inhibit the *Plasmodium falciparum* pyrimidine biosynthetic enzyme (J. Med. Chem., 2007, 50, 186-191). Other carbazole derivatives have been disclosed in WO0129028, WO2010/010027, WO2007/062399, WO2005/074971 and WO02/060867.

Despite of countless efforts to control malaria and its further spread, there is a continued requirement for novel and effective anti-malarial drugs that overcome the emerging resistance to currently available anti-malarial drugs.

It is thus an objective of the present invention to provide novel and effective compounds, for use in the treatment of parasitic diseases such as malaria.

SUMMARY OF THE INVENTION

The present inventors have surprisingly found that compounds of formula (i) and its subformulae as disclosed herein are effective for use in the treatment of parasitic diseases, such as e.g. malaria.

Accordingly, the present invention provides in a first embodiment a compound of formula (i)

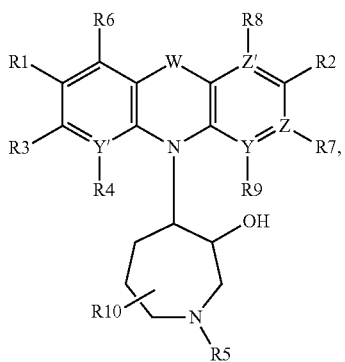

wherein

W is selected from a C-Sp2-Sp2-C bond, O, SO$_2$, S, N

Z is selected from C or N,

Z' is selected from C, or N,

Y' is selected from C or N,

Y is selected from C or N,

R1 denotes H, halogen, CF$_3$, OMe, Alk, Alkoxy, S-Ak, SMe, SO$_2$Me, SO$_2$Alk, NO$_2$, keto, amino, or amide, R2 denotes H, halogen, CF$_3$, OMe, Alkoxy, Alk, S-Ak, SMe, SO$_2$Me, SO$_2$Alkyl, NO$_2$, keto, amino, or amide, R3 denotes H, halogen, CF$_3$, OMe, SO$_2$, Alk, Alkoxy, S-Alkyl, SMe, SO$_2$Me, SO$_2$Alk, NO$_2$, keto, amino, or amide, R4 denotes H, halogen, CF$_3$, OMe, Alk, Alkoxy, S-Alkyl, SMe, SO$_2$Me, SO$_2$Alk, NO$_2$, keto, amino, or amide, R5 denotes H, alkyl, benzyl, amide, sulfonamide, Alk, Alkoxy, NO$_2$, alkoxy, OMe, NO$_2$, keto, amino, or amide, R6 denotes H, alkyl, OMe, SO$_2$, Alk, Alkoxy, S-Alkyl, SMe, SO$_2$Me, SO$_2$Alk, NO$_2$, keto, amino, or amide, R7 denotes H, halogen, SO$_2$, SO$_2$Alk, or S-Alk, Alk, Alkoxy, keto, amino, or amide, R8 denotes H, halogen, CF$_3$, alk, alkoxy, keto, amino, amide, SO$_2$, S-Alk, R9 denotes H, halogen, CF$_3$, OMe, Alk, Alkoxy, S-Alkyl, SMe, SO$_2$Me, SO$_2$Alk, NO$_2$, keto, amino, amide, azepanyl, azepanyl-3-ol, or amino-azepanyl-3-ol R10 denotes H, halogen, CF$_3$, OMe, Alk, Alkoxy, S-Alkyl, SMe, SO$_2$Me, SO$_2$Alk, NO$_2$, keto, aryl, hydroxyl, amino, or amide, and Alk is a branched or linear alkyl group having 1 to 8 carbon atoms or cycloalkyl having 3 to 6 carbon atoms, wherein 1 to 7 H-atoms may be independently replaced by Hal, OR, COOR, CN, NR2, phenyl, linear or branched alkyl having 1, 2 or 3 C atoms, cycloalkyl having 3 to 6 carbon atoms and/or wherein 1 to 3 CH2-groups may be replaced by O, —NRCO—, —CO—, —COO—, —CONR, —NR— or S, or cycloalkyl having 3 to 6 carbon atoms, According to one embodiment the present invention provides a compound according to formula (i), wherein R1 is H, halogen, CF$_3$, NO$_2$.

In one embodiment the present invention provides compounds according to formula (i), wherein R2 is H, halogen, CF$_3$, or NO$_2$.

In one embodiment the inventive compound according to formula (i), wherein R1, R2 are both H, Cl, F, CF$_3$, or NO$_2$.

According to one embodiment the present invention provides for compounds according to the above embodiments, wherein W is a C-Sp2-Sp2-C bond, e.g. a C—C single bond.

According to one embodiment the present invention provides for compounds according to any one of the above embodiments, wherein W is O.

According to one embodiment the present invention provides for compounds according to any one of the above embodiments, wherein W is SO$_2$ In one embodiment the present invention provides for compounds according any one of the above embodiments, wherein W is N.

In one embodiment the present invention provides for compounds according to any one of the above embodiments, wherein W is S.

According to one embodiment the present invention provides for compounds according to any one of the above embodiments, wherein substituents R3, R4, R5, R7, R8, R9 and R10 are H.

In one embodiment, the present invention provides compounds of formula (i) according to any one of the above embodiments, wherein Y is C or N.

In one embodiment the present invention provides compounds of formula (i) according to any one of the above embodiments, wherein Y' is C or N.

In one embodiment, the present invention provides compounds of formula (i) according to any one of the above embodiments, wherein Y' and Z' both are C.

In one embodiment the present invention provides compounds according to formula (i) according to any one of the above embodiments, wherein Z, Z' both are N.

In one embodiment, the present invention provides compounds according to any one of the above embodiments, wherein Y', Z' are both N for formula (i) of the invention.

In one embodiment the present invention provides compounds of formula (i) according to any one of the above embodiments, wherein Z, Z' both are N and Y, Y' both are C.

In one embodiment the present invention provides compounds of formula (i) according to any one of the above embodiments, wherein Z, Z' both are C and Y, Y' both are N.

In one embodiment the present invention provides compounds of formula (i) according to any one of the above embodiments, wherein Z, Z' and Y, Y' are C.

According to one embodiment the present invention provides compounds of formula (i) according to any one of the above embodiments, wherein R1, R2 are both H, Cl, or both are CF$_3$, or both are NO$_2$.

In one embodiment the present invention provides compounds according to formula (i) according to any one of the above embodiments, wherein substituent R1 is H, Cl, F, CF$_3$, or NO$_2$.

In one embodiment the present invention provides compounds according to formula (i) according to any one of the above embodiments, wherein substituent R2 is H, Cl, F, CF$_3$, or NO$_2$.

According to one embodiment the present invention provides compounds accoding to any one of the above embodiments, in which R8 is SO$_2$Alk, or R8 is keto (—CO), is R8 is NO$_2$.

According to one embodiment the present invention provides compounds of formula (i) according to any one of the above embodiments in which R6 is alkoxy or keto (—CO).

In a preferred embodiment the present invention provides compounds of formula (i) according to any one of the above embodiments in which R6 is selected from methoxy, ethoxy, propoxy, or tert-butoxy.

In one embodiment compounds of the present invention of formula (i) according to any one of the above embodiments for which R3 is alkoxy, NO$_2$, or amino (NH$_2$).

In a preferred embodiment the present invention provides for compounds of formula (i) according to any one of the above embodiments in which R3 is selected from methoxy, ethoxy, propoxy, or tert-butoxy.

In one embodiment the present invention provides for compounds of formula (i) according to any one of the above embodiments, wherein R4 selected from H, methoxy, ethoxy, or $NO_2$.

According to one embodiment the present invention provides for compounds of formula (i) according to any one of the above embodiments, wherein R10 is $CF_3$ or keto.

In one embodiment the present invention provides compounds according to any one of the above embodiments, wherein R9 and R10 are both H.

According to one item the present invention provides compounds according to formula (I) as disclosed herein.

In one embodiment, the inventive compounds of formula (i) or any of its subformulae as disclosed herein (e.g. Formula (I)) as defined herein are for use as a medicament, preferably for use as a medicament in the treatment of infectious and parasitic diseases as disclosed herein.

More specifically, the inventive compounds of formula (i) or any of its subformulae as disclosed herein (e.g. Formula (I)) as disclosed herein are for use in the treatment of malaria, or cerebral malaria.

In one embodiment, the present invention provides pharmaceutical compositions, which comprise at least compound according to any one of the above embodiments and/or pharmaceutically acceptable derivatives, tautomers, salts, solvates and stereoisomers thereof, including mixtures thereof in all ratios, and optionally excipients and/or adjuvants.

In a preferred embodiment, the pharmaceutical compositions according to the invention as disclosed above further comprise at least one further pharmaceutically active compound.

In one embodiment, the invention pertains to a pharmaceutical composition as disclosed above for use in the treatment of parasitic disease, whereby according to a more specific embodiment of the present invention, the parasitic disease is selected from the group of malaria, African sleeping sickness (HAT), chagas, leishmaniasis, onchocerciasis, filariasis, schistosomiasis, more specifically, the parasitic disease is malaria.

In one embodiment, the present invention provides kits, which comprise an effective amount of the inventive compound as disclosed above and/or pharmaceutically acceptable derivatives and/or solvates and/or stereoisomers thereof, including mixtures thereof in all ratios, and an effective amount of at least one further pharmaceutically active compound. The inventive compound of formula (i) or any of its subformulae as disclosed herein (e.g. Formula (I)) and the at least one further pharmaceutically active compound may be provided as separate unit dosage forms, or may be provided as a single unit dosage form, which comprises both, the inventive compound according to formula (i) or any of its subformulae as disclosed herein (e.g. Formula (I)) as defined above and the at least one further pharmaceutically active compound.

In one embodiment, the unit dosage form of the inventive kit may be a pill, capsule, lozenge, injectable solution, suppository, or plaster.

According to one item or embodiment, the present invention provides for a process of preparing a compound of formula (I), which comprises the steps of
(a) reacting a compound of formula (II), wherein R1-R8 and Y', Y, Z, Z' are as defined above:

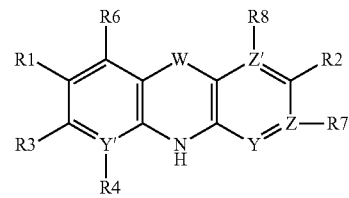

with a compound of formula (III)

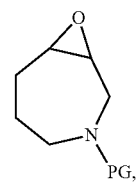

(b) removing the protective group (PG).

According to one embodiment, the present invention provides a method of treatment of a person person inflicted with parasitic disease, wherein the method of treatment comprises administering a pharmacologically effective amount of a compound of formula (i) or any of its subformulae as disclosed herein (e.g. Formula (I)) according to any one of the above embodiments, or a pharmaceutical composition as defined above to a person in need thereof.

In a preferred embodiment, the parasitic disease to be treated by the inventive method is is selected from the group comprising malaria, cerebral malaria, tuberculosis, African sleeping sickness (HAT), chagas, leishmaniasis, onchocerciasis, filariasis and schistosomiasis.

In one embodiment, the inventive method comprises administering to a person in need thereof the inventive compound according to any one of the above embodiments or the pharmaceutical composition as defined above at least once a day, or twice or three times daily, or twice a week, or three times a week, or at least once every 2, 3, 4, 5, 6 days, for at least 1-18 weeks, or for at least 2-16 weeks, or for at least 3, 4, 5, 6, 7, 8, 9, 10, 11, 12, 13, 14, 15 weeks.

In one embodiment, the inventive method as disclosed above comprises administering to a person in need thereof from about 12.5 µg/kg to about 50 mg/kg body weight of the inventive compound as disclosed herein, or of the pharmaceutical composition as disclosed herein.

In more preferably, the parasitic disease to be treated by the inventive method as disclosed above is malaria or cerebral malaria.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of".

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Chemical compounds as disclosed in the present invention are named according to IUPAC nomenclature, unless otherwise indicated, e.g. atoms and/or molecules are denoted by their IUPAC nomenclature.

The described objectives are solved by the present invention, preferably by the subject matter of the appended claims. More preferably, the present invention is solved according to a first embodiment by a compound according to formula (i)

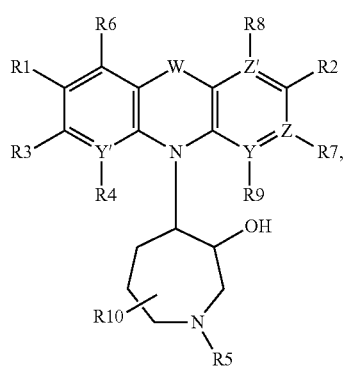

(i)

wherein
W is selected from a C-Sp2-Sp2-C bond, O, $SO_2$, S, N
Z is selected from C or N,
Z' is selected from C, or N,
Y' is selected from C or N,
Y is selected from C or N,
R1 denotes H, halogen, $CF_3$, OMe, Alk, Alkoxy, S-Ak, SMe, $SO_2Me$, $SO_2Alk$, $NO_2$, keto, amino, or amide,
R2 denotes H, halogen, $CF_3$, OMe, Alkoxy, Alk, S-Ak, SMe, $SO_2Me$, $SO_2Alkyl$, $NO_2$, keto, amino, or amide,
R3 denotes H, halogen, $CF_3$, OMe, $SO_2$, Alk, Alkoxy, S-Alkyl, SMe, $SO_2Me$, $SO_2Alk$,
$NO_2$, keto, amino, or amide,
R4 denotes H, halogen, $CF_3$, OMe, Alk, Alkoxy, S-Alkyl, SMe, $SO_2Me$, $SO_2Alk$, $NO_2$, keto, amino, or amide,
R5 denotes H, alkyl, benzyl, amide, sulfonamide, Alk, Alkoxy, $NO_2$, alkoxy, OMe, $NO_2$, keto, amino, or amide,
R6 denotes H, alkyl, OMe, $SO_2$, Alk, Alkoxy, S-Alkyl, SMe, $SO_2Me$, $SO_2Alk$, $NO_2$, keto, amino, or amide,
R7 denotes H, halogen, $SO_2$, $SO_2Alk$, or S-Alk, Alk, Alkoxy, keto, amino, or amide,
R8 denotes H, halogen, CF3, alk, alkoxy, keto, amino, amide, $SO_2$, S-Alk,
R9 denotes H, halogen, $CF_3$, OMe, Alk, Alkoxy, S-Alkyl, SMe, $SO_2Me$, $SO_2Alk$, $NO_2$, keto, amino, amide, azepanyl, azepanyl-3-ol, or amino-azepanyl-3-ol
R10 denotes H, halogen, $CF_3$, OMe, Alk, Alkoxy, S-Alkyl, SMe, $SO_2Me$, $SO_2Alk$, $NO_2$, keto, aryl, hydroxyl, amino, or amide,
and
Alk is a branched or linear alkyl group having 1 to 8 carbon atoms or cycloalkyl having 3 to 6 carbon atoms, wherein 1 to 7H-atoms may be independently replaced by Hal, OR, COOR, CN, $NR_2$, phenyl, linear or branched alkyl having 1, 2 or 3 C atoms, cycloalkyl having 3 to 6 carbon atoms and/or wherein 1 to 3 $CH_2$-groups may be replaced by O, —NRCO—, —CO—, —COO—, —CONR, —NR— or S, or cycloalkyl having 3 to 6 carbon atoms,
and
the pharmaceutically acceptable salts esters and N-oxides thereof, in a racemic form or in an enantiomerically pure form or enriched mixture of the respective enantiomers in all ratios, and/or as a mixture of diastereoisomers in all ratios.

The term "alkyl" as used for the inventive compound according to formula (i) means saturated straight, branched, or cyclic hydrocarbon groups (i.e., cycloalkyl groups). Alkyl may e.g. also refer to groups comprising 1 to 10 carbon atoms, e.g. 1, 2, 3, 4, 5, 6, 7, 8, 9, or 10 carbon atoms. The term "alkyl" as used for the inventive compound may als refer to methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term "heteroalkyl" as used for compounds of formula (I) in the present invention means an alkyl group, having at least one atom within the chain which is not carbon. Preferred heteroatoms include sulfur, oxygen, and nitrogen.

The term "alkoxy" as used with the inventive formula (i) means straight or branched chain alkyl groups linked by an oxygen atom (i.e., —O-alkyl). In particular embodiments, alkoxy refers to oxygen-linked groups comprising 1 to 10 carbon atoms, e.g. 1, 2, 3, 4, 5, 6, 7, 8, 9, or 10 carbon atoms and may e.g. refer to methoxy, ethoxy, -propyloxy, butyloxy, i-butyloxy, pentyloxy, hexyloxy, octyloxy, nonyloxy, decyloxy, including their isomers. Accordingly, the term "OMe" as used with the inventive compound refers to an oxygen atom linked to one carbon atom, e.g. O—CH$_3$.

The term "S-Alkyl" as used for inventive compounds according to formula (i) refers to sulfidyl-alkyl residues, which may comprise branched or linear alkyl group as defined above having 1 to 8 carbon atoms, e.g. 1, 2, 3, 4, 5, 6, 7, or 8 carbon atoms, or cycloalkyl having 3 to 7 carbon atoms, e.g. 3, 4, 5, 6 or 7 carbon atoms, wherein 1 to 7H-atoms, e.g. 2, 3, 4, 5, 6 H-atoms, may be independently replaced by Hal, OR, COOR, CN, NR$_2$, phenyl, linear or branched alkyl having 1, 2 or 3 C atoms, cycloalkyl having 3 to 6 carbon atoms and/or wherein 1 to 3 CH$_2$-groups may be replaced by O, —NRCO—, —CO—, —COO—, —CONR, —NR— or S, or cycloalkyl having 3 to 6 carbon atoms, e.g. 3, 4, 5, or 6 carbon atoms. The term "SMe" as used for the inventive compound refers to a sulfide comprising 1 carbon atom, i.e. —SCH$_3$ (thiomethyl).

The term "SO$_2$Alk" as used with the inventive compound according to formula (i) refers to sulfonylalkyl residues, which may comprise branched or linear alkyl group as defined above having 1 to 8 carbon atoms, e.g. 1, 2, 3, 4, 5, 6, 7, or 8 carbon atoms, or cycloalkyl having 3 to 7 carbon atoms, e.g. 3, 4, 5, 6 or 7 carbon atoms, wherein 1 to 7 H-atoms, e.g. 2, 3, 4, 5, 6 H-atoms, may be independently replaced by Hal, OR, COOR, CN, NR$_2$, phenyl, linear or branched alkyl having 1, 2 or 3 C atoms, cycloalkyl having 3 to 6 carbon atoms and/or wherein 1 to 3 CH$_2$-groups may be replaced by O, —NRCO—, —CO—, —COO—, —CONR, —NR— or S, or cycloalkyl having 3 to 6 carbon atoms, e.g. 3, 4, 5, or 6 carbon atoms. Accordingly, term "SO$_2$Me" as used for the inventive compounds refers to methylsulfonyl residues —SO$_2$CH$_3$. The term "halogen" or "HAL", "hal" as used for the inventive compound according to formula (I) shall refer to fluorine, chlorine, bromine, or iodine. The term "amino" as used with the inventive compounds according to formula (i) or any of its subformulae as disclosed herein refers to a —NH2 group, —NH-alkyl group, or —N(alkyl)$_2$ group wherein alkyl is as defined above.

The term "sulfonamide" as used in the present invention for inventive compounds according to formula (i) refers to a substituent having the structure

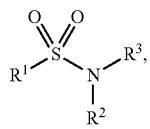

where e.g. R1, R2, R3 can be hydrogen, alkyl, aryl, cycloalkyl, and heterocyclyl. Exemplary sulfonamides used with the inventive compound include e.g. alkylsulfonamides, arylsulfonamides, cycloalkyl sulfonamides, and heterocyclyl sulfonamides.

When a group R, e.g. R1, R2, R3, R4, R5, R6, R7, or R8, Hal, or Alk is present more than once in a compound of the present invention, each group independently denotes one of the meanings as defined herein. The relative stereoconfiguration of of any of the substituents R1, R2, R3, R4, R5, R6, R7 or R8 and adjacent ring substituents in compounds of formula (i) according to the invention may e.g. be in trans, or e.g. in cis configuration, e.g. the relative stereoconfiguration of R1, R2 and adjacent ring substituents may e.g. be in trans, however, cis configuration may also be possible.

Preferred compounds according to the invention are compounds of formula (i), wherein R1 is one of H, halogen (e.g. F, Cl), CF$_3$, or NO$_2$, or R2 is H, halogen, CF$_3$, or NO$_2$, or both R1, R2 are H, halogen, CF$_3$, or NO$_2$, e.g. R1 and R2 may both be F, or Br, or Cl, CF$_3$, or NO$_2$, whereby R1, R2 may be independently chosen from H, Hal, CF$_3$, NO$_2$, e.g. R1 is H, R2 is CF$_3$, or R1 is CF$_3$, R2 is NO$_2$, or R1 is NO$_2$, R2 is H, or R1 is Cl, R2 is NO$_2$, or R1 is F, R2 is Cl, e.g. according to the following structures:

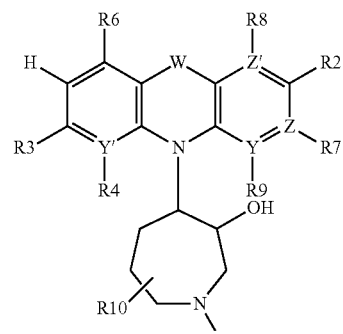

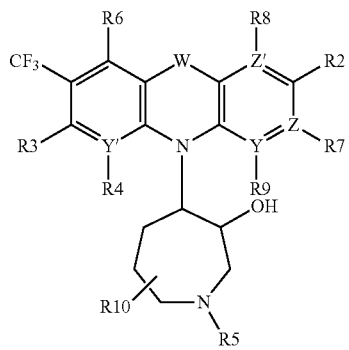

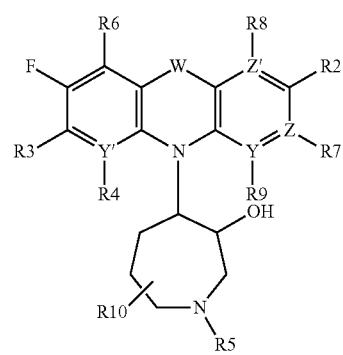

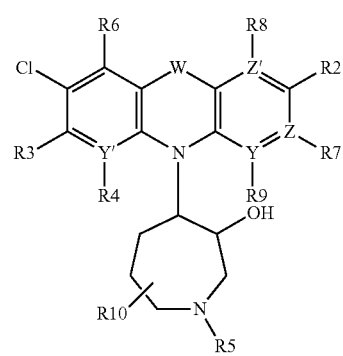

-continued
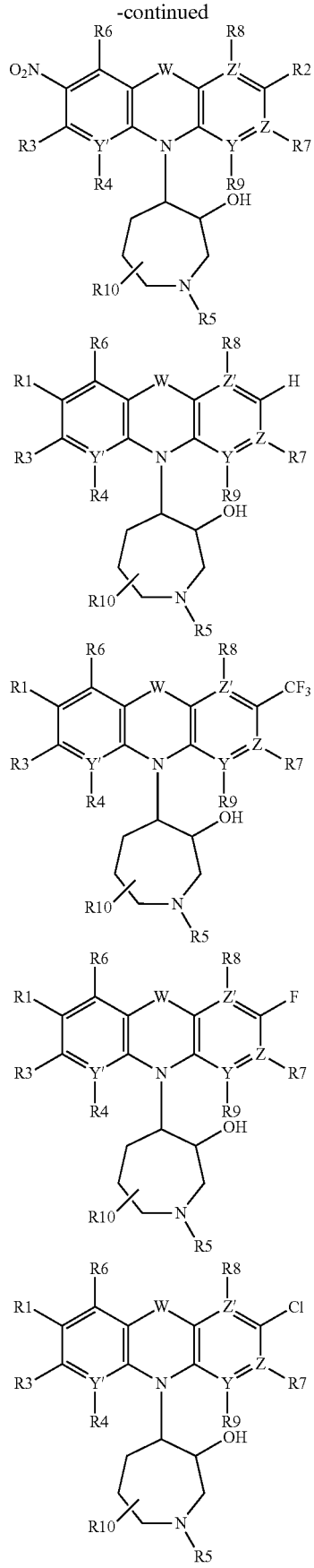
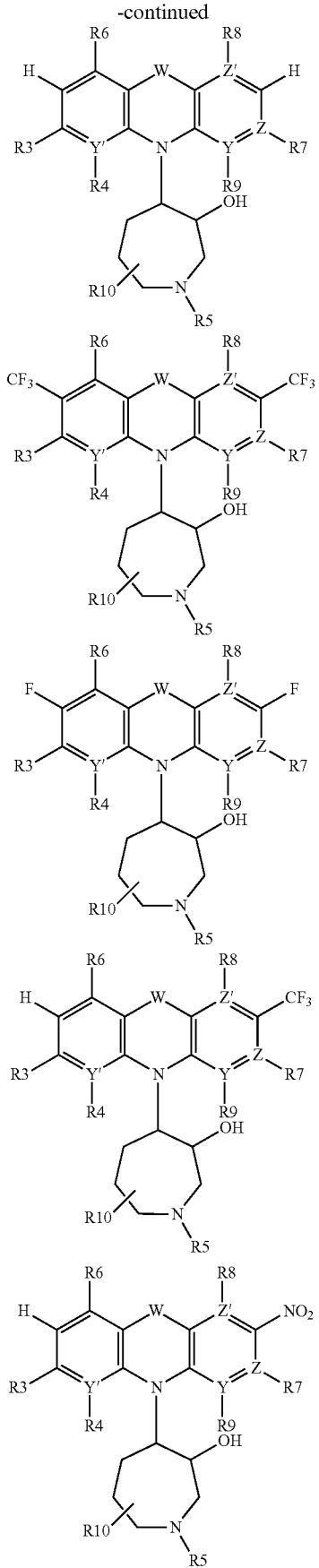

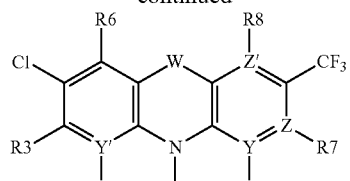
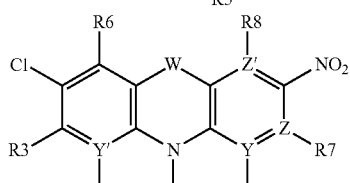
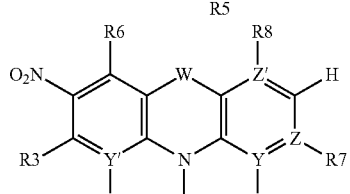
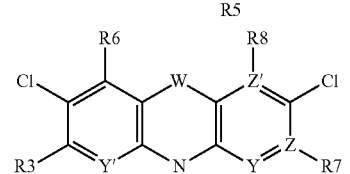
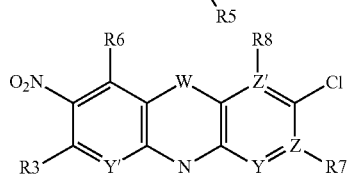
In one embodiment of the present invention, W is a C-Sp2-Sp2-C(C—C single bond) for the inventive compounds according to formula (i) as disclosed above, whereby the substitutents R1, R2, R3, R4, R5, R6, R7, R8, R9, R10 may be as defined above, e.g. inventive compounds of formula (i) may comprise the following subformulae
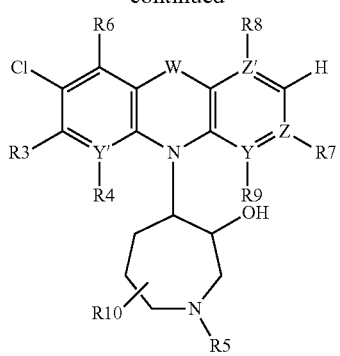
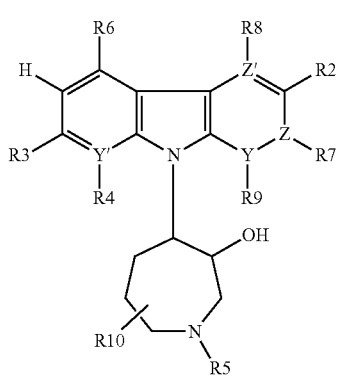
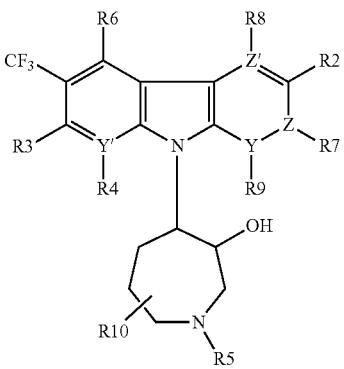

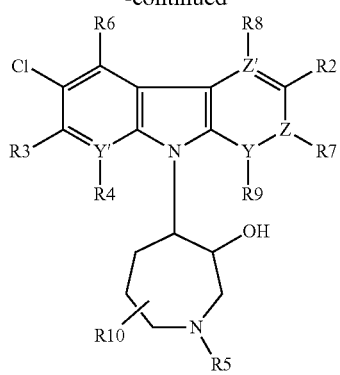
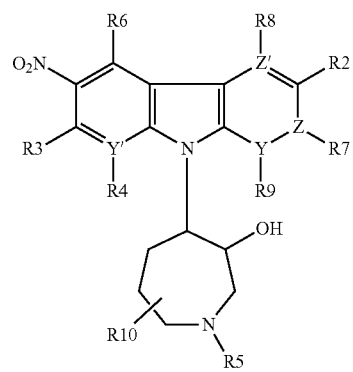
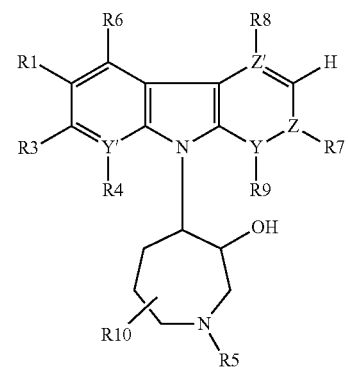
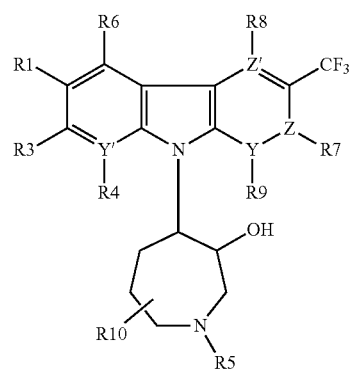
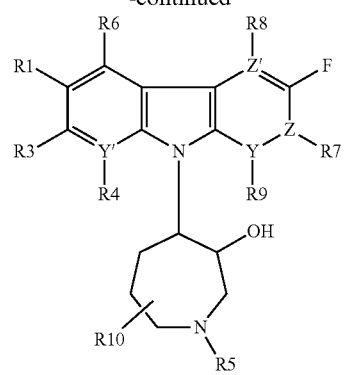
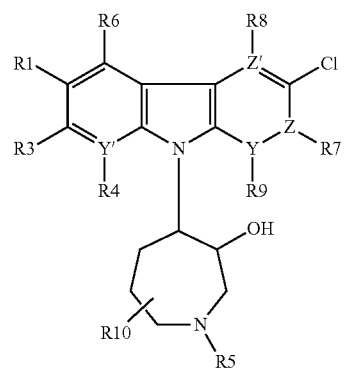
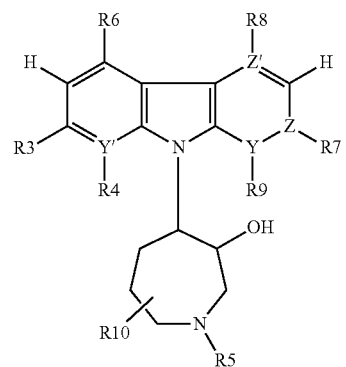
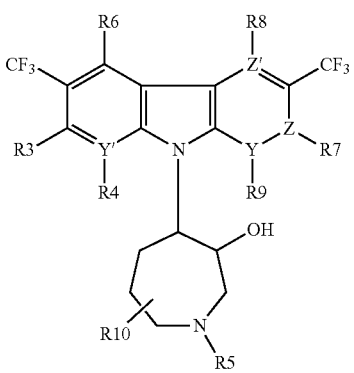

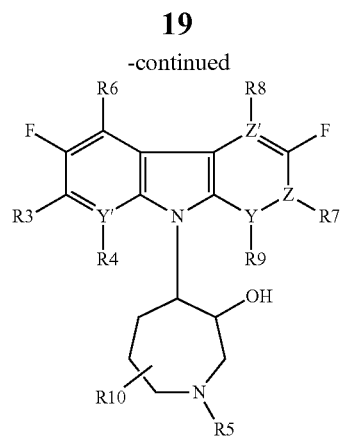
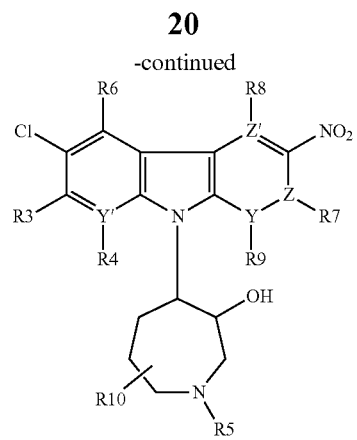
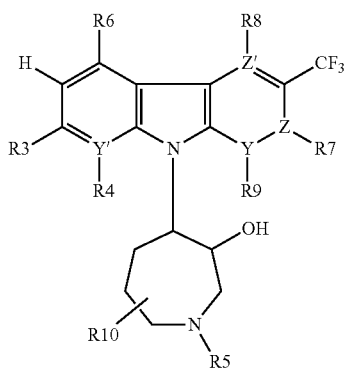
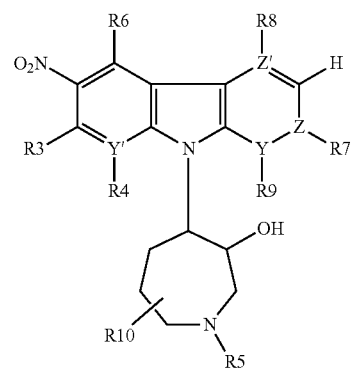
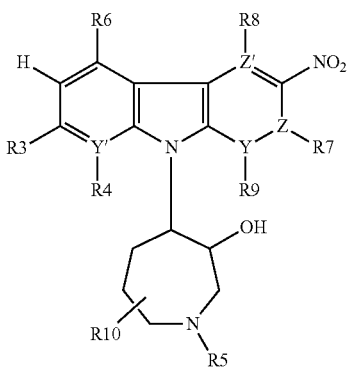
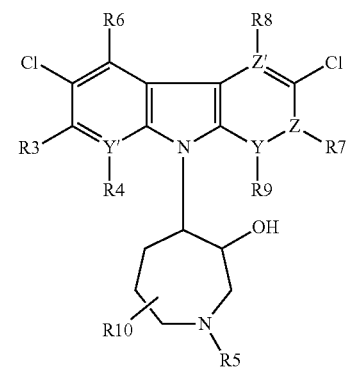
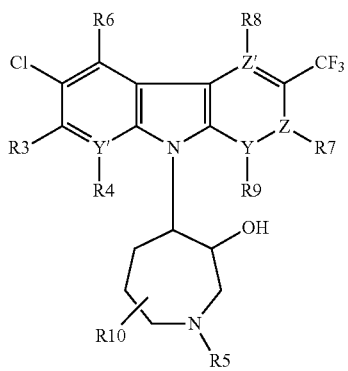
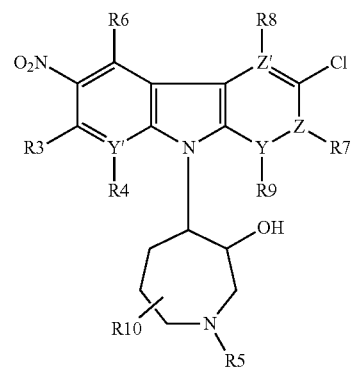

-continued

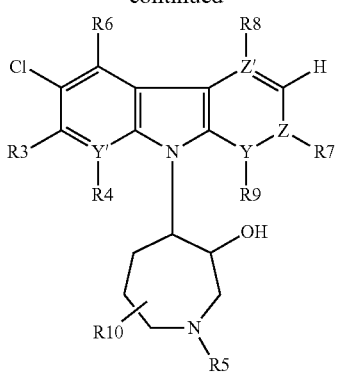

In one embodiment of the present invention, W is O for the inventive compounds according to formula (i) as disclosed above, e.g. inventive compounds of formula (i) may comprise inventive compounds of the following subformula:

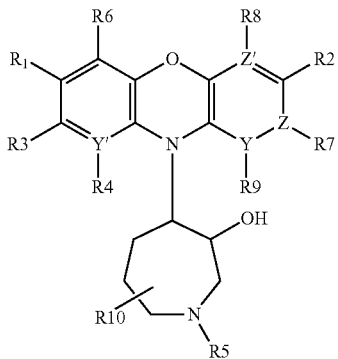

whereby the substitutents R1, R2, R3, R4, R5, R6, R7, R8, R9, R10 may be as defined above, e.g. R1 is H, halogen (e.g. F, Cl), $CF_3$, or $NO_2$, or R2 is H, halogen, $CF_3$, or $NO_2$, or both R1, R2 are H, halogen, $CF_3$, or $NO_2$, e.g. R1 and R2 may both be F, or Br, or Cl, $CF_3$, or $NO_2$, whereby R1, R2 may be independently chosen from H, Hal, $CF_3$, $NO_2$, e.g. R1 is H, R2 is $CF_3$, or R1 is $CF_3$, R2 is $NO_2$, or R1 is $NO_2$, R2 is H, or R1 is Cl, R2 is $NO_2$, or R1 is F, R2 is Cl, e.g. according to the following subformulae

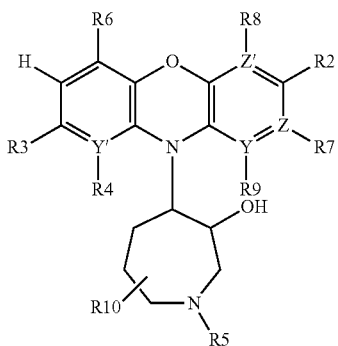

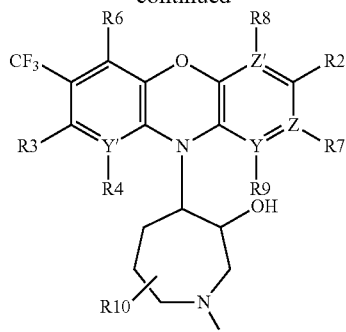

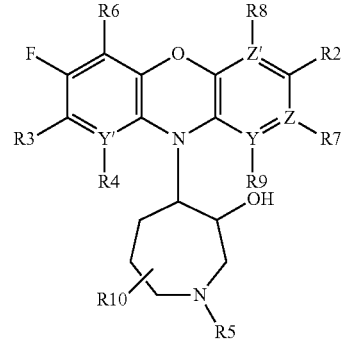

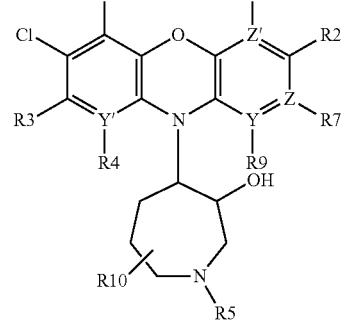

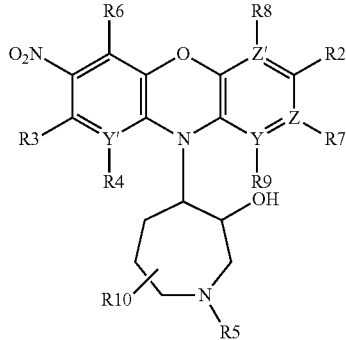

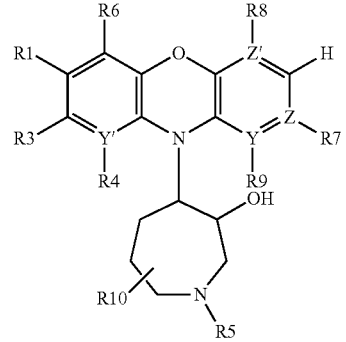

-continued
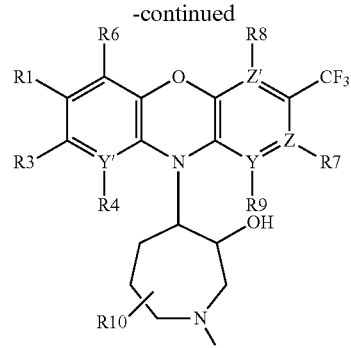
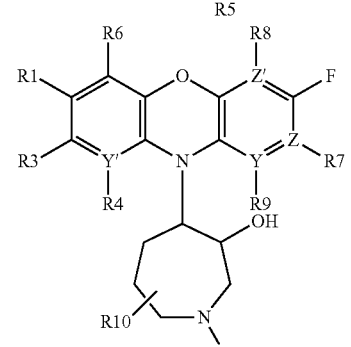
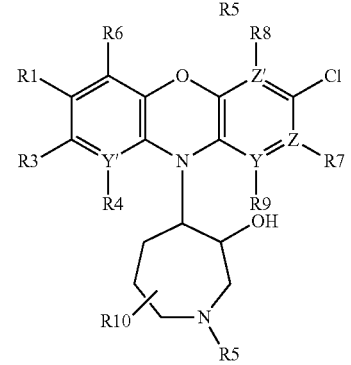
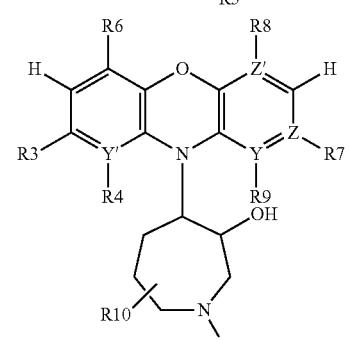
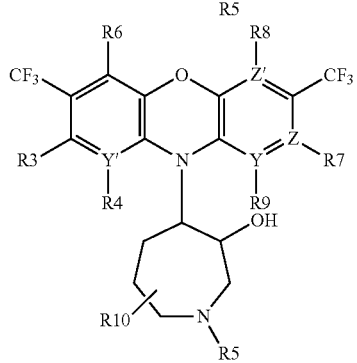
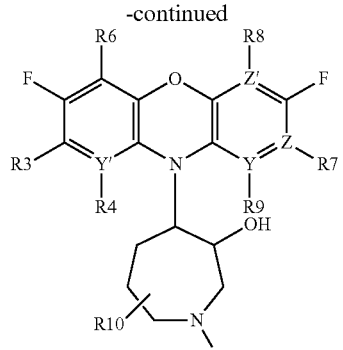
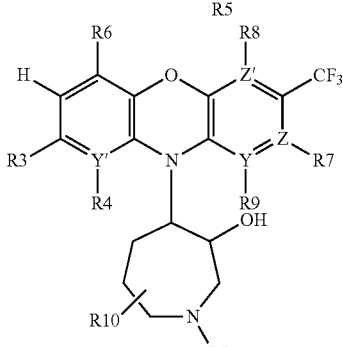
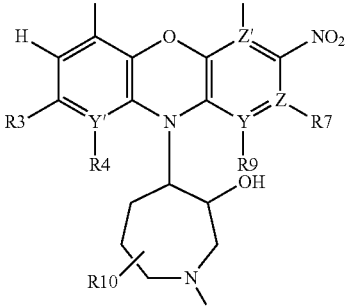
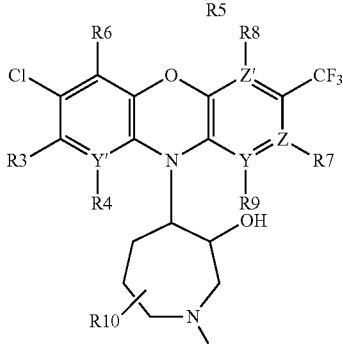
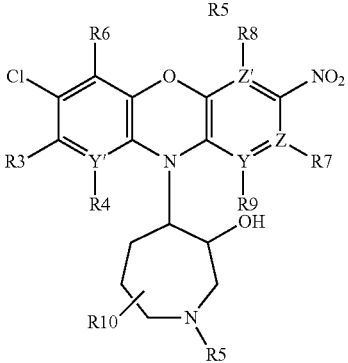

-continued

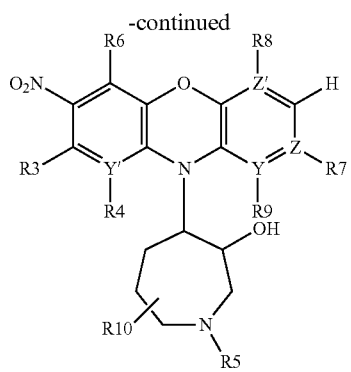

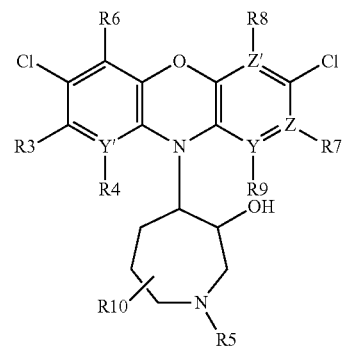

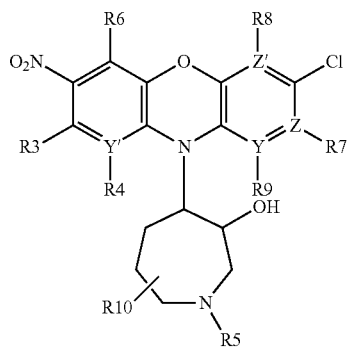

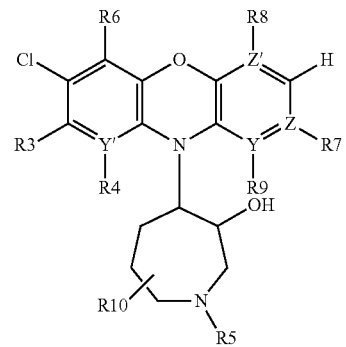

In one embodiment of the present invention, W is SO₂ for the inventive compounds according to formula (i) as disclosed above, e.g. inventive compounds of formula (i) may comprise inventive compounds of the following structure/subformula

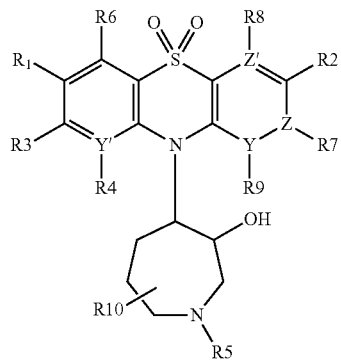

whereby the substitutents R1, R2, R3, R4, R5, R6, R7, R8, R9, R10 may be as defined above, e.g. R1 is H, halogen (e.g. F, Cl), CF₃, or NO₂, or R2 is H, halogen, CF₃, or NO₂, or both R1, R2 are H, halogen, CF₃, or NO₂, e.g. R1 and R2 may both be F, or Br, or Cl, CF₃, or NO₂, whereby R1, R2 may be independently chosen from H, Hal, CF₃, NO₂, e.g. R1 is H, R2 is CF₃, or R1 is CF₃, R2 is NO₂, or R1 is NO₂, R2 is H, or R1 is Cl, R2 is NO₂, or R1 is F, R2 is Cl, e.g. according to the following structures:

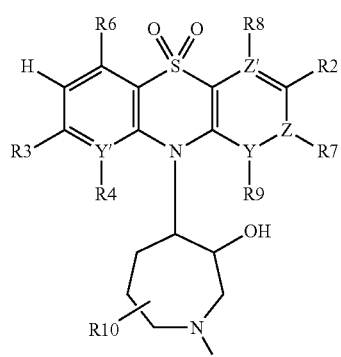

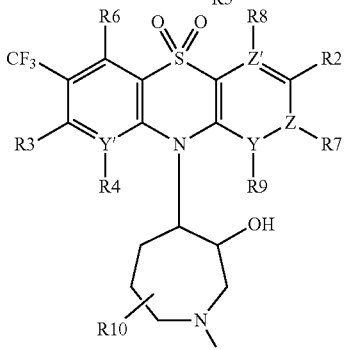

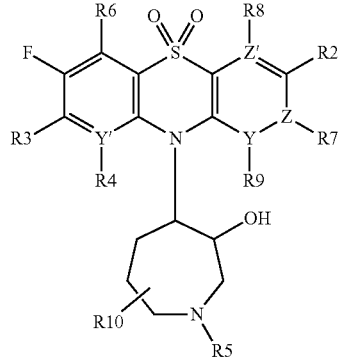

27
-continued
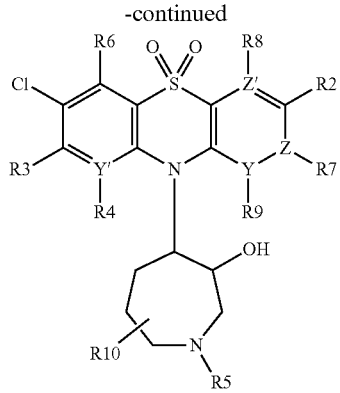
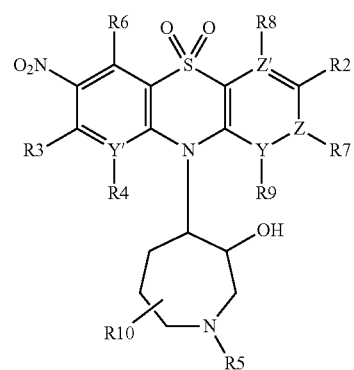
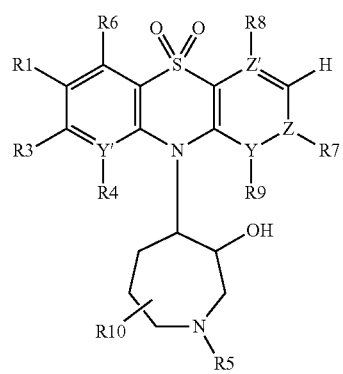
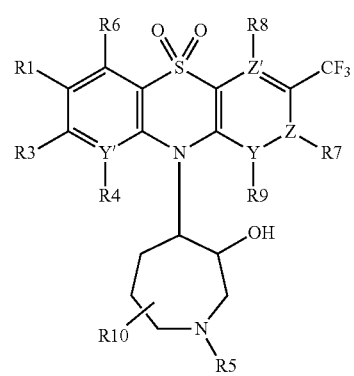
28
-continued
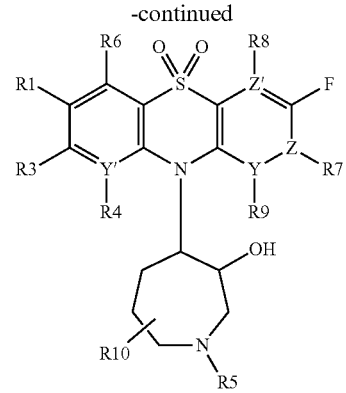
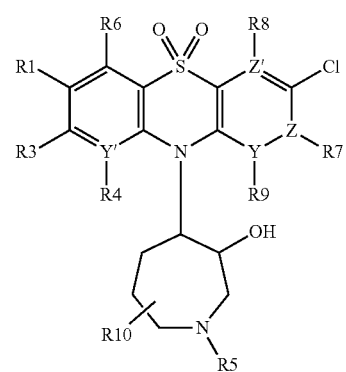
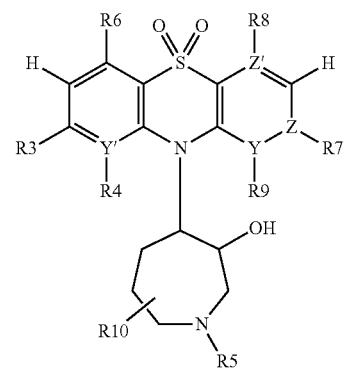
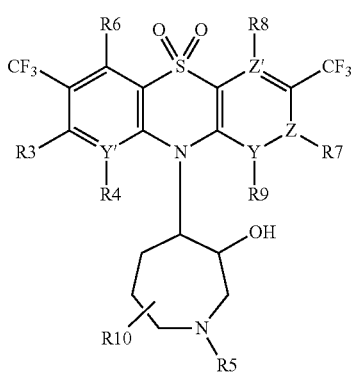

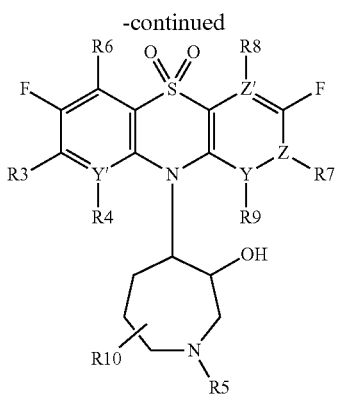
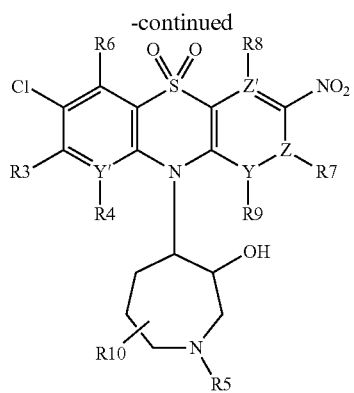
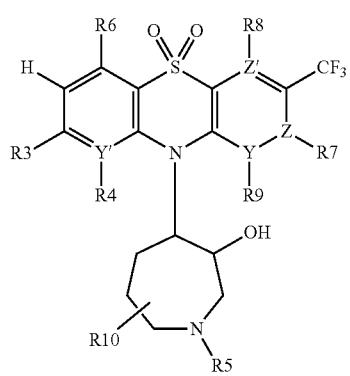
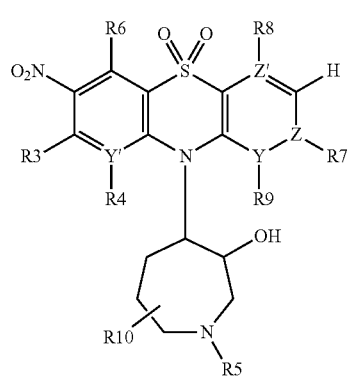
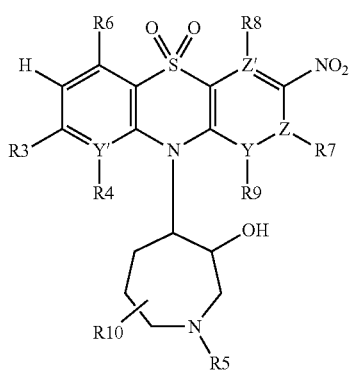
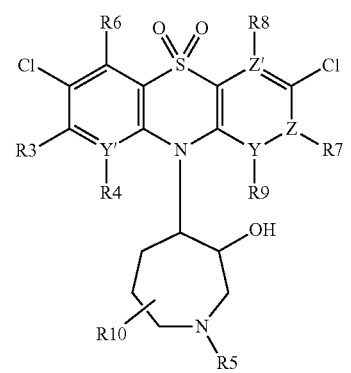
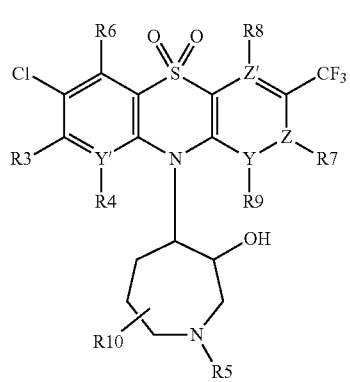
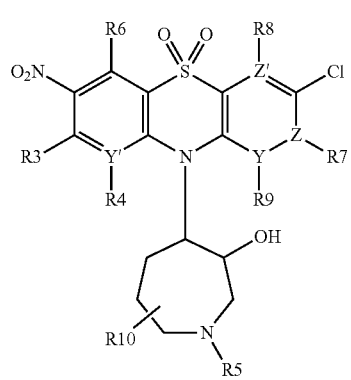

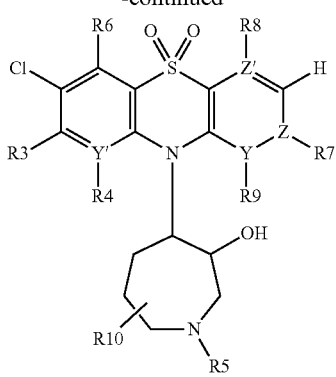

In one embodiment of the present invention, W is N for the inventive compounds according to formula (i) as disclosed above, e.g. inventive compounds of formula (i) may comprise the following structure

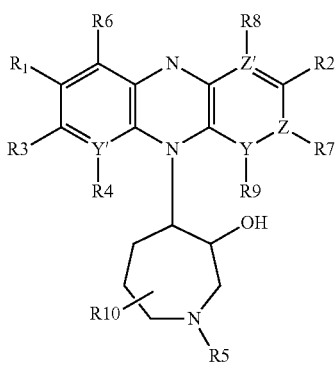

whereby the substitutents R1, R2, R3, R4, R5, R6, R7, R8, R9, R10 may be as defined above, e.g. R1 is H, halogen (e.g. F, Cl), $CF_3$, or $NO_2$, or R2 is H, halogen, $CF_3$, or $NO_2$, or both R1, R2 are H, halogen, $CF_3$, or $NO_2$, e.g. R1 and R2 may both be F, or Br, or Cl, $CF_3$, or $NO_2$, whereby R1, R2 may be independently chosen from H, Hal, $CF_3$, $NO_2$, e.g. R1 is H, R2 is $CF_3$, or R1 is $CF_3$, R2 is $NO_2$, or R1 is $NO_2$, R2 is H, or R1 is Cl, R2 is $NO_2$, or R1 is F, R2 is Cl, e.g. according to the following structures:

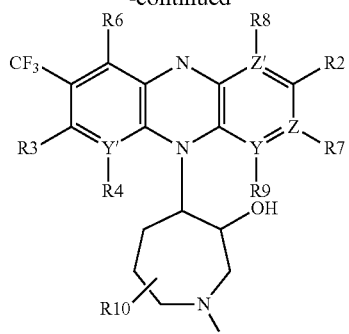

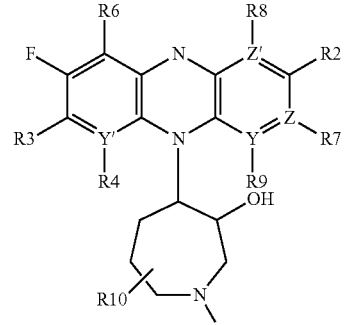

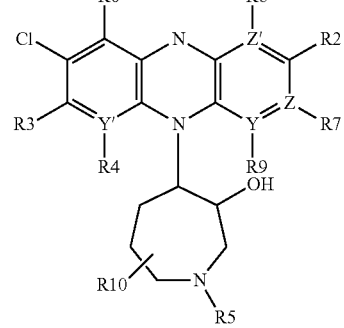

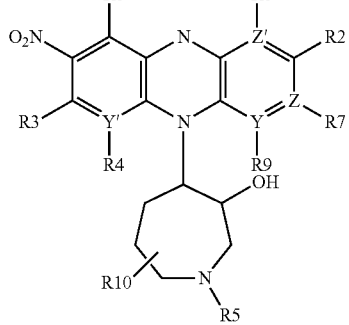

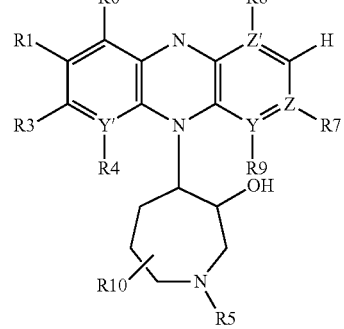

-continued
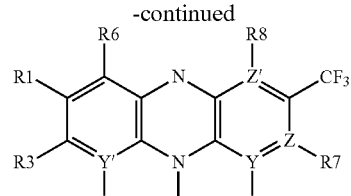
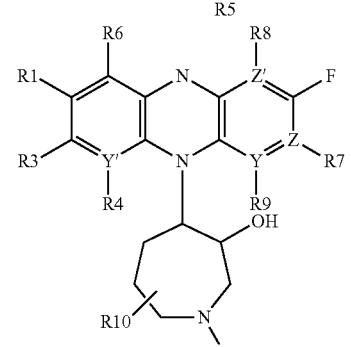
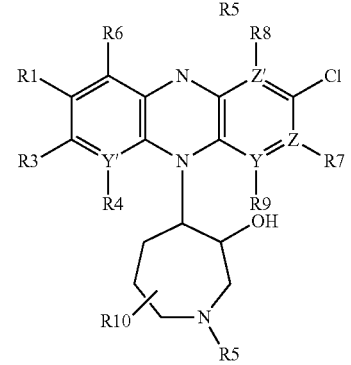
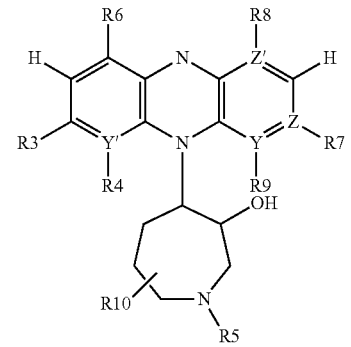
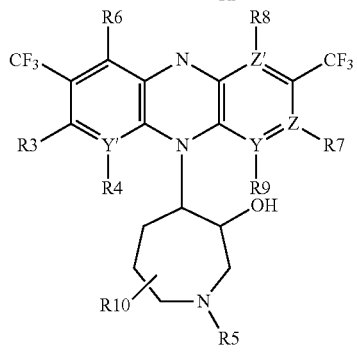
-continued
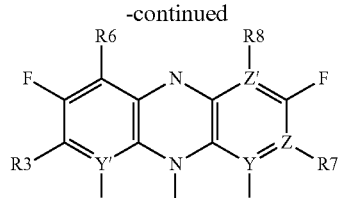
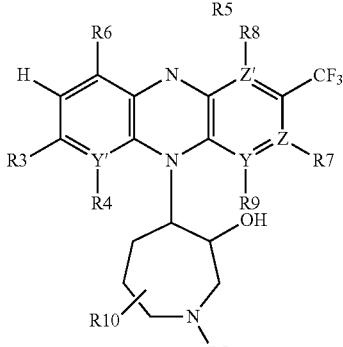
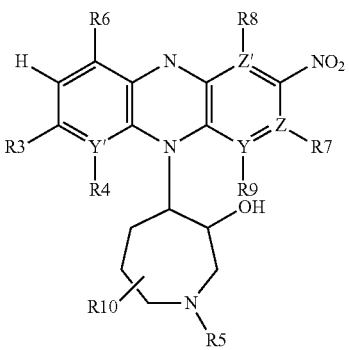
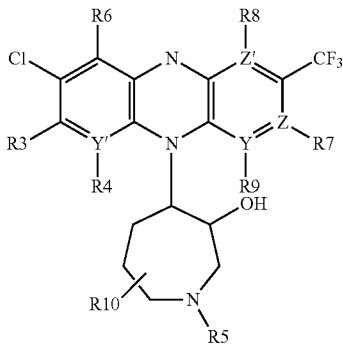
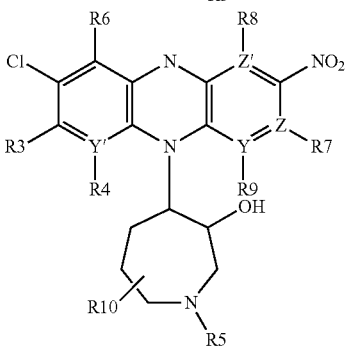

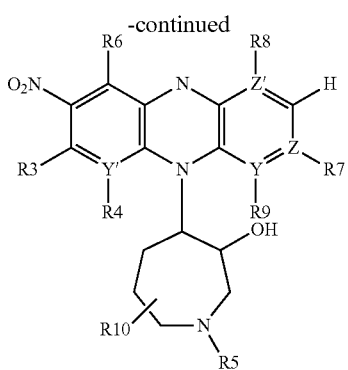

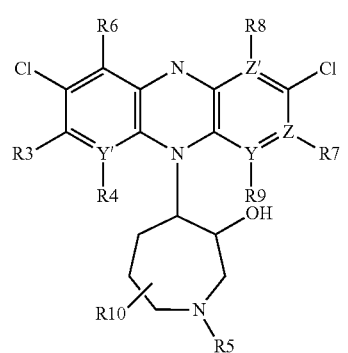

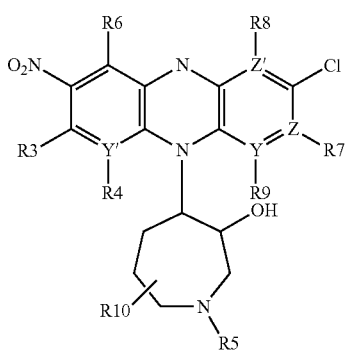

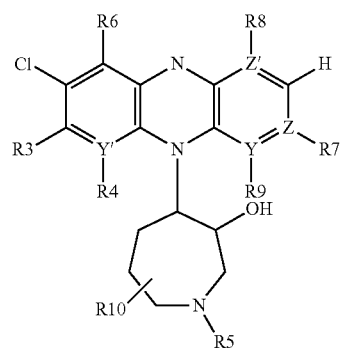

In one embodiment the inventive compounds according to formula (i) comprise substituents R3, R4, R5, R6, R7, R8, R9 and R10 as disclosed above, which e.g. may be H. For example, the inventive compounds according to formula (i) may comprise compounds of the general subformulae as disclosed below:

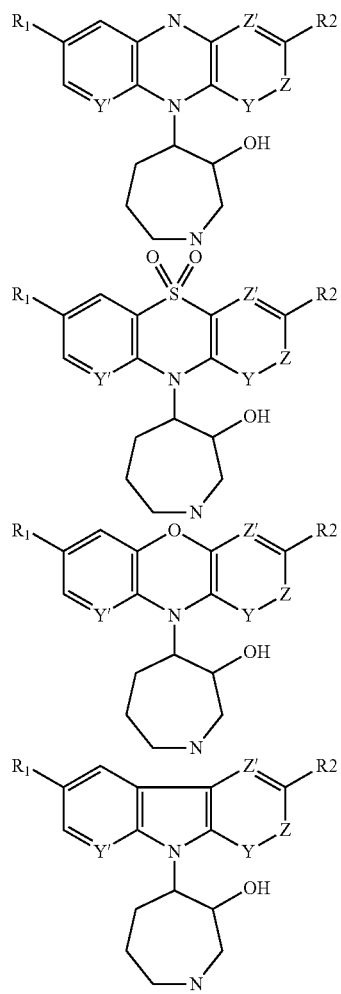

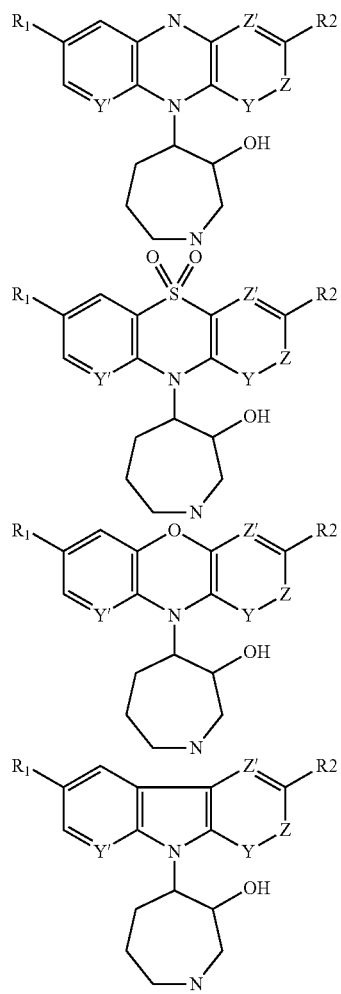

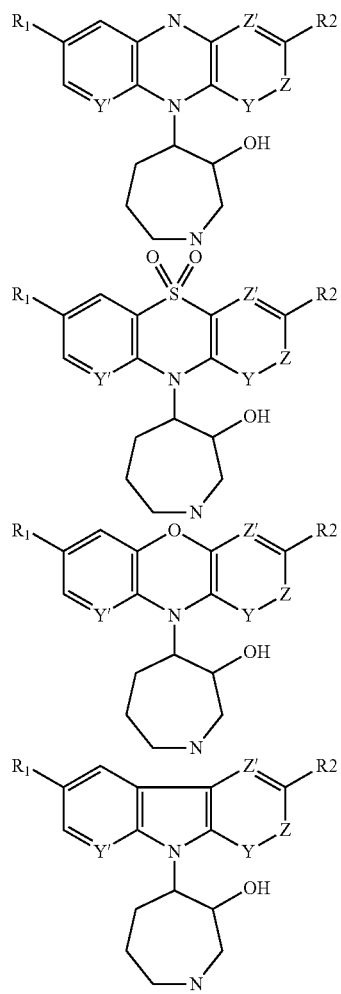

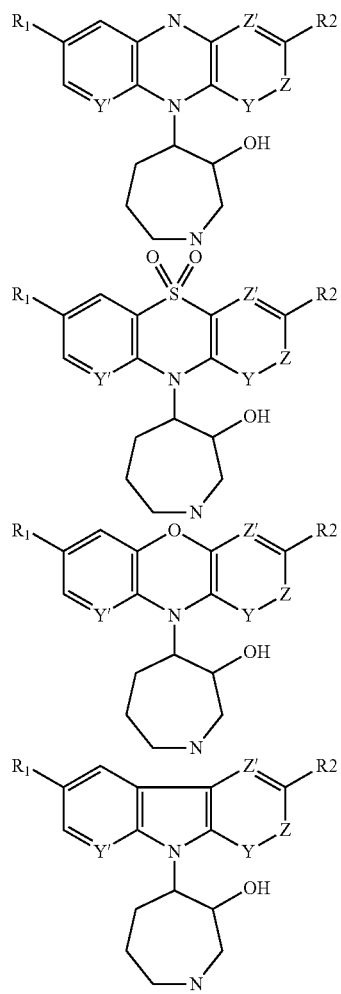

whereby the substitutents R1, R2 may be as defined above, e.g. R1 is H, halogen (e.g. F, Cl), $CF_3$, or $NO_2$, or R2 is H, halogen, $CF_3$, or $NO_2$, or both R1, R2 are H, halogen, $CF_3$, or $NO_2$, e.g. R1 and R2 may both be F, or Br, or Cl, $CF_3$, or $NO_2$, whereby R1, R2 may be independently chosen from H, Hal, $CF_3$, $NO_2$, e.g. R1 is H, R2 is $CF_3$, or R1 is $CF_3$, R2 is $NO_2$, or R1 is $NO_2$, R2 is H, or R1 is Cl, R2 is $NO_2$, or R1 is F, R2 is Cl.

In one embodiment the inventive compounds according to formula (i) or any of its subformulae as disclosed above comprise compounds for which Y may be C or N, e.g. the inventive compounds according to formula (i) may comprise compounds according to the following subformulae:

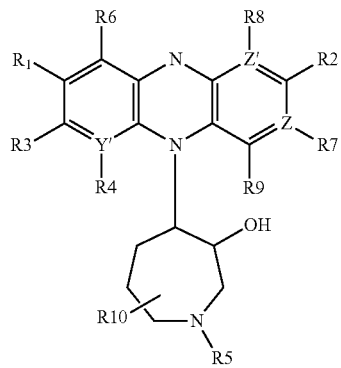

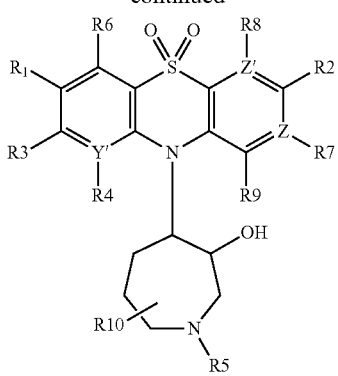

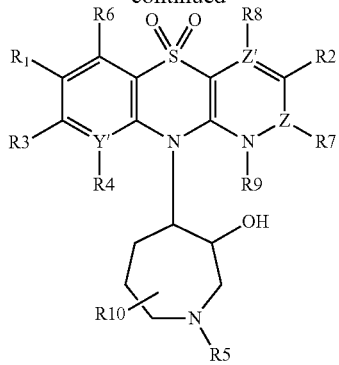

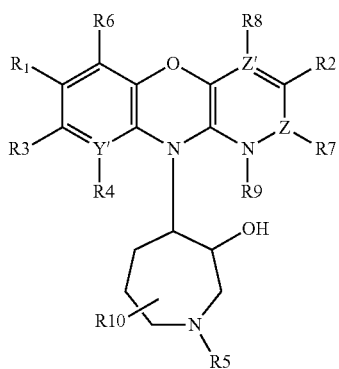

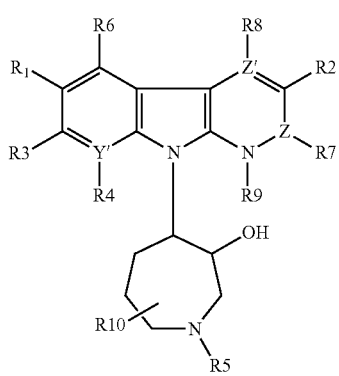

whereby the substitutents R1, R2 may be as defined above, e.g. R1 is H, halogen (e.g. F, Cl), $CF_3$, or $NO_2$, or R2 is H, halogen, $CF_3$, or $NO_2$, or both R1, R2 are H, halogen, $CF_3$, or $NO_2$, e.g. R1 and R2 may both be F, or Br, or Cl, $CF_3$, or $NO_2$, whereby R1, R2 may be independently chosen from H, Hal, $CF_3$, $NO_2$, e.g. R1 is H, R2 is $CF_3$, or R1 is $CF_3$, R2 is $NO_2$, or R1 is $NO_2$, R2 is H, or R1 is Cl, R2 is $NO_2$, or R1 is F, R2 is Cl and e.g. R3, R4, R5, R6, R7, R8, R9 and R10 may be as defined above, e.g. R3-R10 may be H.

In one embodiment the inventive compounds according to formula (i) or any of it subformulae as disclosed above, Y' may be C or N. For example, the inventive compounds may comprise compounds according to the following subformulae:

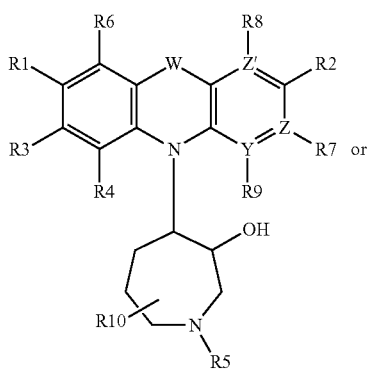

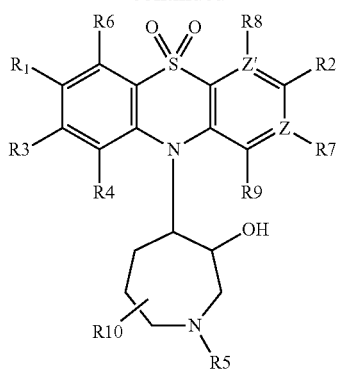

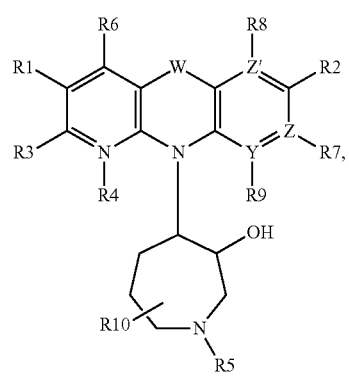

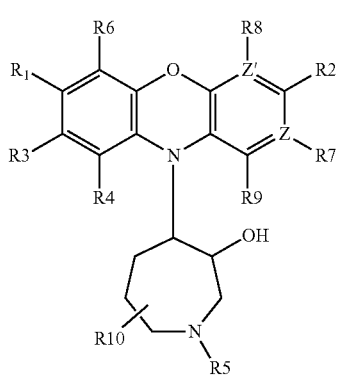

whereby e.g. the substitutents R1, R2, R3, R4, R5, R6, R7, R8, R9 and R10 may be as disclosed above, or e.g. the substitutents R1-R10 may be as disclosed above and Y may be C or N as disclosed above, and e.g. W may be one of a C-Sp2-Sp2-C single bond, N, O, or SO2. For example, substitutents R1, R2, R3, R4, R5, R6, R7, R8, R9 and R10 may as disclosed above independently of each other be any of H, halogen (e.g. F, Cl), CF$_3$, or NO$_2$, or e.g. may be identical, or both R1, R2 are H, halogen, CF$_3$, or NO$_2$, e.g. R1 and R2 may both be F, or Br, or Cl, CF$_3$. For example, for the inventive compounds according to formula (i) or any of its subformulae as disclosed above Y and Y' may be as disclosed above, e.g. Y and Y' are C, or Y, Y' are N, or Y is C and Y' is N, or Y is N and Y' is C. The inventive compounds may e.g. comprise compounds of the following subformulae:

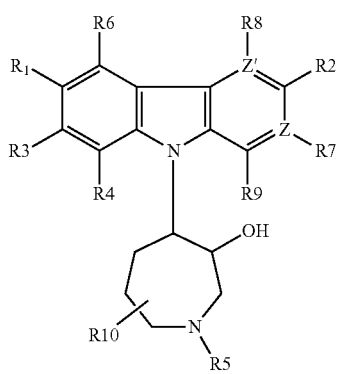

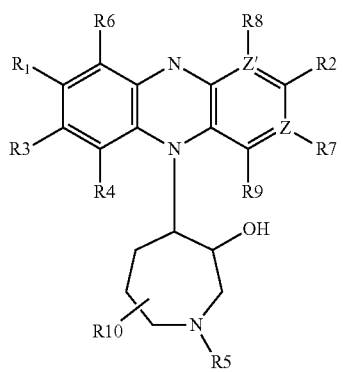

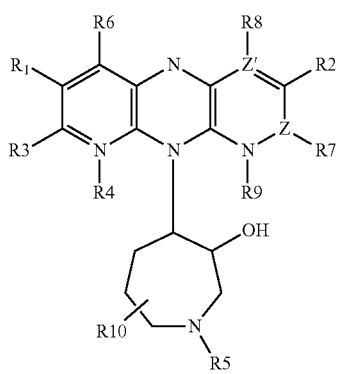

41

-continued

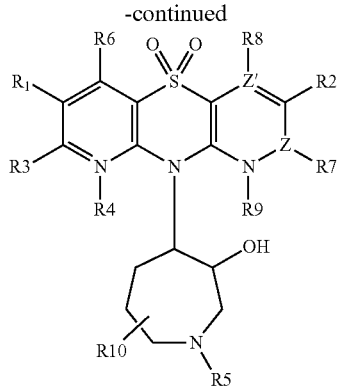

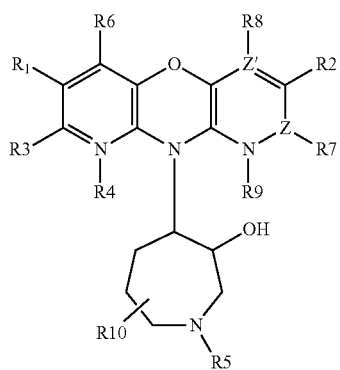

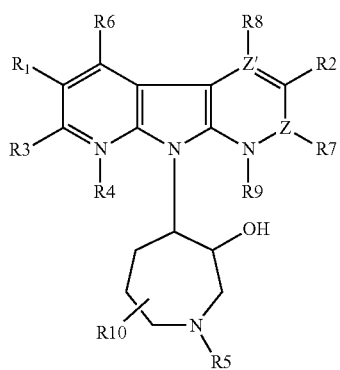

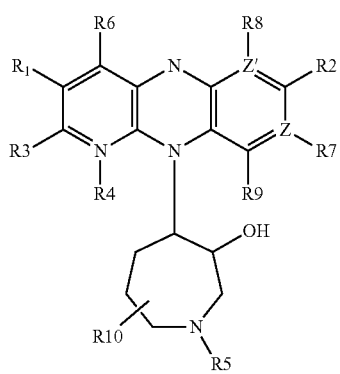

42

-continued

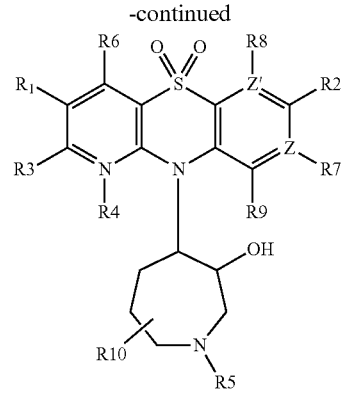

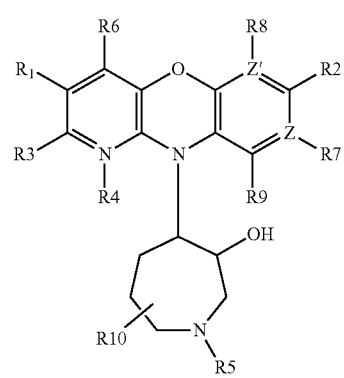

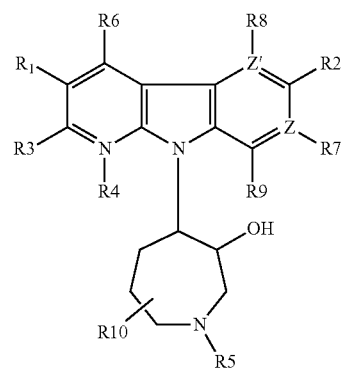

For the inventive compounds according to formula (i) or any of its subformulae as disclosed above R1-R10 may be e.g. be as disclosed above, e.g. R1-R10 may be H, or e.g. R1, R2 may be as disclosed above and R3-R10 may be H as disclosed above.

Compounds according to the invention according to formula (i) or any one of its subformulae for example also comprise compounds, in which Y' and Z' are both C. For example, the inventive compounds may comprise compounds according to the following subformulae

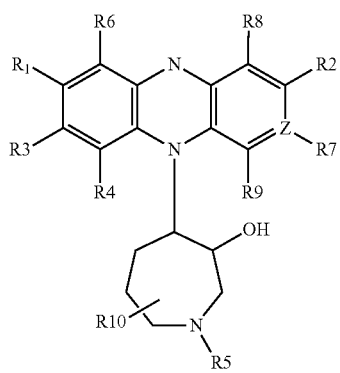
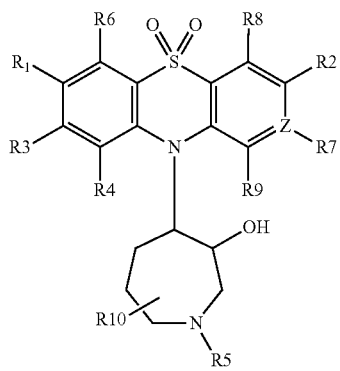
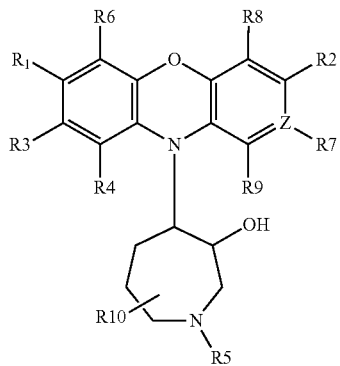
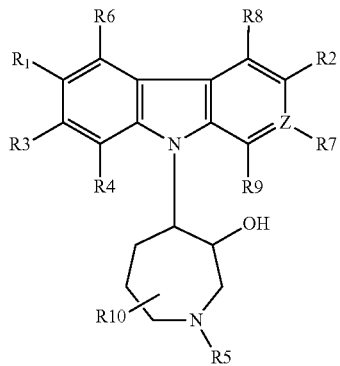
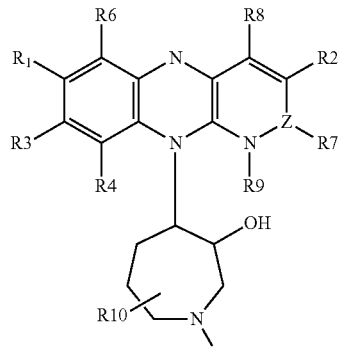
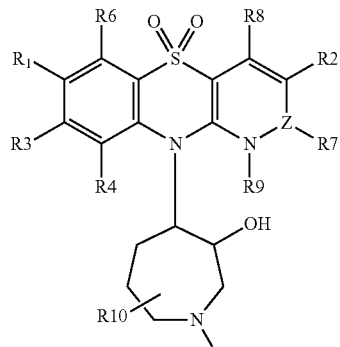
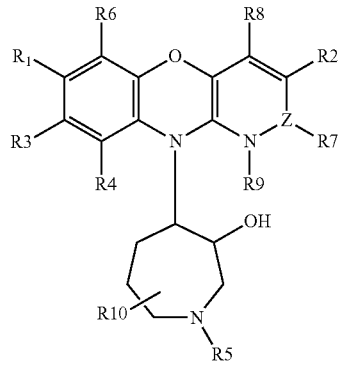
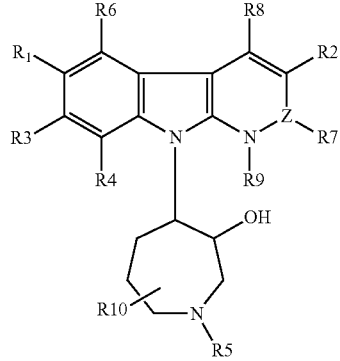
For example, for the inventive compounds according to formula (i) or any of the subformulae as disclosed above R1, R2, R3, R4, R5, R6, R7, R8, R9 and R10 may be as disclosed above.
The inventive compounds also comprise compounds for which both Z and Z' are N. For example, for the inventive compounds Z, Z' are N and e.g. W, Y and Y' may be as disclosed above and R1, R2, R3, R4, R5, R6, R7, R8, R9 and R10 may be as disclosed above. The inventive compounds as disclosed above may e.g. comprise compounds according to the following subformulae
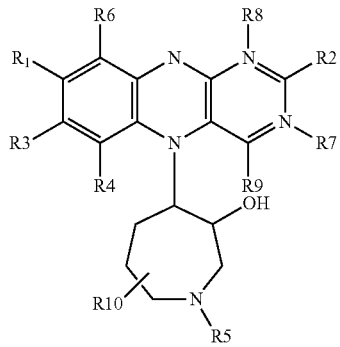
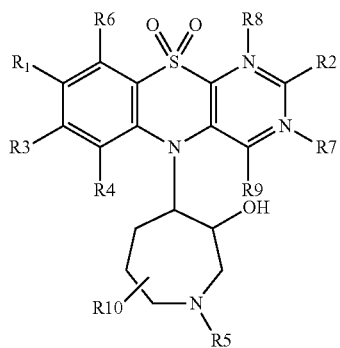
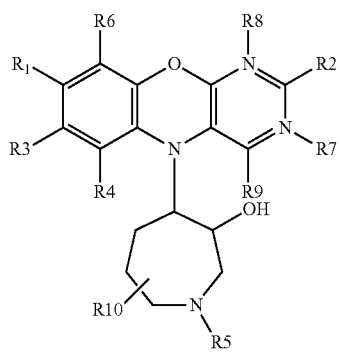
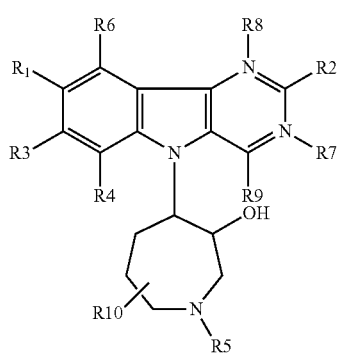
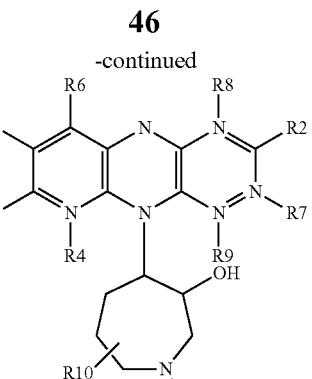
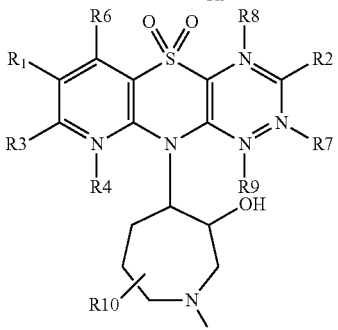
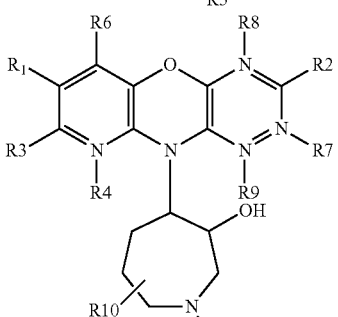
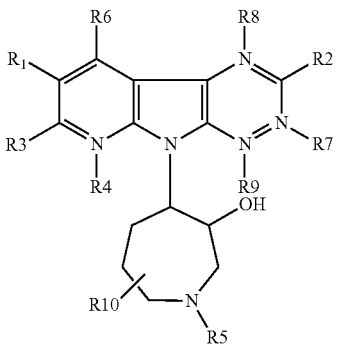
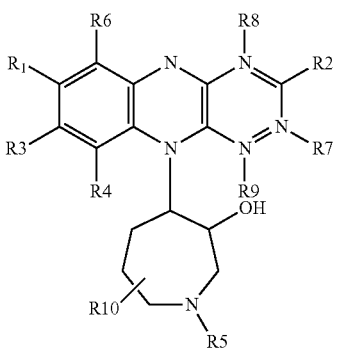

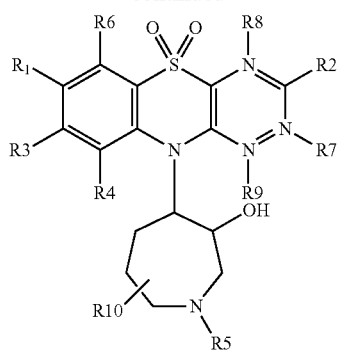
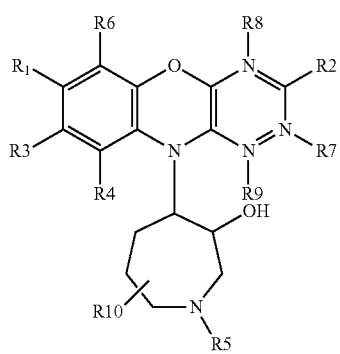
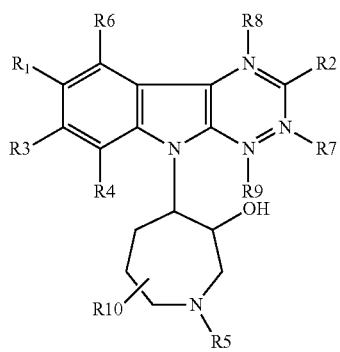
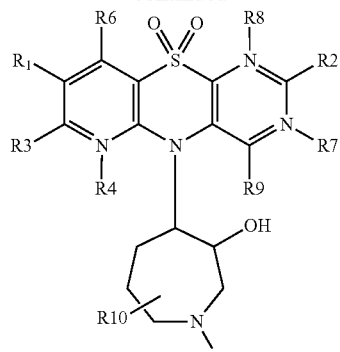
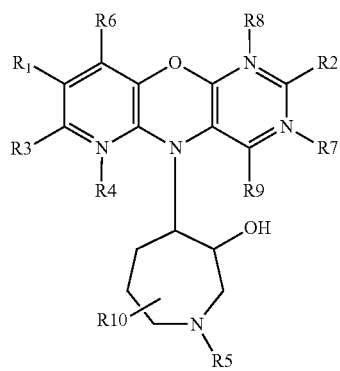
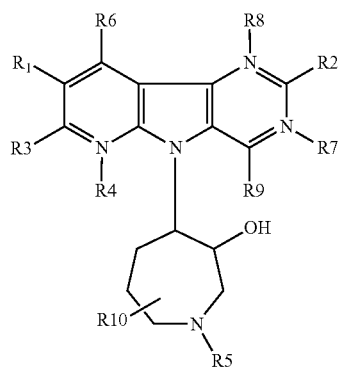
According to one embodiment the inventive compounds of formula (i) or any of its subformulae as disclosed above also comprise compounds in which Y', Z' are both N, e.g. compounds according to the following subformulae
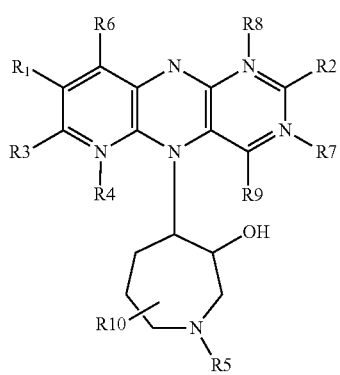
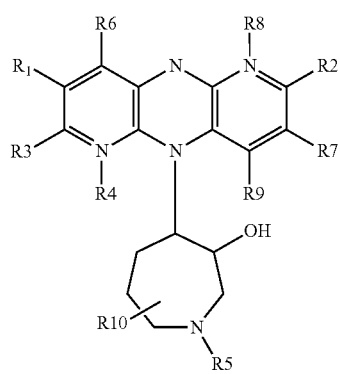

-continued

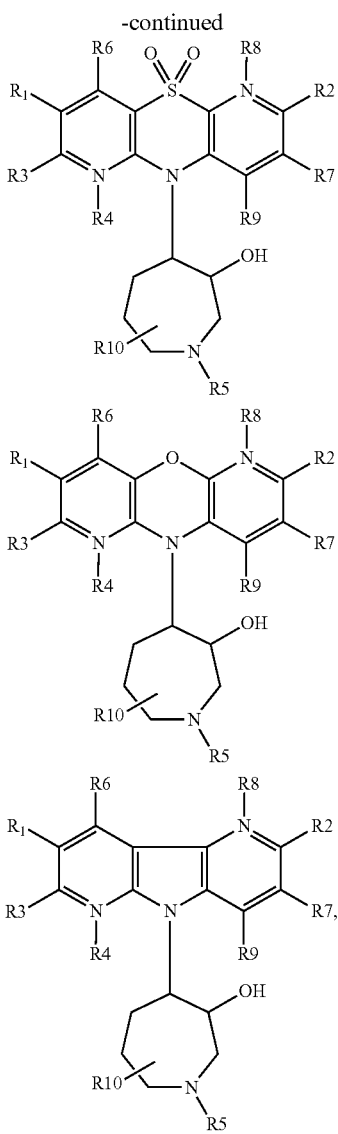

whereby R1, R2, R3, R4, R5, R6, R7, R8, R9 and R10 are as disclosed above for the inventive compounds.

According to one embodiment the inventive compounds of formula (i) or any of its subformulae as disclosed above comprise compounds in which Z, Z' both are N and Y, Y' both are C. For example, the inventive compounds comprise compounds of the subformulae

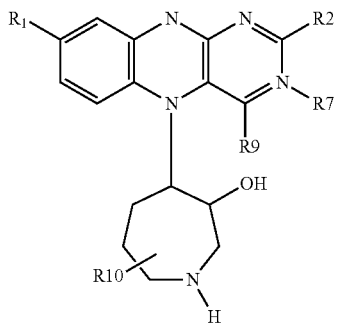

-continued

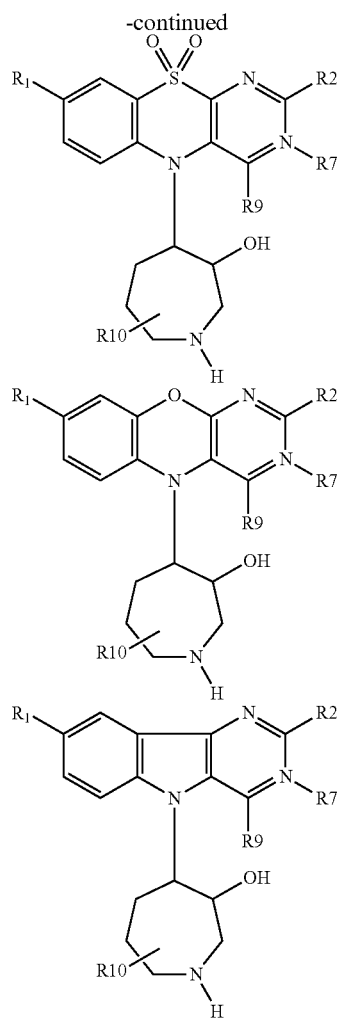

For example, the inventive compounds comprise subformulae as disclosed above, for which substitutents R1, R2 may be as defined above, e.g. R1 is H, halogen (e.g. F, Cl), $CF_3$, or $NO_2$, or R2 is H, halogen, $CF_3$, or $NO_2$, or both R1, R2 are H, halogen, $CF_3$, or $NO_2$, e.g. R1 and R2 may both be F, or Br, or Cl, $CF_3$, or $NO_2$, whereby R1, R2 may be independently chosen from H, Hal, $CF_3$, $NO_2$, e.g. R1 is H, R2 is $CF_3$, or R1 is $CF_3$, R2 is $NO_2$, or R1 is $NO_2$, R2 is H, or R1 is Cl, R2 is $NO_2$, or R1 is F, R2 is Cl and e.g. R3, R4, R5, R6, R7, R8, R9 and R10 may be as defined above, e.g. R3-R10 may be H, or e.g. R7 may be OMe, or e.g. R7 may be keto (—CO). For example, the inventive compounds may comprise compounds of the subformulae

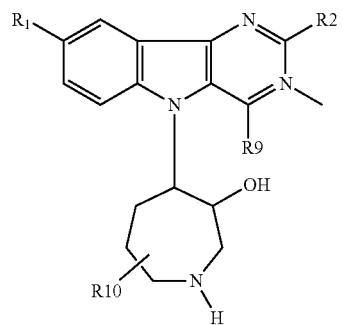

51
-continued
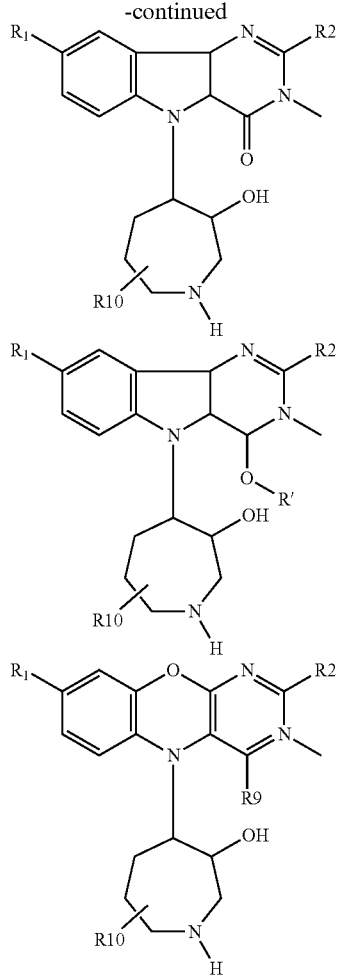
52
-continued
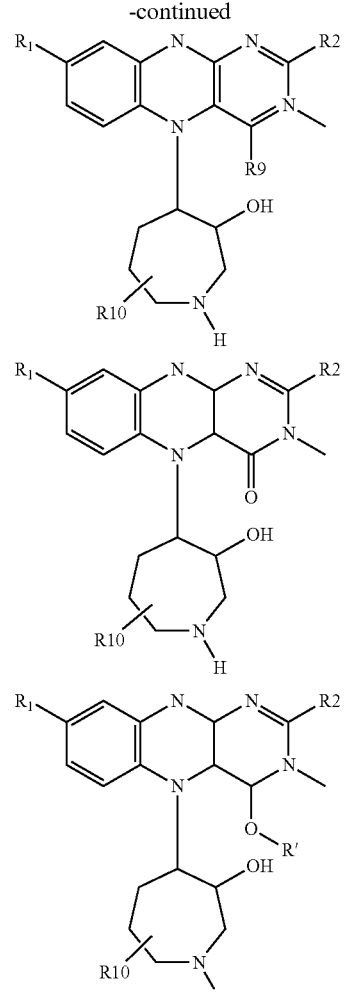

-continued

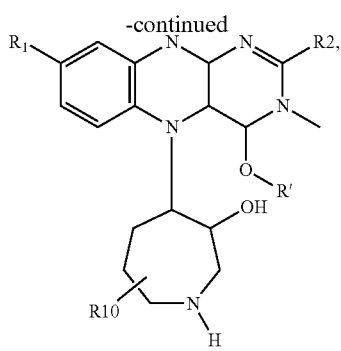

whereby R' is alkyl, e.g. R' may be methyl, ethyl, or propyl. The inventive compounds as disclosed above also comprise the enantiomers of each of the respective subformulae of the invention.

According to one embodiment the compounds of formula (i) or any of its subformulae as disclosed above also comprise compounds for which Z, Z' both are C and Y, Y' both are N. For the inventive compounds the substitutents R1, R2, R3, R4, R5, R6, R7, R8, R9 and R10 are as disclosed above, e.g. R1, R2 may be as disclosed above and R3-R10 may be H, or e.g. R7 is alkyl, or alkoxy, or H and substituents R3, R4, R5, R6, R8, R9 and R10 are H, or e.g. R7 is alkyl, or alkoxy, or e.g. H and substituents R3, R4, R5, R6, R8, and R10 are H and R9 is keto, or e.g. H and substituents R3, R4, R5, R6, R8, and R10 are H and R9 is alkyl, or alkoxy. For example, the inventive compounds comprise the subformulae:

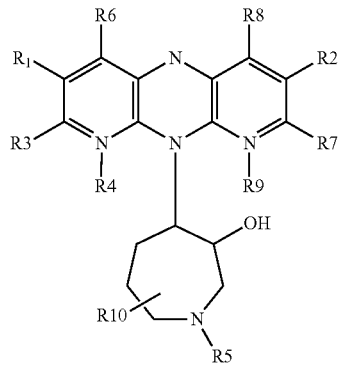

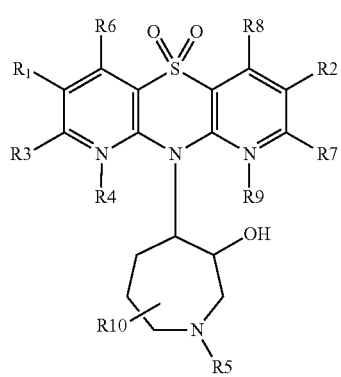

-continued

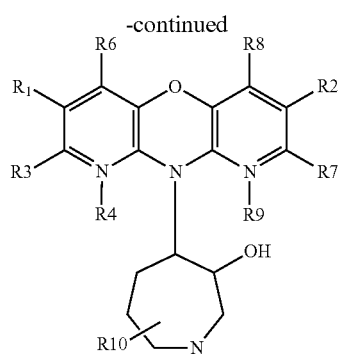

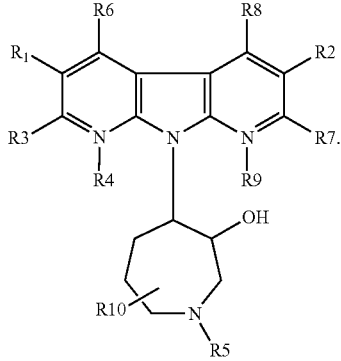

According to one embodiment in the inventive compounds Z, Z' and Y, Y' are C, e.g. the inventive compounds comprise the following subformulae in which R1, R2, R3, R4, R5, R6, R7, R8, R9 and R10 are as disclosed above:

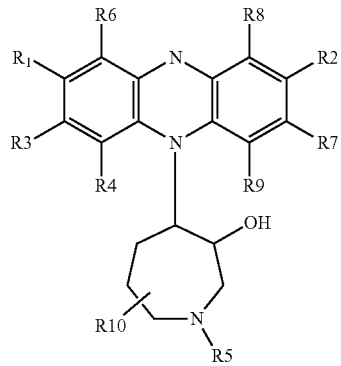

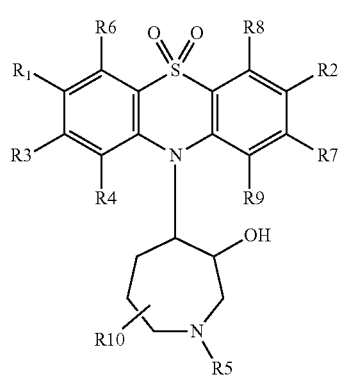

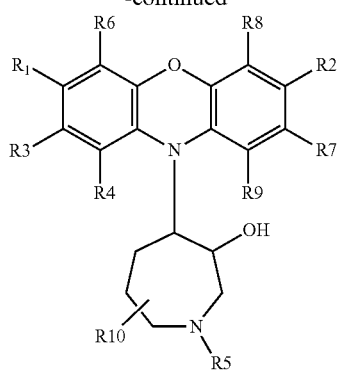
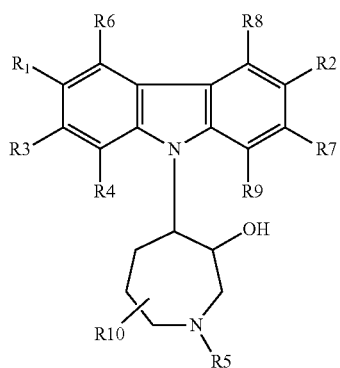
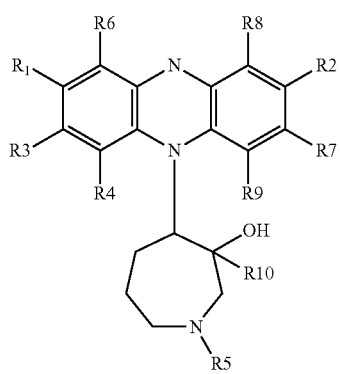
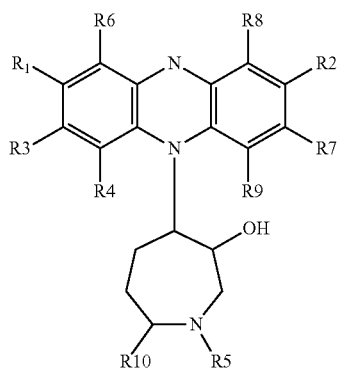
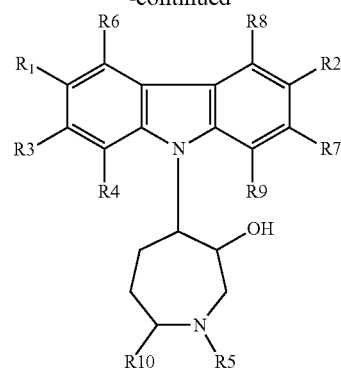
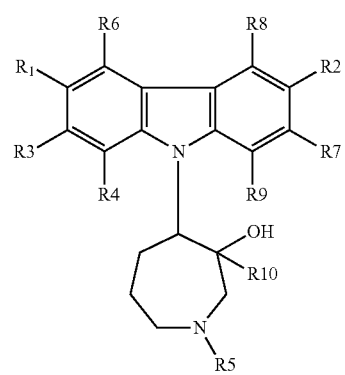
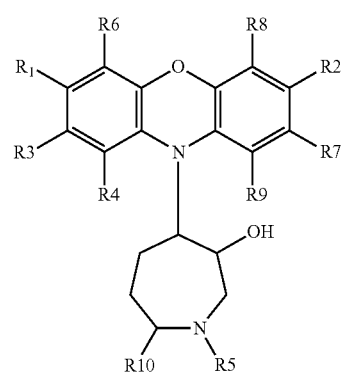
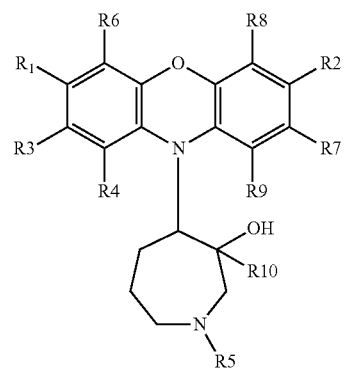

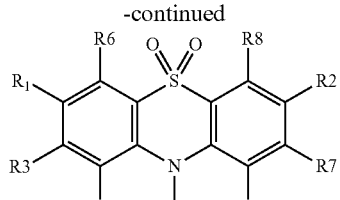
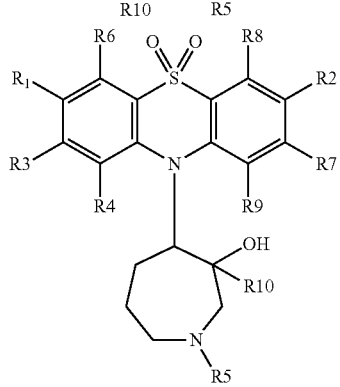
In one embodiment the inventive compounds as disclosed above comprise compounds for which R8 is SO$_2$Alk, keto (—CO) or NO$_2$, e.g. according to any one of the subformulae
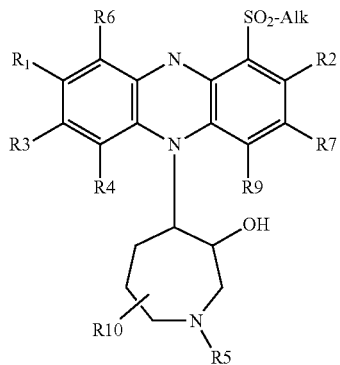
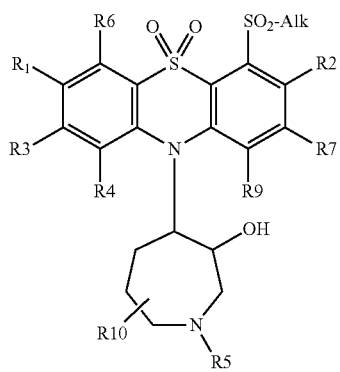
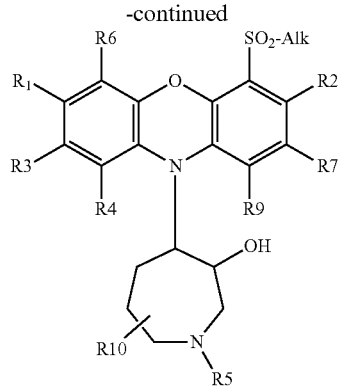
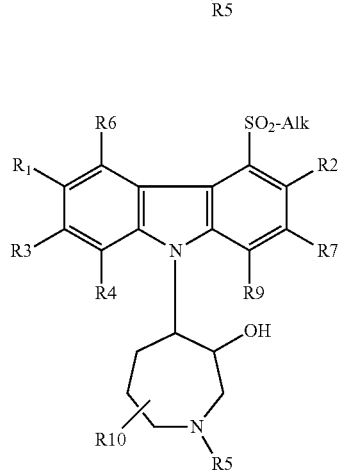
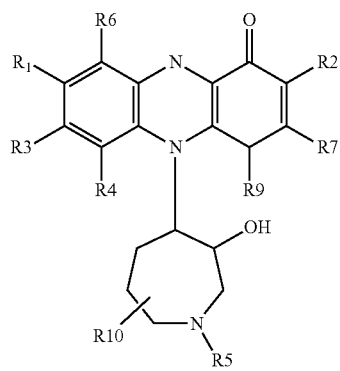
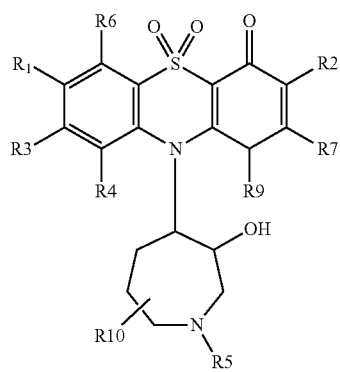

59
-continued

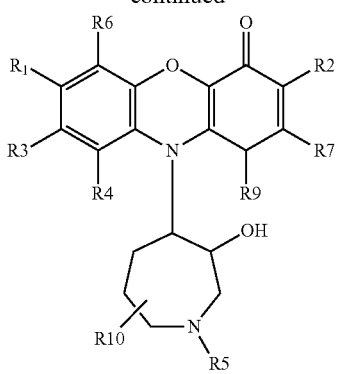

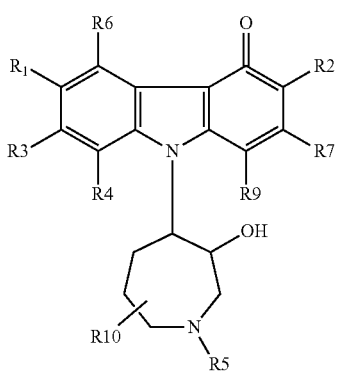

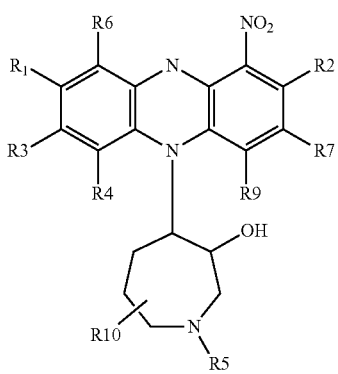

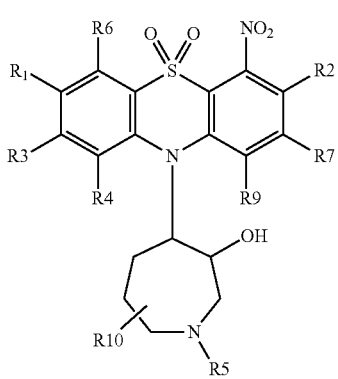

60
-continued

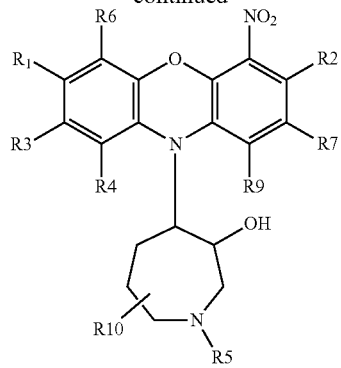

For the inventive compounds according to subformulae as disclosed above, R1, R2, R3, R4, R5, R6, R7, R9 and are R10 are as disclosed above.

In one embodiment the inventive compounds as disclosed above comprise compounds for which R6 is alkoxy or keto. More specifically, R6 may be e.g. methoxy, ethoxy, propoxy, or tert-butoxy. For example, R6 is methoxy, and R1, R2 are as defined above, and R3-R10 are H, or e.g. R6 is alkoxy (e.g. methoxy, ethoxy), and R1, R2 are as defined above and R8 is $NO_2$, keto or $SO_2Alk$.

According to one embodiment the inventive compounds according to formula (i) or any of its subformulae as disclosed above comprise compounds in which R3 is alkoxy, $NO_2$, or amino ($NH_2$). The term amino as used with the inventive compounds, refers to a nitrogen radical bonded to two substituents and can be represented as: —NH2, —NHR or —NR2, wherein each R is aliphatic, aryl, heterocyclyl or heteroaryl;

In a more preferred embodiment, R4 is selected from H, methoxy, ethoxy, or $NO_2$ for the inventive compounds.

According to a more preferred embodiment, substitutent R10 of the inventive compounds as disclosed above, e.g. according to formula (i) or any of its subformulae as disclosed above, is is $CF_3$ or keto. For example, the inventive compounds may comprise the below subformulae, whereby the substitutents R1, R2, R3, R4, R5, R6, R7, R8, R9 are as disclosed above:

61
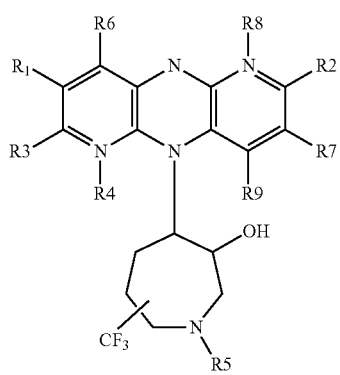
62
-continued
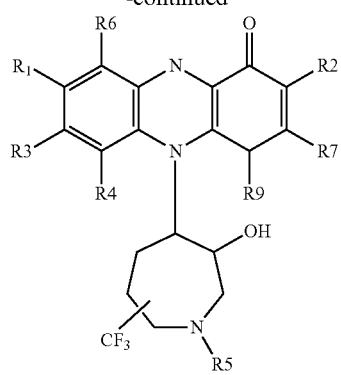
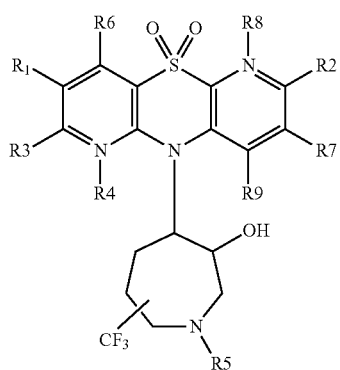
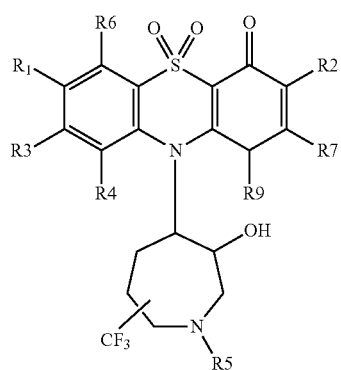
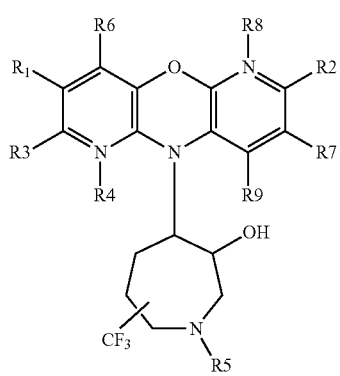
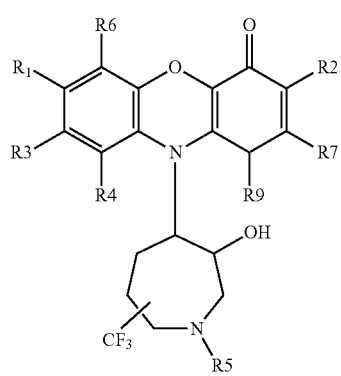
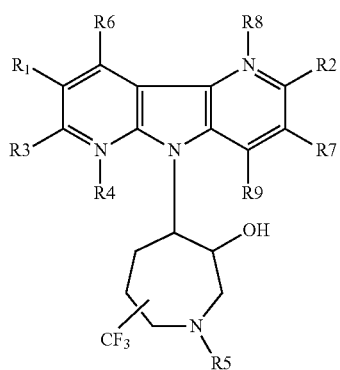
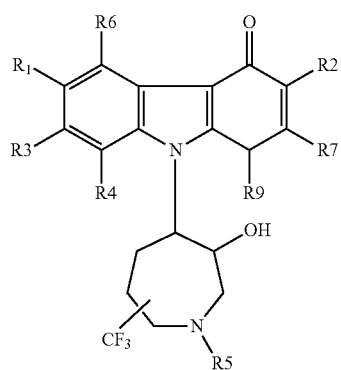

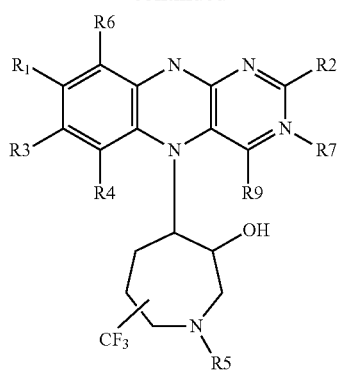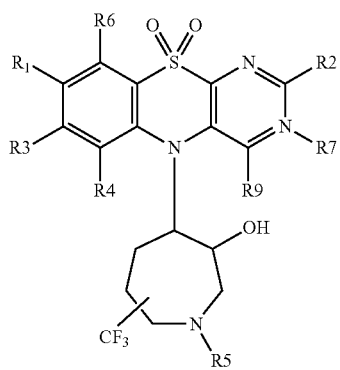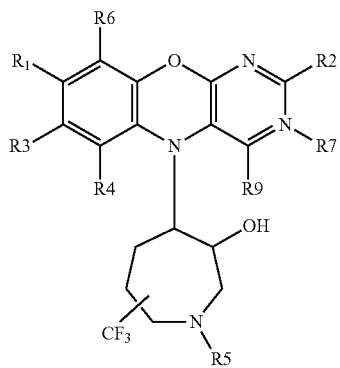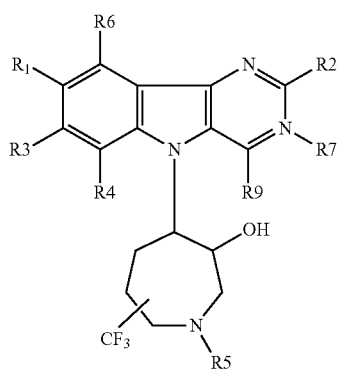
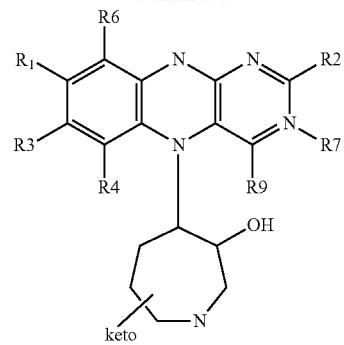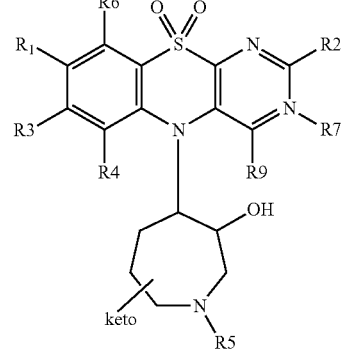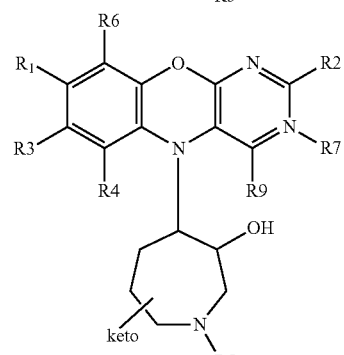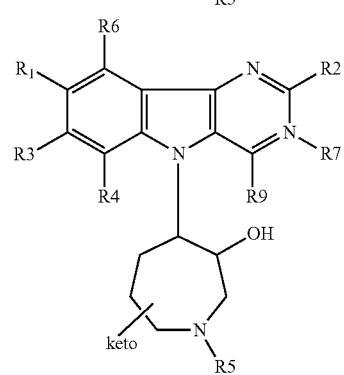
The inventive compounds as disclosed above also comprise isomers with regard to R10, which may be located on different carbon atoms of the azepanyl-3-ol ring, e.g. R10 may be positioned at C2, C3, C5, C6 or C7, e.g. the inventive compounds may comprise compounds according to the below subformulae which also encompass enantiomers of the respective subformula:

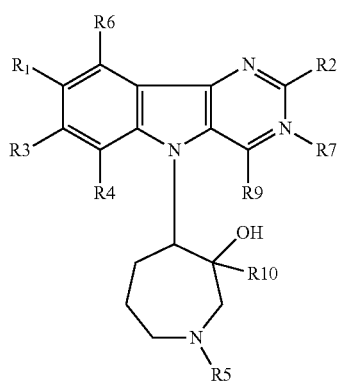
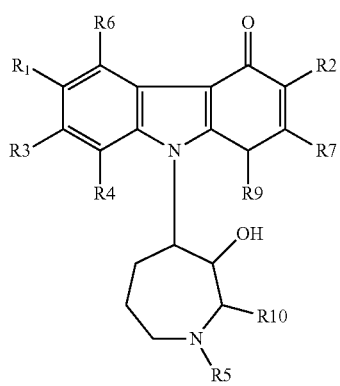
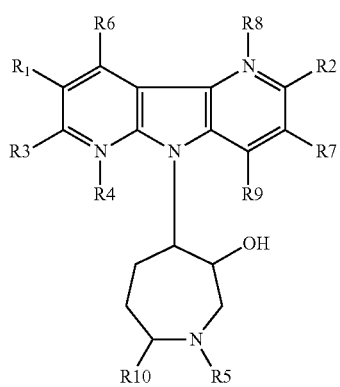
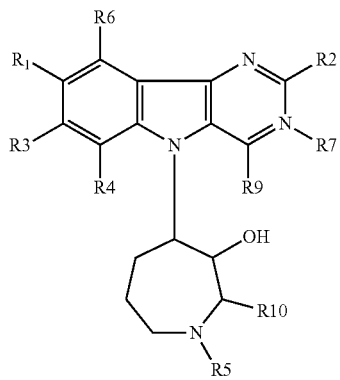
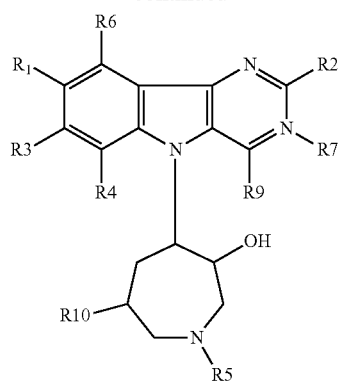
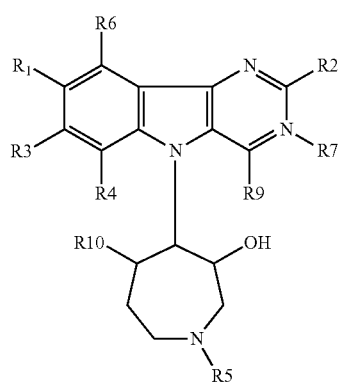
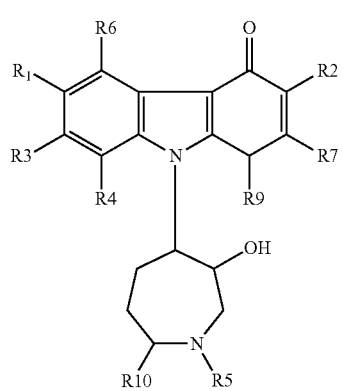
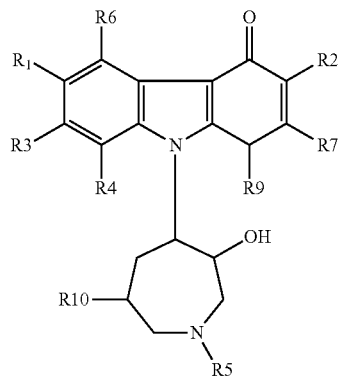

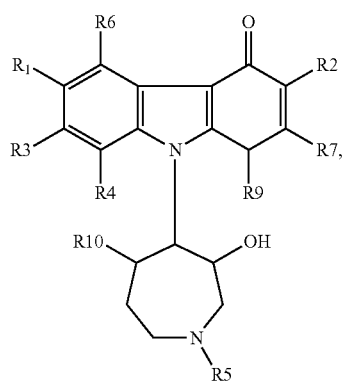

wherein R1, R2, R3, R4, R5, R6, R7, R9 and R10 are as disclosed above, e.g.

According to a more preferred embodiment the inventive compounds comprise compounds 25-31 and their respective enantiomers, e.g. compound 25 ((3R,4R)-4-[(8-chloro-5H-pyrimido[5,4-b]indol-4-yl)amino]azepan-3-ol, compound 26 ((3R,4R)-4-(3-chloro-6-nitro-carbazol-9-yl)azepan-3-ol, compound 27 (5R,6R)-5-(3,6-dichloro-9H-carbazol-9-yl)-6-hydroxyazepan-2-one, compound 28 (3R,4R)-4-[8-chloro-2-(trifluoromethyl)pyrimido[5,4-b]indol-5-yl]-7-methyl-azepan-3-ol, compound 30 (8-chloro-5-[(3R,4R)-3-hydroxyazepan-4-yl]-3H-pyrimido[5,4-b]indol-4-one, compound 31 (3R,4R)-4-(8-chloro-4-methoxy-pyrimido[5,4-b]indol-5-yl)azepan-3-ol, e.g.

(compound 25) AND Enantiomer

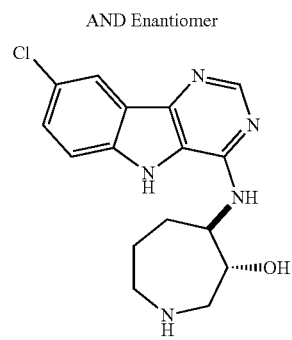

(compound 26) AND Enantiomer

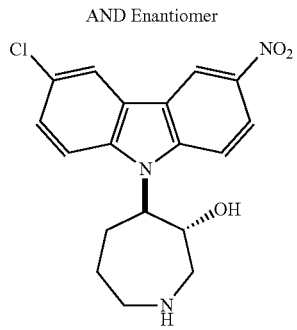

(compound 27) AND Enantiomer

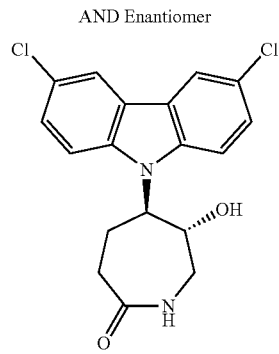

(compound 28) AND Enantiomer

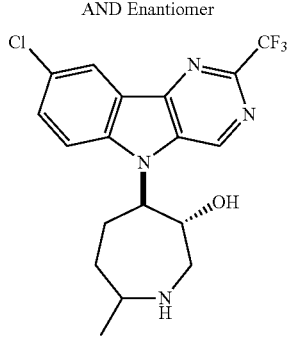

(compound 29) AND Enantiomer

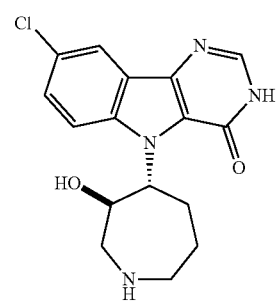

(compound 31) AND Enantiomer

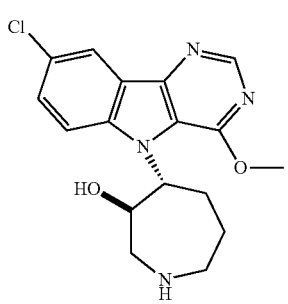

According to one item (e.g. item 1), the present invention also provides compounds of formula (I)

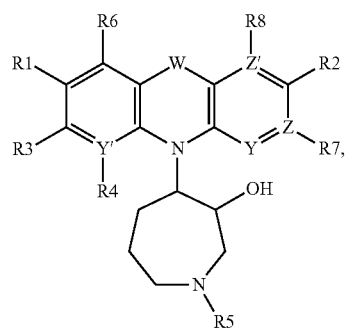

(I)

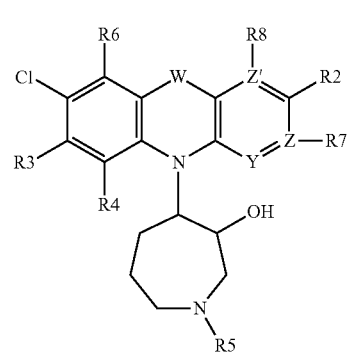

(IIa)

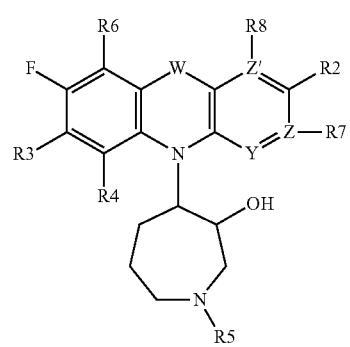

(IIb)

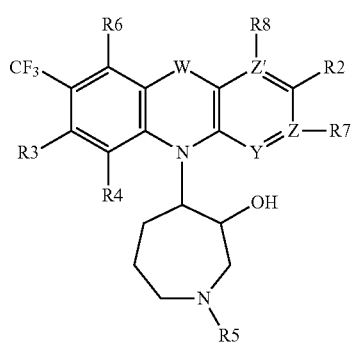

(IIc)

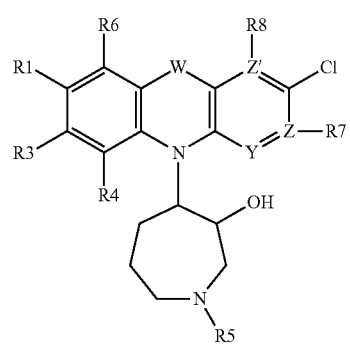

(IId)

wherein

W is selected from a C-Sp2-Sp2-C bond, O, SO$_2$, S,

Z is selected from C or N,

Z' is selected from C, or N,

Y' is selected from C or N,

Y is selected from C or N,

R1 denotes halogen, CF$_3$, OMe, Alkoxy, S-Alk, SMe, SO$_2$Me, SO$_2$Alk

R2 denotes halogen, CF$_3$, OMe, Alkoxy, S-Alk, SMe, SO$_2$Me, SO$_2$Alkyl,

R3 denotes halogen, CF$_3$, OMe, SO$_2$, SO$_2$Ak, Alkoxy, S-Alkyl, SMe, SO$_2$Me, SO$_2$Alk R4 denotes halogen, CF$_3$, OMe, SO$_2$Alk, Alkoxy, S-Alkyl, SMe, SO$_2$Me, SO$_2$Alk R5 denotes H, alkyl, benzyl, amide, sulfonamide, R6 denotes H, alkyl, OMe, SO$_2$, SO$_2$Ak, Alkoxy, S-Alkyl, SMe, SO$_2$Me, SO$_2$Alk R7 denotes H, SO$_2$, SO$_2$Alk, or S-Alk, R8 denotes H, SO$_2$, or S-Alk, and Alk is a branched or linear alkyl group having 1 to 8 carbon atoms or cycloalkyl having 3 to 6 carbon atoms, wherein 1 to 7 H-atoms may be independently replaced by Hal, OR, COOR, CN, NR$_2$, phenyl, linear or branched alkyl having 1, 2 or 3 C atoms, cycloalkyl having 3 to 6 carbon atoms and/or wherein 1 to 3 CH$_2$-groups may be replaced by O, —NRCO—, —CO—, —COO—, —CONR, —NR— or S, or cycloalkyl having 3 to 6 carbon atoms, and the pharmaceutically acceptable salts esters and N-oxides thereof, in a racemic form or in an enantiomerically pure form or enriched mixture of the respective enantiomers in all ratios, and/or as a mixture of diastereoisomers in all ratios.

Compounds according to the invention comprise compounds of formula (I), wherein R1 is hal, or CF$_3$, R2 is HAL, or CF$_3$, more preferred are inventive compounds of formula (I), wherein both R1 and R2 are HAL, or both R1, R2 are CF$_3$, e.g. R1 and R2 may both be F, or Br, or Cl, or CF$_3$, e.g. compounds having the structure

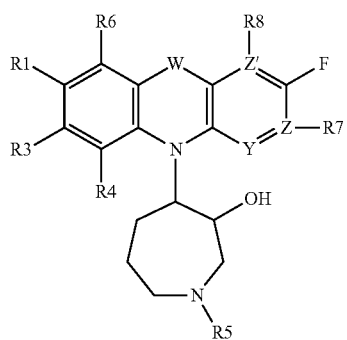
(IIe)
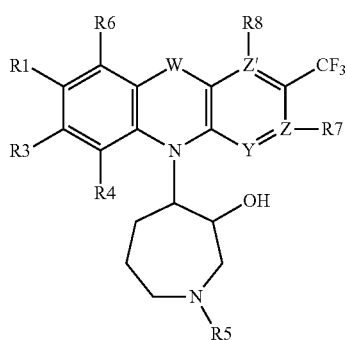
(IIf)
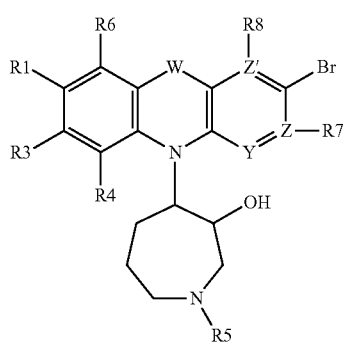
(IIg)
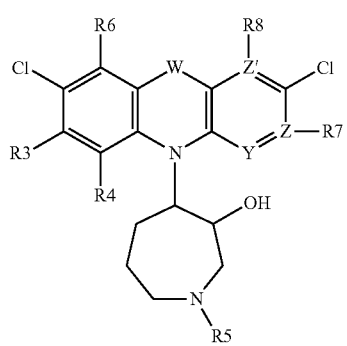
(IIh)
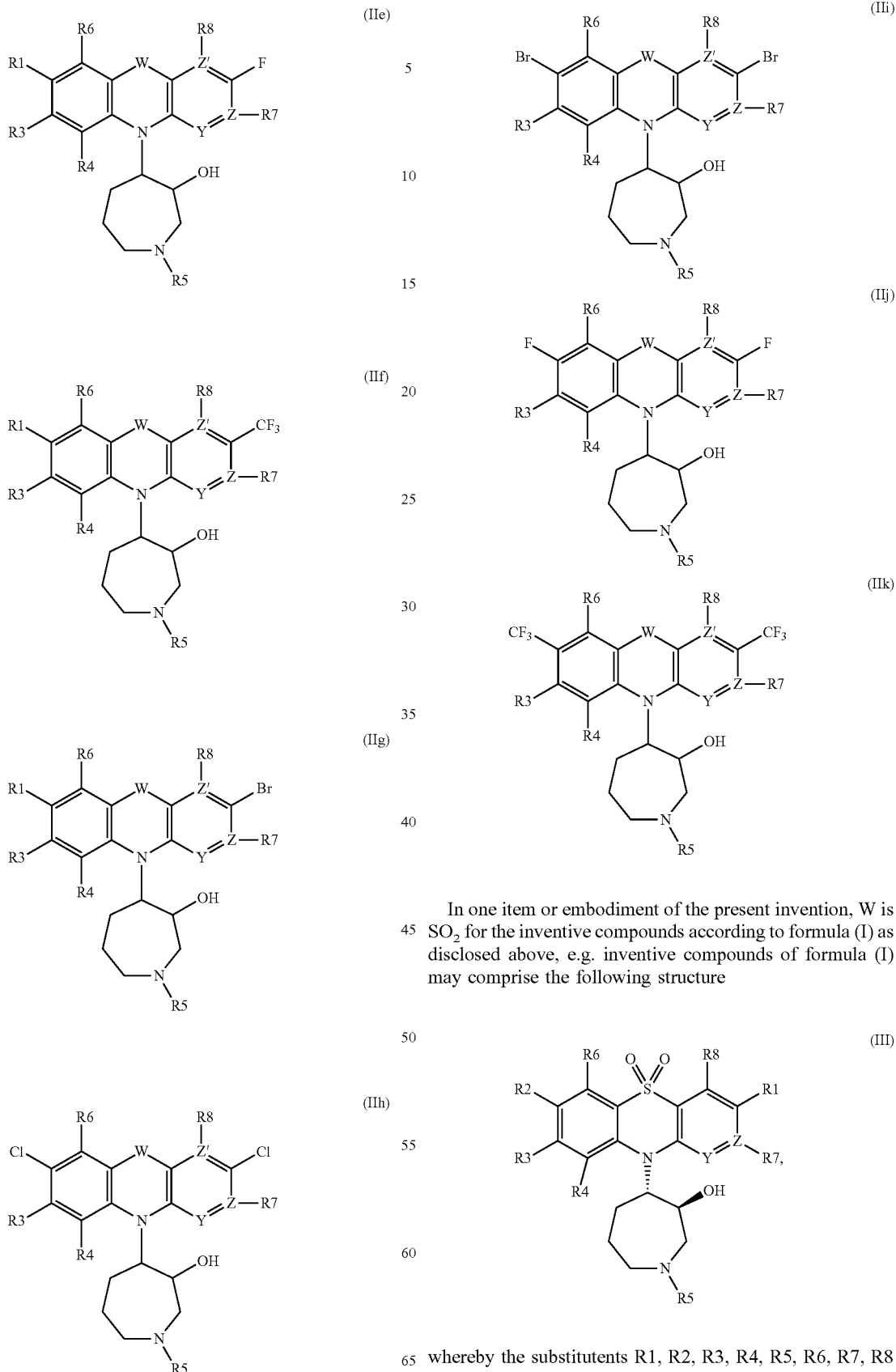
In one item or embodiment of the present invention, W is SO₂ for the inventive compounds according to formula (I) as disclosed above, e.g. inventive compounds of formula (I) may comprise the following structure
whereby the substitutents R1, R2, R3, R4, R5, R6, R7, R8 may be as defined above. For example R1 may be Hal, or CF₃, e.g. F, Cl, or CF₃, R2 may be Hal, Cl, F, or CF₃.

Preferably, in the inventive compound according to formula (III), R1, R2 are both Hal, or CF$_3$, e.g. R1 and R2 are both F, Cl, or CF$_3$.

In a one item or embodiment, the substitutents R3, R4, R5, R6, R7 and R8 of the inventive compound according to formula (I), or its subformulae as disclosed above, e.g. structures (IIa)-(IIk), (III), are all H. According to one preferred item or embodiment of the present invention R3-R8 are all H as defined above and R1, R2 are as defined above, e.g. R1 and R2 are both Cl, or CF$_3$, or F, and W may e.g. be a C-Sp2-Sp2-C bond, O, or S, or R4, R5, R6 are all H and R1, R2, R7 and R8 Accordingly, the inventive compound may e.g. have a structure according to any one of formulae (IVa), (IVb), (IVc), (IVd):

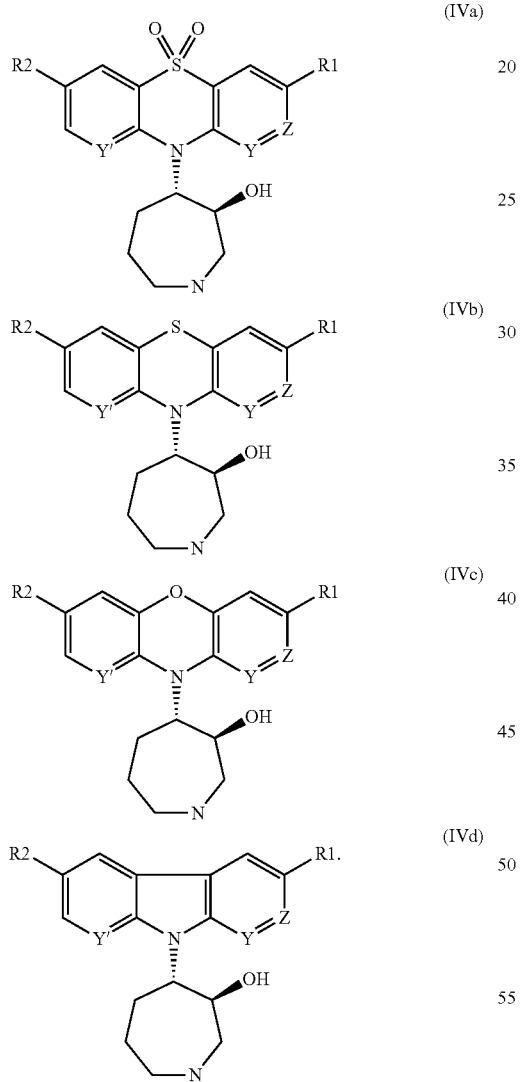

More preferred are compounds according to any one of the structures (IVa)-(IVd), wherein Y' is C.

In one item or embodiment, the inventive compounds according to formula (I) may comprise compounds in which both, Y' and Z' are C. Accordingly, the inventive compounds may e.g. include compounds of the general structures (Va)-(Vd'):

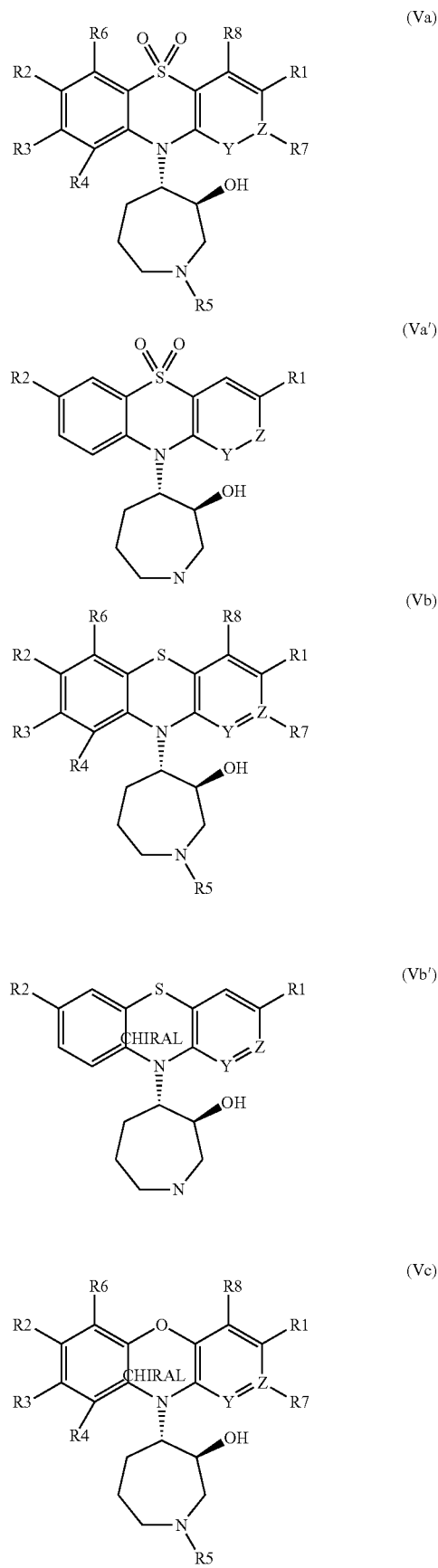

-continued

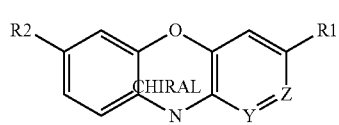
(Vc')

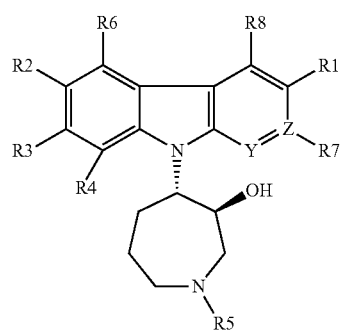
(Vd)

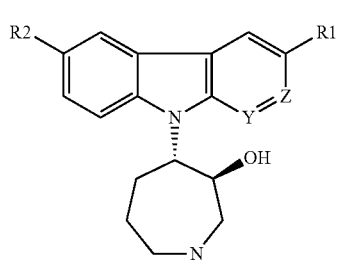
(Vd')

According to one item or embodiment, for the inventive compounds (Va)-(Vd') the substitutents R1, R2 are both HAL, or CF$_3$, e.g. R1, R2 are both Cl, or both F, or both CF$_3$. In the inventive compounds as disclosed above the substituents R3, R4, R5, R6, R7, R8 may e.g. all be H, and R1, R2 may be F, Cl, or CF$_3$, or e.g. R3 is OMe and R1, R2 are both Cl, or CF3 and R4, R5, R6, R7 and R8 are all H, or e.g. R4 is OMe and R1, R2 are both Cl, or CF$_3$ and R3, R5, R6, R7 and R8 are all H, or e.g. R7 is SO$_2$ and R1, R2 are both Cl, or CF$_3$ and R3, R4, R5, R6 and R8 are all H, or e.g. or e.g. R8 is SO$_2$ and R1, R2 are both Cl, or CF$_3$ and R3, R4, R5, R6 and R7 are all H.

Compounds according to the invention may for example also comprise compounds, in which Y=N, e.g. inventive compounds as disclosed above, wherein Y=N, or e.g. for which Y=N and Z=C, or Z=N. For example, the inventive compounds may comprise the following structures:

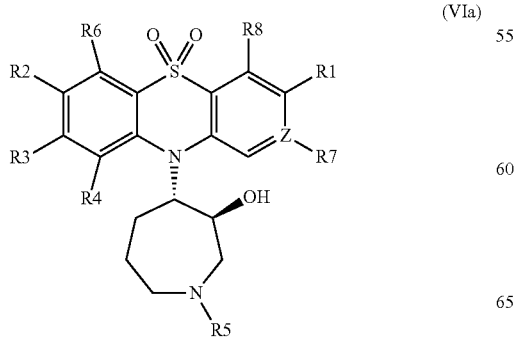
(VIa)

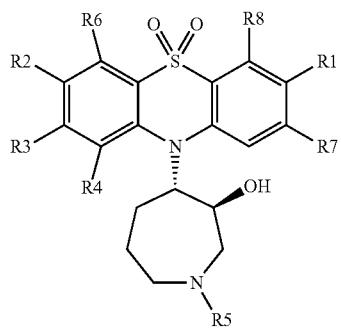
(VIb)

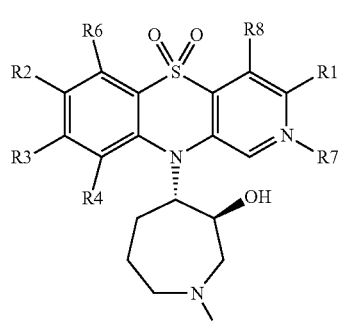
(VIc)

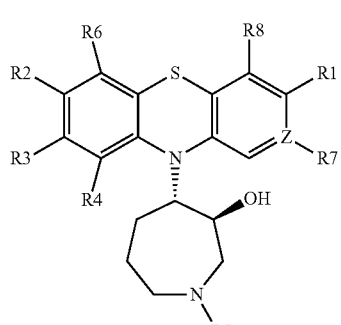
(VId)

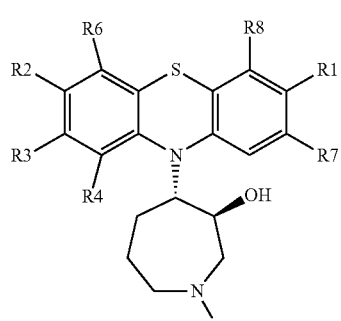
(VIe)

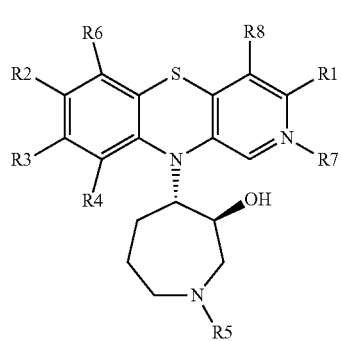
(VIf)

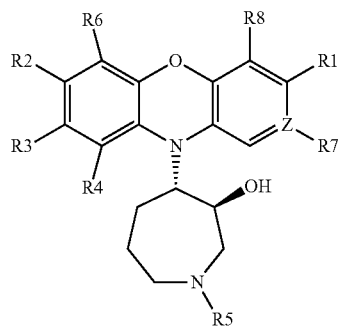 (VIg)

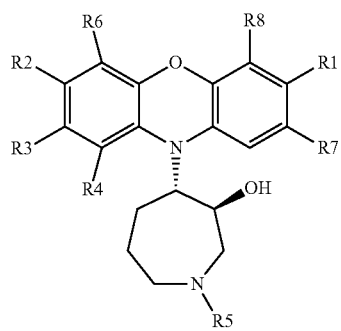 (VIh)

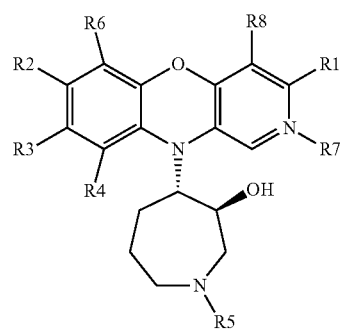 (VIi)

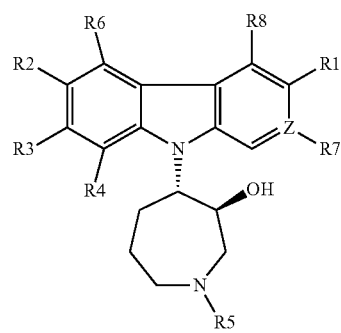 (VIj)

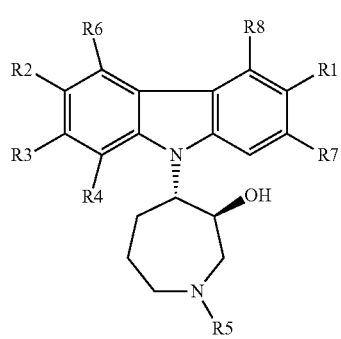 (VIk)

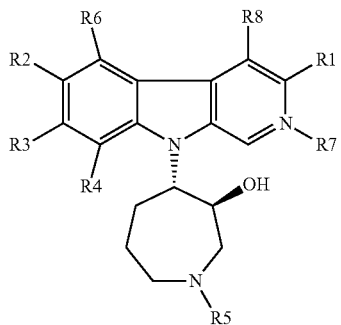 (VIl)

In one item or embodiment, the substituent R1, or R2 for the inventive compounds as disclosed above is selected from F, Cl, or CF$_3$, preferably, both substituents R1 and R2 are both selected from F, Cl, or CF$_3$, e.g. both R1, R2 are F, or R1, R2 are both Cl, or R1, R2 are both CF$_3$. For example, R1, R2 are both Cl, and R3, R4, R5, R6, R7, R8 are H, or e.g. R1, R2 are both CF$_3$ and R3, R4, R5, R6, R7, R8 are H as disclosed below, e.g. R1, R2 are as disclosed above and R7, or R8 may be SO$_2$Alk, e.g. SO$_2$Me.

The inventive compounds may also comprise compounds, in which e.g. R1, R2 are both Cl, or CF$_3$ and any of the substitutents R3-R8 may be SO$_2$, e.g. R1, R2 are both Cl and R8 is SO$_2$Me, or e.g. R1, R2 are both CF$_3$ and R7 is SO$_2$Me, or e.g. R1, R2 are both CF$_3$ and R8 is SO$_2$Me, e.g. compounds of the following structures:

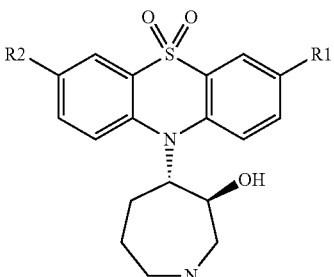 (VIIa)

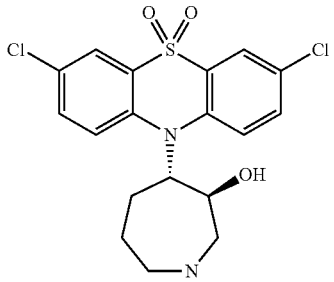 (VIIb)

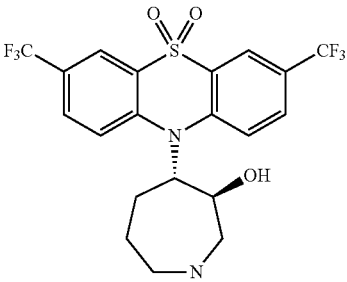 (VIIc)

-continued
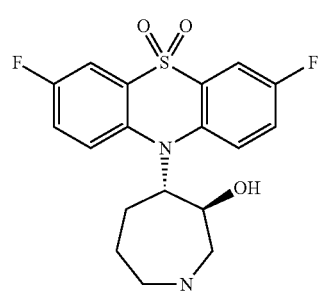
(VIId)
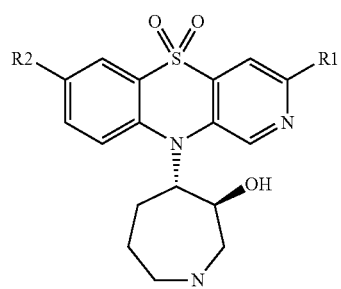
(VIIe)
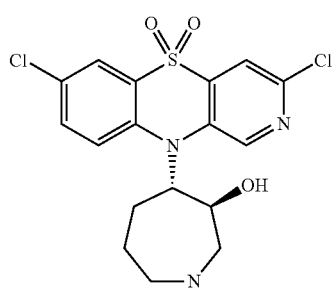
(VIIf)
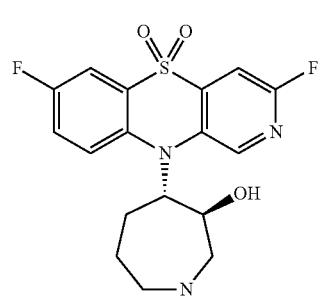
(VIIg)
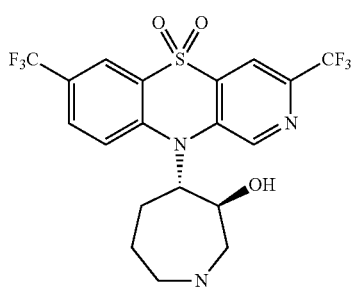
(VIIh)
-continued
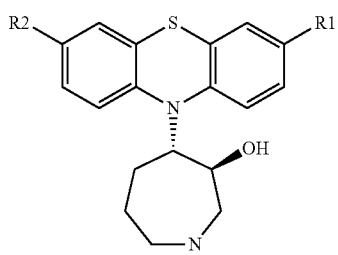
(VIIi)
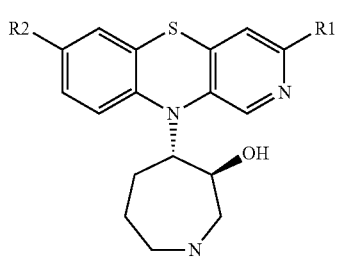
(VIIj)
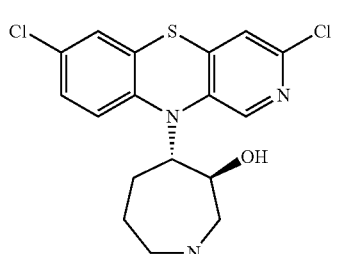
(VIIk)
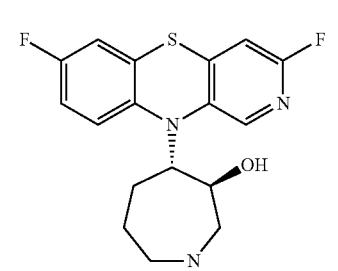
(VIIl)
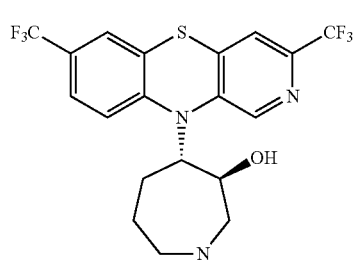
(VIIm)
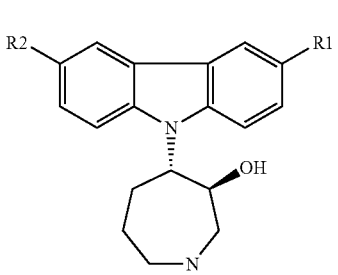
(VIIn)

-continued (VIIo)

(VIIp)

(VIIq)

(VIIr)

(VIIr)

(VIIs)

-continued (VIIt)

(VIIu)

(VIIv)

(VIIw)

(VIIx)

83
-continued
(VIIy)
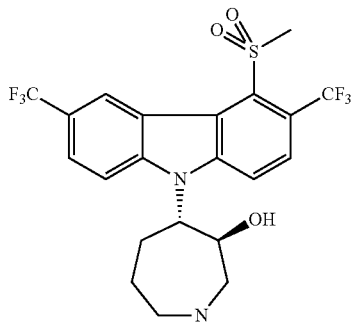
(VIIz)
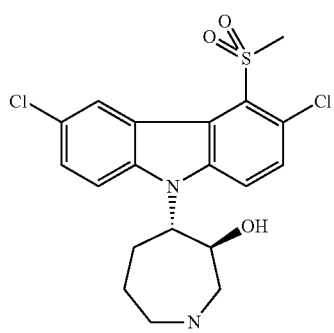
(VIIaa)
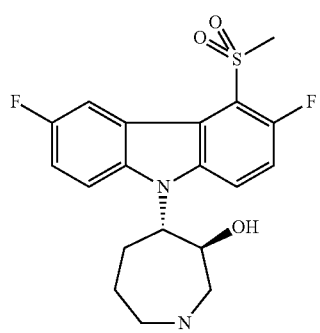
Preferred inventive compounds of formula (I) are compounds 1-16 as disclosed below:
| Compound No. | Structure |
|---|---|
| 1 | 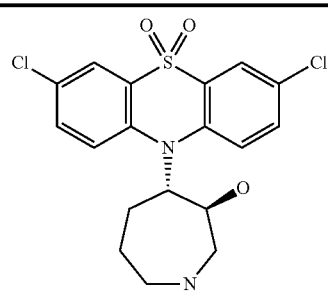 |
84
-continued
| Compound No. | Structure |
|---|---|
| 2 | 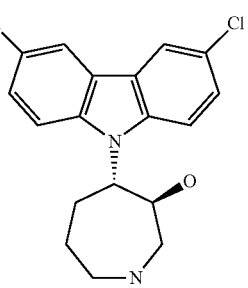 |
| 3 | 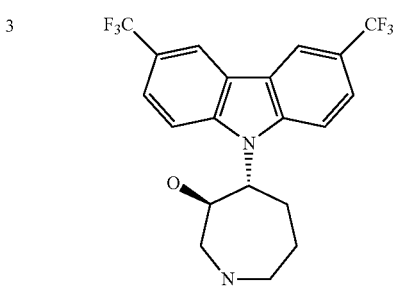 |
| 4 | 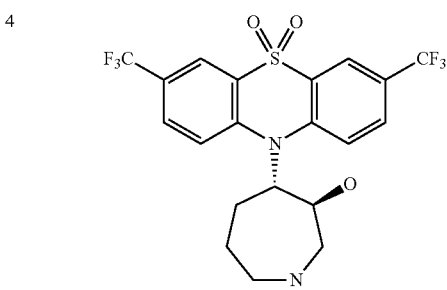 |
| 5 | 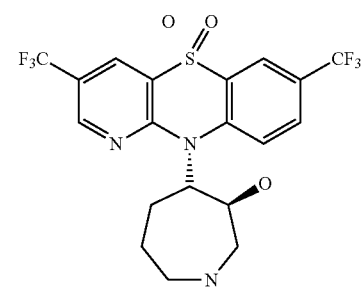 |
| 6 | 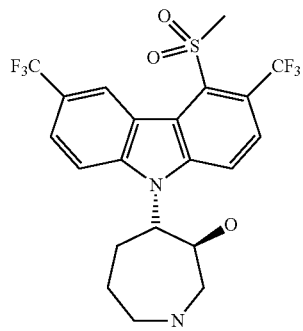 |

| Compound No. | Structure |
|---|---|
| 7 | (structure) |
| 8 | (structure) |
| 9 | (structure) |
| 10 | (structure) |
| 11 | (structure) |
| 12 | (structure) |
| 13 | (structure) |
| 14 | (structure) |
| 15 | (structure) |
| 16 | (structure) |

The compounds of the present invention encompasses pure enantiomers of formula (i) or any of its subformulae as disclosed above (e.g. Formula (I)), as well mixtures thereof in all ratios for all compounds as disclosed above, e.g. for all compounds according to claims 1-28 as disclosed above, or e.g. according to items 1-26 as disclosed herein.

The present invention encompasses compounds of Formula (i) or any of its subformulae as disclosed above (e.g. Formula (I)), as well as their use as a medicament, e.g. for use as a medicament in human and/or veterinarian use.

In one embodiment the present invention pertains the use of compounds of formula or any of its subformulae as disclosed above (e.g. Formula (I)), or any compounds according to its subformulae as disclosed above, such as e.g. compounds 1-31, in the treatment or prevention of parasitic and infectious diseases (in humans as well as in other mammals). Said parasitic and infectious diseases include in particular malaria, cerebral malaria, HAT (human African trypanosomiasis), tuberculosis, chagas (American Trypanosomiasis), leishmaniasis, onchocerciasis, filariasis, and schistosomiasis.

The compounds of the present invention may be used for or in the treatment of parasitic and/or infectious disease selected from the group comprising Acanthamoeba Infection, Acanthamoeba Keratitis Infection, Alveolar Echinococcosis (Echinococcosis, Hydatid Disease), Amebiasis (*Entamoeba histolytica* Infection), Ancylostomiasis (Hookworm, Cutaneous Larva Migrans [CLM]), Angiostrongyliasis (*Angiostrongylus* Infection), Anisakiasis (*Anisakis* Infection, *Pseudoterranova* Infection), Ascariasis (*Ascaris* Infection, Intestinal Roundworms), Babesiosis (*Babesia* Infection), Balantidiasis (*Balantidium* Infection), Baylisascariasis (*Baylisascaris* Infection, Racoon Roundworm), *Bilharzia* (Schistosomiasis), *Blastocystis hominis* Infection, Body Lice Infestation (Pediculosis), Capillariasis (*Capillaria* Infection), Cercarial Dermatitis (Swimmer's Itch), *Chilomastix mesnili* Infection (Nonpathogenic [Harmless] Intestinal Protozoa), Clonorchiasis (*Clonorchis* Infection), CLM (Cutaneous Larva Migrans, Ancylostomiasis, Hookworm), "Crabs" (Pubic Lice), Cryptosporidiosis (*Cryptosporidium* Infection), Cutaneous Larva Migrans (CLM, Ancylostomiasis, Hookworm), Cyclosporiasis (*Cyclospora* Infection), Cysticercosis (Neurocysticercosis), Cystoisopora Infection (Cystoisosporiasis) formerly *Isospora* Infection, Diarrhea, *Dientamoeba fragilis* Infection, Diphyllobothriasis (*Diphyllobothrium* Infection), *Dipylidium caninum* Infection (dog or cat tapeworm infection), Dracunculiasis (Guinea Worm Disease), Dog tapeworm (*Dipylidium caninum* Infection), Echinococcosis (Alveolar Echinococcosis, Hydatid Disease), Elephantiasis (Filariasis, Lymphatic Filariasis), *Endolimax nana* Infection (Nonpathogenic [Harmless] Intestinal Protozoa), *Entamoeba coli* Infection (Nonpathogenic [Harmless] Intestinal Protozoa), *Entamoeba dispar* Infection (Nonpathogenic [Harmless] Intestinal Protozoa), *Entamoeba hartmanni* Infection (Nonpathogenic [Harmless] Intestinal Protozoa), *Entamoeba histolytica* Infection (Amebiasis), *Entamoeba polecki*, Enterobiasis (Pinworm Infection), Fascioliasis (*Fasciola* Infection), Fasciolopsiasis (*Fasciolopsis* Infection), Filariasis (Lymphatic Filariasis, Elephantiasis), Foodborne Diseases, Giardiasis (Giardia Infection), Gnathostomiasis (*Gnathostoma* Infection), Guinea Worm Disease (Dracunculiasis), Head Lice Infestation (Pediculosis), Heterophyiasis (Heterophyes Infection), Hydatid Disease (Alveolar Echinococcosis), Hymenolepiasis (*Hymenolepis* Infection), Hookworm Infection (Ancylostomiasis, Cutaneous Larva Migrans [CLM]), Intestinal Roundworms (Ascariasis, *Ascaris* Infection), *Iodamoeba buetschlii* Infection (Nonpathogenic [Harmless] Intestinal Protozoa), *Isospora* Infection (see Cystoisospora Infection), Kala-azar (Leishmaniasis, *Leishmania* Infection), Keratitis (*Acanthamoeba* Infection), Leishmaniasis (Kala-azar, *Leishmania* Infection), Lice Infestation (Body, Head, or Pubic Lice, Pediculosis, Pthiriasis), Loaiasis (*Loa loa* Infection), Lymphatic filariasis (Filariasis, Elephantiasis), Malaria (*Plasmodium* Infection), Microsporidiosis (Microsporidia Infection), Mite Infestation (Scabies), *Naegleria* Infection, Neurocysticercosis (Cysticercosis), Nonpathogenic (Harmless) Intestinal Protozoa, Ocular Larva Migrans (Toxocariasis, *Toxocara* Infection, Visceral Larva Migrans), Onchocerciasis (River Blindness), Opisthorchiasis (*Opisthorchis* Infection), Paragonimiasis (*Paragonimus* Infection), Pediculosis (Head or Body Lice Infestation), Pthiriasis (Pubic Lice Infestation), Pinworm Infection (Enterobiasis), *Plasmodium* Infection (Malaria), *Pneumocystis jirovecii* Pneumonia, *Pseudoterranova* Infection (Anisakiasis, *Anisakis* Infection), Pubic Lice Infestation ("Crabs," Pthiriasis), Raccoon Roundworm Infection (Baylisascariasis, *Baylisascaris* Infection), River Blindness (Onchocerciasis), Scabies, Schistosomiasis (*Bilharzia*), Sleeping Sickness (Trypanosomiasis, African; African Sleeping Sickness), Strongyloidiasis (*Strongyloides* Infection), Swimmer's Itch (Cercarial Dermatitis), Taeniasis (*Taenia* Infection, Tapeworm Infection), Tapeworm Infection (Taeniasis, *Taenia* Infection), Toxocariasis (*Toxocara* Infection, Ocular Larva Migrans, Visceral Larva Migrans), Toxoplasmosis (*Toxoplasma* Infection), Travelers' Diarrhea, Trichinellosis (Trichinosis), Trichinosis (Trichinellosis), Trichomoniasis (*Trichomonas* Infection), Trichuriasis (Whipworm Infection, *Trichuris* Infection), Trypanosomiasis, African (African Sleeping Sickness, Sleeping Sickness), Visceral Larva Migrans (Toxocariasis, *Toxocara* Infection, Ocular Larva Migrans), Waterborne Diseases, Whipworm Infection (Trichuriasis, *Trichuris* Infection).

In a preferred embodiment, the inventive compounds as disclosed above may be used for or in the treatment of parasitic and infectious diseases selected from the group constisting of malaria, African sleeping sickness (HAT), chagas, leishmaniasis, onchocerciasis, filariasis, schistosomiasis, Cryptosporidiosis (*Cryptosporidium* Infection), *Entamoeba coli* Infection (Nonpathogenic [Harmless] Intestinal Protozoa), *Entamoeba dispar* Infection (Nonpathogenic [Harmless] Intestinal Protozoa), *Entamoeba hartmanni* Infection (Nonpathogenic [Harmless] Intestinal Protozoa), *Entamoeba histolytica* Infection (Amebiasis), *Entamoeba polecki*, Toxoplasmosis (*Toxoplasma* Infection), Zoonotic Diseases (Diseases spread from animals to people), more preferably, the parasitic disease to be treated by the inventive compounds are selected from the group comprising malaria, African sleeping sickness (HAT), chagas, leishmaniasis, schistosomiasis.

In an even more preferred embodiment, the inventive compounds are for use in the treatment of malaria, or cerebral malaria.

In another specific embodiment, the present invention provides a pharmaceutical composition comprising at least one compound of Formula (i) or or any of its subformulae as disclosed above (e.g. Formula (I)), and/or pharmaceutically acceptable derivatives, tautomers, salts, solvates and stereoisomers thereof, including mixtures thereof in all ratios, and optionally excipients and/or adjuvants. The inventive pharmaceutical composition may be applied in human medicine as well as in e.g. veterinary medicine.

In more specific embodiment, the present invention provides a pharmaceutical composition comprising at least one compound of formula (i) or any of its subformulae as disclosed above (e.g. Formula (I)), or related formulae as disclosed above and/or pharmaceutically acceptable derivatives, tautomers, salts, solvates and stereoisomers thereof, including mixtures thereof in all ratios, and at least one further pharmaceutically active compound. The further pharmaceutically active compound to be combined with the at least one inventive compound of formula or any of its subformulae as disclosed above (e.g. Formula (I)), may be selected from the group of anti-malarial drugs, such as e.g.

chloroquine, amodiaquine, proguanil, sulphonamides, mefloquine, atovaquone, primaquine, artemisinin and artemisinin-derivatives, halofantrine, doxycycline, tetracycline, or clindamycin. Accordingly, the at least one compound according to formula or any of its subformulae as disclosed above (e.g. Formula (I)), of the invention or compounds according to any of its subformulae disclosed above may e.g. be combined with chloroquine, or e.g. may be combined with artemisinin and artemisinin-derivatives. The inventive pharmaceutical composition may e.g. also comprise at least one inventive compound according formula (I) or any of its subformulae as disclosed above and e.g. artesunate and amodiaquine, or e.g. artesunate and mefloquine, or e.g. artesunate and lumefantrine, or e.g. artesunate and sulfadoxine/pyrimethamine, or e.g. artesunate and pyronaridine.

The inventive pharmaceutical compositions may comprise the at least one compound according to formula or any of its subformulae as disclosed above (e.g. Formula (I)), and the at least one further pharmaceutically active compound as disclosed above in any given ratio or weight. For example, the inventive pharmaceutical compositions may comprise at least one inventive compound according to formula (i) or any of its subformulae as disclosed above (e.g. Formula (I)), or any of its subformulae and the at least one further pharmaceutically active compounds in a relative ratio of from about 1:100 to about 100:1, or e.g. from about 2, 3, 4, 5, 6, 7, 8, 9, 10: 90, 91, 92, 93, 94, 95, 96, 97, 98 or 99, or e.g. from about 2:50 to about 50:2, or e.g. from about 3:75 to about 75:3, or e.g. from about 4:70 to about 70:4, or e.g. from about 1, 2, 3, 4, 5, 6, 7, 8, 9, 10 to about 10, 9, 8, 7, 6, 5, 4, 3, 2, 1. If the inventive the pharmaceutical composition comprises more than one, e.g. two or three, additional pharmaceutically active compounds, the relative ratios shall pertain to the sum of all relative abundances, or cumulative weight of all further pharmaceutically active compounds in the pharmaceutical composition.

A therapeutically effective amount of a compound of the formula (i) or any of its subformulae as disclosed above (e.g. Formula (I)), according to the invention depends on a number of factors, including, for example, the age and weight of the individual to be treated, the precise condition that requires treatment, and its severity, the nature of the formulation and the method and/or route of administration, and is ultimately determined by the treating physican or veterinarian. However, an effective amount of a compound according to the invention may e.g. be generally in the range from about 0.1 to about 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

Pharmaceutical compositions according to the invention can be administered in the form of dosage units which comprise a predetermined amount of active compound per dosage unit. Such a unit can comprise, for example, 0.5 mg to 1 g, preferably 1 mg to 700 mg, particularly preferably from about 5 mg to about 100 mg, or from about 10 mg to about 90 mg, or from about 15 mg to about 85 mg, or from about 20 mg to about 80 mg, or from about 25 mg to about 75 mg, or from about 40 mg to about 65 mg, or from about 45 mg to about 60 mg, or from about 100 mg to about 700 mg, or from about 125 mg to about 675 mg, or from about 125 mg to about 650 mg, or from about 150 mg to about 625 mg, or from about 175 mg to about 600 mg, or from about 200 mg, 250 mg, 300 mg, 350 mg, 400 mg to about 400 mg, 450 mg, 500 mg, 550 mg, or e.g. about 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5, 47.5 mg, 50 mg, 55 mg, 60, mg, 75 mg, 80 mg, 85 mg, 90 mg, 100 mg, 110 mg, 112.5 mg, 125 mg, 150 mg, 160 mg, 175 mg, 180 mg, 190 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, or about 700 mg of a at least one compound according to the invention, depending on the condition to be treated, the method and route of administration, the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of the at least one compound of the invention. Furthermore, pharmaceutical formulations of this type can be prepared using a process which is generally known in the pharmaceutical art.

Without being bound thereto, the inventive pharmaceutical composition will contain or release sufficient active compound of formula (i) or any of its subformulae as disclosed above (e.g. Formula (I)), or its tautomers, salts, solvates and stereoisomers to provide a dose of about 10, 20, 50, or 100 nanograms per kilogram body weight (ng/kg) to about 1, 2.5, 5, 10, 15, 20, 25, 27.5, 30, 35, 45, 50, 75 milligrams per kilogram body weight (mg/kg), preferably about 10 micrograms per kilogram (μg/kg) to about 50 mg/kg, e.g. from about 12.5 μg/kg, 25 μg/kg, 50 μg/kg, 75 μg/kg, 100 μg/kg, 125 μg/kg, 150 μg/kg, 175 μg/kg, 200 μg/kg, 250 μg/kg, 300 μg/kg, 350 μg/kg, 400 μg/kg, 450 μg/kg, 500 μg/kg, 600 μg/kg, 750 μg/kg, 1 mg/kg, 2.5 mg/kg, 5 mg/kg, 7.5 mg/kg, 10 mg/kg to about 10 mg/kg, 12.5 mg/kg, 15 mg/kg, 17.5 mg/kg, 20 mg/kg, 22.5 mg/kg, 25 mg/kg, 27.5 mg/kg, 30 mg/kg, 35 mg/kg, 40 mg/kg, 45 mg/kg, 50 mg/kg of active compound of formula (I) or a salt thereof to the subject. Accordingly, the inventive pharmaceutical composition will contain or release sufficient active compound of Formula (I) to provide a dose of, for example, from about 0.005 mg/m², 0.01 mg/m², 0.1 mg/m² to about 2.5 mg/m², 5.0 mg/m², 7.5 mg/m², 10 mg/m², 15 mg/m², 20 mg/m², 25 mg/m², 50 mg/m², 100 mg/m², 250 mg/m², computed according to the Dubois method, in which the body surface area of a subject (m²) is computed using the subject's body weight (wt) given in kg and the subject's height given in cm: $m^2 = (wt^{0.425} \times height^{0.725}) \times 7,184 \times 10^{-3}$, although in some embodiments the methods may be performed by administering a compound or salt or composition in a dose outside this range. In some of these embodiments, the method includes administering sufficient active compound of formula (I) to provide a dose of from about 0.01, 0.02, 0.05, 0.1, 0.25, 0.5, 1.0, 2.5, 5, 7.5, 10, 12.5, 15, 17.5, 20, 22.5, 25, 27.5, 30, 35, 40, 45, 50 mg/m² to about 50, 52.5, 55, 57.5, 60, 65, 70, 75, 80, 85, 90, 95, 100, 125, 150, 175, 200 mg/m² to the subject, for example, a dose of from about 0.1, 0.2, 0.3, 0.4, 0.5, 0.75, 1, 2, 3, 4, 5, 6, 7, 8, 9 mg/m² to about 10, 11, 12, 12.5, 13, 14, 15, 17.5, 20, 22.5, 25, 27.5, 30, 32.5, 35, 37.5, 40, 45, 50 mg/m².

The inventive pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations according to the invention which are adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

The compounds of the formula (i) or any of its subformulae as disclosed above (e.g. Formula (I)), according to the invention and salts thereof, solvates and physiologically and/or pharmaceutically active derivatives thereof can also be administered in the form of liposome delivery systems, such as, for exam-pie, small unilamellar vesicles, large unilamellar vesicles and multilamellar vesicles. Liposomes can be formed from various phospholipids, such as, for example, cholesterol, stearylamine or phosphatidylcholines.

The compounds of the formula (i) or any of its subformulae as disclosed above (e.g. Formula (I)), and the salts, solvates and physiologically and/or pharmaceutically active derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, polyepsiloncaprolactone, polyhydroxybutyric acid, polyorthoesters, polyacetals, polydihydroxypyrans, polycyanoacrylates and crosslinked or amphipathic block copolymers of hydrogels.

Pharmaceutical composition of the invention may also be provided as formulations adapted for transdermal administration, which can be administered as independent plasters for extended, close contact with the epidermis of the individual to be treated. Thus, for example, the active compound can be delivered from the plaster by iontophoresis, as described in general terms in Pharmaceutical Research, 3(6), 318 (1986).

Pharmaceutical compositions of the invention may e.g. also be adapted for topical administration and may be formulated as ointments, creams, suspensions, lotions, powders, solutions, pastes, gels, sprays, aerosols or oils.

For the treatment of the eye or other tissues such as e.g. mucosal tissues, such as for example the oral cavity, the inventive compositions and formulations are preferably applied as topical ointment or cream.

In the case the pharmaceutical composition of the invention is to be formulated to be given as ointment, the active compound may e.g. be employed either with a paraffinic or a water-miscible cream base. Alternatively, the active compound according to formula (i) or any of its subformulae as disclosed above (e.g. Formula (I)), or any subformula of the invention may e.g. be formulated to give a cream with an oil-in-water cream base or a water-in-oil base.

Pharmaceutical compositions of the invention, which are adapted for topical application to the eye include e.g. eye drops, in which the active compound is dissolved or suspended in a suitable carrier, in particular an aqueous solvent.

Pharmaceutical compositions according to the invention adapted for topical application in the mouth encompass lozenges, pastilles and mouthwashes, those adapted (formulated) for rectal administration may, e.g. be administered in the form of suppositories or enemas.

Pharmaceutical compositions of the invention, which are adapted for nasal administration in which for example the carrier substance is a solid, comprise a coarse powder having a particle size, in the range e.g. of about 10, 15, 20, 25, 30, 35, 40, 45, 50, 55, 60, 70, 80, 90, 100, 110, 125, 150 to about 160, 170, 180, 190, 200, 225, 250, 300, 400, 500 µm, which is administered in the manner in which snuff is taken, e.g. by rapid inhalation via the nasal passages from a container containing the powder held close to the nose. Suitable formulations for administration as nasal spray or nose drops with a liquid as carrier substance encompass active-compound solutions in water or oil.

The inventive pharmaceutical compositions or formulations adapted for administration by inhalation encompass finely particulate dusts or mists, which can be generated by various types of pressurized dispensers with aerosols, nebulisers or insufflators. Pharmaceutical formulations of the invention adapted for vaginal administration can be administered as pessaries, tampons, creams, gels, pastes, foams or spray formulations.

Pharmaceutical formulations according to the invention, which are adapted for parenteral administration, include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

The inventive pharmaceutical compositions as disclosed above may also comprise other agents commonly used in the art with respect to the particular type of formulation; thus, for example, compositions which are suitable for oral administration may comprise flavours or sweetener and/or antioxidants.

A combined treatment of this type can be achieved with the aid of simultaneous, consecutive or separate dispensing of the individual components of the treatment. Combination products of this type employ the compounds according to the invention.

In one embodiment, the pharmaceutical composition of the invention as disclosed above may be used in the treatment of a parasitic disease as defined above. Preferably, the inventive pharmaceutical composition is used for the treatment of parasitic diseases selected from the group of malaria, cerebral malaria, African sleeping sickness (HAT), chagas, leishmaniasis, onchocerciasis, filariasis, schistosomiasis, more preferably the parasitic disease is malaria, or cerebral malaria. Accordingly, the inventive pharmaceutical composition for use in the treatment of a parasitic disease, e.g. malaria, or cerebral malaria, may be administered as disclosed above, e.g. in any of the dosing regimens and dosings disclosed above. The most effective amount of the inventive pharmaceutical composition to be provided to the person in need thereof is to be determined by the attending medical personnel or physician.

In another specific embodiment, the invention provides a kit comprising, which comprises
 (a) an effective amount of at least one compound of formula (i) or any of its subformulae as disclosed herein (e.g. Formula (I)), and/or pharmaceutically acceptable derivatives and/or solvates and/or stereoisomers thereof, including mixtures thereof in all ratios, and
 (b) an effective amount of at least one further pharmaceutically active compound, wherein the at least one compound of formula (i) or or any of its subformulae as disclosed herein (e.g. Formula (I)), and at least one further pharmaceutically active compound may be provided as separate unit dosage forms, or may be provided as a single unit dosage form comprising both (a) and (b), optionally, the unit dosage forms may further comprise anti-oxidants.

The antioxidant or antioxidants which may be optionally comprised in the unit dosage form according to the invention, are chosen such that they do not interfere with the pharmaceutical effect or efficacy of the at least one inventive compound comprised in the unit dosage form, or with the pharmaceutical effect or efficacy of the at least one further pharmaceutically active compound.

In the inventive kit the at least one further pharmaceutically active compound may e.g. be selected from the group of anti-malarials as disclosed above, e.g. chloroquine, amodiaquine, proguanil, sulphonamides, mefloquine, atovaquone, primaquine, artemisinin and artemisinin-derivatives, halofantrine, doxycycline, tetracycline, clindamycin, or e.g. pain relievers, or e.g. anti-inflammatory agents, such as e.g. non-steroidal anti-inflammatory drugs (NSAIDs).

More specifically, the unit dosage form comprised in the kit of the invention may e.g. be a pill, capsule, lozenge, injectable solution, suppository or plaster, or single-use syringe or auto-injector comprising an individual dose of the inventive compound of formula (i) or any of its subformulae as disclosed herein (e.g. Formula (I)), or of a pharmaceutical composition comprising at least one compound of formula (i) or any of its subformulae as disclosed herein (e.g. Formula (I)), or mixtures thereof in any ratio as defined above and optionally at least one further pharmaceutically active compound as defined above.

According to a general process, compounds of formula (i) or any of its subformulae as disclosed above (e.g. Formula (I)), can be converted to alternative compounds of formula (i) or e.g. any of its subformulae as disclosed above (e.g. Formula (I)), employing suitable inter-conversion techniques well-known by a person skilled in the art.

In one item the present invention provides a process for preparing compounds of formula (I) and its subformulae as disclosed above. In general, the synthesis pathways for any individual compounds of formula (I), or any of its subformulae as disclosed above, e.g. subformulae (II)-(VIIaa), or e.g. any one of the inventive compounds 1-16, depends on the specific substituents of each molecule, on the availability of intermediates or transformation of commercially available starting materials into key intermediates, such factors being appreciated by the one ordinary skilled in the art. For all the protection and deprotection methods, see e.g. Philipp J. Kocienski in "Protecting groups", Georg Thieme Verlag Stuttgart, New York, 1994 and Theodora W. Greene and Peter G. Wuts in "Protective groups in organic synthesis", Wiley Interscience, 3rd Edition 1999.

The inventive compounds according to formula (I) or any of its subformulae as disclosed above may e.g. be obtained by reacting a suitable intermediate such as, e.g. 8-oxa-5-azabicyclo[5.1.0]octane, or any suitable derivate thereof, which will allow for the coupling reaction to proceed to yield an inventive compound according to formula (I). For example, amino functions in the intermediates used for the synthesis of the inventive compounds, may be protected by protecting groups (PG), such as e.g. BOC-(tert-butyloxycarbonyl), FMOC-(9-fluorenylmethyloxycarbonyl), Cbz-(carbobenzyloxy), MeOZ-(p-methoxybenzyl carbonyl), Ac-(acetyl), Bz-(benzoyl), PMB-(-methoxybenzyl), tosyl, or sulfonamide groups. For example, one 8-oxa-5-azabicyclo [5.1.0]octane-derivative which may be used in the coupling reactions is tert-butyl 8-oxa-5-azabicyclo[5.1.0]octane-5-carboxylate. Suitable intermediates for use for the synthesis of the inventive compounds according to formula (I) include, but are not limited to e.g. 3,6-difluoro-9H-carbazole, 3,6-dichloro-9H-carbazole, 3,6-bis(trifluoromethyl)-9H-carbazole, 3,6-dichloro-9H-pyrido[2,3-b]indole, 3,7-dichloro-10H-phenoxazine, 3,7-dichloro-10H-phenothiazine, 3,6-bis(trifluoromethyl)-9H-pyrido[2,3-b]indole, 6-chloro-2,3,4,9-tetrahydro-1H-carbazole, 3,6-bis(trifluoromethyl)-9H-pyrido[3,4-b]indole: 3,6-dichloro-2-methoxy-9H-carbazole, 3,6-dichloro-1-methoxy-9H-carbazole, 2-(methylsulfonyl)-3,6-bis(trifluoromethyl)-9H-carbazole, 4-(methylsulfonyl)-3,6-bis(trifluoromethyl)-9H-carbazole.

For example, tert-butyl 8-oxa-5-azabicyclo[5.1.0]octane-5-carboxylate may be reacted with any one of the above intermediates under suitable reaction conditions, which will allow for the coupling reaction to proceed amd to yield as a major reaction product, e.g. >20% w/w, >30% w/w, >40% w/w, >50% w/w, >60% w/w, >70% w/w, >80% w/w the inventive compound of formula (I), or e.g. any of its subformulae (II)-(VIIaa). The reaction product may comprise all stereoisomers, enantiomers diastereoisomers of the inventive compounds. If required, chiral resolution may be carried out for the isolation of individual stereoisomers according to any technology known in the art, e.g. such as those disclosed in Porter (1991) Pure & Appl. Chem Vol. 63, No. 8, pp-1119-22, or Davankov (1997) Pure & Appl. Chem. Vol. 69, No. 7, pp-1469-74.

Substituted carbazoles, which may be used for the synthesis of the inventive compounds according to formula (I), may be prepared by standard methods known to those skilled in the art. For example, carbazole-derivatives for which R1, R2 may be as disclosed above, e.g. R1, R2 may be both F, or Cl, or $CF_3$ and for which W is a C-Sp2-Sp2-C single bond, or e.g. compounds for which W is O and R1, R2 are as disclosed above, e.g. Cl, F, or $CF_3$, may e.g. be obtained according to the reaction schemes disclosed below (reaction schemes (Ai-iv), which is described in further detail in the appended examples, or as disclosed in e.g. Tetrahedron 64 (2008) 6038-6050, U.S. Pat. Appl. Publ., US20130040977.

Reaction Schemes (Ai-Aiii)

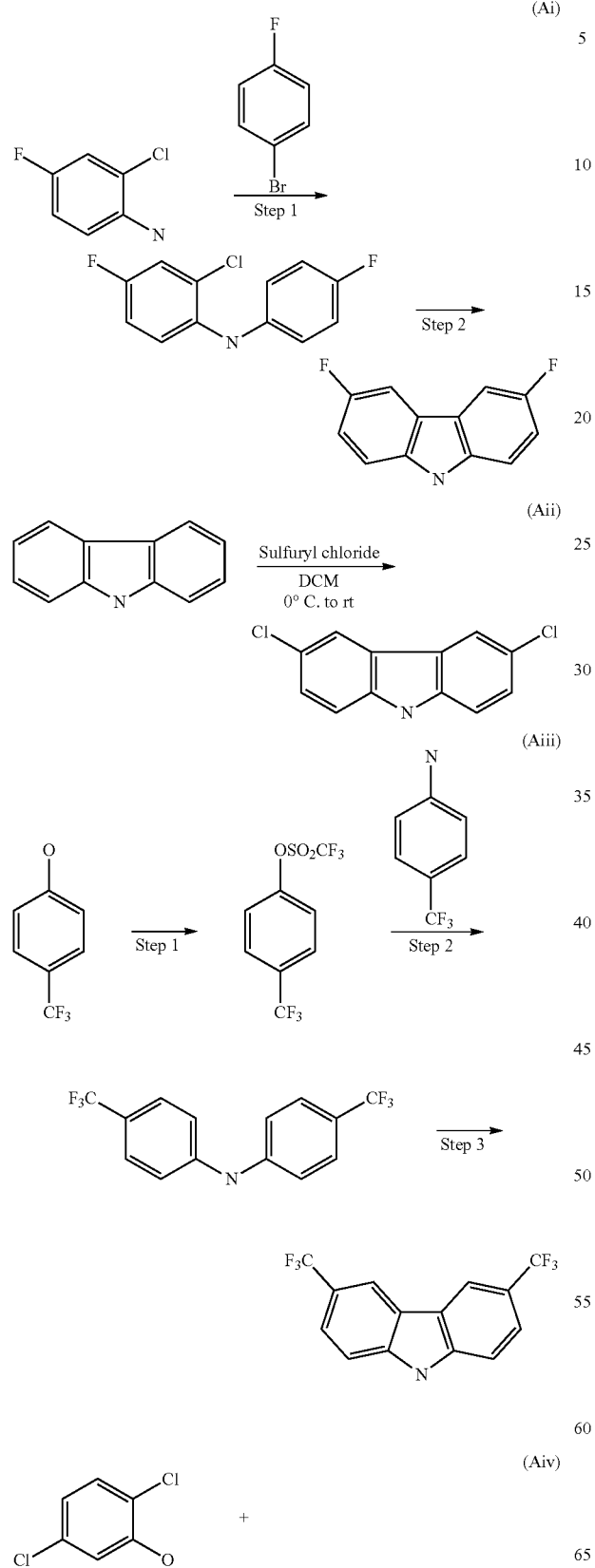

Typically, compounds of general formula (I) of the invention for which the substituents R1-R8 may be as disclosed above and which may e.g. be obtained by way of a reaction as disclosed in reaction scheme (B), whereby "EWG" denotes an "electron withdrawing group", whereby EWG may be e.g. an atom or e.g. functional group that removes electron density from a conjugated π system via resonance or inductive electron withdrawal.

Reaction Scheme (B)

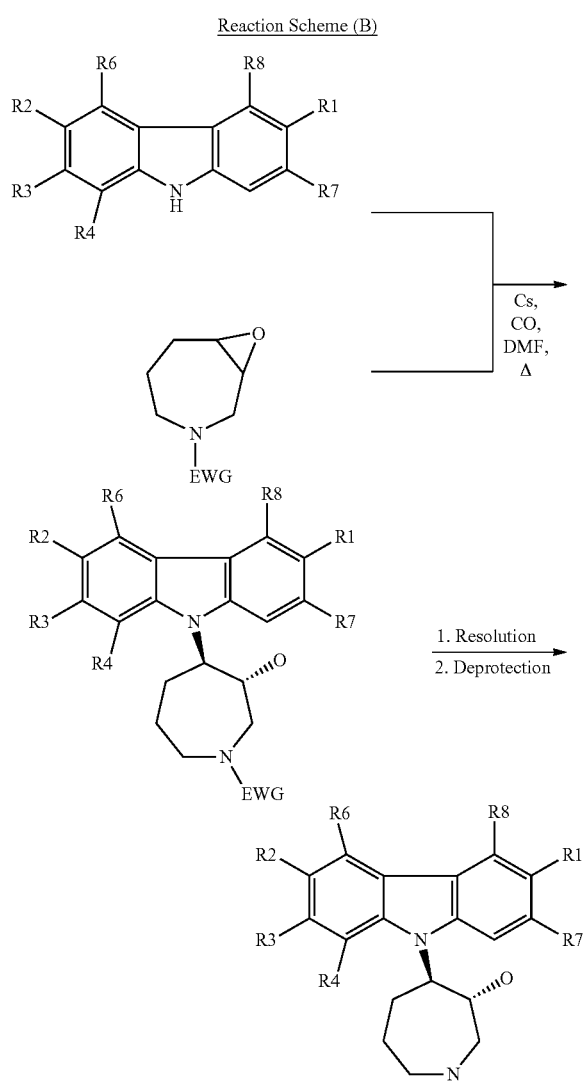

However, certain compounds of formula (I) of the invention may require different syntheses strategies, which differ from that of reaction scheme (B).

According to one item or embodiment, the present invention pertains to a method of treating a person inflicted with parasitic disease, wherein the method comprises: adiministering an pharmacologically effective amount of a compound of formula (I) of the invention or any of its subformulae as disclosed above (e.g. Formula (I)), or a pharmaceutical composition as disclosed above to a person in need thereof.

More specifically, the method of treatment according to the invention pertains to the treatment of a parasitic disease, which is selected from the group comprising malaria, cerebral malaria, tuberculosis, African sleeping sickness (HAT), chagas, leishmaniasis, onchocerciasis, filariasis and schistosomiasis.

More specifically, the inventive method of treatment comprises administering to a person in need thereof the inventive compound according to formula (I) or any of its subformulae as disclosed above (e.g. Formula (I)), or the pharmaceutical composition as disclosed above at least once a day, or twice or three times daily, or twice a week, or three times a week, or at least once every 2, 3, 4, 5, 6 days, for at least 1-18 weeks, or for at least 2-16 weeks, or for at least 3, 4, 5, 6, 7, 8, 9, 10, 11, 12, 13, 14, 15 weeks.

According to one item or embodiment the inventive method as disclosed above comprises administering to a person in need thereof from about the inventive compound or of the inventive pharmaceutical composition in an amount or dosing as disclosed above, e.g. from about 10 micrograms per kilogram (μg/kg) to about 50 mg/kg body weight, e.g. from about 12.5 μg/kg, μg/kg, 50 μg/kg, 75 μg/kg, 100 μg/kg, 125 μg/kg, 150 μg/kg, 175 μg/kg, 200 μg/kg, 250 μg/kg, 300 μg/kg, 350 μg/kg, 400 μg/kg, 450 μg/kg, 500 μg/kg, 600 μg/kg, 750 μg/kg, 1 mg/kg, 2.5 mg/kg, 5 mg/kg, 7.5 mg/kg, 10 mg/kg to about 10 mg/kg, 12.5 mg/kg, 15 mg/kg, 17.5 mg/kg, 20 mg/kg, 22.5 mg/kg, 25 mg/kg, 27.5 mg/kg, 30 mg/kg, 35 mg/kg, 40 mg/kg, 45 mg/kg, 50 mg/kg body weight.

More preferably, the inventive method of treatment as disclosed above pertains to the treatment of malaria or cerebral malaria.

In a more specific embodiment or item, the present invention also pertains to the preparation of compounds 1-31 according to formula (i) or any of its subformulae as disclosed herein (e.g. compounds according to Formula (I)) of the invention, as well as the corresponding reaction intermediates, which may e.g. be used for the synthesis of the inventive compounds of formula (i) or any of its subformulae as disclosed herein, such as e.g. Formula (i), the syntheses of which will be described in the appended examples:

INTERMEDIATES

Intermediate 1 tert-Butyl 8-oxa-3-azabicyclo[5.1.0]octane-3-carboxylate (int 1)

Intermediate 2

3,6-difluoro-9H-carbazole (int 2)

Intermediate 3

3,6-dichloro-9H-carbazole (int 3)

Intermediate 4

3,6-bis(trifluoromethyl)-9H-carbazole (int 4)

Intermediate 5

3,6-dichloro-9H-pyrido[2,3-b]indole (int 5)

Intermediate 6

3,7-dichloro-10H-phenoxazine (int 6)

Intermediate 7

3,7-dichloro-10H-phenothiazine (int 7)

Intermediate 8

3,6-bis(trifluoromethyl)-9H-pyrido[2,3-b]indole (int 8)

Intermediate 9

6-chloro-2,3,4,9-tetrahydro-1H-carbazole (int 9)

Intermediate 10

3,6-bis(trifluoromethyl)-9H-pyrido[3,4-b]indole (int 10)

Intermediate 11

3,6-dichloro-1-methoxy-9H-carbazole (int 11)

Intermediate 12

3,6-dichloro-2-methoxy-9H-carbazole (int 12)

Intermediate 13

3,6-dichloro-4-methoxy-9H-carbazole (int 13)

Intermediate 14

2-(methylthio)-3,6-bis(trifluoromethyl)-9H-carbazole (int 14)

Intermediate 15

4-(methylthio)-3,6-bis(trifluoromethyl)-9H-carbazole (int 15)

Intermediate 16

Synthesis of 7-methoxy-2,8-bis(trifluromethyl)-5H-pyrido[3,2-b]indole (int 16)

Intermediate 17

Synthesis of 7-methoxy-2,8-bis(trifluoromethyl)-5H-pyrido[3,2-b]indole (int 17)

Intermediate 18

N-(4-chloro-2-methoxyphenyl)-6-(trifluoromethyl)pyridin-3-amine (int 18)

Intermediate 19

N-(4-chloro-2-methoxyphenyl)-6-(trifluoromethyl)pyridin-3-amine (int 19)

Intermediate 20

3,6-bis(trifluoromethyl)-9H-pyrrolo[2,3-b:5,4-c']di pyridine (int 20)

Intermediate 21

3,6-bis(trifluoromethyl)-9H-pyrrolo[2,3-b:5,4-c']di pyridine (int 21)

Intermediate 22

3-chloro-6-nitro-9H-carbazole (int 22)

Intermediate 23 tert-Butyl 4-methyl 8-oxa-3-azabicyclo[5.1.0]octane-3-carboxylate (int 23)

Compounds

Compound 1:
3,7-dichloro-10-((3R,4R)-3-hydroxyazepan-4-yl)-10H-phenothiazine 5,5-dioxide,
3,7-dichloro-10-((3S,4S)-3-hydroxyazepan-4-yl)-10H-phenothiazine 5,5-dioxide Compound 2:
(3R,4R)-4-(3,6-dichloro-9H-carbazol-9-yl)azepan-3-ol
(3S,4S)-4-(3, 6-dichloro-9H-carbazol-9-yl)azepan-3-ol Compound 3:
(3R,4R)-4-[3,6-bis(trifluoromethyl)-9H-carbazol-9-yl]azepan-3-ol
(3S,4S)-4-[3,6-bis(trifluoromethyl)-9H-carbazol-9-yl]azepan-3-ol Compound 6:
(3R,4R)-4-[4-methylsulfonyl-3,6-bis(trifluoromethyl)carbazol-9-yl]azepan-3-ol,
(3S,4S)-4-[4-methylsulfonyl-3, 6-bis(trifluoromethyl)carbazol-9-yl]azepan-3-ol Compound 7:
(3R,4R)-4-[2-methylsulfonyl-3, 6-bis(trifluoromethyl)carbazol-9-yl]azepan-3-ol,
(3S,4S)-4-[2-methylsulfonyl-3,6-bis(trifluoromethyl)carbazol-9-yl]azepan-3-ol Compound 8:
(3S,4S)-4-(3,6-dichloro-1-methoxy-9H-carbazol-9-yl)azepan-3-ol,
(3R,4R)-4-(3,6-dichloro-1-methoxy-9H-carbazol-9-yl)azepan-3-ol Compound 9:
(3R,4R)-4-(3,6-dichloro-2-methoxy-9H-carbazol-9-yl)azepan-3-ol,
(3S,4S)-4-(3, 6-dichloro-2-methoxy-9H-carbazol-9-yl)azepan-3-ol Compound 10:
(3R,4R)-4-(3,7-dichloro-10H-phenoxazin-10-yl)azepan-3-ol,
(3S,4S)-4-(3,7-dichloro-10H-phenoxazin-10-yl)azepan-3-ol Compound 14:
(3R,4R)-4-[13,6-bis(trifluoromethyl)pyrido[2,3-b]indol-9-yl]azepan-3-ol,
(3S,4S)-4-[3,6-bis(trifluoromethyl)pyrido[2,3-b]indol-9-yl]azepan-3-ol Compound 15:
(3R,4R)-4-[3,6-bis(trifluoromethyl)pyrido[3,4-b]indol-9-yl]azepan-3-ol,
(3S,4S)-4-[3,6-bis(trifluoromethyl)pyrido[3,4-b]indol-9-yl]azepan-3-ol Compound 16:
(3R,4R)-4-(2,8-bis(trifluoromethyl)-5H-pyrido[3,2-b]indol-5-yl)azepan-3-ol
(3S,4S)-4-(2,8-bis(trifluoromethyl)-5H-pyrido[3,2-b]indol-5-yl)azepan-3-ol Compound 17:
(3R,4R)-4-(7-methoxy-2,8-bis(trifluoromethyl)-5H-pyrido[3,2-b]indol-5-yl)azepan-3-ol Compound 18:
(3S,4S)-4-(7-methoxy-2,8-bis(trifluoromethyl)-5H-pyrido[3,2-b]indol-5-yl)azepan-3-ol Compound 19:
(3R,4R)-4-(8-chloro-6-methoxy-2-(trifluoromethyl)-5H-pyrido[3,2-b]indol-5-yl)azepan-3-ol Compound 20:
(3S,4S)-4-(8-chloro-6-methoxy-2-(trifluoromethyl)-5H-pyrido[3,2-b]indol-5-yl)azepan-3-ol Compound 21:
(3R,4R)-4-(8-chloro-2-(trifluoromethyl)-5H-pyrimido[5,4-b]indol-5-yl)azepan-3-ol
Compound 22:
(3S,4S)-4-(8-chloro-2-(trifluoromethyl)-5H-pyrimido[5,4-b]indol-5-yl)azepan-3-ol
Compound 23:
(3R,4R)-4-(2,8-bis(trifluoromethyl)-5H-pyrrolo[2,3-b:4,5-b']dipyridin-5-yl)azepan-3-ol
Compound 24:
(3S,4S)-4-(2, 8-bis(trifluoromethyl)-5H-pyrrolo[2, 3-b:4,5-b']dipyridin-5-yl)azepan-3-ol
Compound 25:
Synthesis of (3R,4R)-4-((8-chloro-5H-pyrimido[5,4-b]indol-4-yl)amino)azepan-3-ol
Compound 26:
((3R,4R)-4-(3-chloro-6-nitro-carbazol-9-yl)azepan-3-ol,
Compound 27:
(5R,6R)-5-(3,6-dichloro-9H-carbazol-9-yl)-6-hydroxyazepan-2-one
Compound 28:
(3R,4R)-4-[8-chloro-2-(trifluoromethyl)pyrimido[5,4-b]indol-5-yl]-7-methyl-azepan-3-ol
Compound 30:
(8-chloro-5-[(3R,4R)-3-hydroxyazepan-4-yl]-3H-pyrimido[5,4-b]indol-4-one
Compound 31:
((3R,4R)-4-(8-chloro-4-methoxy-pyrimido[5,4-b]indol-5-yl)azepan-3-ol), The present invention also comprises the subsequent items:

Item 1:
A compound of formula (I)

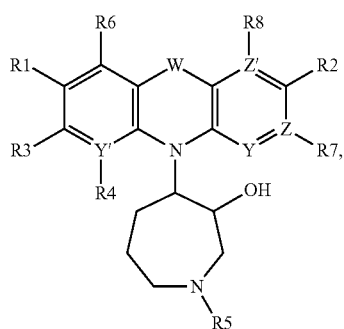

(I)

wherein
W is selected from a C-Sp2-Sp2-C bond, O, SO$_2$, S,
Z is selected from C or N,
Z' is selected from C, or N,
Y' is selected from C or N,
Y is selected from C or N,
R1 denotes halogen, CF$_3$, OMe, Alkoxy, S-Ak, SMe, SO$_2$Me, SO$_2$Alk
R2 denotes halogen, CF$_3$, OMe, Alkoxy, S-Ak, SMe, SO$_2$Me, SO$_2$Alkyl,
R3 denotes halogen, CF$_3$, OMe, SO$_2$, Alkoxy, S-Alkyl, SMe, SO$_2$Me, SO$_2$Alk
R4 denotes halogen, CF$_3$, OMe, Alkoxy, S-Alkyl, SMe, SO$_2$Me, SO$_2$Alk
R5 denotes H, alkyl, benzyl, amide, sulfonamide,
R6 denotes H, alkyl, OMe, SO$_2$, Alkyl, SMe, SO$_2$Me, SO$_2$Alk
R7 denotes H, SO$_2$, SO$_2$Alk, or S-Alk,
R8 denotes H, SO$_2$, or S-Alk,
and
Alk is a branched or linear alkyl group having 1 to 8 carbon atoms or cycloalkyl having 3 to 6 carbon atoms, wherein 1 to 7H-atoms may be independently replaced by Hal, OR, COOR, CN, NR$_2$, phenyl, linear or branched alkyl having 1, 2 or 3 C atoms, cycloalkyl having 3 to 6 carbon atoms and/or wherein 1 to 3 CH$_2$-groups may be replaced by O, —NRCO—, —CO—, —COO—, —CONR, —NR— or S, or cycloalkyl having 3 to 6 carbon atoms,
and
the pharmaceutically acceptable salts esters and N-oxides thereof, in a racemic form or in an enantiomerically pure form or enriched mixture of the respective enantiomers in all ratios, and/or as a mixture of diastereoisomers in all ratios.

Item 2:
Compound according to item 1, wherein R1 is halogen, or CF$_3$.
Item 3:
Compound according to item 1 or item 2, wherein R2 is halogen, or CF$_3$.
Item 4:
Compound according to any one of items 1-3, wherein R1, R2 are both Cl, or both F, or both are CF$_3$.
Item 5:
Compound according to any one of items 1-4, wherein W is SO$_2$.
Item 6:
Compound according to any one of items 1-5, wherein R3, R4, R5, R7 and R8 are H.
Item 7:
Compound according to any one of items 1-6, wherein Y' and Z' both are C.
Item 8:
Compound according to any one of items 1-7, wherein R1, R2 are both Cl, or both are CF$_3$.
Item 9:
Compound according to any one of items 1-8, wherein W is a C-Sp2-Sp2-C bond.
Item 10:
Compound according to any one of items 1-9, wherein Y is C.
Item 11:
Compound according to any one of items 1-10, wherein Y is N.
Item 12:
Compound according to item 11, wherein R1 is Cl, F, or CF$_3$.
Item 13:
Compound according to item 12, wherein R2 is Cl, F, or CF$_3$.
Item 14:
Compound according to item 13, wherein R1, R2 are both Cl, or both are CF$_3$.
Item 15:
Compound according to any one of items 9-14, wherein R8 is SO$_2$Alk.
Item 16:
Compound according to any one of items 9-15, wherein R6 is alkoxy.

Item 17:
Compound according to item 16, wherein R6 is OMe.
Item 18:
Compound according to any one of items 9-17, wherein R3 is alkoxy.
Item 19:
Compound according to any one of items 9-18, wherein R3 is OMe.
Item 20:
Compound according to any one of items 1-19, wherein W is O.
Item 21:
Compound according to item 20, wherein Y is C or N.
Item 22:
Compound according to item 20 or item 21, wherein R2 is Cl, F, or CF$_3$.
Item 23:
Compound according to any one of items 20-22, wherein R2 is CF$_3$.
Item 24:
Compound according to any one of items 20-23, wherein Y is O and Z' is N or C.
Item 25:
Compound according to any one of items 20-24, wherein Y is N and Z' is O.
Item 26:
Compound according to any one of items 1-25, wherein the compound is selected from the group comprising:

| Compound No. | Structure |
|---|---|
| 1 | 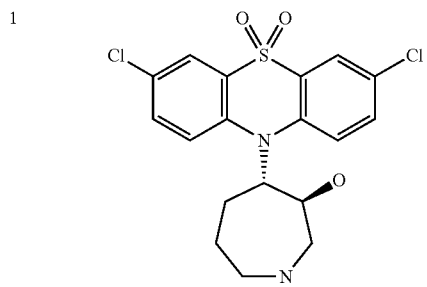 |
| 2 | 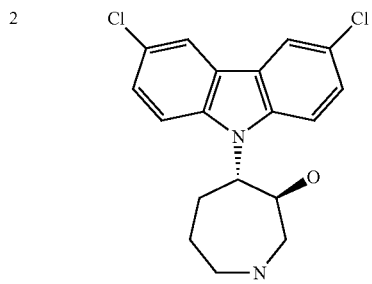 |
| 3 | 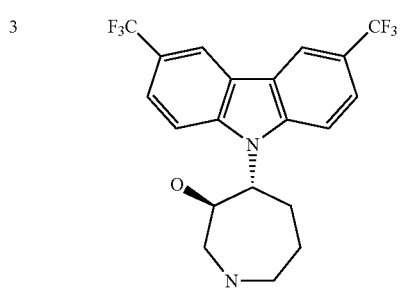 |

-continued

| Compound No. | Structure |
|---|---|
| 4 | 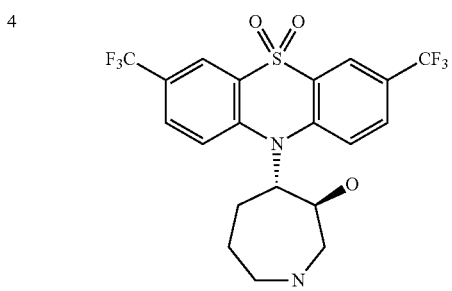 |
| 5 | 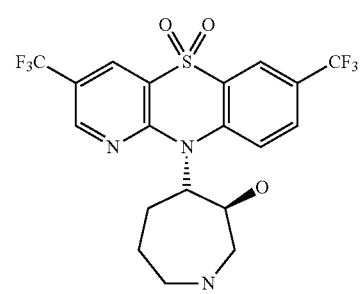 |
| 6 | 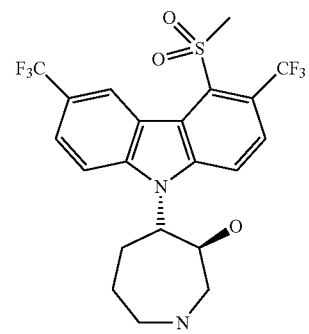 |
| 7 | 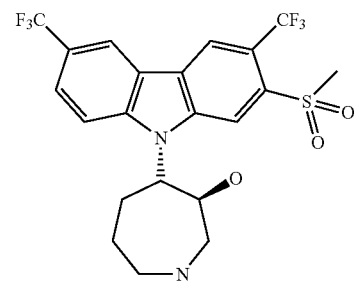 |
| 8 | 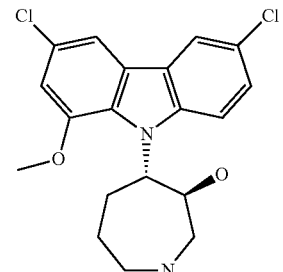 |

| Compound No. | Structure |
|---|---|
| 9 | [structure: 6,8-dichloro-7-methoxy carbazole N-substituted with hydroxy-azepane] |
| 10 | [structure: 3,7-dichloro-phenoxazine N-substituted with hydroxy-azepane] |
| 11 | [structure: bis-CF3 pyrido-indole with methylsulfonyl, N-substituted with hydroxy-azepane (HN)] |
| 12 | [structure: dichloro pyrido-phenoxazine N-substituted with hydroxy-azepane] |
| 13 | [structure: bis-CF3 pyrido-indole with methylsulfonyl, N-substituted with hydroxy-azepane (HN)] |

| Compound No. | Structure |
|---|---|
| 14 | [structure: bis-CF3 α-carboline N-substituted with hydroxy-azepane] |
| 15 | [structure: bis-CF3 β-carboline N-substituted with hydroxy-azepane] |
| 16 | [structure: bis-CF3 pyrido-indole N-substituted with hydroxy-azepane] |

Item 27:
A compound of formula (I) according to any one of items 1-26 for use as a medicament.

Item 28:
A compound of formula (I) according to any one of items 1-27 for use in the treatment or prevention of infectious and parasitic diseases.

Item 29:
A compound for use according to item 28, wherein the parasitic diseases is selected from malaria, tuberculosis, African sleeping sickness (HAT), chagas, leishmaniasis, onchocerciasis, filariasis, schistosomiasis, or one of the following diseases: *Acanthamoeba* Infection, *Acanthamoeba Keratitis* Infection, African Sleeping Sickness (African trypanosomiasis), Alveolar Echinococcosis (Echinococcosis, Hydatid Disease), Amebiasis (*Entamoeba histolytica* Infection), American Trypanosomiasis (Chagas Disease), Ancylostomiasis (Hookworm, Cutaneous Larva Migrans [CLM]), Angiostrongyliasis (*Angiostrongylus* Infection), Anisakiasis (*Anisakis* Infection, *Pseudoterranova* Infection), Ascariasis (*Ascaris* Infection, Intestinal Roundworms), Babesiosis (*Babesia* Infection), Balantidiasis (*Balantidium* Infection), Baylisascariasis (*Baylisascaris* Infection, Racoon Roundworm), *Bilharzia* (Schistosomiasis), *Blastocystis hominis* Infection, Body Lice Infestation (Pediculosis), Capillariasis (Capillaria Infection), Cercarial Dermatitis (Swimmer's Itch), Chagas Disease (American Trypanosomiasis), *Chilomastix mesnili* Infection (Non-pathogenic [Harmless] Intestinal Protozoa), Clonorchiasis (*Clonorchis* Infection), CLM (Cutaneous Larva Migrans, Ancylostomiasis, Hookworm), "Crabs" (Pubic Lice), Cryptosporidiosis (*Cryptosporidium* Infection), Cutaneous Larva Migrans (CLM, Ancylostomiasis, Hookworm), Cyclosporiasis (*Cyclospora* Infection), Cysticercosis (Neurocysticercosis), Cystoisopora Infection (Cystoisosporiasis) formerly *Isospora* Infection, Diarrhea, *Dientamoeba fragilis* Infection, Diphyllobothriasis (*Diphyllobothrium* Infection), *Dipylidium caninum* Infection (dog or cat tapeworm infection), Dracunculiasis (Guinea Worm Disease), Dog tapeworm (*Dipylidium caninum* Infection), Echinococcosis (Alveolar Echinococcosis, Hydatid Disease), Elephantiasis (Filariasis, Lymphatic Filariasis), *Endolimax nana* Infection (Nonpathogenic [Harmless] Intestinal Protozoa), *Entamoeba coli* Infection (Nonpathogenic [Harmless] Intestinal Protozoa), *Entamoeba dispar* Infection (Nonpathogenic [Harmless] Intestinal Protozoa), *Entamoeba hartmanni* Infection (Nonpathogenic [Harmless] Intestinal Protozoa), *Entamoeba histolytica* Infection (Amebiasis), *Entamoeba polecki*, Enterobiasis (Pinworm Infection), Fascioliasis (*Fasciola* Infection), Fasciolopsiasis (*Fasciolopsis* Infection), Filariasis (Lymphatic Filariasis, Elephantiasis), Foodborne Diseases, Giardiasis (Giardia Infection), Gnathostomiasis (*Gnathostoma* Infection), Guinea Worm Disease (Dracunculiasis), Head Lice Infestation (Pediculosis), Heterophyiasis (Heterophyes Infection), Hydatid Disease (Alveolar Echinococcosis), Hymenolepiasis (*Hymenolepis* Infection), Hookworm Infection (Ancylostomiasis, Cutaneous Larva Migrans [CLM]), Intestinal Roundworms (Ascariasis, *Ascaris* Infection), *Iodamoeba buetschlii* Infection (Nonpathogenic [Harmless] Intestinal Protozoa), *Isospora* Infection (see Cystoisospora Infection), Kala-azar (Leishmaniasis, *Leishmania* Infection), Keratitis (*Acanthamoeba* Infection), Leishmaniasis (Kala-azar, *Leishmania* Infection), Lice Infestation (Body, Head, or Pubic Lice, Pediculosis, Pthiriasis), Loaiasis (*Loa loa* Infection), Lymphatic filariasis (Filariasis, Elephantiasis), Malaria (*Plasmodium* Infection), Microsporidiosis (Microsporidia Infection), Mite Infestation (Scabies), *Naegleria* Infection, Neurocysticercosis (Cysticercosis), Nonpathogenic (Harmless) Intestinal Protozoa, Ocular Larva Migrans (Toxocariasis, *Toxocara* Infection, Visceral Larva Migrans), Onchocerciasis (River Blindness), Opisthorchiasis (*Opisthorchis* Infection), Paragonimiasis (*Paragonimus* Infection), Pediculosis (Head or Body Lice Infestation), Pthiriasis (Pubic Lice Infestation), Pinworm Infection (Enterobiasis), *Plasmodium* Infection (Malaria), *Pneumocystis jirovecii* Pneumonia, *Pseudoterranova* Infection (Anisakiasis, *Anisakis* Infection), Pubic Lice Infestation ("Crabs," Pthiriasis), Raccoon Roundworm Infection (Baylisascariasis, *Baylisascaris* Infection), River Blindness (Onchocerciasis), Scabies, Schistosomiasis (*Bilharzia*), Sleeping Sickness (Trypanosomiasis, African; African Sleeping Sickness), Strongyloidiasis (*Strongyloides* Infection), Swimmer's Itch (Cercarial Dermatitis), Taeniasis (*Taenia* Infection, Tapeworm Infection), Tapeworm Infection (Taeniasis, *Taenia* Infection), Toxocariasis (*Toxocara* Infection, Ocular Larva Migrans, Visceral Larva Migrans), Toxoplasmosis (*Toxoplasma* Infection), Travelers' Diarrhea, Trichinellosis (Trichinosis), Trichinosis (Trichinellosis), Trichomoniasis (*Trichomonas* Infection), Trichuriasis (Whipworm Infection, *Trichuris* Infection), Trypanosomiasis, African (African Sleeping Sickness, Sleeping Sickness), Trypanosomiasis, American (Chagas Disease), Visceral Larva Migrans (Toxocariasis, *Toxocara* Infection, Ocular Larva Migrans), Waterborne Diseases, Whipworm Infection (Trichuriasis, *Trichuris* Infection).

Item 30:

A compound for use according to item 28 or 29, wherein the parasitic disease is malaria, or cerebral malaria.

Item 31:

Pharmaceutical composition comprising at least one compound according to any one of items 1-26 and/or pharmaceutically acceptable derivatives thereof, tautomers, salts, solvates and stereoisomers thereof, including mixtures thereof in all ratios, and optionally excipients and/or adjuvants and/or a carrier.

Item 32:

Pharmaceutical composition according to item 31 comprising at least one further pharmaceutically active compound.

Item 33:

Pharmaceutical composition according to item 31 or item 32 for use in the treatment of parasitic disease.

Item 34:

Pharmaceutical composition for use according to item 33, wherein the parasitic disease is selected from the group of malaria, cerebral malaria, African sleeping sickness (HAT), chagas, leishmaniasis, onchocerciasis, filariasis, schistosomiasis.

Item 35:

Pharmaceutical composition for use according to item 33 or item 34, wherein the parasitic disease is malaria, or cerebral malaria.

Item 36:

Kit comprising:
  (a) an effective amount of at least one compound of formula (I) or any of its subformulae according to any one of items 1-26 and/or pharmaceutically acceptable derivatives and/or solvates and/or stereoisomers thereof, including mixtures thereof in all ratios, and
  (b) an effective amount of at least one further medicament active compound, wherein said compound of formula (I) and said at least one further pharmaceutically active compound may are provided as separate unit dosage forms, or are provided as a single unit dosage form comprising both (a) and (b).

Item 37:

Kit according to item 36, wherein the unit dosage form is a pill, capsule, lozenge, injectable solution, suppository or plaster.

Item 38:

A process for preparing a compound of formula (I) comprising the steps of
  (a) reacting a compound of formula (II), wherein R1-R8 and Y', Y, Z, Z' are as defined in item 1:

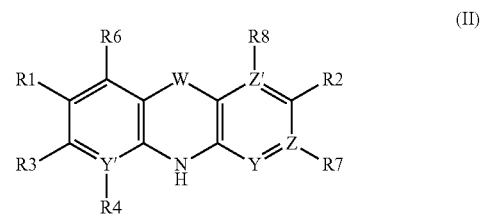

with a compound of formula (III)

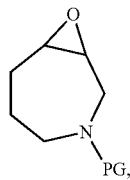

wherein PG denotes a protecting group,
(b) removing the protective group PG.

Item 39:
Method of treating a person inflicted with parasitic disease, wherein the method comprises: administering a pharmacologically effective amount of a compound of formula (I) according to any one of items 1-26, or a pharmaceutical composition according to item 31 or item 32 to a person in need thereof.

Item 40:
Method according to item 39, wherein the parasitic disease is selected from the group comprising malaria, cerebral malaria, tuberculosis, African sleeping sickness (HAT), chagas, leishmaniasis, onchocerciasis, filariasis and schistosomiasis.

Item 41:
Method according to item 39 or item 40, wherein the method comprises administering to a person in need thereof a pharmacologically effective amount the inventive compound according to any one of items 1-28, or the pharmaceutical composition according to item 34 or item 35 at least once a day, or twice or three times daily, or twice a week, or three times a week, or at least once every 2, 3, 4, 5, 6 days, for at least 1-18 weeks, or for at least 2-16 weeks, or for at least 3, 4, 5, 6, 7, 8, 9, 10, 11, 12, 13, 14, 15 weeks.

Item 42:
Method according to any one of items 39-41, wherein the method comprises administering to a person in need thereof from about 12.5 µg/kg, 25 µg/kg, 50 µg/kg, 75 µg/kg, 100 µg/kg, 125 µg/kg, 150 µg/kg, 175 µg/kg, 200 µg/kg, 250 µg/kg, 300 µg/kg, 350 µg/kg, 400 µg/kg, 450 µg/kg, 500 µg/kg, 600 µg/kg, 750 µg/kg, 1 mg/kg, 2.5 mg/kg, 5 mg/kg, 7.5 mg/kg, 10 mg/kg to about 10 mg/kg, 12.5 mg/kg, 15 mg/kg, 17.5 mg/kg, 20 mg/kg, 22.5 mg/kg, 25 mg/kg, 27.5 mg/kg, 30 mg/kg, 35 mg/kg, 40 mg/kg, 45 mg/kg, 50 mg/kg of the compound according to any one of items 1-26, or of the pharmaceutical composition according to item 31 or item 32.

Item 43:
Method according to any one of items 39-42, wherein the parasitic disease is malaria, or cerebral malaria.

EXAMPLES

The following Examples are intended to further illustrate the invention. They are not intended to limit the subject matter or scope of the invention thereto.

The following abbreviations may be used throughout the appended examples and the specification as provided above:
Ac (acetyl), ABS (enantiopure form), ACN (acetonitrile), brs (broad singlet), Boc (tert-butoxycarbonyl), d (doublet), DCE (dichloroethane), DCM (dichloromethane), DMF (dimethylformamide), DMSO (dimethylsulfoxide), EA (ethyl acetate), equiv. (equivalent), ESI (electro-spray ionization), Et (ethyl), Et$_2$O (diethyl ether), EtOAc (ethyl acetate), h (hour), HPLC (high performance liquid chromatography), L (liter), LC (liquid chromatography), MD Autoprep (mass directed preparative HPLC), MeOH (methanol), MeOD (deuterated methanol), mg (milligram), min (minute), mL (milliliter), PL (microliter), M.P. (melting point), mm (millimeter), µm (micrometer), mmol (millimole), m (multiplet), MS (mass spectrometry), NMR (nuclear magnetic resonance), PE (petroleum ether), q (quadruplet), RAC (racemic mixture) Rt (retention time), rt (room temperature), on (overnight), s (singlet), SFC (supercritical fluid chromatography) SPE (solid phase extraction), TBAF (tetrabutylammonium fluoride), TFA (trifluoroacetic acid), THF (tetrahydrofuran), t (triplet), UPLC (ultra performance liquid chromatography).

Throughout the examples, LCMS, GCMS-Analysis, HPLC-Analysis, UPLC, CHIRAL HPLC analyses were done according to the protocols disclosed below:

LCMS-Analysis:
Method A:
Method A—10 mM Ammonium acetate in water; B—ACN; Flow: 1.2 mL/min.
Column-ZORBAX XDB C18 (50×4.6 mm-5 µm) dual MODE
Method B:
Method A—0.1% HCOOH; B—ACN; Flow: 1.2 mL/min.
Column-Atlantis dC18 (50×4.6 mm-5 µm) dual MODE
Method C:
Method A—0.1% HCOOH; B—MEOH; Flow: 1.2 mL/min.
Column-Atlantis dC18 (50×4.6 mm-5 µm) dual MODE
Method D:
Method A—0.1% HCOOH; B—ACN Flow: 1.2 mL/min.
Column-X-terra MS C8 (50×4.6 mm-5 µm) dual MODE
Method E:
Method A—0.1% HCOOH; B—ACN Flow=1.5 mL/min.
Column-ZORBAX XDB C18 (50×4.6 mm-5 µm) positive Mode
Method F:
Method A—0.1% HCOOH; B—0.075% HCOOH IN ACN Flow=1.0 mL/min
Column-PHENOMENEX GEMINI NX C18 (50×4.6 mm-3 µm) dual MODE GCMS-Analysis:
Method A:
AcqMethod DB5MS_SPLITTER1.M
Method B:
AcqMethod HP-1MS UPLC-Analysis:
Method A:
Acquity HSS T3 C18 (2.1×50 mm-1.8 µm)
Acq. Method: 595FA.olp % B: 0 min=5% 2.0 min=95% 2.5 min=5% 3.0 min=5%

HPLC-Analysis:
Method A:
Method A: 0.1% TFA in water; B: ACN; Flow: 1.0 mL/min
Column: WELCHROM C18 (250×4.6 mm-5 µm)
Method B:
Method A: 0.1% TFA in water; Flow: 1.0 mL/min
Column: Atlantis dC18 (250×4.6 mm-5 µm)
Method C:
Method A: 0.1% TFA in water B: Methanol; Flow: 1.0 mL/min
Column: XDB-C18 (50×4.6 mm-1.8 µm)
Method D:
Method A: 10 mM NH$_4$OAC in water, Flow: 0.7 mL/min
Column: phenomenex Gemini NX C18 (150×4.6 mm-5 µm)

Method E:
Method A: 0.1% TFA in water; B: ACN; Flow: 1.0 mL/min
  Column: SYNCRONIS C18 (250×4.6 mm-5 μm)
Method F:
Method A: 0.1% TFA in water B: Methanol; Flow: 1.0 mL/min
  Column: Atlantis dC18 (250×4.6 mm-5 μm)
Method G:
  Method A: HEXANE: IPA (95:05) Flow: 0.8 mL/min
  Column: YMC-PACK silica (250×4.6 mm-5 μm)
CHIRAL HPLC:
Method A:
Method: A: HEXANE: I/PA (80:20) Flow: 1.0 mL/min
  Column: CHIRAL PAK IA (250×4.6 mm-5μ)
Method B:
Method: A: HEXANE: ETHANOL (90:10); Flow: 1.0 mL/min
  Column: CHIRAL PAK AD-H (250×4.6 mm-5μ)
Method C:
Method: A: HEXANE: ETHANOL (90:10); Flow: 1.0 mL/min.
  Column: PHENOMENEX LUX C-4 (250×4.6 mm-5μ)
Method D:
Method A: 0.1% DEA in HEXANE: IPA (90:10)
  Column: CHIRAL PAK IC (250×4.6 mm-5μ)
Method E:
Method A: HEXANE: ETHANOL (95:05)
  Column: CHIRAL PAK IC (250×4.6 mm-5μ)
Method F:
Method A: HEXANE: ETHANOL (80:20); Flow: 1.0 mL/min
  Column: CHIRAL PAK AD-H (250×4.6 mm-5μ)
Method G:
Method A: HEXANE: ETHANOL (40:60); Flow: 1.0 mL/min
  Column: CHIRAL PAK AD-H (250×4.6 mm-5μ)
Method H:
Method A: 0.1% DEA IN HEXANE: IPA (95:05); Flow: 1.0 mL/min
  Column: CHIRAL PAK IA (250×4.6 mm-5μ)
Method I:
Method A: HEXANE: ETHANOL (60:40); Flow: 1.0 mL/min
  Column: PHENOMENEX LUX C-4 (250×4.6 mm-5μ)
Method J:
Method A: HEXANE: ETHANOL (95:05); Flow: 1.0 mL/min
  Column: PHENOMENEX LUX C-4 (250×4.6 mm-5μ)
Method K:
Method A: HEXANE: IPA (90:10); Flow: 1.0 mL/min
  Column: CHIRAL PAK AD-H (250×4.6 mm-5μ)
Method L:
Method A: HEXANE: EtOH (70:30); Flow: 1.0 mL/min
  Column: CHIRAL PAK IA (250×4.6 mm-5μ)
Method M
Method A: 0.1% DEA IN HEXANE: ETHANOL (50:50) Flow: 1.0 mL/min
  Column: CHIRAL PAK IA (250×4.6 mm-5μ)
Method N:
Method A: HEXANE: ETHANOL (30:70) Flow: 1.0 mL/min
  Column: CHIRAL PAK ADH (250×4.6 mm-5μ)

Example 1

Synthesis of tert-Butyl 8-oxa-3-azabicyclo[5.1.0]octane-3-carboxylate (intermediate 1, int 1)

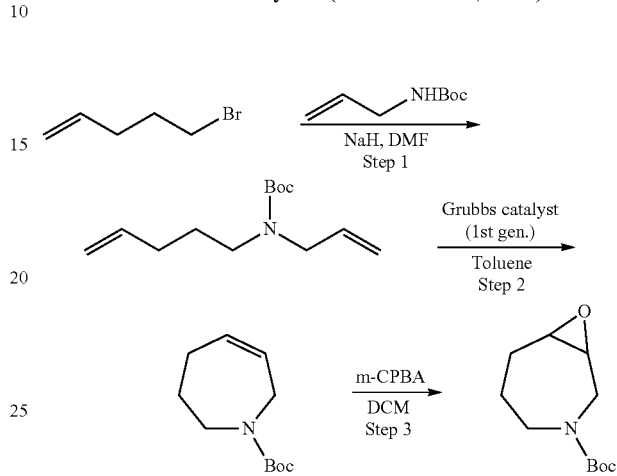

Step 1: To a suspension of sodium hydride (9.54 g, 238 mmol) in DMF (50 mL), tert-butyl N-allylcarbamate (23.0 g, 146 mmol) in DMF (100 mL) was added in a drop wise fashion at 0° C. The mixture was stirred at room temperature for approximately for 30 minutes and cooled to 0° C. whereupon 5-bromo-1-pentene (24.0 g, 175 mmol) in DMF (100 mL) was added in to it. After complete addition, the reaction mixture brought to room temperature and stirred for 1 h. The reaction mixture was partitioned between ethyl acetate and water. The organic layer washed with water, brine, dried over anhydrous sodium sulfate, filtered and concentrated. The crude product was further purified by silica gel chromatography using 0-5% of ethyl acetate/hexane to afford yellowish oil as product (Yield: 29.0 g, 88%).

$^1$H NMR (300 MHz, DMSO-d6): δ 5.71-5.79 (m, 2H), 4.92-5.10 (m, 4H), 3.73 (d, J=4.68 Hz, 2H), 3.08 (t, J=7.10 Hz, 2H), 1:92-1.99 (m, 2H), 1.52 (t, J=7.14 Hz, 2H), 1.36 (s, 9H).

Step 2: To a solution of the boc intermediate (7.0 g, 31.1 mmol) in toluene (250 mL) Grubb's first generation catalyst (1.28 g, 1.55 mmol) was added (Before adding the catalyst, reaction mixture should be degassed using N$_2$). The reaction mixture was heated at 80° C. for 1 h, concentrated to remove toluene and the residue directly taken for column chromatography using 25-30% dichloromethane/hexane to afford 2.0 g of colorless oil as product (Yield: 32.7%).

$^1$H NMR (400 MHz, DMSO-d6): δ 5.69-5.72 (m, 2H), 3.81-3.82 (m, 2H), 3.43 (t, J=6.00 Hz, 2H), 2.13-2.21 (m, 2H), 1.70-1.76 (m, 2H), 1.41 (s, 1H).

Step 3: 3-chloroperoxybenzoic acid (2.1 g, 12.8 mmol) was added to a solution of tert-butyl 2,3,4,7-tetrahydro-1H-azepine-1-carboxylate (2.0 g, 10.1 mmol) in dichloromethane (20 mL) at 0° C. The mixture was stirred at room temperature overnight and then a 10% solution of Na$_2$S$_2$O$_3$ was added and the mixture basified with a saturated solution of Na$_2$CO$_3$. The organic layer was separated, dried (Na$_2$SO$_4$), filtered and the solvent evaporated in vacuo.

Crude product was further purified by silica gel chromatography using 4-8% of ethylacetate/hexane to afford 1.0 g of tert-butyl 8-oxa-3-azabicyclo[5.1.0]octane-3-carboxylate as colorless oil (Yield: 46.2%).

$^1$H NMR (400 MHz, DMSO-d6): δ 3.55-3.65 (m, 2H), 3.13-3.14 (m, 2H), 2.50-2.70 (m, 2H), 2.10-2.15 (m, 2H), 1.93-2.02 (m, 2H), 1.38 (s, 9H).

Example 2

Synthesis of 3, 6-bis(trifluoromethyl)-9H-pyrido[2,3-b]indole (intermediate 3, int 3)

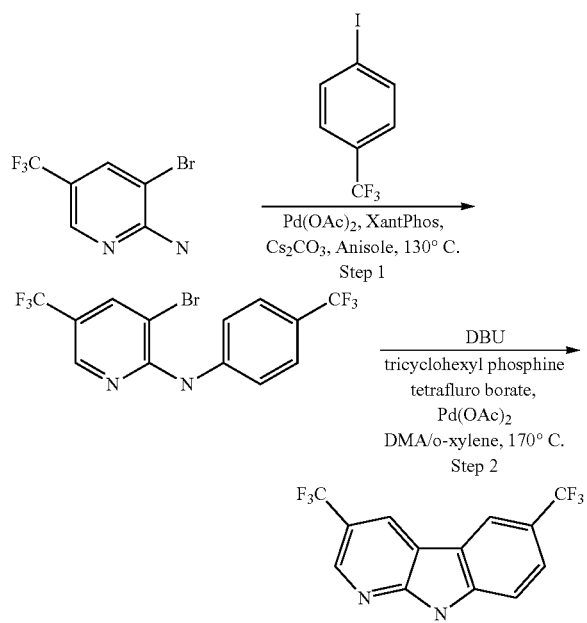

Step 1:

In a sealed tube, 2-amino-3-bromo-5-trifluoromethyl pyridine (2.0 g, 8.2 mmol), 4-iodo benzotrifluoride (2.25 g, 8.2 mmol), Xant-phos (0.425 g, 0.82 mmol) and cesium carbonate (4.0 g, 12.3 mmol) were mixed in anisole (30 mL). The resulting mixture was purged with argon, added Pd(OAc)$_2$ (0.276 g, 1.23 mmol) and heated at 130° C. for 12 h. After completion of the reaction, the reaction mixture was filtered through Celite® bed and concentrated under vacuum. The residue obtained was diluted with ethyl acetate (200 mL), washed with water, brine solution and dried over anhydrous Na$_2$SO$_4$. The organic phase was concentrated and purified by the column chromatography (230-400 size mesh) to get the yellow solid 3-bromo-5-(trifluoromethyl)-N-(4-(trifluoromethyl)phenyl)pyridin-2-amine (1.2 g, 37.7%).

LCMS: (Method B) 385 (M+H), RT. 4.02 min, $^1$H NMR (400 MHz, DMSO-d6): δ 8.47 (d, J=0.80 Hz, 1H), 8.00 (d, J=0.40 Hz, 1H), 7.80 (d, J=8.4 Hz, 2H), 7.63 (d, J=8.4 Hz, 2H), 7.42 (s, 1H).

Step 2:

In a sealed tube, 3-bromo-5-(trifluoromethyl)-N-(4-(trifluoromethyl)phenyl)pyridin-2-amine (1.1 g, 2.8 mmol), DBU (0.87 g, 5.7 mmol) and tricyclohexyl phosphine tetrafluoro borate (0.103 g, 0.28 mmol) were mixed in DMA/o-xylene (1:2) (18 mL). The resulting mixture was purged with argon, added Pd(OAc)$_2$ (0.031 g, 0.014 mmol) and heated at 170° C. for 24 h. After completion of the reaction, the solvent was concentrated under vacuum. The residue obtained was diluted with ethyl acetate (150 mL), washed with water, brine solution and dried over anhydrous Na$_2$SO$_4$. The organic phase was concentrated and purified by column chromatography (60-120 size mesh) to afford 3,6-bis(trifluoromethyl)-9H-pyrido[2,3-b]indole (0.440 g, 50.5%) as white solid.

LCMS: (Method B) 305 (M+H), RT. 3.56 min, $^1$H NMR (400 MHz, DMSO-d6): δ 12.76 (s, 1H), 9.23 (d, J=2.12 Hz, 1H), 8.86 (m, 2H), 7.86 (m, 1H), 7.75 (d, J=8.56 Hz, 1H).

Example 3

Synthesis of 3, 7-dichloro-10H-phenothiazine (intermediate 4, int 4)

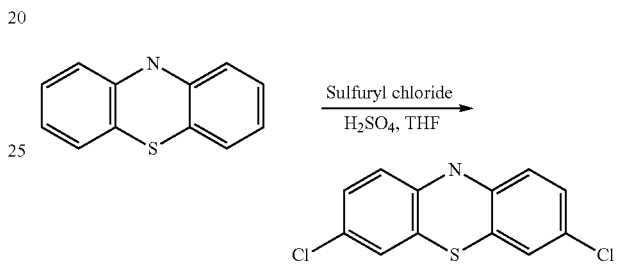

To a solution of phenothiazine (5.0 g, 25 mmol) in THF (70 mL), 2 drops of con H$_2$SO$_4$ was added followed by N-chloro succinimide (6.6 g, 50 mmol) at 0° C. and the reaction mixture stirred at same temperature for another 30 minutes. Then the reaction mixture was concentrated to remove THF, the solid obtained was re-crystallized from dichloromethane. The suspension was filtered, to afford pure product (5.0 g, 74.6%) of 3,7-dichloro-10H-phenothiazine as green color solid.

$^1$H NMR (400 MHz, DMSO-d6): δ 8.84 (s, 1H), 7.02-7.04 (m, 4H), 6.63 (d, J=9.20 Hz, 2H).

Example 4

Synthesis of 3, 6-difluoro-9H-carbazole (intermediate 5, int 5)

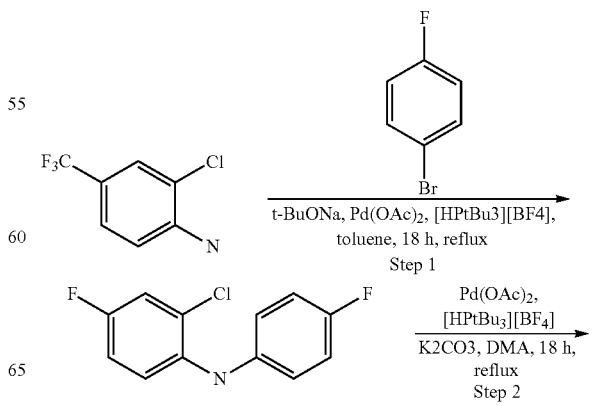

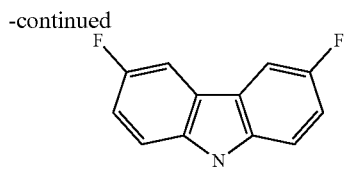

Step 1: 2-Chloro-4-fluoroaniline (3.0 g, 20.6 mmol) and 4-fluoro-1-bromo benzene (3.6 g, 20.6 mmol) were added to NaOtBu (9.9 g, 103.0 mmol), Pd(OAc)$_2$ (0.231 g, 1.03 mmol) and [HPtBu$_3$][BF$_4$] (0.42 g, 1.4 mmol) suspended in toluene (120 mL). The reaction was then heated to reflux for 18 h, allowed to cool and concentrated to remove toluene. The residue was extracted with dichloromethane (2×100 mL), dried (Na$_2$SO$_4$), then filtered and the solvent removed under reduced pressure. The crude product was purified by column chromatography using silica gel 230-400 mesh to get the desired colorless product 2-chloro-4-fluoro-N-(4-fluorophenyl)aniline (2.0 g, 41%).

GC MS: (Method B) 239.0 (M+H), RT-4.73 min $^1$H NMR (400 MHz, DMSO-d6): δ 7.28 (s, 1H), 7.01-7.16 (m, 5H), 6.89-6.88 (m, 1H), 5.84 (s, 1H).

Step 2: 2-Chloro-4-fluoro-N-(4-fluorophenyl)aniline (1.6 g, 6.6 mmol) was added to potassium carbonate (4.6 g, 33.3 mmol), Pd(OAc)$_2$ (0.074 g, 0.33 mmol) and [HPtBu$_3$][BF$_4$] (0.14 g, 4.67 mmol) suspended in DMA (48 mL). The reaction then stirred at reflux temperature for 18 h, reaction mixture was diluted with water, extracted with ethyl acetate. The organic layer was dried over anhydrous sodium sulfate, filtered, and concentrated under reduced pressure. The crude product was purified by column chromatography using silica gel 230-400 mesh to give intermediate 5 (int 5) (1.26 g, 93%) as white solid.

LCMS: (Method B) 202.0 (M+H), RT-3.18 min, $^1$H NMR (400 MHz, DMSO-d6): δ 8.00 (s, 1H), 7.67-7.68 (m, 2H), 7.35-7.36 (m, 2H), 7.17-7.18 (m, 2H).

Example 5

Synthesis of 3, 6-dichloro-9H-carbazole (intermediate 6, int 6)

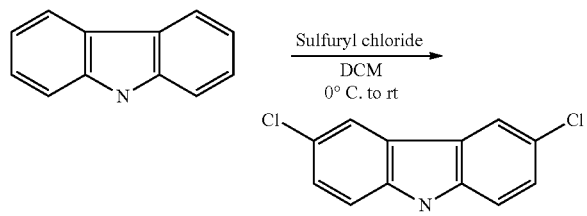

To a 3-neck, 100 mL round-bottomed flask equipped with septum, a mechanical stirrer and a thermometer, was added carbazole (5.0 g, 2.9 mmol) and dichloromethane (50 mL) The suspension was cooled to 0° C. With vigorous stirring, sulfuryl chloride (4.8 mL, 5.9 mmol) was added drop wise at such rate, that the temperature did not exceed 2° C. Following the addition, the cooling bath was removed and the reaction mixture was stirred for another 4 h at room temperature. The solid precipitated was filtered off, washed with dichloromethane and dried to give 4.4 g of raw 3,6-dichlorocarbazole contaminated with traces of 3-chlorocarbazole. The residue was suspended in 0.1 L of hexane and boiled for 0.5 h to remove the traces of 3-chlorocarbazole. The suspension was filtered, giving pure product (3.0 g, 42.9%).

$^1$H NMR (400 MHz, DMSO-d6): δ 11.58 (s, 1H), 8.28 (d, J=2.0 Hz, 2H) 7.52 (d, J=8.6 Hz, 2H), 7.42 (dd, J=8.6 Hz, J=2.0 Hz, 2H)

Example 6

Synthesis of 3, 6-bis(trifluoromethyl)-9H-carbazole (intermediate 7, int 7)

(See Also U.S. Pat. Appl. Publ. 20130040977)

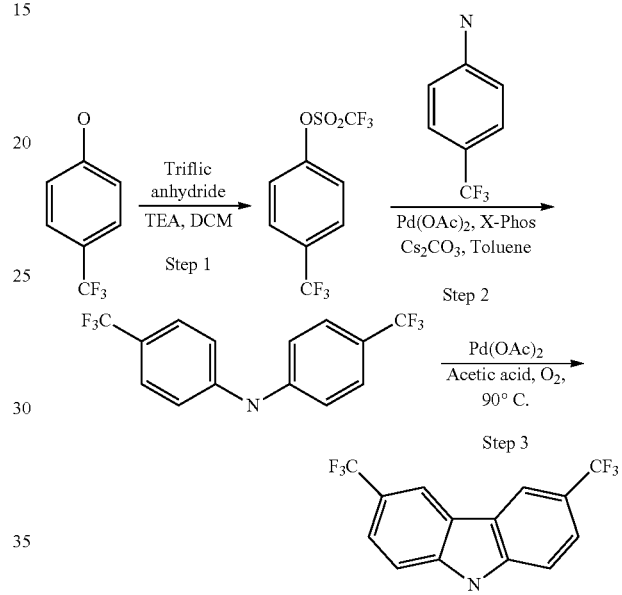

Step 1: To a solution of 4-trifluoromethylphenol (25.0 g, 154 mmol) in dichloromethane (100 mL) was added pyridine (14.6 mL, 185 mmol) and stirred. To this stirred solution was added solution of triflic anhydride (27.9 mL, 169 mmol) in dichloromethane (100 mL) at 0° C. The mixture was stirred at 0° C. for 1 h, and then room temperature for 2.5 h. The reaction was quenched with 25 mL of water and the organic phase saturated with NaHCO$_3$, 1M HCl and brine, then dried with MgSO$_4$ and concentrated to give crude product. The crude product was further purified by silica gel chromatography using 5% ethyl acetate/petroleum ether to afford 27.4 g of colorless oil as product (Yield 60.4%).

$^1$H NMR (400 MHz, CDCl$_3$): δ7.74-7.76 (m 2H), 7.27-7.29 (m, 2H).

Step 2: The product of step 1 (5.0 g, 16.9 mmol), 4-(trifluoromethyl)aniline (3.01 g, 18.6 mmol), Pd(OAc)$_2$ (0.38 g, 1.69 mmol), XPhos (1.2 g, 2.5 mmol) and Cs$_2$CO$_3$ (6.6 g, 20.2 mmol), was added toluene (100 mL) and stirred at 100° C. for 3 h in a sealed tube under nitrogen. After cooling, the crude mixture was diluted with ethyl acetate and washed with brine. The organic layer was dried with MgSO$_4$ and concentrated. The crude product was further purified by silica gel chromatography using 0-5% of EtOAc/Hex to afford 5.0 g of the diaryl amine as a colorless oil (Yield: 96%).

LCMS: (Method B) 304 (M+H), RT. 3.59 min, $^1$H NMR (400 MHz, CDCl$_3$): δ9.10 (s, 1H), 7.58-7.59 (m, 4H), 7.25-7.27 (m, 4H).

Step 3: To bis(4-(trifluoromethyl)phenyl)amine (5.4 g, 17.6 mmol), was added acetic acid (54 mL) and Pd(OAc)$_2$ (0.397 g, 1.76 mmol) and heated to 90° C. for 12 h under an oxygen balloon. Solid NaHCO$_3$ was added to quench the reaction and the mixture was diluted with ethyl acetate. The organic layer was dried with MgSO$_4$ and concentrated to give crude product. It was further purified by silica gel chromatography using 25% ethyl acetate/petroleum ether to afford 2.8 g of white solid (Yield: 56%).

LCMS: (Method B) 303 (M+H), RT. 2.83 min,
$^1$H NMR (400 MHz, CDCl$_3$): δ12.12 (s, 1H), 8.81 (s, 2H), 7.75-7.77 (m, 2H), 7.73 (d, J=8.00 Hz, 2H).

Example 7

Synthesis of 3, 6-dichloro-9H-pyrido[2, 3-b]indole (intermediate 8, int 8)

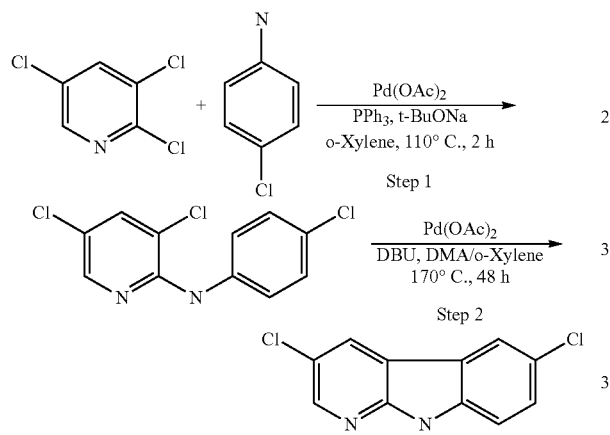

Step 1:

In a sealed tube, 2,3,5-trichloro pyridine (8.0 g, 44 mmol), 4-chloro aniline (6.17 g, 49 mmol), triphenyl phosphine (1.16 g, 44 mmol) and sodium-tert-butoxide (5.09 g, 53 mmol) were mixed in o-xylene (80 mL). The resulting mixture was purged with argon, added Pd(OAc)$_2$ (0.49 g, 2.2 mmol) and heated at 110° C. for 12 h. After completion of the reaction, the reaction mixture was filtered through Celite® bed and concentrated under vacuum. The residue obtained was diluted with ethyl acetate (200 mL), washed with water, brine solution and dried over anhydrous Na$_2$SO$_4$. The organic phase was concentrated and purified by the column chromatography (60-120 size mesh) to get the yellow solid 3,5-dichloro-N-(4-chlorophenyl)pyridin-2-amine (7.0 g, 58.23%).

LCMS: (Method B) 275 (M+H), RT. 3.69 min,
$^1$H NMR (400 MHz, DMSO-d6): δ 8.68 (s, 1H), 8.14 (d, J=2.28 Hz, 1H), 8.04 (d, J=2.32 Hz, 1H), 7.68-7.66 (m, 2H), 7.34-7.32 (m, 2H).

Step 2:

In a sealed tube, 3,5-dichloro-N-(4-chlorophenyl)pyridin-2-amine (4.0 g, 14.7 mmol), DBU (4.4 g, 29.5 mmol) and tricyclohexyl phosphine tetrafluoro borate (0.54 g, 1.47 mmol) were mixed in DMA/o-xylene (1:2) (50 mL). The resulting mixture was purged with argon, added Pd(OAc)$_2$ (0.16 g, 0.73 mmol) and heated at 170° C. for 48 h. After completion of the reaction, the solvent was concentrated under vacuum. The residue obtained was diluted with ethyl acetate (150 mL), washed with water, brine solution and dried over anhydrous Na$_2$SO$_4$. The organic phase was concentrated and purified by column chromatography (60-120 size mesh) to afford 3,6-dichloro-9H-pyrido[2,3-b]indole intermediate 8 (int 8) (1.2 g, 34.6%) as yellow solid.

LCMS: (Method B) 235 (M+H), RT. 3.34 min,
$^1$H NMR (400 MHz, DMSO-d6): δ 12.17 (s, 1H), 8.74 (s, 1H), 8.46 (s, 1H), 8.33 (s, 1H), 7.52-7.51 (m, 2H).

Example 8

Synthesis of 3, 7-dichloro-10H-phenoxazine (intermediate 9, int 9)

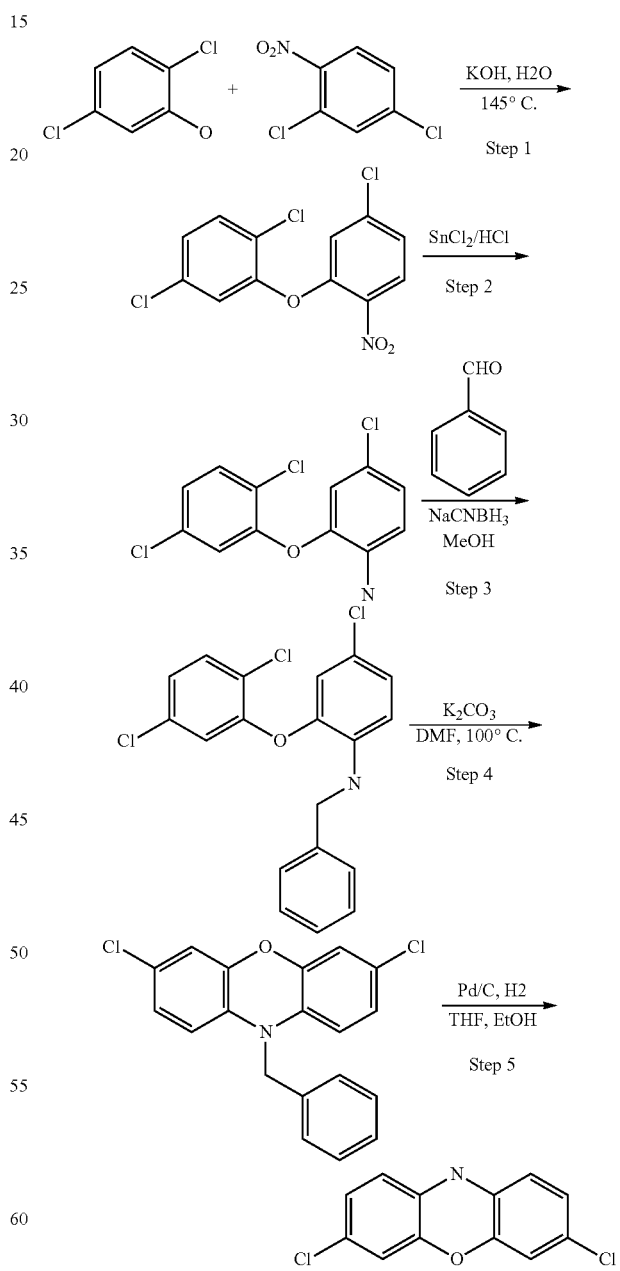

Step 1: A mixture of (9.78 g, 60 mmol) of 2,5-dichlorophenol and (11.58 g, 60 mmol) of 1,4-dichloro-2-nitrobenzene was heated to 120-125° C., stirring commenced, a solution of 4.0 g of KOH pellets (85%) in 2.6 mL of water was added drop wise in to it and temperature was raised to 145° C. and maintained for a further 18 h. The hot solution was poured in to a stirred solution of 1 mL of 30% of aqueous NaOH in 100 mL of water. The initially formed oil become solid in few minutes, filtered and re-crystallized from ethanol to get 1,4-dichloro-2-(5-chloro-2-nitrophenoxy)benzene as yellow solid (11.5 g, 59.9%).

$^1$H NMR (400 MHz, DMSO-d6): δ 8.26 (d, J=2.80 Hz, 1H), 7.76-7.78 (m, 1H), 7.68 (d, J=8.40 Hz, 1H), 7.36-7.41 (m, 2H), 7.20 (d, J=8.8 Hz, 1H).

Step 2: To a solution of 1,4-dichloro-2-(5-chloro-2-nitrophenoxy)benzene (13.0 g, 40.88 mmol) in ethanol (150 mL):H$_2$O (50 mL) mixture, SnCl$_2$.H$_2$O (36.8 g, 163.7 mmol) was added and the reaction mixture heated to 90° C. for 12 h. The reaction mixture was concentrated and the residue was basified using 10% sodium hydroxide solution and extracted with ethyl acetate. The organic layer was separated, dried (Na$_2$SO$_4$), filtered and the solvent evaporated in vacuo. The crude product was further purified by silica gel chromatography using 0-3% of ethyl acetate/hexane to afford 4-chloro-2-(2,5-dichlorophenoxy)aniline (7.0 g, 59.8%) as brownish oil.

$^1$H NMR (400 MHz, DMSO-d6): δ 7.59 (d, J=8.56 Hz, 1H), 7.18-7.21 (m, 1H), 6.74-6.85 (m, 3H), 6.53-6.56 (s, 1H), 5.41 (s, 2H).

Step 3: To a solution of 4-chloro-2-(2,5-dichlorophenoxy) aniline (4.0 g, 13.8 mmol) in MeOH (100 mL), benzaldehyde (1.17 g, 11.1 mmol) and 2 drops of acetic acid were added and stirred the reaction mixture at room temperature for 2 h. After 2 h, the reaction mixture was cooled to 0° C. and NaBH$_4$ (0.62 g, 16.6 mmol) was added. Upon complete addition, warm the reaction mixture to room temperature and stir for 1 h. Reaction mixture quenched with ice and concentrated in vacuo and to the residue was partitioned between water and ethyl acetate. The organic layer was separated, dried (Na$_2$SO$_4$), filtered and the solvent evaporated in vacuo. Crude product with 18% mass by UPLC was taken as such for the next step.

Step 4: To a stirred solution of N-benzyl-4-chloro-2-(2, 5-dichlorophenoxy)aniline (0.95 g, 1.1 mmol) in DMF was added potassium carbonate (0.33 g, 2.3 mmol) and the reaction mixture was stirred at 100° C. for 12 h. After completion of reaction, reaction mixture was diluted with ethyl acetate (100 mL), washed with water, brine solution and dried over anhydrous Na$_2$SO$_4$. Crude product was re-crystallized from methanol, filtered, dried to obtain 10-benzyl-3,7-dichloro-1 OH-phenoxazine (0.4 g, 47% as white solid.

$^1$H NMR (300 MHz, DMSO-d6): δ 7.34-7.36 (m, 1H), 7.26-7.28 (m, 3H), 6.71 (s, 4H), 6.53 (s, 2H), 4.91 (s, 2H).

Step 5: A flask was charged 10-benzyl-3,7-dichloro-10H-phenoxazine (1.0 g, 2.9 mmol), ethanol (50 mL), THF (50 mL) and 10% Pd/C. The mixture was subjected to hydrogenation using bladder at RT for 30 min. After 3 h the reaction mixture was filtered through a pad of celite and the solvent removed under reduced pressure. The filtrate was evaporated and purified by flash chromatography using 0-5% of EtOAc/Hex to afford (0.4 g, 54.7%) as off white solid.

$^1$H NMR (300 MHz, DMSOd6): δ 8.59 (s, 1H), 6.55-6.63 (m, 4H), 6.40-6.43 (m, 2H).

Example 9

Synthesis of 3, 6-bis(trifluoromethyl)-9H-pyrido[3,4-b]indole (intermediate 10, int 10)

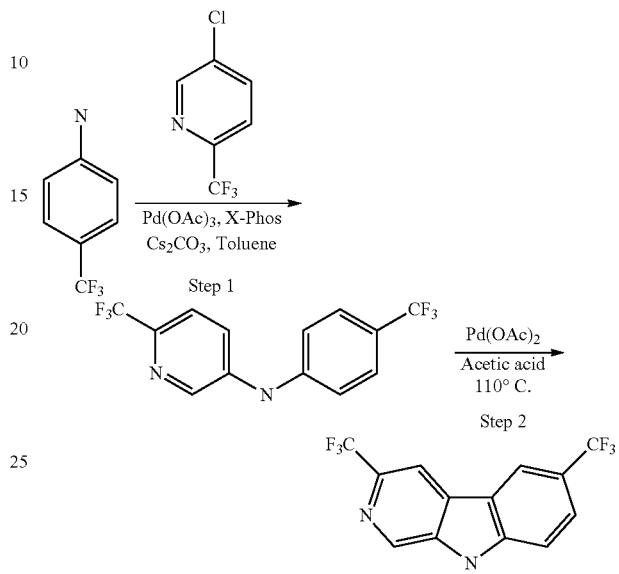

Step 1: In a sealed tube, 5-chloro 2-trifluoromethyl pyridine (5.0 g, 27.5 mmol), 4-(trifluoromethyl)aniline (4.88 g, 30.0 mmol), XPhos (0.944 g, 0.13 mmol) and Cs$_2$CO$_3$ (13.4 g, 41.2 mmol), were mixed in toluene (100 mL). The resulting mixture was purged with argon, added Pd(OAc)$_2$ (0.62 g, 0.275 mmol) and stirred at 110° C. for 12 h. After completion of the reaction, the reaction mixture was filtered through Celite® bed and concentrated under vacuum. The residue obtained was diluted with ethyl acetate and washed with brine. The organic layer was dried with MgSO$_4$ and concentrated. The crude product was further purified by silica gel chromatography using 0-5% of ethyl acetate/hexane to afford 4.75 g of the 6-(trifluoromethyl)-N-(4-(trifluoromethyl)phenyl)pyridin-3-amine as a white solid (Yield: 56.3%).

LCMS: (Method B) 307 (M+H), RT. 3.55 min, $^1$H NMR (300 MHz, CDCl$_3$): δ 8.48 (d, J=2.3 Hz, 1H), 7.54-7.61 (m, 4H), 7.22-7.27 (m, 1H), (s, 1H).

Step 2: To 6-(trifluoromethyl)-N-(4-(trifluoromethyl)phenyl)pyridin-3-amine (4.75 g, 15 mmol) was added acetic acid (50 mL) and Pd(OAc)$_2$ (3.48 g, 15 mmol) and heated to 100° C. for 12 h. After completion of the reaction, the reaction mixture was filtered through Celite® bed and concentrated under vacuum. The residue obtained was diluted with ethyl acetate (200 mL), washed with 10% sodium bicarbonate solution, water and brine solution. The organic layer was dried over anhydrous Na$_2$SO$_4$ and concentrated. The crude product was further purified by silica gel chromatography using 0-14% of ethyl acetate/hexane to afford 0.75 g of the 3,6-bis(trifluoromethyl)-9H-pyrido[3,4-b]indole.

LCMS: (Method E) 305 (M+H), RT. 3.43 min, $^1$H NMR (400 MHz, CDCl$_3$): δ 8.75-8.78 (m, 1H), 7.88 (d, J=8.50 Hz, 1H), 7.77-7.82 (m, 2H), 7.58 (d, J=8.60 Hz, 1H).

Example 10

Synthesis of 3,6-dichloro-1-methoxy-9H-carbazole (intermediate 11, int 11)

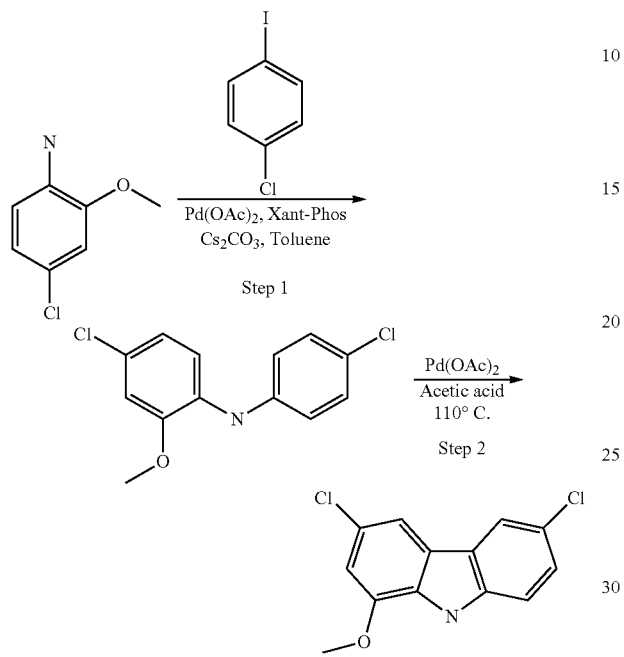

Step 1: In a sealed tube, 4-chloro 2-anisidine (1.0 g, 6.3 mmol), 4-iodo chloro benzene (1.51 g, 6.3 mmol), Xant-Phos (0.33 g, 0.63 mmol) and $Cs_2CO_3$ (6.19 g, 19.0 mmol), were mixed in toluene (20 mL). The resulting mixture was purged with argon, added $Pd(OAc)_2$ (0.213 g, 0.95 mmol) and stirred at 110° C. for 12 h. After completion of the reaction, the reaction mixture was filtered through Celite® bed and concentrated under vacuum. The residue obtained was diluted with ethyl acetate and washed with brine. The organic layer was dried with $MgSO_4$ and concentrated. The crude product was further purified by silica gel chromatography using 0-1% of ethyl acetate/hexane to afford 0.5 g of the 4-chloro-N-(4-chlorophenyl)-2-methoxyaniline as a white solid (Yield: 29.4%)

LCMS: (Method B) 268 (M+H), RT. 3.87 min, 92.28% (Max).

$^1$H NMR (400 MHz, DMSO-d6): δ 7.64 (s, 1H), 7.21 (dd, J=5.20, 6.20 Hz, 2H), 7.14-7.16 (m, 1H), 7.06 (d, J=2.40 Hz, 1H), 6.89-7.00 (m, 2H), 6.88 (d, J=2.40 Hz, 1H), 3.82 (s, 1H).

Step 2: To 4-chloro-N-(4-chlorophenyl)-2-methoxyaniline (0.5 g, 1.86 mmol) was added acetic acid (5 mL) and $Pd(OAc)_2$ (0.12 g, 0.55 mmol) and heated to 100° C. for 12 h. After completion of the reaction, the reaction mixture was filtered through Celite® bed and concentrated under vacuum. The residue obtained was diluted with ethyl acetate (20 mL), washed with 10% sodium bicarbonate solution, water and brine solution. The organic layer was dried over anhydrous $Na_2SO_4$ and concentrated. The crude product was further purified by silica gel chromatography using 0-5% of ethyl acetate/hexane to afford 0.25 g of the 3,6-dichloro-1-methoxy-9H-carbazole int 11. (Yield: 50.4%)

LCMS: (Method B) 366 (M+H), RT. 3.72 min, $^1$H NMR (400 MHz, DMSO-d6): δ 8.24 (s, 1H), 7.87 (s, 1H), 7.48 (d, J=8.40 Hz, 1H), 7.40 (d, J=8.40 Hz, 1H), 7.05 (s, 1H).

Example 11

Synthesis of 3, 6-dichloro-2-methoxy-9H-carbazole int 12 and 3, 6-dichloro-4-methoxy-9H-carbazole int 13

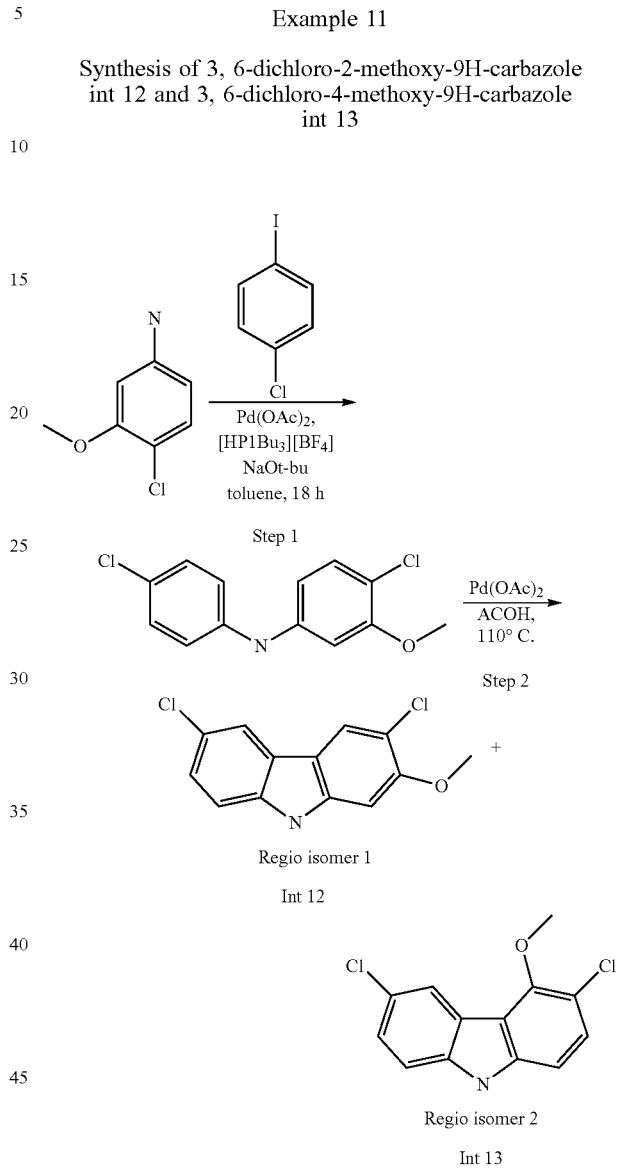

Step 1:

4-chloro-3-methoxy aniline (2.0 g, 12.6 mmol), 1-chloro-4-iodobenzene (3.33 g, 13.9 mmol), and sodium-tert-butoxide (6.04 g, 63 mmol) were taken in toluene (15 mL). The resulting mixture was purged with nitrogen, added $Pd(OAc)_2$ (0.141 g, 0.63 mmol), [HPtBu₃][BF₄] (0.255 g, 0.88 mmol) and heated at 110° C. for 12 h. After completion of the reaction, the reaction mixture was filtered through celite bed and concentrated under vacuum. The residue obtained was diluted with ethyl acetate (200 mL) washed with water, brine solution and dried over anhydrous $Na_2SO_4$. The organic phase was concentrated and purified by the column chromatography (230-400 size mesh) to get the white solid 4-chloro-N-(4_chlorophenyl)-3-methoxy aniline (1.2 g, 35.2%).

$^1$H NMR (400 MHz, DMSO-d6): δ 8.46 (s, 1H), 7.22-7.28 (m, 3H), 7.08-7.10 (m, 2H), 6.75 (s, 1H), 6.64 (d, J=8.68 Hz, 1H), 3.80 (s, 3H).

Step 2: In a sealed tube, 4-chloro-N-(4_chlorophenyl)-3-methoxyaaniline (1.5 g, 5.5 mmol), Pd(OAC)₂ were taken in ACOH (5 mL) and heated the reaction mixture at 120° C. for 24 h. Reaction mixture was diluted with ethyl acetate (150 mL), washed with water, brine solution and dried over anhydrous Na₂SO₄. The organic phase was concentrated and purified by column chromatography (230-400 size mesh) to afford Int 12 & Int 13 as yellow solid.

Int 12: (0.2 g, 13.5%)
LCMS: (Method B) 266 (M+H), RT. 3.62 min.
¹H NMR 400 MHz, DMSO-d6: δ 11.42 (s, 1H), 8.26 (s, 1H), 8.17 (d, J=1.60 Hz, 1H), 7.46 (d, J=8.60 Hz, 1H), 7.31-7.33 (s, 1H), 7.14 (s, 1H), 3.94 (s, 3H).

Int 13: (0.05 g, 3.5%)
¹H NMR (400 MHz, DMSO-d6): δ 8.41 (d, J=1.60 Hz, 1H), 8.32-8.33 (m, 1H), 8.21-8.24 (m, 1H), 7.96-7.99 (m, 1H), 7.72 (s, 1H), 4.13 (s, 3H).

Example 12

Synthesis of 2-(methylthio)-3,6-bis(trifluoromethyl)-9H-carbazole (intermediate 14, int 14) and 4-(methylthio)-3, 6-bis(trifluoromethyl)-9H-carbazole (intermediate 15, int 15)

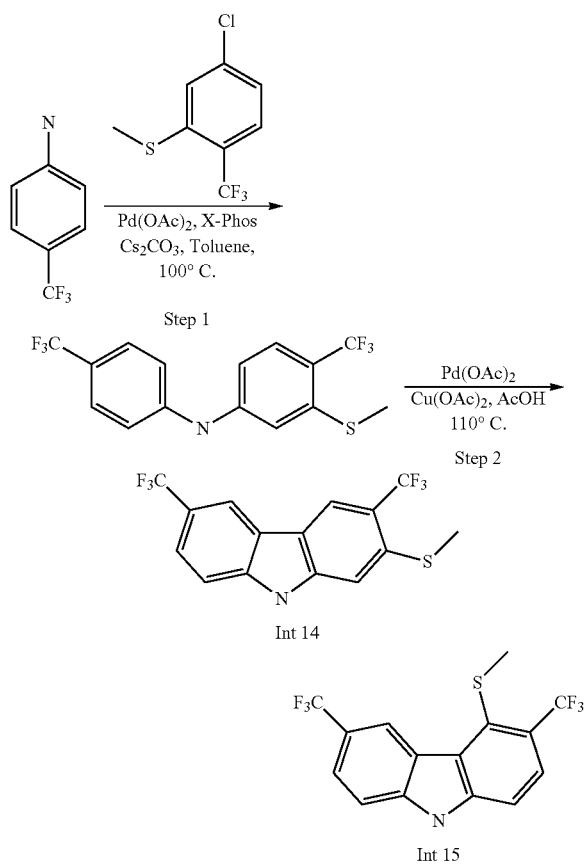

Step 1: In a sealed tube, 4-chloro 2-methyl thiol-trifluoromethyl benzene (2.0 g, 8.8 mmol), 4-(trifluoromethyl) aniline (1.56 g, 9.7 mmol), XPhos (0.30 g, 0.44 mmol) and Cs₂CO₃ (4.3 g, 13.2 mmol) were mixed in toluene (20 mL). The resulting mixture was purged with argon, added Pd(OAc)₂ (0.395 g, 1.76 mmol) and stirred at 110° C. for 12 h. After completion of the reaction, the reaction mixture was filtered through Celite® bed and concentrated under vacuum. The residue obtained was diluted with ethyl acetate (200 mL), washed with water, brine solution and dried over anhydrous Na₂SO₄ and concentrated. The crude product was further purified by silica gel chromatography using 0-5% of ethyl acetate/hexane to afford 0.9 g of the 3-(methylthio)-4-(trifluoromethyl)-N-(4-(trifluoromethyl)phenyl)aniline as a yellow solid (Yield: 29%).

LCMS: (Method B) 350 (M+H), RT. 3.91 min,

Step 2: To 3-(methylthio)-4-(trifluoromethyl)-N-(4-(trifluoromethyl)phenyl)aniline (0.9 g, 2.56 mmol) was added acetic acid (10 mL), Pd(OAc)₂ (0.575 g, 2.56 mmol) and Cu(OAc)₂ (1.02 g, 5.12 mmol) and heated to 120° C. for 18 h in sealed tube. After completion of the reaction, the reaction mixture was filtered through Celite® bed and concentrated under vacuum. The residue obtained was diluted with ethyl acetate (200 mL), washed with ammonia solution, water, brine solution and dried over anhydrous Na₂SO₄ and concentrated. The crude product was further purified by silica gel chromatography using ethyl acetate/petroleum ether to afford elution 1 as 4-(methylthio)-3,6-bis(trifluoromethyl)-9H-carbazole Int 15 (0.20 g, 22.3%) and 2-(methylthio)-3,6-bis(trifluoromethyl)-9H-carbazole Int 14 (0.13 g, 14.5%) as elution 2.

Int 15
LCMS: (Method B) 348 (M+H), RT. 3.90 min.
¹H NMR (400 MHz, CDCl₃): δ 9.26 (s, 1H), 8.65 (s, 1H), 7.76-7.84 (m, 2H), 7.51-7.58 (m, 2H), 2.48 (s, 3H).

Int 14
LCMS: (Method B) 348 (M+H), RT. 3.74 min.
¹H NMR (400 MHz, CDCl₃): δ 8.31-8.39 (m, 3H), 7.70 (d, J=8.40 Hz, 1H), 7.52 (d, J=8.80 Hz, 1H), 7.42 (s, 1H), 2.61 (s, 3H).

Example 13

Synthesis of: (3R,4R)-4-[2-methylsulfonyl-3, 6-bis(trifluoromethyl)carbazol-9-yl]azepan-3-ol, (3S,4S)-4-[2-methylsulfonyl-3, 6-bis(trifluoromethyl)carbazol-9-yl]azepan-3-ol (compound 7)

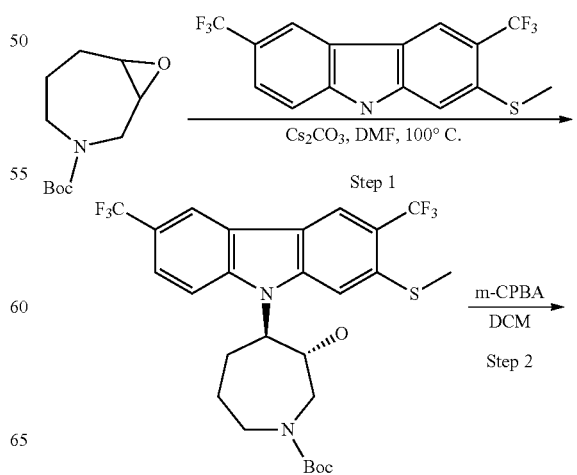

-continued

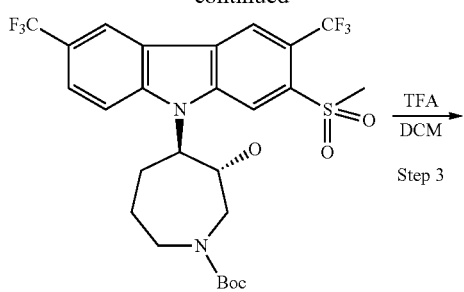

Step 3 TFA/DCM

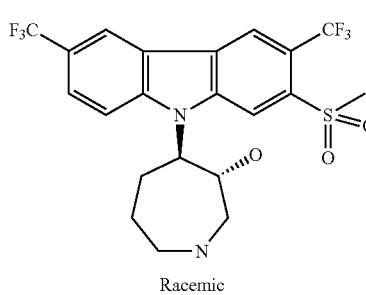

Racemic

Step 1: To a stirred solution of 2-(methylthio)-3,6-bis(trifluoromethyl)-9H-carbazole Int 14 (0.1 g, 0.29 mmol) in dry N, N-dimethyl formamide (1 mL) was added cesium carbonate (0.139 g, 0.429 mmol) under $N_2$ atmosphere and the reaction mixture was stirred at 100° C. for 1 h. After 1 h, Int 1 (0.057 g, 0.27 mmol) was added to the reaction mixture and the stirring continued at 100° C. for 48 h. After completion, the reaction mass was diluted with water, extracted over ethyl acetate, washed with water, brine solution and dried over anhydrous $Na_2SO_4$. The organic phase was concentrated and the regio isomers were purified by the flash column chromatography (230-400 size mesh) as elution 1 (non polar) was regio isomer 1 (0.030 g, 19.1%)

LCMS: (Method B) 563 (M+H), RT. 3.93 min,

Step 2: 3-chloroperoxybenzoic acid (0.018 g, 0.109 mmol) was added to a solution of boc intermediate (0.030 g, 0.054 mmol) in dichloromethane (1 mL) at 0° C. The mixture was stirred at room temperature overnight. After the completion of reaction, the reaction mass was washed with saturated solution of $Na_2CO_3$, water and brine solution. The organic layer was separated, dried ($Na_2SO_4$), filtered and the solvent evaporated in vacuo. Crude product was further purified by silica gel chromatography using 46% of ethyl acetate/hexane to afford 0.30 g as white solid (Yield: 53%).

LCMS: (Method B) 615 (M+H), RT. 3.69 min,

Step 3: Deprotection was done in HCl-dioxane. Crude was then purified by reverse phase prep to obtain compound 7 (0.010 g, 40.3%)

LCMS: (Method B) 481 (M+H), RT. 2.45 min,

HPLC: (Method A) RT 11.67 min, $^1$H NMR (400 MHz, DMSO-d6): b 9.13-9.22 (m, 4H), 8.65 (s, 1H), 8.31 (d, J=9.20 Hz, 1H), 7.95 (d, J=8.00 Hz, 1H), 5.66 (s, 1H), 5.08-5.10 (m, 1H), 4.60-4.80 (m, 1H), 3.62 (s, 3H), 3.50-3.52 (m, 1H), 3.02-3.10 (m, 1H), 2.80-2.90 (m, 1H), 2.15-2.18 (m, 1H).

Example 14

Synthesis of (3R,4R)-4-[4-methylsulfonyl-3, 6-bis(trifluoromethyl)carbazol-9-yl]azepan-3-ol, (3S,4S)-4-(4-(methylsulfonyl)-3,6-bis(trifluoromethyl)-9H-carbazol-9-yl)azepan-3-ol, (compound 6)

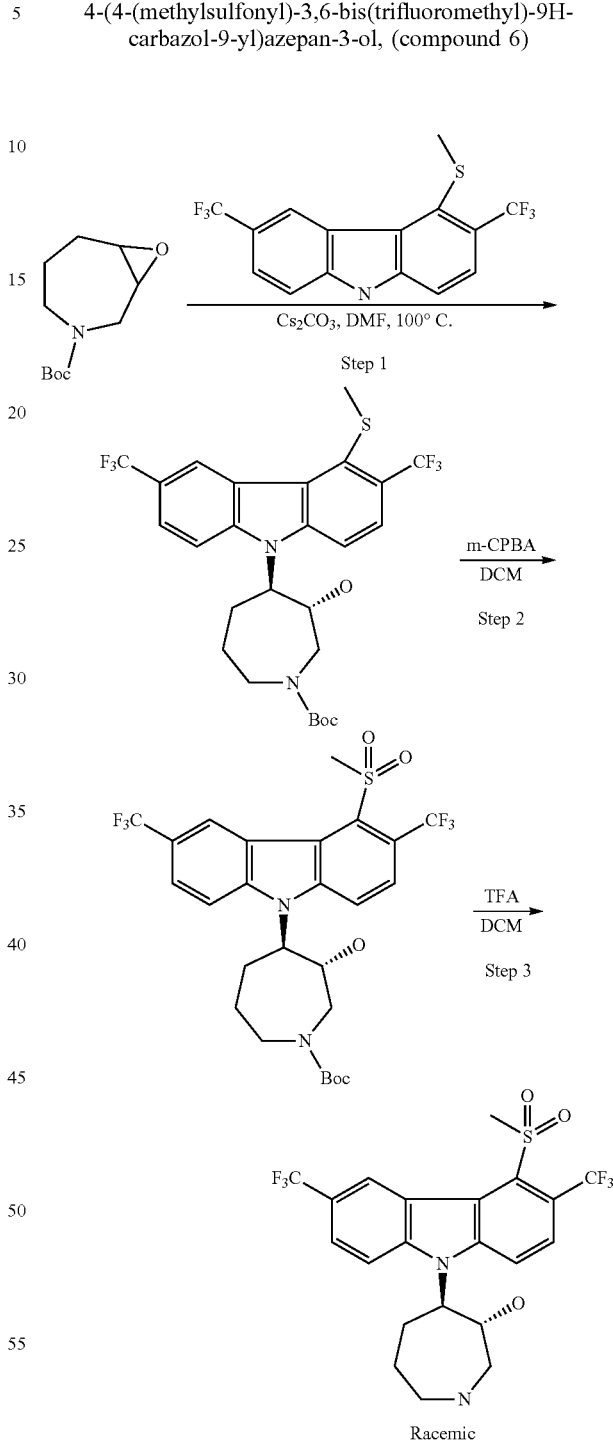

Step 1: To a stirred solution of 2-(methylthio)-3,6-bis(trifluoromethyl)-9H-carbazole Int 15 (0.1 g, 0.29 mmol) in dry N, N-dimethyl formamide (1 mL) was added cesium carbonate (0.139 g, 0.429 mmol) under $N_2$ atmosphere and the reaction mixture was stirred at 100° C. for 1 h. After. 1 h, Int 1 (0.057 g, 0.28 mmol) was added to the reaction mixture and the stirring continued at 100° C. for 48 h. After completion, the reaction mass was diluted with water, extracted over ethyl acetate, washed with water, brine solution and dried over anhydrous Na$_2$SO$_4$. The organic phase was concentrated and the regio isomers were purified by the flash column chromatography (230-400 size mesh) as elution 1 (non polar) was regio isomer 1 (0.030 g, 19.1%)

LCMS: (Method B) 563 (M+H), RT. 3.93 min,

Step 2: 3-chloroperoxybenzoic acid (0.018 g, 0.109 mmol) was added to a solution of boc intermediate (0.030 g, 0.054 mmol) in dichloromethane (1 mL) at 0° C. The mixture was stirred at room temperature overnight. After the completion of reaction, the reaction mass was washed with saturated solution of Na$_2$CO$_3$, water and brine solution. The organic layer was separated, dried (Na$_2$SO$_4$), filtered and the solvent evaporated in vacuo. Crude product was further purified by silica gel chromatography using 46% of ethyl acetate/hexane to afford 0.30 g as white solid (Yield: 53%).

LCMS: (Method B) 615 (M+H), RT. 3.69 min,

Step 3: Deprotection was done in HCl-dioxane. Crude was then purified by reverse phase prep to obtain compound 6

LCMS: (Method B) 481 (M+H), RT. 2.45 min,

HPLC: (Method A) RT 11.67 min, $^1$H NMR (400 MHz, DMSO-d6): δ 9.13-9.22 (m, 4H), 8.65 (s, 1H), 8.31 (d, J=9.20 Hz, 1H), 7.95 (d, J=8.00 Hz, 1H), 5.66 (s, 1H), 5.08-5.10 (m, 1H), 4.60-4.80 (m, 1H), 3.62 (s, 3H), 3.50-3.52 (m, 1H), 3.02-3.10 (m, 1H), 2.80-2.90 (m, 1H), 2.15-2.18 (m, 1H).

Example 15

Synthesis of 3, 7-dichloro-10-((3R,4R)-3-hydroxyazepan-4-yl)-10H-phenothiazine 5,5-dioxide, 3, 7-dichloro-10-((3S,4S)-3-hydroxyazepan-4-yl)-10H-phenothiazine 5,5-dioxide, (compound 1)

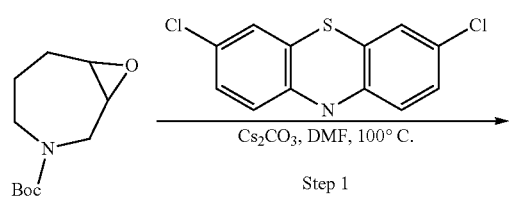

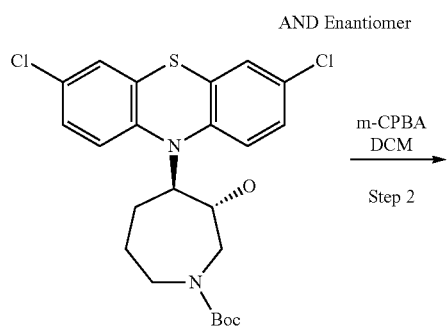

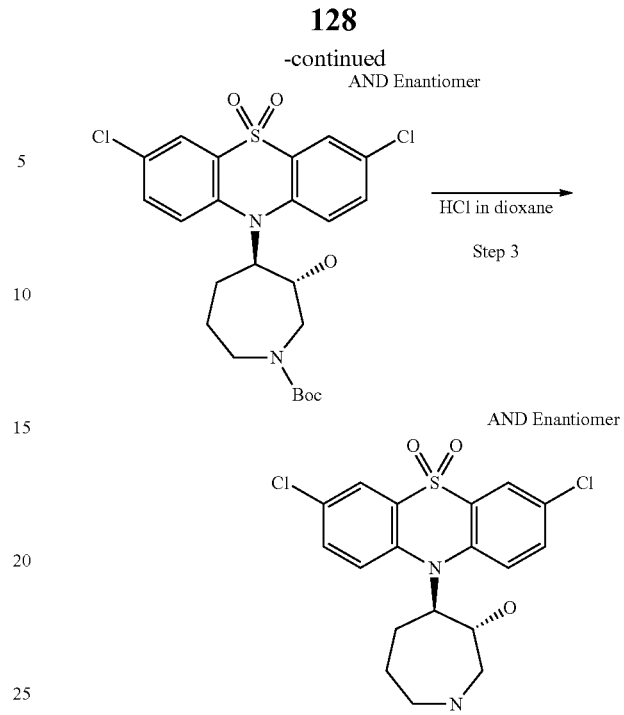

Step 1: To a solution of 3,7-dichloro-10H-phenothiazine int 4 (1.0 g, 3.7 mmol) in dry N,N-dimethyl formamide (2 mL) was added cesium carbonate (2.4 g, 7.4 mmol) under N$_2$ atmosphere and the reaction mixture stirred at 80° C. for 1 h. After 1 h, int 1 (1.18 g, 5.5 mmol) was added to the reaction mixture and allowed to stir at 100° C. for 5 days. After completion of the reaction, the reaction mass was diluted with water, extracted over ethyl acetate, washed with water, brine solution and dried over anhydrous Na$_2$SO$_4$. Organic phase was concentrated and the regio isomers purified by the flash column chromatography (230-400 size mesh) as elution 1 (non polar) was regio isomer 1 and elution 2 was the regio isomer 2 (only traces observed).

Yield: (Elution 1) (Regio isomer 1) 0.15 g, 8.8%

HPLC: (Method F) RT 7.08 min,

Step 2: m-chloroperoxybenzoic acid (0.134 g, 0.7 mmol) was added to a solution of tert-butyl-4-(3,7-dichloro-10H-phenothiazin-10-yl)-3-hydroxyazepane-1-carboxylate (0.15 g, 0.3 mmol) in dichloromethane (2 mL) at 0° C. The mixture was stirred at room temperature overnight the mixture basified with a saturated solution of Na$_2$CO$_3$. The organic layer was separated, dried (Na$_2$SO$_4$), filtered and the solvent evaporated in vacuo. Crude product was further purified by silica gel chromatography using 25-30% of ethyl acetate/hexane to afford 0.057 g of the product as colorless solid.

Compound I (Racemic): 0.057 g, 38%.

HPLC: (Method B) RT 11.37 min,

Step 3: Same protocol was followed for all compounds which involved de-protection of the boc group.

Compound 1 (Racemic): 0.035 g, 77.7%

LCMS: (Method B) 415 (M+H), RT. 2.35 min,

HPLC: (Method A) RT 11.03 min, $^1$H NMR 400 MHz, DMSO-d6: δ 7.96 (d, J=1.60 Hz, 2H), 7.77 (s, 4H), 5.84 (s, 1H), 4.65 (s, 1H), 4.45 (t, J=9.80 Hz, 1H), 3.47-3.50 (m, 1H), 3.26-3.40 (m, 3H), 3.03-3.05 (m, 1H), 2.02-2.06 (m, 3H).

Example 16

Synthesis of (3R,4R)-4-(3,6-dichlorocarbazol-9-yl)azepan-3-ol, (3S,4S)-4-(3, 6-dichloro-9H-carbazol-9-yl)azepan-3-ol (compound 2)

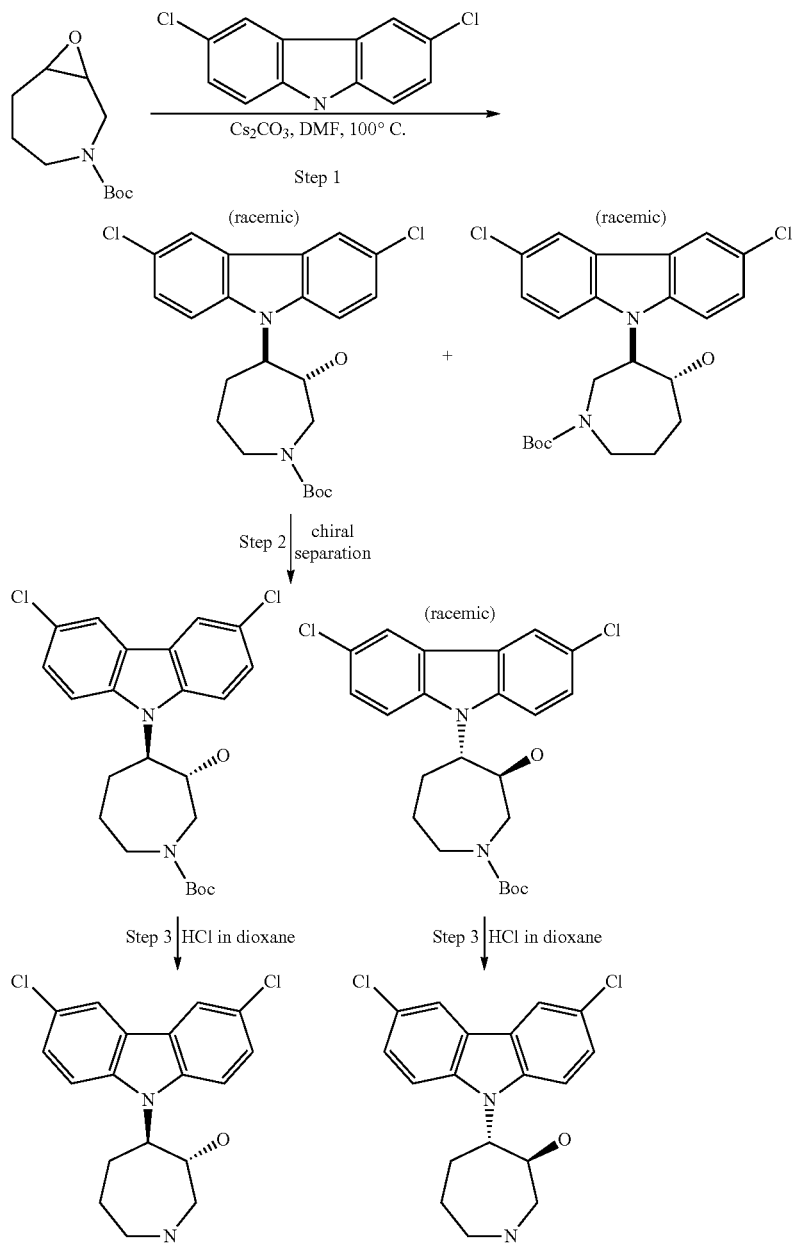

Step 1: To a stirred solution of 3,6-dichloro-9H-carbazole (int 6) (0.8 g, 3.3 mmol) in dry N, N-dimethyl formamide (5 mL), was added cesium carbonate (2.2 g, 6.7 mmol) under $N_2$ atmosphere and the reaction mixture was stirred at RT for 1 h. After 1 h, int 1 (0.56 g, 2.6 mmol) was added to the reaction mixture and allowed to stir at 100° C. for 18 h. After completion of reaction, reaction mixture was diluted with ethyl acetate (100 mL), washed with water, brine solution and dried over anhydrous $Na_2SO_4$. Organic phase was concentrated and the regio-isomers were purified by the flash column chromatography (230-400 size mesh) as elution 1 (non polar) was regio isomer 1 (0.25 g, 12.3%) and elution 2 was the regio isomer 2 (0.15 g, 7.4%).

LCMS: (Method A) 350.0 (M+H), RT. 3.7 min,

HPLC: (Method C) RT 16.8 min,

Step 2:

The regio isomer 1 was submitted for chiral preparative purification using Method H and obtained 0.09 g of isomer 1 and 0.075 g of isomer 2. After de-protection of the respective individual isomers using HCl in dioxane, isomer 1 and isomer 2 were obtained.

Isomer 1:
HPLC: (Method B) RT 16.8 min, 99.1% (Max)
CHIRAL HPLC: (Method J)—RT 9.58 min,
Isomer 2:
HPLC: (Method B) RT 16.8 min, 97.2% (Max)
CHIRAL HPLC: (Method J)—RT 14.65 min
Isomer 1: (0.06 g, 86%)
LCMS: (Method B) 350 (M+H), RT. 2.7 min,
HPLC: (Method B) RT 12.1 min,
$^1$H NMR (400 MHz, DMSO-d6): δ 9.43 (s, 2H), 8.33 (s, 2H), 7.93 (s, 1H), 7.73 (s, 1H), 7.46 (s, 2H), 5.46 (d, J=5.60 Hz, 1H), 4.76 (t, J=9.6 Hz, 1H), 4.59 (s, 1H), 3.24-3.48 (m, 3H), 3.08-3.20 (m, 1H), 2.61-2.70 (m, 1H), 2.04-2.21 (m, 2H), 1.83-1.85 (m, 1H).

Isomer 2: (0.05 g, 86.2%)
LCMS: (Method B) 350 (M+H), RT. 2.7 min,
HPLC: (Method B) RT 12.1 min,
$^1$H NMR (400 MHz, DMSO-d6): δ 9.39 (s, 2H), 8.33 (s, 2H), 7.97 (s, 1H), 7.72 (s, 1H), 7.47 (s, 2H), 5.47 (d, J=5.60 Hz, 1H), 4.75 (t, J=9.4 Hz, 1H), 4.57-4.59 (m, 1H), 3.40-3.44 (m, 1H), 3.24-3.32 (m, 2H), 3.09-3.12 (m, 1H), 2.63-2.66 (m, 1H), 2.04-2.15 (m, 2H), 1.83-1.86 (m, 1H).

Example 17

Synthesis of (3R,4R)-4-[3,6-bis(trifluoromethyl)carbazol-9-yl]azepan-3-ol, (3S,4S)-4-[3, 6-bis(trifluoromethyl)carbazol-9-yl]azepan-3-ol, (compound 3)

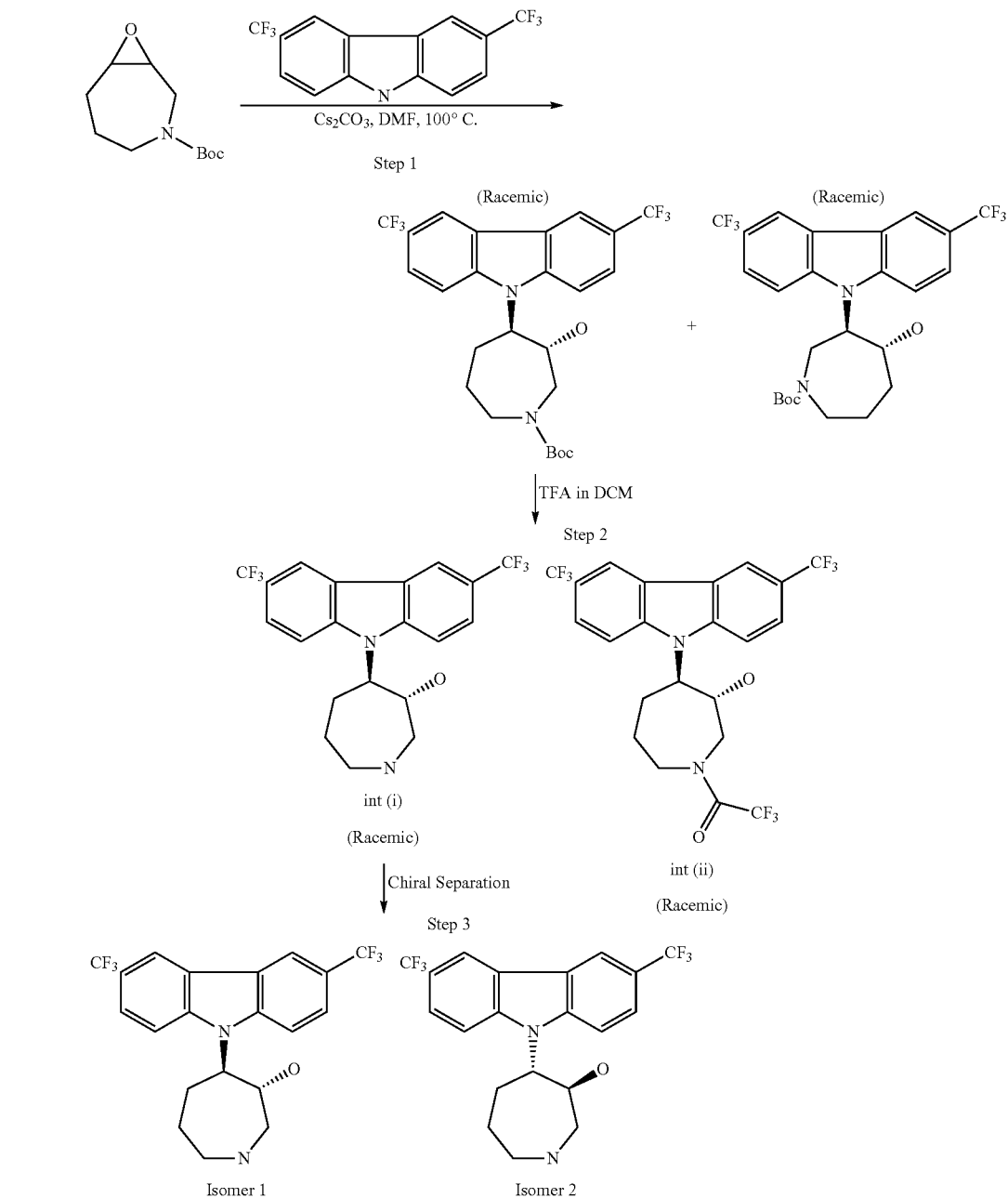

Step 1: To a stirred solution of 3,6-ditrifluoromethyl-9H-carbazole int 8 (2.0 g, 6.5 mmol) in dry N, N-dimethyl formamide (4 mL), was added cesium carbonate (3.17 g, 9.75 mmol) under $N_2$ atmosphere and the reaction mixture was stirred at RT for 1 h. After 1 h, int 1 (1.8 g, 8.5 mmol) was added to the reaction mixture and allowed to stir at 100° C. for 7 days. After completion, the reaction mass was diluted with water, extracted over ethyl acetate, washed with water, brine solution and dried over anhydrous $Na_2SO_4$. Organic phase was concentrated and the regio isomers were purified by the flash column chromatography (230-400 size mesh) as elution 1 (non polar) was regio isomer 1 (1.2 g, 35.2%)

LCMS: (Method B) 517.0 (M+H), RT.4.06 min,

Step 2: To a stirred solution of Boc protected intermediate (1.2 g, 2.4 mmol) in dichloromethane, trifluoroacetic acid (0.545 mL, 7.3 mmol) was added after cooling to 0° C. and stirred at room temperature overnight. After completion, the reaction mixture was washed with 10% sodiumbicarbonate solution, water, brine solution and dried over anhydrous $Na_2SO_4$. Organic phase was concentrated and purified by the flash column chromatography (230-400 size mesh) as elution 1 was int (ii) (0.3 g, 25.2%) and elution 2 was int (i) (0.62 g, 64.1%).

Int (i):

LCMS: (Method B) 417 (M+H), RT. 2.62 min,

HPLC: (Method B) RT 12.70 min, $^1$H NMR (400 MHz, DMSO-d6): δ 9.05 (s, 2H), 8.86-8.90 (m, 2H), 7.81-8.09 (m, 4H), 5.52 (d, J=5.2 Hz, 1H), 4.88 (t, J=9.40 Hz, 1H), 4.58-4.59 (m, 1H), 3.46-3.50 (m, 1H), 3.12-3.19 (m, 1H), 2.66-2.71 (m, 1H), 2.07-2.33 (m, 2H), 1.93-1.97 (m, 1H).

Int (ii):

UPLC: (Method A) 513 (M+H), RT. 1.93 min,

HPLC: (Method B) RT 15.62 min, $^1$H NMR (400 MHz, DMSO-d6): δ 8.86-8.88 (m, 2H), 7.75-8.08 (m, 4H), 5.34-5.35 (m, 1H), 4.76-4.80 (m, 1H), 4.32-4.34 (m, 1H), 4.04-4.09 (m, 1H), 3.81-3.85 (m, 2H), 3.47-3.53 (m, 1H), 1.05 (s, 2H), 1.96-1.99 (m, 1H).

Isomer 1 & Isomer 2:

The regio isomer 1 int (i) was submitted for chiral preparative purification using Method K and obtained 0.070 g, of isomer 1 and 0.070 g, of isomer 2.

(Isomer 1): (0.070 g, 70%)

LCMS: (Method B) 317.0 (M+H), RT. 2.62 min

HPLC: (Method B) RT 12.95 min,

CHIRAL HPLC: (Method M)—RT 4.93 min, $^1$H NMR (400 MHz, DMSO-d6): δ 8.83-8.86 (m, 2H), 7.92-8.00 (m, 2H), 7.77 (s, 2H), 4.72-4.78 (m, 2H), 4.21-4.22 (m, 1H), 3.03-3.04 (m, 2H), 2.86-2.91 (m, 1H), 2.67-2.70 (m, 2H), 1.72-1.82 (m, 3H).

Isomer 2: (0.070 g, 70%)

LCMS: (Method B) 317.0 (M+H), RT. 2.63 min,

HPLC: (Method B) RT 12.69 min,

CHIRAL HPLC: (Method M)—RT 8.87 min, $^1$H NMR (400 MHz, DMSO-d6): δ 9.06 (s, 2H), 8.86-8.90 (m, 2H), 8.09 (s, 2H), 7.80-7.93 (m, 3H), 5.53 (d, J=7.20 Hz, 1H), 4.85-4.88 (m, 1H), 4.59 (s, 1H), 3.46-3.49 (m, 1H), 3.15 (s, 1H), 2.62-2.72 (m, 1H), 2.07 (s, 2H), 1.93-1.95 (m, 1H).

Example 18

Synthesis of (3R,4R)-4-[3,6-bis(trifluoromethyl) pyrido[2, 3-b]indol-9-yl]azepan-3-ol, (3S,4S)-4-[3, 6-bis(trifluoromethyl)pyrido[2,3-b]indol-9-yl]azepan-3-ol, (compound 14)

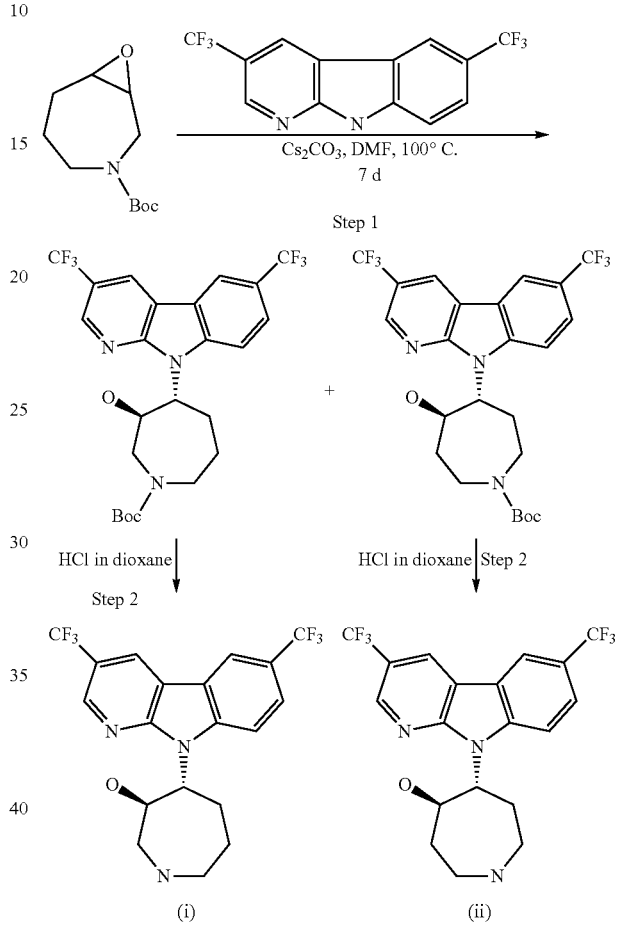

Step 1: To a solution of 3, 6-bis(trifluoromethyl)-9H-pyrido[2,3-b]indole int3 (0.3 g, 0.98 mmol) in dry N,N-dimethyl formamide (3 mL), was added cesium carbonate (0.481 g, 1.479 mmol) under $N_2$ atmosphere and the reaction mixture stirred at 100° C. for 1 h. After 1 h, int 1 (0.273 g, 1.28 mmol) was added to the reaction mixture and allowed to stir at 100° C. for 7 days. After completion of the reaction, the reaction mass was diluted with water, extracted over ethyl acetate, washed with water, brine solution and dried over anhydrous $Na_2SO_4$. Organic phase was concentrated and the regio isomers separated from crude by reverse phase preparative HPLC to get 0.2 g mixture of both regio isomers, which was then separated by normal phase preparative HPLC to isolate 0.14 g of regio isomer 1 and 0.04 g of regio isomer 2.

Yield: (Elution 1) (Regio isomer 1) 0.140 g, 27.4%

HPLC: (Method G) RT 6.84 min,

Yield: (Elution 2) (Regio-isomer 2) 0.040 g, 7.8%

HPLC: (Method G) RT 9.35 min,

Step 2: Same protocol was followed for all compounds which involved de-protection of the boc group.

Compound 14 (i) (Racemic): 0.030 g,
LCMS: (Method B) 418 (M+H), RT. 2.54 min,
HPLC: (Method B) RT 12.62 min,
$^1$H NMR (400 MHz, DMSO-d6): δ 9.28 (s, 3H), 8.89-8.92 (m, 2H), 8.21-8.23 (m, 1H), 7.92 (d, J=8.40 Hz, 1H), 5.52 (d, J=4.40 Hz, 1H), 5.18-5.21 (m, 1H), 4.80 (s, 1H), 3.56-3.64 (m, 1H), 3.46-3.49 (m, 1H), 3.32 (s, 1H), 3.15 (s, 1H), 2.66-2.71 (m, 1H), 1.97-2.07 (m, 3H).

Compound 14 (ii) (Racemic): 0.031 g, 95.09%
LCMS: (Method B) 336 (M+H), RT. 2.44 min,
HPLC: (Method B) RT 11.72 min,
$^1$H NMR (400 MHz, DMSO-d6): δ 9.40 (br s, 1H), 9.32 (d, J=1.92 Hz, 1H), 8.92 (d, J=6.52 Hz, 2H), 8.05-8.07 (m, 1H), 7.97-7.99 (m, 1H), 5.10 (d, J=4.92 Hz, 1H), 4.49 (s, 1H), 4.03-4.09 (m, 2H), 3.49-3.65 (m, 3H), 2.30-2.33 (m, 2H), 1.91 (s, 2H).

Example 19

Synthesis of (3S,4S)-4-(3, 6-dichloro-1-methoxy-9H-carbazol-9-yl)azepan-3-ol, (3R,4R)-4-(3, 6-dichloro-1-methoxy-9H-carbazol-9-yl)azepan-3-ol, (compound 8)

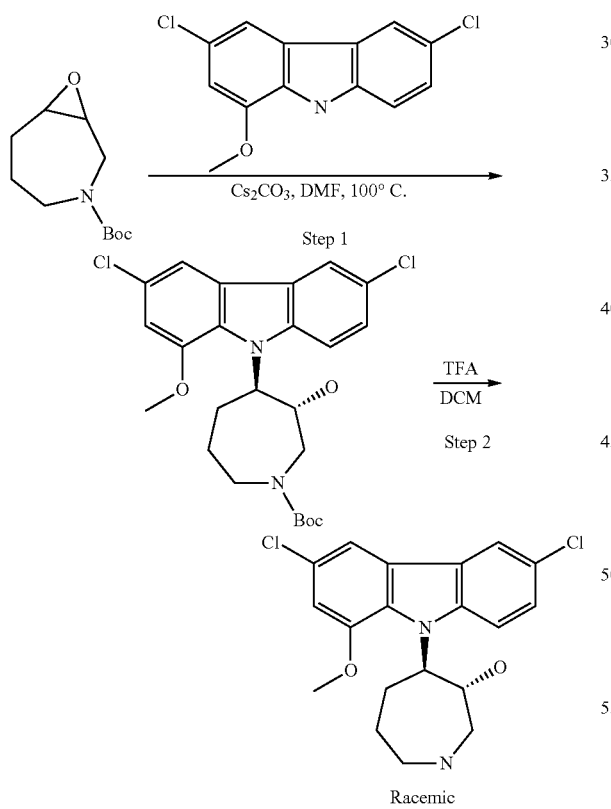

Racemic

Step 1: To a stirred solution of 3,6-dichloro-1-methoxy-9H-carbazole int 11 (0.5 g, 1.87 mmol) in dry N, N-dimethyl formamide (5 mL), was added cesium carbonate (0.917 g, 2.81 mmol) under N$_2$ atmosphere and the reaction mixture was stirred at RT for 1 h. After 1 h, Int 1 (0.48 g, 2.25 mmol) was added to the reaction mixture and allowed to stir at 100° C. for 7 days. After completion, the reaction mass was diluted with water, extracted over ethyl acetate, washed with water, brine solution and dried over anhydrous Na$_2$SO$_4$. Organic phase was concentrated and the regio isomers were purified by the flash column chromatography (230-400 size mesh) as elution 1 (non polar) was regio isomer 1 (0.06 g, 6.6%).
LCMS: (Method B) 379 (M+H), RT. 4.17 min,
Compound 8: (0.030 g, 63.2%)
LCMS: (Method B) 381 (M+H), RT. 2.52 min,
HPLC: (Method A) RT 12.31 min,
$^1$H NMR (400 MHz, DMSO-d6): δ 8.70-9.09 (m, 2H), 8.29-8.32 (m, 1H), 8.26 (d, J=2.00 Hz, 1H), 7.80-7.82 (m, 1H), 7.40-7.44 (m, 1H), 7.08-7.18 (m, 1H), 5.50-5.60 (m, 1H), 4.54-4.77 (m, 2H), 3.98 (s, 3H), 3.37-3.50 (m, 2H), 3.07-3.26 (m, 2H), 1.73-2.08 (m, 4H).

Example 20

Synthesis of (3R,4R)-4-(3, 6-dichloro-2-methoxy-carbazol-9-yl)azepan-3-ol, (3S,4S)-4-(3, 6-dichloro-2-methoxy-carbazol-9-yl)azepan-3-ol, (compound 9)

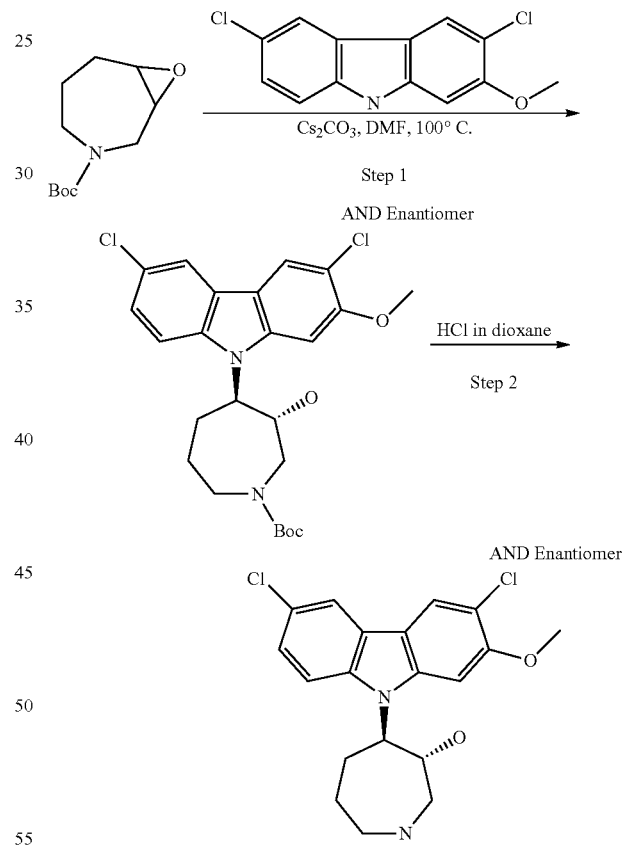

Step 1: To a solution of 3,6-dichloro-2-methoxy-9H-carbazole Int 12 (0.2 g, 0.6 mmol) in dry N,N-dimethyl formamide (1 mL), was added cesium carbonate (0.488 g, 1.5 mmol) under N2 atmosphere and the reaction mixture stirred at 80° C. for 1 h. After 1 h, tert-butyl 8-oxa-5-azabicyclo[5.1.0]octane-5-carboxylate (0.102 g, 0.4 mmol) was added to the reaction mixture and allowed to stir at 80° C. for 18 h. After completion of the reaction, the reaction mass was diluted with water, extracted over ethyl acetate, washed with water, brine solution and dried over anhydrous Na2SO$_4$. Organic phase was concentrated and the regio isomers purified by the flash column chromatography (230-

400 size mesh) as elution 1 (non polar) was regio isomer 1 and elution 2 was the regio isomer 2 (only traces observed).

Yield: (Elution 1) (Regio isomer 1) 0.07 g, 19.4%

LCMS: (Method B) 423 (M+H), RT.3.56 min,

Step 2: Same protocol was followed for all compounds which involved de-protection of the boc group.

Compound 9 (Racemic): 0.05 g, 90.9%

LCMS: (Method B) 379 (M+H), RT. 2.5 min,

HPLC: (Method B) RT 12.27 min, $^1$H NMR (400 MHz, DMSO-d6): δ 9.28 (s, 1H), 8.34-8.36 (m, 1H), 8.23-8.29 (m, 1H), 7.86-7.88 (m, 1H), 7.31-7.44 (m, 2H), 5.48 (d, J=8.40 Hz, 1H), 4.56-4.80 (m, 2H), 4.02 (s, 1H), 3.49-3.57 (m, 1H), 3.04-3.13 (m, 1H), 2.52-2.68 (m, 2H), 2.05-2.17 (m, 3H), 1.84-1.88 (m, 1H).

Example 21

Synthesis of (3S,4S)-4-(3, 6-dichloro-1-methoxy-9H-carbazol-9-yl)azepan-3-ol, (3R,4R)-4-(3, 6-dichloro-1-methoxy-9H-carbazol-9-yl)azepan-3-ol, (compound 8)

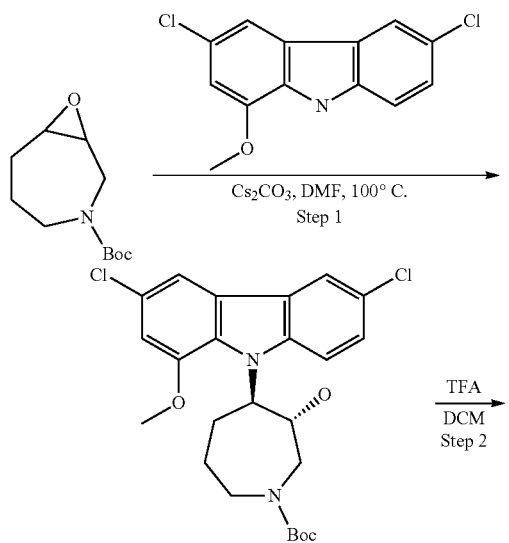

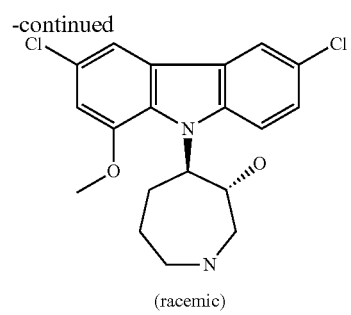

(racemic)

Step 1: To a stirred solution of 3,6-dichloro-1-methoxy-9H-carbazole int 11 (0.5 g, 1.87 mmol) in dry N, N-dimethyl formamide (5 mL), was added cesium carbonate (0.917 g, 2.81 mmol) under $N_2$ atmosphere and the reaction mixture was stirred at RT for 1 h. After 1 h, Int 1 (0.48 g, 2.25 mmol) was added to the reaction mixture and allowed to stir at 100° C. for 7 days. After completion, the reaction mass was diluted with water, extracted over ethyl acetate, washed with water, brine solution and dried over anhydrous $Na_2SO_4$. Organic phase was concentrated and the regio isomers were purified by the flash column chromatography (230-400 size mesh) as elution 1 (non polar) was regio isomer 1 (0.06 g, 6.6%).

LCMS: (Method B) 379 (M+H), RT. 4.17 min

Compound 8: (0.030 g)

LCMS: (Method B) 381 (M+H), RT. 2.52 min,

HPLC: (Method A) RT 12.31 min $^1$H NMR (400 MHz, DMSO-d6): δ 8.70-9.09 (m, 2H), 8.29-8.32 (m, 1H), 8.26 (d, J=2.00 Hz, 1H), 7.80-7.82 (m, 1H), 7.40-7.44 (m, 1H), 7.08-7.18 (m, 1H), 5.50-5.60 (m, 1H), 4.54-4.77 (m, 2H), 3.98 (s, 3H), 3.37-3.50 (m, 2H), 3.07-3.26 (m, 2H), 1.73-2.08 (m, 4H).

Example 22

Synthesis of (3R,4R)-4-(3, 7-dichloro-10H-phenoxazin-10-yl)azepan-3-ol, (3S,4S)-4-(3, 7-dichloro-10H-phenoxazin-10-yl)azepan-3-ol, (compound 10)

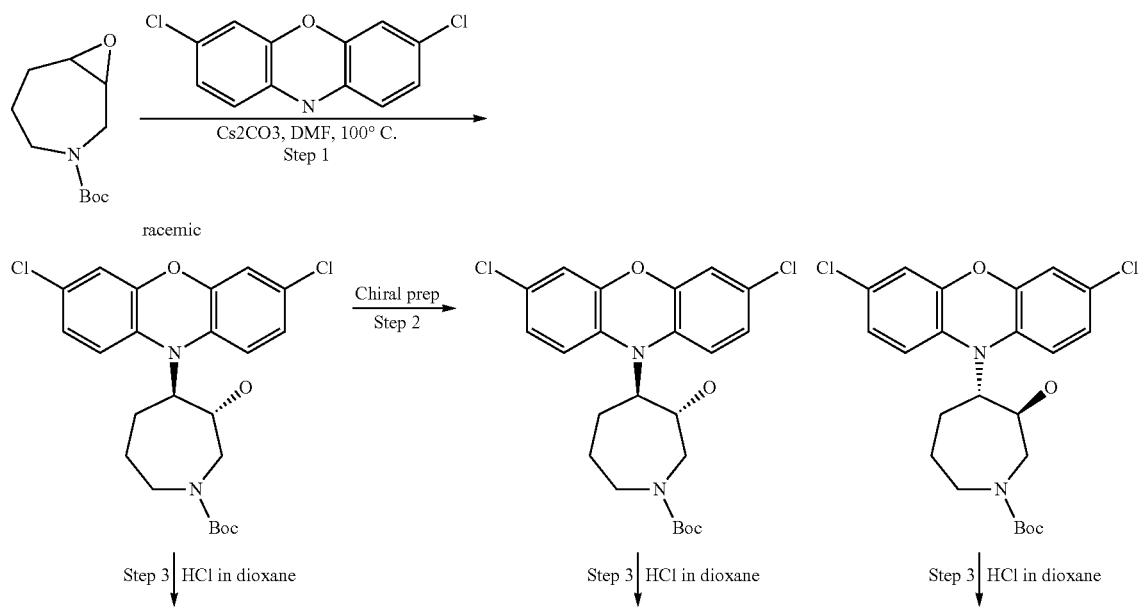

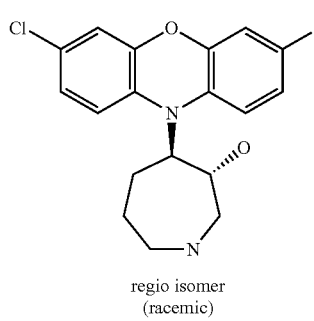

regio isomer
(racemic)

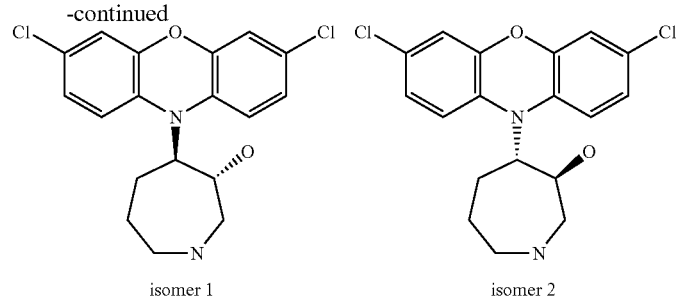

isomer 1　　　　　　isomer 2

Step 1: To a solution of 3,7-dichloro-10H-phenoxazine Int 9 (0.55 g, 2.18 mmol) in dry N,N-dimethyl formamide (3 mL), was added cesium carbonate (1.41 g, 4.3 mmol) under $N_2$ atmosphere and the reaction mixture stirred at 80° C. for 1 h. After 1 h, int 1 (0.371 g, 1.74 mmol) was added to the reaction mixture and allowed to stir at 80° C. for 18 h. After completion of the reaction, the reaction mass was diluted with water, extracted over ethyl acetate, washed with water, brine solution and dried over anhydrous $Na_2SO_4$. Organic phase was concentrated and the regio isomers purified by the flash column chromatography (230-400 size mesh) as elution 1 (non polar) was regio isomer 1 and elution 2 was the regio isomer 2.

Regio isomer 1 (Racemic) was de-protected using standard protocol and obtained as HCl salt (0.017 g, 89.4%).

LCMS: (Method B) 366 (M+H), RT. 2.47 min,

HPLC: (Method A) RT 11.37 min, $^1$H NMR (400 MHz, MeOD): δ 6.89 (s, 2H), 6.80-6.82 (m, 2H), 6.72-6.74 (m, 2H), 4.58 (s, 1H), 3.97-3.99 (m, 1H), 3.56-3.59 (m, 1H), 3.44-3.47 (m, 2H), 3.14 (t, J=12.60 Hz, 1H), 2.38-2.48 (m, 1H), 2.12-2.17 (m, 1H), 2.01-2.04 (m, 2H).

Yield: (Elution 1) (Regio isomer 1) 0.17 g, 17%.

HPLC: (Method C) RT 7.35 min,

Isomers 1, 2:

The regio-isomer-1 (0.17 g) was submitted for chiral SFC purification using Method K and obtained 0.035 g of isomer 1 and 0.030 g of isomer 2. After de-protection of the respective individual isomers, Isomer 1 and Isomer 2 obtained.

Isomer 1: 0.025 g, 92.5%

LCMS: (Method B) 366 (M+H), RT. 2.49 min,

HPLC: (Method B) RT 12.13 min, $^1$H NMR (400 MHz, DMSO-d6): δ 9.21 (s, 1H), 8.94 (s, 1H), 6.89 (s, 2H), 6.82-6.83 (m, 2H), 6.75-6.81 (m, 2H), 5.84 (d, J=4.80 Hz, 1H), 4.43-4.44 (m, 1H), 3.89 (t, J=9.5 Hz, 1H), 3.42-3.48 (m, 1H), 3.23-3.25 (m, 2H), 2.99-2.04 (m, 1H), 2.28-2.32 (m, 1H), 1.91-1.98 (m, 3H).

Isomer 2: 0.020 g, 86.9%

LCMS: (Method B) 366 (M+H), RT. 2.48 min,

HPLC: (Method B) RT 12.12 min, $^1$H NMR 400 MHz, DMSO-d6: δ 9.16 (s, 1H), 8.89 (s, 1H), 6.89 (s, 2H), 6.80-6.83 (m, 2H), 6.75-6.77 (m, 2H), 5.85 (d, J=4.80 Hz, 1H), 4.44 (d, J=4.40 Hz, 1H), 3.89 (t, J=9.40 Hz, 1H), 3.42-3.48 (m, 1H), 3.23-3.27 (m, 2H), 2.99-3.04 (m, 1H), 2.30-0.00 (m, 1H), 1.91-1.96 (m, 3H).

Example 23

Synthesis of (3R,4R)-4-[3,6-bis(trifluoromethyl) pyrido[3, 4-b]indol-9-yl]azepan-3-ol, (3S,4S)-4-[3, 6-bis(trifluoromethyl)pyrido[3, 4-b]indol-9-yl]azepan-3-ol, (compound 15)

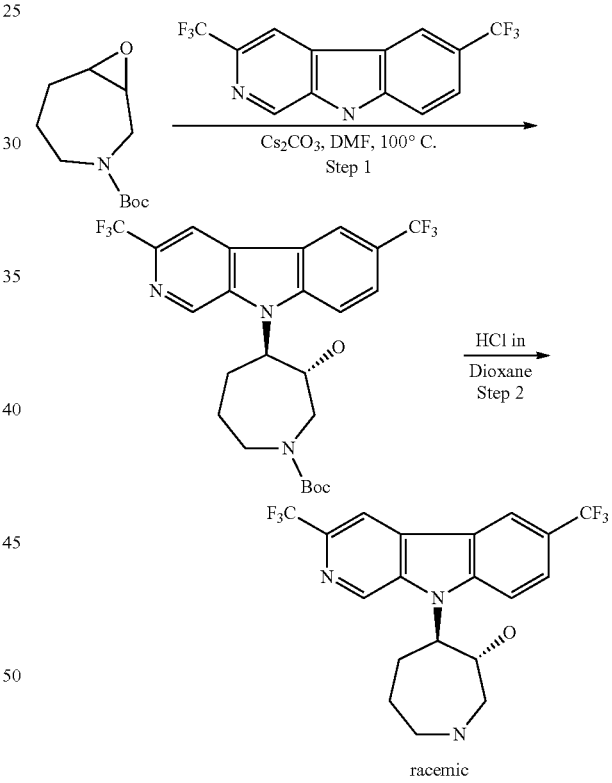

racemic

Step 1: To a stirred solution of 3,6-bis(trifluoromethyl)-9H-pyrido[3,4-b]indole (int 10) (0.20 g, 0.66 mmol) in dry N, N-dimethyl formamide (3 mL) was added cesium carbonate (0.321 g, 0.99 mmol) under $N_2$ atmosphere and the reaction mixture was stirred at 100° C. for 1 h. After 1 h, int 1 (0.141 g, 0.66 mmol) was added to the reaction mixture and the stirring continued at 100° C. for 48 h. After completion, the reaction mass was diluted with water, extracted over ethyl acetate, washed with water, brine solution and dried over anhydrous $Na_2SO_4$. The organic phase was concentrated and the regio isomers were purified by the flash column chromatography (230-400 size mesh) as elution 1 (non polar) was regio isomer 1 (0.02 g, 6%)
LCMS: (Method B) 404 (M+H), RT. 2.36 min,
Compound 15: (0.015 g, 93.6%)
LCMS: (Method B) 481 (M+H), RT. 2.45 min,
HPLC: (Method D) RT 9.93 min, 88.55% (Max)
$^1$H NMR (400 MHz, DMSO-d6): δ 9.46 (s, 1H), 9.34 (s, 1H), 8.79 (s, 1H), 8.59 (s, 1H), 8.41 (s, 1H), 8.22-8.28 (m, 1H), 7.91-8.06 (m, 2H), 5.36 (s, 1H), 5.12 (s, 1H), 4.60 (s, 1H), 3.81 (s, 1H), 3.57 (d, J=8.00 Hz, 1H), 3.35-3.44 (m, 2H), 2.20-2.23 (m, 1H), 1.94-1.96 (m, 1H).

Example 24

Synthesis of (3R,4R)-4-[2, 8-bis(trifluoromethyl)pyrido[3, 2-b]indol-5-yl]azepan-3-ol, (3S,4S)-4-[2, 8-bis(trifluoromethyl)pyrido[3, 2-b]indol-5-yl]azepan-3-ol, (compound 16)

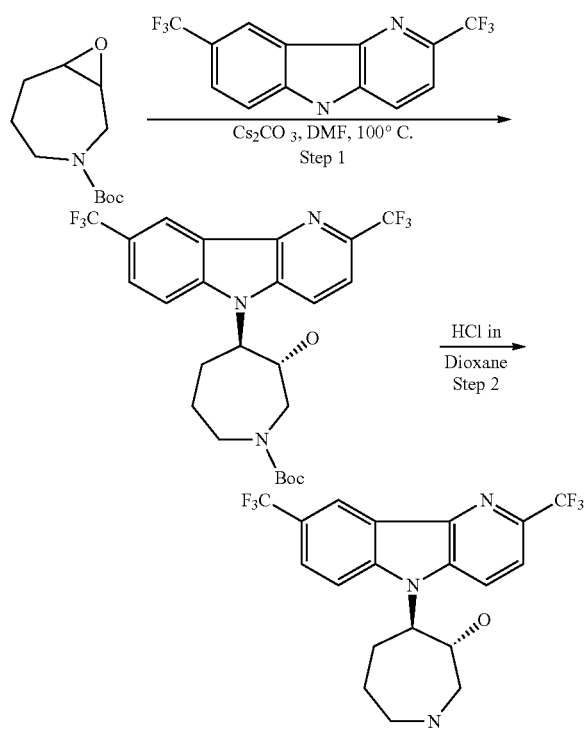

Example 25

Synthesis of 7-methoxy-2,8-bis(trifluromethyl)-5H-pyrido[3,2-b]indole (int 16)

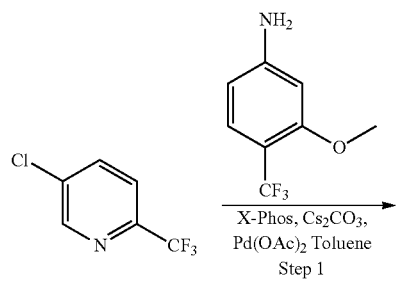

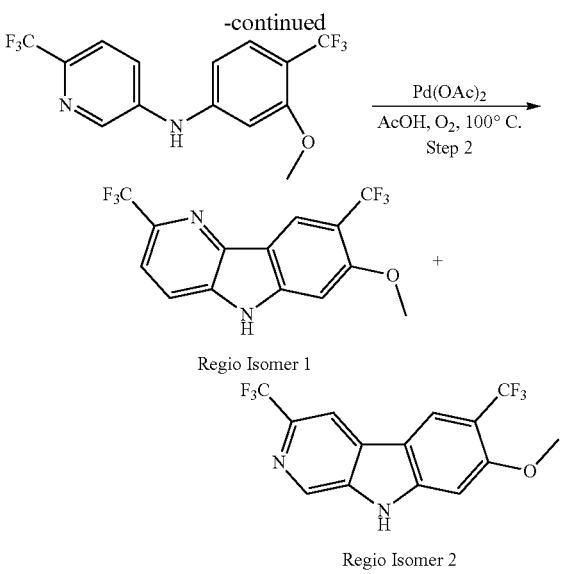

Step 1:
In a sealed tube 3-methoxy-4-trifluromethylaniline (5.0 g, 26 mmol), 5-chloro-2-trifluromethylpyridine (4.7 g, 26 mmol) and Cs$_2$CO$_3$ (10.97 g, 33.8 mmol) were mixed in toluene (100 mL) and the resulting mixture was purged with nitrogen, added Pd(OAc)$_2$ (0.88 g, 3.9 mmol) and X-phos (0.62 g, 1.3 mmol) and heated at 100° C. for 12 h. After completion of the reaction, the reaction mixture was filtered through Celite® bed and concentrated under vacuum. The residue obtained was diluted with ethyl acetate (250 mL), washed with water, brine solution and dried over anhydrous Na$_2$SO$_4$. The organic phase was concentrated and purified by the column chromatography (230-400 size mesh) to get the desired product N-(3-methoxy-4-(trifluoromethyl)phenyl-6-(trifluoromethyl)pyridine-3-amine (6.2 g, 71.2%).
LC MS: 335 (M–H), RT-3.5 min, 99.75% (max)
Method A—0.1% HCOOH; B—ACN Flow=1.5 mL/min.
Column-Atlantis dc18 (50×4.6 mm-5 μm) negative Mode
$^1$H NMR (300 MHz, DMSO-d6): δ 9.36 (s, 1H), 8.54 (d, J=3.66 Hz, 1H), 7.72-7.77 (m, 2H), 7.50 (d, J=8.52 Hz, 1H), 6.83-6.92 (m, 2H), 3.87 (s, 3H).
Step 2: N-(3-methoxy-4-(trifluoromethyl)phenyl-6-(trifluoromethyl)pyridine-3-amine (6.2 g, 18.4 mmol) and Pd(OAc)$_2$ (4.1 g, 18.4 mmol) was taken in acetic acid (70 mL) and heated to 100° C. for 12 h under an oxygen balloon. After completion of the reaction, the reaction mixture was filtered through Celite® bed and concentrated under vacuum. The residue obtained was diluted with ethyl acetate (250 mL), washed with NaHCO$_3$ solution, water, brine solution and dried over anhydrous Na$_2$SO$_4$ and concentrated. The crude product was first purified by silica gel chromatography using ethyl acetate/petroleum ether and further purified by preparative HPLC afford Regio isomer 1 as 7-methoxy-2,8-bis(trifluromethyl)-5H-pyrido[3,2-b]indole (0.46 g, 7.5%) and Regio isomer 2 as 7-methoxy-3,6-bis(trifluromethyl)-9H-pyrido[3,4-b]indole (0.25 g, 4%).
Regio isomer 1 (int 16):
LCMS: 335 (M+H), RT-3.39 min, 99.61% (Max), positive mode
Method A—0.1% HCOOH; B—ACN Flow=1.5 mL/min.
Column-ZORBAX XDB C18 (50×4.6 mm-5 μm) positive Mode
$^1$H NMR: (300 MHz, DMSO-d6): δ 12.14 (s, 1H), 8.39 (s, 1H), 8.12 (d, J=8.46 Hz, 1H), 7.86 (d, J=8.43 Hz, 1H), 7.36 (s, 1H), 4.06 (s, 3H).

Regio isomer 2 (int 17):
LCMS: 335.0 (M+H), RT-3.35 min, 99.09% (max)
Method A—0.1% HCOOH; B—ACN Flow=1.5 mL/min.
Column-ZORBAX XDB C18 (50×4.6 mm-5 µm) positive Mode
$^1$H NMR: (300 MHz, DMSO-d6): δ 12.29 (s, 1H), 9.01 (s, 1H), 8.82 (s, 2H), 7.35 (s, 1H), 4.02 (s, 3H).

Example 26

Synthesis of N-(4-chloro-2-methoxyphenyl)-6-(trifluoromethyl)pyridin-3-amine (int 18, int 19)

Step 1:
In a sealed tube 4-chloro-2-anisidine (3.0 g, 19.0 mmol), 5-chloro-2-trifluromethylpyridine (3.8 g, 20.9 mmol) and $Cs_2CO_3$ (8.02 g, 24.7 mmol) were mixed in toluene (50 mL). The resulting mixture was purged with nitrogen, added $Pd(OAc)_2$ (0.64 g, 2.8 mmol) and X-phos (0.45 g, 0.95 mmol) and heated at 140° C. for 12 h. After completion of the reaction, the reaction mixture was filtered through Celite® bed and concentrated under vacuum. The residue obtained was diluted with ethyl acetate (200 mL), washed with water, brine solution and dried over anhydrous $Na_2SO_4$. The organic phase was concentrated and purified by the column chromatography (230-400 size mesh) to get the desired product N-(4-chloro-2-methoxyphenyl)-6-(trifluoromethyl)pyridin-3-amine (3.5 g, 61.4%).
LC MS: 303.0 (M+H), RT-3.45 min, 96.03% (max)
Method A—0.1% HCOOH; B—ACN Flow=1.5 mL/min.
Column-ZORBAX XDB C18 (50×4.6 mm-5 µm) positive Mode
$^1$H NMR (300 MHz, DMSO-d6): δ 8.42 (s, 1H), 8.27 (d, J=2.58 Hz, 1H), 7.58 (d, J=8.7 Hz, 1H), 7.21-7.27 (m, 2H), 7.16 (d, J=2.16 Hz, 1H), 6.97 (dd, J=2.17, 9.80 Hz, 1H), 3.81 (s, 3H).
Step 2: N-(4-chloro-2-methoxyphenyl)-6-(trifluromethyl)pyridine-3-amine (3.5 g, 11.5 mmol) and $Pd(OAc)_2$ (2.6 g, 11.5 mmol) was taken in acetic acid (40 mL) and heated to 100° C. for 12 h under an oxygen balloon. After completion of the reaction, the reaction mixture was filtered through Celite® bed and concentrated under vacuum. The residue obtained was diluted with ethyl acetate (200 mL), washed with $NaHCO_3$ solution, water, brine solution and dried over anhydrous $Na_2SO_4$ and concentrated. The crude product was further purified by silica gel chromatography using ethyl acetate/petroleum ether to afford Regio isomer 1 as 8-chloro-6-methoxy-2-trifluromethyl-5H-pyrido[3,2-b]indole (0.8 g, 23%) and Regio isomer 2 as 6-chloro-8-methoxy-3-trifluromethyl-9H-pyrido[3,4-b]indole (0.7 g, 20%).
Regio isomer 1 (int 18)
LC MS: 301.0 (M+H), RT-3.43 min, 98.0% (max)
Method A—0.1% HCOOH; B—ACN Flow=1.5 mL/min.
Column-ZORBAX XDB C18 (50×4.6 mm-5 µm) positive Mode
$^1$H NMR: (300 MHz, DMSO-d6): δ 12.23 (s, 1H), 8.05 (d, J=8.4 Hz, 1H), 7.80-7.89 (m, 2H), 7.23 (s, 1H), 4.04 (s, 3H).
Regio isomer 2 (int 19):
LCMS: 301.0 (M+H), RT-3.45 min, 92.5% (Max), positive mode
Method A—0.1% HCOOH; B—ACN Flow=1.5 mL/min.
Column-ZORBAX XDB C18 (50×4.6 mm-5 µm) positive Mode $^1$H NMR: (300 MHz, DMSO-d6): δ 12.45 (s, 1H), 8.97 (s, 1H), 8.76 (s, 1H), 8.11 (s, 1H), 7.23 (s, 1H), 4.04 (s, 3H).

Example 27

Synthesis of 3,6-bis(trifluoromethyl)-9H-pyrrolo[2,3-b:5,4-c']di pyridine (Int B, int 20, int 21)

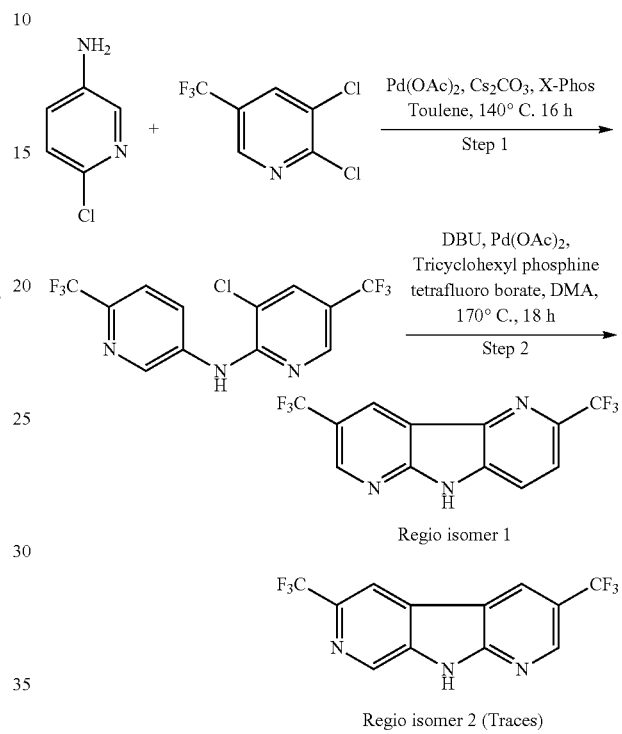

Step 1: In a sealed tube 2-chloropyridin-3-amine (4.0 g, 24.0 mmol), 2,3-dichloro-5-(trifluoromethyl)pyridine (7.99 g, 37 mmol), and $Cs_2CO_3$ (11.98 g, 37 mmol) were mixed in toluene (50 mL). The resulting mixture was purged with nitrogen, added $Pd(OAc)_2$ (0.55 g, 2.4 mmol) and X-Phos (0.58 g, 1.2 mmol) and heated at 140° C. for 12 h. After completion of the reaction, the reaction mixture was filtered through Celite® bed and concentrated under vacuum. The residue obtained was diluted with ethyl acetate (200 mL), washed with water, brine solution and dried over anhydrous $Na_2SO_4$. The organic phase was concentrated and purified by the column chromatography (60-120 size mesh) to get the yellow solid 3-chloro-5-(trifluoromethyl)-N-(6-(trifluoromethyl)pyridin-3-yl)pyridin-2-amine (1.2 g, 15.03%).
LCMS: 340 (M–H), RT. 3.64 min, 99.16% (max)
Method A—0.1% HCOOH; B—ACN; Flow: 1.2 mL/min.
Column-Atlantis dC18 (50×4.6 mm-5 µm) dual MODE.
$^1$H NMR (300 MHz, DMSO-d6): δ 9.55 (s, 1H), 9.07 (s, 1H), 8.53 (s, 1H), 8.35 (d, J=8.46 Hz, 8.33 (s, 1H), 7.87 (d, J=8.67 Hz, 1H).
Step 2: In a sealed tube, 3-chloro-5-(trifluoromethyl)-N-(6-(trifluoromethyl)pyridin-3-yl)pyridin-2-amine (1.4 g, 4.1 mmol) was added to DBU (1.24 g, 8.2 mmol), tricyclohexyl phosphine tetrafluoro borate (0.15 g, 0.4 mmol), $Pd(OAc)_2$ (0.046 g, 0.02 mmol), suspended in DMA (15 mL). The reaction mixture was purged for 15 minutes and stirred at 170° C. for 18 h. After completion of the reaction, the reaction mixture was filtered through Celite® bed and concentrated under vacuum. The residue obtained was diluted with ethyl acetate (200 mL), washed with water, brine solution and dried over anhydrous $Na_2SO_4$. The organic phase was concentrated and purified by preparative chromatography to get 3, 6-bis(trifluoromethyl)-9H-pyrrolo[2,3-b:5,4-c']di pyridine Int B (0.33 g, 26.4%).

LCMS: 306 (M+H), RT. 3.14 min, 99.61% (max)
Method A—0.1% HCOOH; B—ACN Flow=1.5 mL/min. Column-ZORBAX XDB C18 (50×4.6 mm-5 µm) positive Mode
$^1$H NMR (400 MHz, DMSO-d6): δ 13.2 (s, 1H), 9.39 (d, J=1.64, 1H), 9.13 (s, 1H), 9.05 (d, J=1.5 Hz, 1H), 8.98 (s, 1H).

Example 28

Synthesis of 3-chloro-6-nitro-9H-carbazole (int 22)

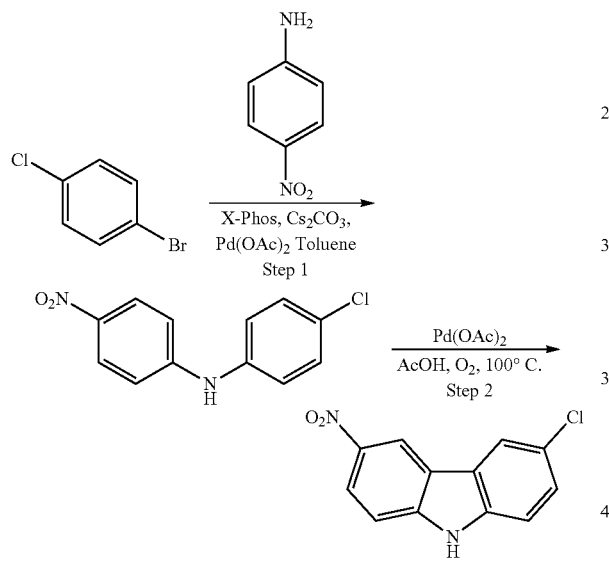

Step 1:
In a sealed tube 4-nitroaniline (1.0 g, 7.23 mmol), 4-bromo chlorobenzene (1.66 g, 8.68 mmol) and $Cs_2CO_3$ (3.05 g, 9.39 mmol) were mixed in toluene (10 mL). The resulting mixture was purged with nitrogen, added $Pd(OAc)_2$ (0.24 g, 0.1 mmol) and X-phos (0.17 g, 0.03 mmol) and heated at 100° C. for 12 h. After completion of the reaction, the reaction mixture was filtered through Celite® bed and concentrated under vacuum. The residue obtained was diluted with ethyl acetate (150 mL), washed with water, brine solution and dried over anhydrous $Na_2SO_4$. The organic phase was concentrated and purified by the column chromatography (230-400 size mesh) to get the desired product 4-chloro-N-4-nitrophenylaniline (1.2 g, 66.6%).

LC MS: 247 (M−H), RT-3.41 min, 98.3% (max)
Method A—0.1% HCOOH; B—ACN Flow=1.5 mL/min. Column-ZORBAX XDB C18 (50×4.6 mm-5 µm) negative Mode
$^1$H NMR (400 MHz, DMSO-d6): δ 9.36 (s, 1H), 8.10 (d, J=9.20 Hz, 2H), 7.41 (dd, J=2.00, 6.80 Hz, 2H), 7.25 (d, J=8.80 Hz, 2H), 7.07 (d, J=9.20 Hz, 2H).

Step 2: 4-Chloro-N-4-nitrophenylaniline (1.22 g, 4.9 mmol) and $Pd(OAc)_2$ (1.1 g, 4.9 mmol) was taken in acetic acid (12 mL) and heated to 100° C. for 12 h under an oxygen balloon. After completion of the reaction, the reaction mixture was filtered through Celite® bed and concentrated under vacuum. The residue obtained was diluted with ethyl acetate (100 mL), washed with $NaHCO_3$ solution, water, brine solution and dried over anhydrous $Na_2SO_4$ and concentrated. The crude product was first purified by silica gel chromatography using ethyl acetate/petroleum ether 3-chloro-6-nitro-9H-carbazole (0.39 g, 35.5%).

LC MS: 245 (M+H), RT-3.31 min, 99.62% (max)
Method A—0.1% HCOOH; B—ACN Flow=1.5 mL/min. Column-ZORBAX XDB C18 (50×4.6 mm-5 µm) negative Mode
$^1$H NMR: (400 MHz, DMSO-d6: δ 12.21 (s, 1H), 9.28 (s, 1H), 8.55 (s, 1H), 8.32 (dd, J=2.12, 9.02 Hz, 1H), 7.45-7.67 (m, 3H).

Example 29

Synthesis of (3R,4R)-4-(8-chloro-2-(trifluoromethyl)-5H-pyrimido[5,4-b]indol-5-yl)-7-methyl-azepan-3-ol (compound 28)

Synthesis of tert-Butyl 4-methyl 8-oxa-3-azabicyclo[5.1.0]octane-3-carboxylate (int 23)

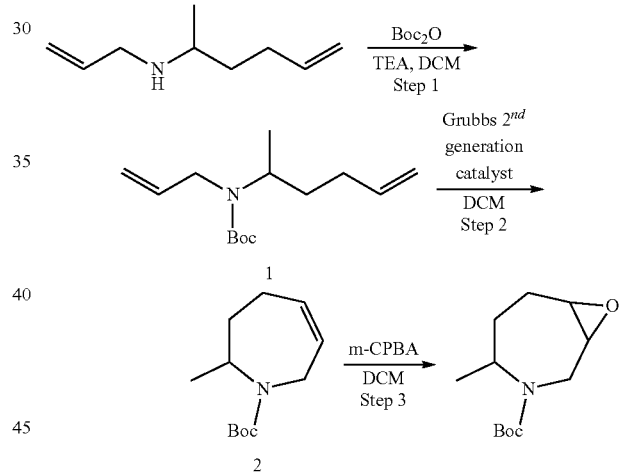

Step 1: To the ice cooled solution of N-allylhex-5-en-2-amine hydrochloride (2.0 g, 11.3 mmol) in THF (75 mL), DMAP (2.08 g, 17.1 mmol) and boc anhydride (2.95 g, 13.5 mmol) was added and stirred at RT overnight. The reaction mixture was partitioned between DCM and water, dried over $Na_2SO_4$ and concentrated. The crude product was first purified by silica gel chromatography using ethyl acetate/petroleum ether to afford 1 (1.7 g, 62.9%).

$^1$H NMR (400 MHz, DMSO-d6): δ 5.74-5.84 (m, 2H), 4.93-5.15 (m, 4H), 4.06 (s, 1H), 3.64-3.67 (m, 2H), 1.93-1.94 (m, 2H), 1.50-1.70 (m, 1H), 1.39 (s, 9H), 1.07 (s, 3H).

Step 2: To a solution of 1 (1.7 g, 7.1 mmol) in DCM (170 mL) Grubb's second generation catalyst (0.116 g, 0.142 mmol) was added (Before adding the catalyst reaction mixture should be degassed using $N_2$) and heated the reaction mixture at 40° C. for 1 h. Reaction mixture concentrated to remove toluene and the residue directly taken for column chromatography using ethyl acetate/petroleum to afford 2 (1.2 g, 80%).

$^1$H NMR (300 MHz, DMSO-d6): δ 5.62 (s, 2H), 3.98-4.23 (m, 2H), 3.53-3.59 (m, 1H), 2.28 (s, 1H), 1.96-2.06 (m, 1H), 1.79-1.91 (m, 1H), 1.50-1.69 (m, 1H), 1.40 (s, 9H), 1.06 (s, 3H).

Step 3: 3-Chloroperoxybenzoic acid (2.1 g, 8.1 mmol) was added to the ice cooled solution of 2 (1.2 g, 5.6 mmol) in DCM (20 mL) at 0° C. The mixture was stirred at room temperature overnight and then a 10% solution of Na$_2$S$_2$O$_3$ was added and the mixture basified with a saturated solution of Na$_2$CO$_3$. The organic layer was separated, dried (Na$_2$SO$_4$), filtered and the solvent evaporated in vacuo. Crude product was further purified by silica gel chromatography using EtOAc/Hex to afford tert-Butyl 4-methyl 8-oxa-3-azabicyclo[5.1.0]octane-3-carboxylate as colorless oil (0.48 g, 37.2%).

$^1$H NMR (300 MHz, DMSO-d6): δ 3.93-4.03 (m, 1H), 3.85-3.90 (m, 1H), 3.27 (d, J=3.87 Hz, 1H), 3.04 (s, 1H), 2.86-2.91 (m, 1H), 2.00-2.28 (m, 1H), 1.61-1.71 (m, 1H), 1.42 (s, 9H), 1.19-1.42 (m, 2H), 1.06 (s, 3H).

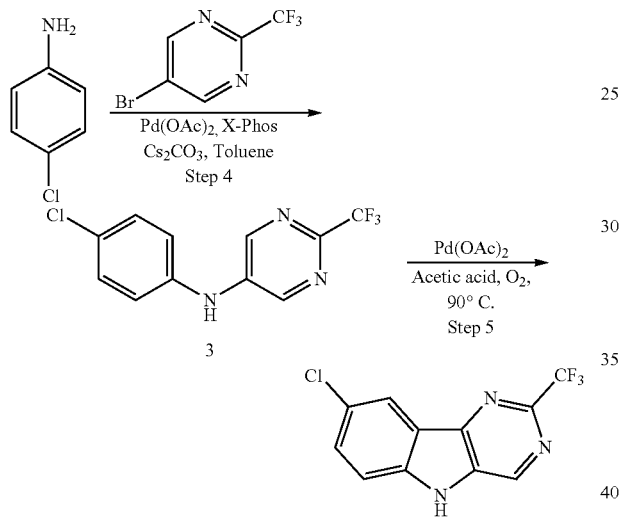

Step 4: In a sealed tube 4-chloroaniline (3.1 g, 24.3 mmol), 5-bromo-2-trifluromethylpyrimidine (5 g, 22 mmol) and Cs$_2$CO$_3$ (9.29 g, 28.6 mmol) were mixed in toluene (50 mL). The resulting mixture was purged with nitrogen, added Pd(OAc)$_2$ (0.74 g, 3.3 mmol) and X-phos (0.524 g, 1.1 mmol) and heated at 100° C. for 12 h. After completion of the reaction, the reaction mixture was filtered through Celite® bed and concentrated under vacuum. The residue obtained was diluted with ethyl acetate (200 mL), washed with water, brine solution and dried over anhydrous Na$_2$SO$_4$. The organic phase was concentrated and purified by the column chromatography (230-400 size mesh) to get the desired product N-(4-chlorophenyl)-2-(trifluoromethyl)pyrimidine-5-amine 3 (5.5 g, 91.6%).

LC MS: 272.0 (M−H), RT-3.23 min, 98.09% (max)
Method A—0.1% HCOOH; B—ACN Flow=1.5 mL/min
Column-ZORBAX XDB C18 (50×4.6 mm-5 µm) Dual Mode $^1$H NMR (400 MHz, DMSO-d6): δ 9.23 (s, 1H), 8.65 (s, 2H), 7.39 (d, J=1.92 Hz, 2H), 7.28 (d, J=1.84 Hz, 2H).

Step 5: N-(4-chlorophenyl)-2-(trifluoromethyl)pyrimidine-5-amine 3 (5.5 g, 20.1 mmol) and Pd(OAc)$_2$ (4.5 g, 20.1 mmol) was taken in acetic acid (50 mL) and heated to 100° C. for 12 h under an oxygen balloon. After completion of the reaction, the reaction mixture was filtered through Celite® bed and concentrated under vacuum. The residue obtained was diluted with ethyl acetate (200 mL), washed with NaHCO$_3$ solution, water, brine solution and dried over anhydrous Na$_2$SO$_4$ and concentrated. The crude product was further purified by silica gel chromatography using ethyl acetate/petroleum ether to afford as 8-chloro-2-triflurom-ethyl-5H-pyrimido[5,4-b]indole (2.0 g, 37.3%).

LC MS: 272 (M+H), RT-3.14 min, 94.16% (max)
Method A—0.1% HCOOH; B—ACN Flow=1.5 mL/min.
Column-ZORBAXXDB C18 (50×4.6 mm-5 µm) dual Mode $^1$H NMR (300 MHz, DMSO-d6): δ 12.51 (s, 1H), 9.34 (s, 1H), 8.39 (s, 1H), 7.81 (s, 2H).

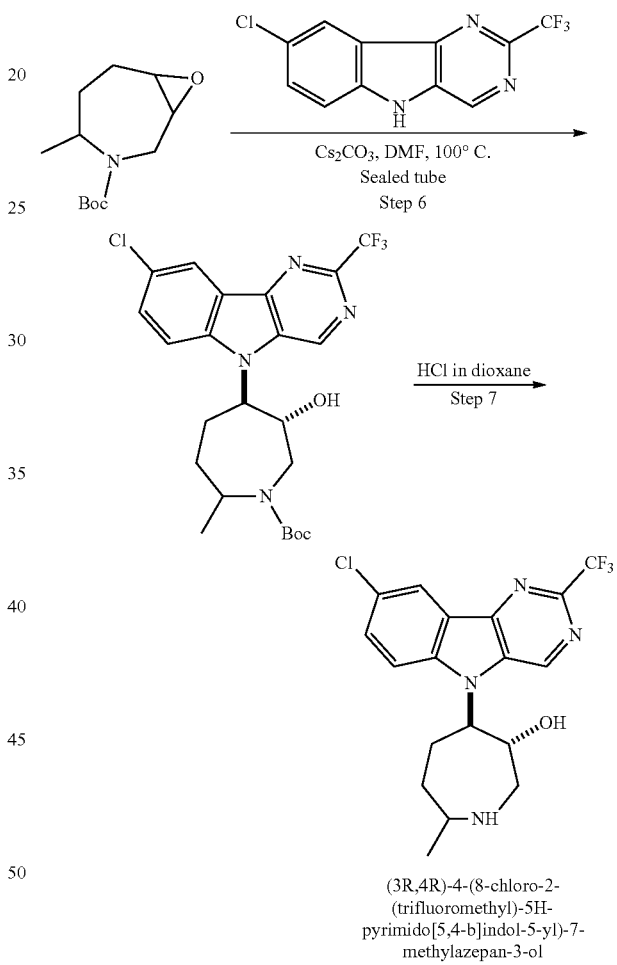

(3R,4R)-4-(8-chloro-2-(trifluoromethyl)-5H-pyrimido[5,4-b]indol-5-yl)-7-methylazepan-3-ol Step 6: To a stirred solution of 8-chloro-2-trifluromethyl-5H-pyrimido[5,4-b]indole (0.48 g, 1.7 mmol) in dry N,N-dimethyl formamide (3 mL), was added cesium carbonate (0.83 g, 2.6 mmol) under N$_2$ atmosphere and the reaction mixture was stirred at RT for 1 h. After 1 h, tert-Butyl 4-methyl 8-oxa-3-azabicyclo[5.1.0]octane-3-carboxylate (0.48 g, 2.1 mmol) was added to the reaction mixture and allowed to stir at 120° C. for 7 days. After completion of reaction, reaction mixture was diluted with ethyl acetate (100 mL), washed with water, brine solution and dried over anhydrous Na₂SO₄. Organic phase was concentrated and purified by preparative HPLC to obtain the boc intermediate (0.11 g, 12.5%).

LCMS: 499 (M+H), RT. 3.81 min, 97.99% (Max).
Method A—0.1% HCOOH; B—ACN Flow=1.5 mL/min.
Column-ZORBAX XDB C18 (50×4.6 mm-5 µm)
HPLC: RT 14.70 min, 95.94% (Max).
Method A: 10 mM NH4OAC in water; B: MeOH; Flow: 1.0 mL/min
COLUMN: Phenomenex Gemini-NX C18 (150×4.6 mm-3 µm)
¹H NMR (400 MHz, CD₃OD): δ 9.34-9.39 (m, 1H), 8.45-8.48 (m, 1H), 7.77-7.97 (m, 2H), 4.71-4.87 (m, 1H), 3.90-4.07 (m, 3H), 1.94-2.17 (m, 5H), 1.43 (s, 9H) 1.13 (s, 3H).

Step 7:

De-protection of the of the above boc intermediate using HCl in dioxane, (3R,4R)-4-(8-chloro-2-(trifluoromethyl)-5H-pyrimido[5,4-b]indol-5-yl)-7-methylazepan-3-ol (compound 28) was obtained. (0.013 g, 86.6%)

LCMS: 399 (M+H), RT. 2.22 min, 93.15% (Max).
Method A—0.1% HCOOH; B—ACN Flow=1.5 mL/min.
Column-ZORBAX XDB C18 (50×4.6 mm-5 µm)
HPLC: RT 10.275 min, 92.09% (Max).
Method A: 10 mM NH4OAC in water; B: MeOH; Flow: 1.0 mL/min
COLUMN: Phenomenex Gemini-NX C18 (150×4.6) mm-3µ
¹H NMR (400 MHz, CD₃OD): δ 9.38 (s, 1H), 8.49 (s, 1H), 7.82 (s, 2H), 5.19-5.24 (m, 1H), 4.57-4.58 (m, 1H), 4.36 (s, 1H), 3.56-3.69 (m, 2H), 2.37-2.42 (m, 1H), 2.12-2.16 (m, 3H), 1.50 (s, 3H).

Example 30

Synthesis of (3R,4R)-4-((8-chloro-5H-pyrimido[5,4-b]indol-4-yl)amino)azepan-3-ol (compound 25)

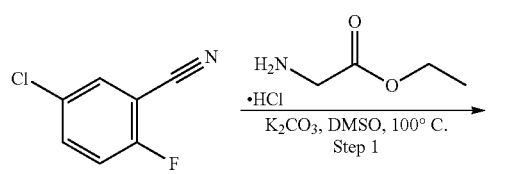

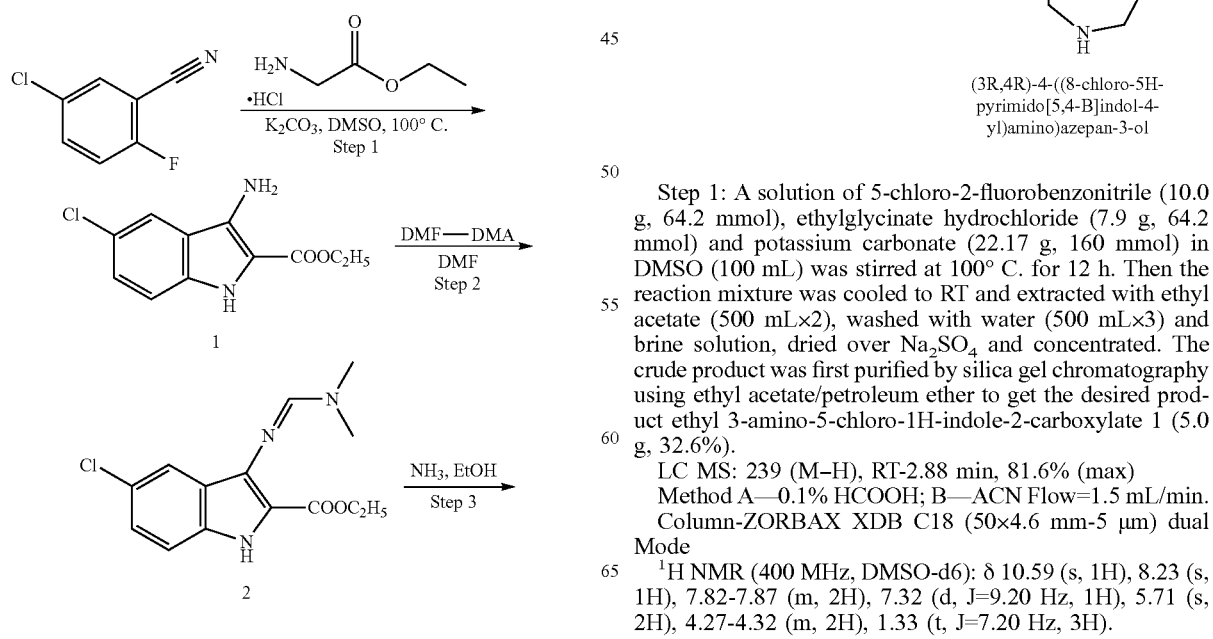

Step 1: A solution of 5-chloro-2-fluorobenzonitrile (10.0 g, 64.2 mmol), ethylglycinate hydrochloride (7.9 g, 64.2 mmol) and potassium carbonate (22.17 g, 160 mmol) in DMSO (100 mL) was stirred at 100° C. for 12 h. Then the reaction mixture was cooled to RT and extracted with ethyl acetate (500 mL×2), washed with water (500 mL×3) and brine solution, dried over Na₂SO₄ and concentrated. The crude product was first purified by silica gel chromatography using ethyl acetate/petroleum ether to get the desired product ethyl 3-amino-5-chloro-1H-indole-2-carboxylate 1 (5.0 g, 32.6%).

LC MS: 239 (M–H), RT-2.88 min, 81.6% (max)
Method A—0.1% HCOOH; B—ACN Flow=1.5 mL/min.
Column-ZORBAX XDB C18 (50×4.6 mm-5 µm) dual Mode
¹H NMR (400 MHz, DMSO-d6): δ 10.59 (s, 1H), 8.23 (s, 1H), 7.82-7.87 (m, 2H), 7.32 (d, J=9.20 Hz, 1H), 5.71 (s, 2H), 4.27-4.32 (m, 2H), 1.33 (t, J=7.20 Hz, 3H).

Step 2: To a solution of ethyl-3-amino-5-chloro-1H-indole-2-carboxylate 1 (5.0 g, 20.9 mmol) in DMF (10 mL) was added 10 mL of N,N-dimethyl formamide dimethyl acetal and stirred at 100° C. for 2 h. After the completion of the reaction, the reaction mixture was cooled to RT and concentrated under vacuum. The residue obtained was diluted with ethyl acetate (100 mL), washed with water, brine solution and dried over anhydrous $Na_2SO_4$ and concentrated. The crude product was purified by silica gel chromatography using ethyl acetate/petroleum ether to afford 2 (2.5 g, 40.6%).

$^1$H NMR (400 MHz, DMSO-d6): δ 7.78 (s, 1H), 7.49 (d, J=2.00 Hz, 1H), 7.31 (d, J=8.80 Hz, 1H), 7.19 (dd, J=2.2 & 8.4 Hz, 1H), 4.19-4.25 (m, 2H), 2.99 (s, 6H), 1.27 (t, J=7.20 Hz, 3H).

Step 3: To a solution of 2 (2.5 g, 8.5 mmol) in ethanol (20 mL) was added $NH_4OH$ solution (20 mL) and heated at 70° C. overnight. The volatiles were removed in vacuo, the solid obtained was filtered and washed with ethyl acetate/pet ether mixture and dried to obtain 3 (1.5 g, 83.3%).

LC MS: 218 (M–H), RT-2.23 min, 92.3% (max)
Method A—0.1% HCOOH; B—ACN Flow=1.5 mL/min.
Column-ZORBAX XDB C18 (50×4.6 mm-5 μm) negative Mode $^1$H NMR (300 MHz, DMSO-d6): δ 12.30 (s, 2H), 8.00 (d, J=9.96 Hz, 1H), 7.56 (d, J=8.73 Hz, 1H), 7.47 (d, J=6.75 Hz, 1H).

Step 4: 3 (1.5 g, 6.8 mmol) was placed in $POCl_3$ (15 mL) and triethyl amine hydrochloride was added and the mixture was heated to 100° C. overnight. The reaction was cooled to RT and the excess $POCl_3$ was evaporated under vacuum. The residue was dissolved in anhydrous DCM (50 mL) and added dropwise to a rapidly stirred solution of saturated aqueous sodium bicarbonate (50 mL) and DCM (50 mL) at 0° C. The mixture was stirred for 1 h, then the aqueous phase was extracted with DCM (3×0.50 mL). The organic phases were washed with saturated aqueous sodium bicarbonate (1×50 mL), water (1×50 mL), and brine (1×50 mL), then dried over $MgSO_4$, filtered, and concentrated to afford 4 (1.0 g, 62.5%).

LC MS: 239 (M+H), RT-2.88 min, 97.8% (max)
Method A—0.1% HCOOH; B—ACN Flow=1.5 mL/min.
Column-ZORBAXXDB C18 (50×4.6 mm-5 μm)

$^1$H NMR: (400 MHz, DMSO-d6): δ 12.59 (s, 1H), 8.90 (s, 1H), 8.29 (s, 1H), 7.71-7.77 (m, 2H),

Step 5: To a solution of 4 (0.1 g, 0.42 mmol) in isopropyl alcohol (2.0 mL), DIPEA (0.108 g, 0.8 mmol) and tert butyl (3R,4R)-4-amino-3-hydroxyazepeneas-1-carboxylate (0.116 g, 0.5 mmol) was added, the mixture was heated to 100° C. overnight. The reaction mixture was cooled to RT and concentrated under vacuum. The residue obtained was diluted with ethyl acetate (100 mL), washed with water, brine solution and dried over anhydrous $Na_2SO_4$ and concentrated. The crude product was purified by silica gel chromatography using ethyl acetate/petroleum ether to obtain 5 (0.03 g, 16.6%).

LC MS: 432.2 (M+H), RT-3.31 min, 99.62% (max)
Method A—0.1% HCOOH; B—ACN Flow=1.5 mL/min.
Column-ZORBAX XDB C18 (50×4.6 mm-5 μm)

$^1$H NMR (400 MHz, $CD_3OD$): b 8.40 (s, 1H), 8.15 (d, J=1.84 Hz, 1H), 7.58 (d, J=8.80 Hz, 1H), 7.51 (d, J=8.72 Hz, 1H), 4.16-4.18 (m, 1H), 3.75-3.77 (m, 1H), 3.50-3.71 (m, 3H), 3.12-3.22 (m, 1H), 2.17-2.20 (m, 1H), 1.91-1.95 (m, 3H), 1.48 (s, 9H).

Step 6: De-protection of the of the above boc intermediate using HCl in dioxane (3R,4R)-4-((8-chloro-5H-pyrimido[5,4-b]indol-4-yl)amino)azepan-3-ol was obtained (0.016 g, 84.2%).

LCMS: 332 (M+H), RT 1.759 min, 98.53% (Max).
Method A—0.1% TFA; B—ACN Flow=1.5 mL/min.
Column-ZORBAX XDB C18 (50×4.6 mm-5 μm) positive Mode
HPLC: RT 7.93 min, 97.7% (Max).
Method A: 0.1% TFA in water, B: ACN; Flow: 1.0 mL/min
COLUMN: Welchrom C18 (250×4.6 mm-5 μm)

$^1$H NMR (400 MHz, $CD_3OD$): δ 8.81 (s, 1H), 8.17 (d, J=2.02 Hz, 1H), 7.81 (d, J=8.92 Hz, 1H), 7.70 (dd, J=2.04, 8.96 Hz, 1H), 4.33-4.34 (m, 1H), 3.62-3.72 (m, 2H), 3.40-3.50 (m, 3H), 2.20-2.40 (m, 2H), 2.08-2.11 (m, 2H).

Example 31

Synthesis of 8-chloro-5-((3R,4R)-3-hydroxyazepan-4-yl)-3,5-dihydro-4H-pyrimido[5,4-b]indol-4-one (compound 30)

Step 1: To a stirred solution of 8-chloro-3,5-dihydro-4H-pyrimido[5,4-b]indole-4-one (0.5 g, 2.2 mmol) in dry DMF (3 mL), was added cesium carbonate (1.1 g, 3.4 mmol) under $N_2$ atmosphere and the reaction mixture was stirred at RT for 1 h. After 1 h, Int A1 (0.61 g, 2.8 mmol) was added to the reaction mixture and allowed to stir at 100° C. for 7 days. After completion of reaction, reaction mixture was diluted with ethyl acetate (100 mL), washed with water, brine solution and dried over anhydrous Na₂SO₄. Organic phase was concentrated and purified by preparative HPLC was isolated (0.06 g, 6.1%).

LCMS: 433 (M+H), RT. 2.94 min, 99.47% (Max).

Method A—0.1% HCOOH; B—ACN Flow=1.5 mL/min.

Column-ZORBAX XDB C18 (50×4.6 mm-5 μm)

HPLC: RT 5.63 min, 92.96% (Max).

Method A: 0.1% TFA in water, B: MeOH; Flow: 1.0 mL/min

COLUMN: Atlantis dC18 (50×4.6 mm-5 μm)

¹H NMR (400 MHz, CD₃OD): δ 8.22 (d, J=8.80 Hz, 1H), 8.07 (s, 1H), 7.56 (d, J=8.80 Hz, 1H), 7.45 (d, J=2.00 Hz, 1H), 4.33-4.38 (m, 1H), 3.92-3.98 (m, 1H), 3.64-3.65 (m, 2H), 3.36-3.37 (m, 1H), 3.11-3.17 (m, 2H), 2.02-2.12 (m, 1H), 1.94-1.96 (m, 2H), 1.50 (s, 9H).

Step 2:

De-protection of the of the above boc intermediate using HCl in dioxane, 8-chloro-5-((3R,4R)-3-hydroxyazepan-4-yl)-3,5-dihydro-4H-pyrimido[5,4-b]indol-4-one was obtained (0.012 g, 80%).

LCMS: 333 (M+H), RT. 1.92 min, 95.39% (Max).

Method A—0.1% HCOOH; B—ACN Flow=1.5 mL/min.

Column-ZORBAX XDB C18 (50×4.6 mm-5 μm) positive Mode

HPLC: RT 6.69 min, 94.68% (Max).

Method A: 10 mM NH₄OAC in water; B: MeOH; Flow: 1.0 mL/min

COLUMN: Phenomenex Gemini-NX C18 (150×4.6 mm-3 μm).

¹H NMR (400 MHz, CD₃OD): δ 8.70 (s, 1H), 8.10 (s, 1H), 7.62-7.62 (m, 1H), 7.54-7.54 (m, 1H), 4.62-4.63 (m, 2H), 3.70-3.72 (m, 1H), 3.49-3.49 (m, 2H), 3.15-3.32 (m, 1H), 2.60-2.70 (m, 1H), 2.15-2.30 (m, 2H), 2.00-2.10 (m, 1H).

Example 32

Synthesis of (3R,4R)-4-(8-chloro-4-methoxy-5H-pyrimido[5,4-b]indol-5-yl)azepan-3-ol compound 31)

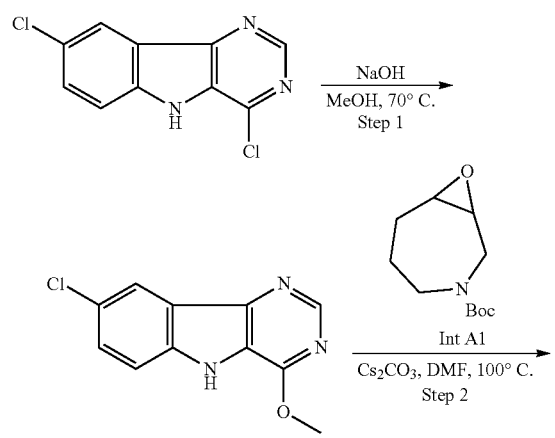

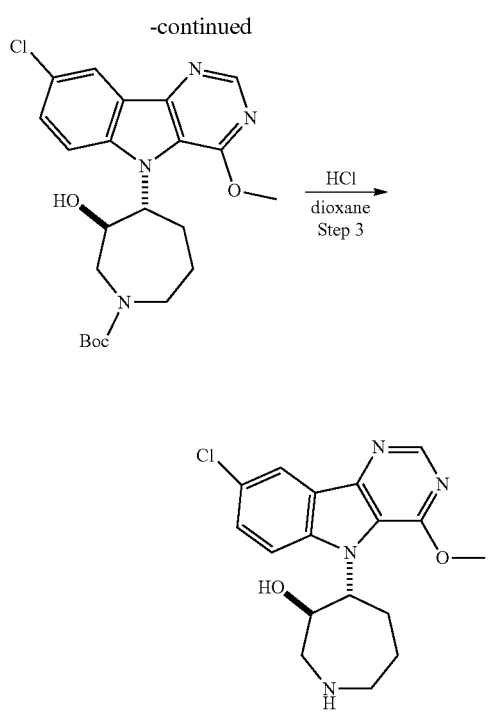

(3R,4R)-4-(8-chloro-4-methoxy-5H-pyrimido[5,4-b]indol-5-yl)azepan-3-ol

Step 1: To a stirred solution of 4,8-dichloro-5H-pyrimido[5,4-b]indole (0.30 g, 1.24 mmol) in methanol (10.0 mL), was added sodium hydroxide (0.074 g, 1.87 mmol) and the reaction mixture was stirred at 70° C. overnight. After completion, the reaction mixture was diluted with ethyl acetate (100 mL), washed with water, brine solution and dried over anhydrous Na₂SO₄.

Organic phase was concentrated to afford 8-chloro-4-methoxy-5H-pyrimido[5,4-b]indole (0.28 g, 96.5%).

LCMS: 234.0 (M+H), RT. 2.67 min, 98.54% (Max).

Method A—0.1% HCOOH; B—ACN Flow=1.5 mL/min.

Column-ZORBAX XDB C18 (50×4.6 mm-5 μm) positive Mode

¹H NMR (400 MHz, DMSO-d6): δ 8.56 (s, 1H), 8.10 (d, J=2.00 Hz, 1H), 7.60 (d, J=8.8 Hz, 1H), 7.51 (dd, J=2.0 & 8.8 Hz, 1H), 4.13 (s, 3H).

Step 2: To a stirred solution of 8-chloro-4-methoxy-5H-pyrimido[5,4-b]indole (0.28 g, 1.20 mmol) in dry N, N-dimethyl formamide (3.0 mL), was added cesium carbonate (0.59 g, 1.80 mmol) under N₂ atmosphere and the reaction mixture was stirred at RT for 1 h. After 1 h, Int A1 (0.384 g, 1.80 mmol) was added to the reaction mixture and allowed to stir at 100° C. for 7 days. After completion of reaction, reaction mixture was diluted with ethyl acetate (100 mL), washed with water, brine solution and dried over anhydrous Na₂SO₄. Organic phase was concentrated and purified by preparative HPLC to afford 0.020 g (3.72%) of the desired product.

LCMS: 447.0 (M+H), RT. 3.26 min, 95.54% (Max).

Method A—0.1% HCOOH; B—ACN Flow=1.5 mL/min.

Column-ZORBAX XDB C18 (50×4.6 mm-5 μm) positive Mode

Step 3:

De-protection of the above boc intermediate using HCl in dioxane, (3R,4R)-4-(8-chloro-4-methoxy-5H-pyrimido[5,4-b]indol-5-yl)azepan-3-ol (0.010 g, 66.6%)

LCMS: 347.2 (M+H), RT. 2.05 min, 97.72% (Max)

Method A—0.1% formic acid in water; B—Acetonitrile flow=1.5 ML/MIN

Column-Zorbax XDBC18 (50×4.6 mm-5 μm)

HPLC: RT 7.36 min, 96.16% (Max)

Method: 10 mM NH4OAC in water, B: Acetonitrile flow: 1.0 ml\min

Column: Phenomenex Gemini-NX C18 (150×4.6 mm, 3 μm)

$^1$H NMR (400 MHz, CD$_3$OD): δ 8.48 (s, 1H), 8.10 (d, J=1.60 Hz, 1H), 7.66-7.68 (m, 1H), 7.59 (dd, J=2.00, 8.80 Hz, 1H), 4.56-4.60 (m, 2H), 4.26 (s, 3H), 3.45-3.50 (m, 2H), 3.14-3.31 (m, 1H), 2.60-2.69 (m, 1H), 2.17-2.24 (m, 2H), 2.00-2.17 (m, 1H).

Example 33

Synthesis of (3R,4R)-4-[7-methoxy-2,8-bis(trifluoromethyl)pyrido[3,2-b]indol-5-yl]azepan-3-ol (compound 17) and (3S,4S)-4-(7-methoxy-2,8-bis(trifluoromethyl)-5H-pyrido[3,2-b]indol-5-yl)azepan-3-ol (regio isomer 1=int 16)

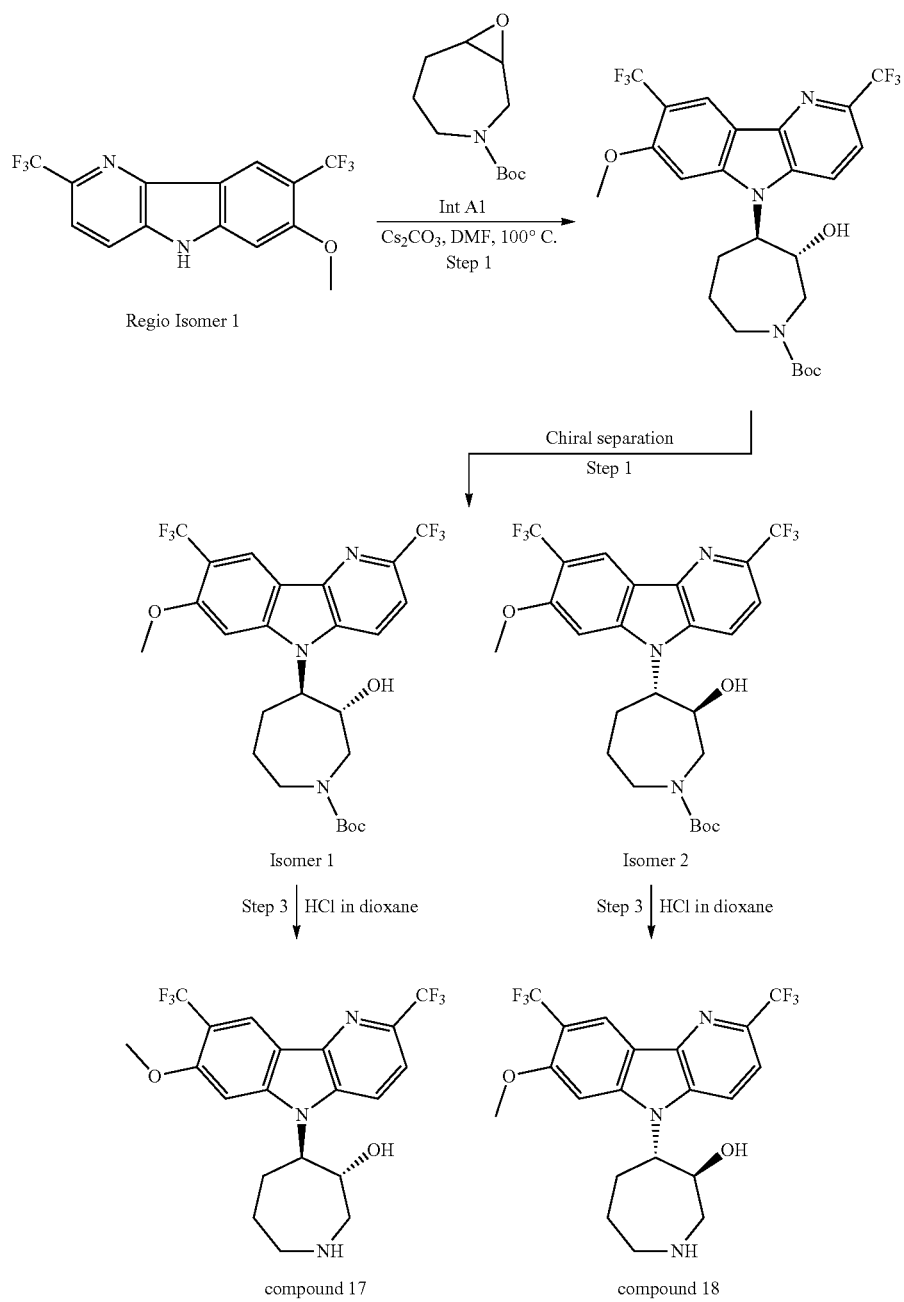

Step 1: To a stirred solution of regio isomer 1 (int 16) (0.46 g, 1.3 mmol) in dry N, N-dimethyl formamide (5 mL), was added cesium carbonate (0.633 g, 1.9 mmol) under $N_2$ atmosphere and the reaction mixture was stirred at RT for 1 h. After 1 h, Int A1 (0.36 g, 1.6 mmol) was added to the reaction mixture and allowed to stir at 100° C. for 7 days. After completion of reaction, reaction mixture was diluted with ethyl acetate (100 mL), washed with water, brine solution and dried over anhydrous $Na_2SO_4$. Organic phase was concentrated and purified by the flash column chromatography (230-400 size mesh) and elution 1 (non-polar) was isolated (0.15 g, 20%).

LCMS: 549 (M+H), RT. 3.24 min, 99.9% (Max).
Method A—0.1% HCOOH; B—ACN Flow=1.5 mL/min.
Column-ZORBAX XDB C18 (50×4.6 mm-5 μm) positive Mode Chiral HPLC: RT 6.94 min, 49.68% (Max), 12.90 min, 49.92% (Max)

Method A: HEXANE: IPA (90:10)
Column: CHIRAL PAK IA (250×4.6 mm-5μ)

$^1$H NMR: (400 MHz, MeOD): δ 9.15 (s, 1H), 8.95 (s, 1H), 8.60 (d, J=10.52 Hz, 1H), 7.47 (d, J=12.00 Hz, 1H), 4.87-4.89 (m, 2H), 4.69-4.71 (m, 2H), 4.04 (s, 3H), 3.94-3.99 (m, 2H), 3.47-3.49 (m, 1H), 2.55-2.57 (m, 2H), 2.03-2.11 (m, 1H), 1.58 (s, 9H).

Step 2:
This boc intermediate was submitted for chiral preparative purification using the above method and obtained 0.05 g of isomer 1 and 0.06 g of isomer 2.

ISOMER1:
CHIRAL HPLC: RT 7.03 min, 99.22% (Max)
Method A: HEXANE: IPA (90:10)
Column: CHIRAL PAK IA (250×4.6 mm-5μ)

ISOMER2:
CHIRAL HPLC: RT 12.22 min, 94% (Max)
Method A: HEXANE: IPA (90:10)
Column: CHIRAL PAK IA (250×4.6 mm-5μ)

Step 3:
After de-protection of the respective individual isomers using HCl in dioxane, compound 17 and compound 18 were obtained.

Compound 17: (0.027 g, 83.3%)
LCMS: 448 (M+H), RT. 2.57 min, 99.54% (Max)
Method A—0.1% HCOOH; B—ACN Flow=1.5 mL/min.
Column-ZORBAX XDB C18 (50×4.6 mm-5 μm) positive Mode
HPLC: RT 9.6 min, 99.09% (Max)
Method A: 0.1% TFA in water, Flow: 0.7 mL/min
Column: Atlantic dC18 (50×4.6 mm-5 μm)
$^1$H NMR (400 MHz, DMSO-d6): δ 8.43-8.50 (m, 2H), 7.90 (s, 1H), 7.60 (s, 1H), 4.90-4.91 (m, 1H), 4.55 (s, 1H), 4.07 (s, 3H), 3.29-3.48 (m, 4H), 3.16-3.20 (m, 1H), 2.02-2.10 (m, 3H).

Compound 18: (0.035 g, 100%)
LCMS: 448 (M+H), RT; 2.56 min, 99.07% (Max)
Method A—0.1% HCOOH; B—ACN Flow=1.5 mL/min.
Column-ZORBAX XDB C18 (50×4.6 mm-5 μm) positive Mode
HPLC: RT 12.02 min, 98.48% (Max)
Method A: 0.1% TFA in water, Flow: 0.7 mL/min
Column: Atlantic dC18 (50×4.6 mm-5 μm)
$^1$H NMR: (400 MHz, DMSO-d6): δ 8.44 (s, 2H), 7.91 (s, 1H), 7.57 (s, 1H), 4.86-4.87 (m, 1H), 4.54-4.56 (m, 1H), 4.05 (s, 3H), 3.40-3.55 (m, 4H), 3.20-3.25 (m, 1H), 2.33-2.49 (m, 3H).

Example 34

Synthesis of (5R,6R)-5-(3,6-dichloro-9H-carbazol-9-yl)-6-hydroxyazepan-2-one (compound 27)

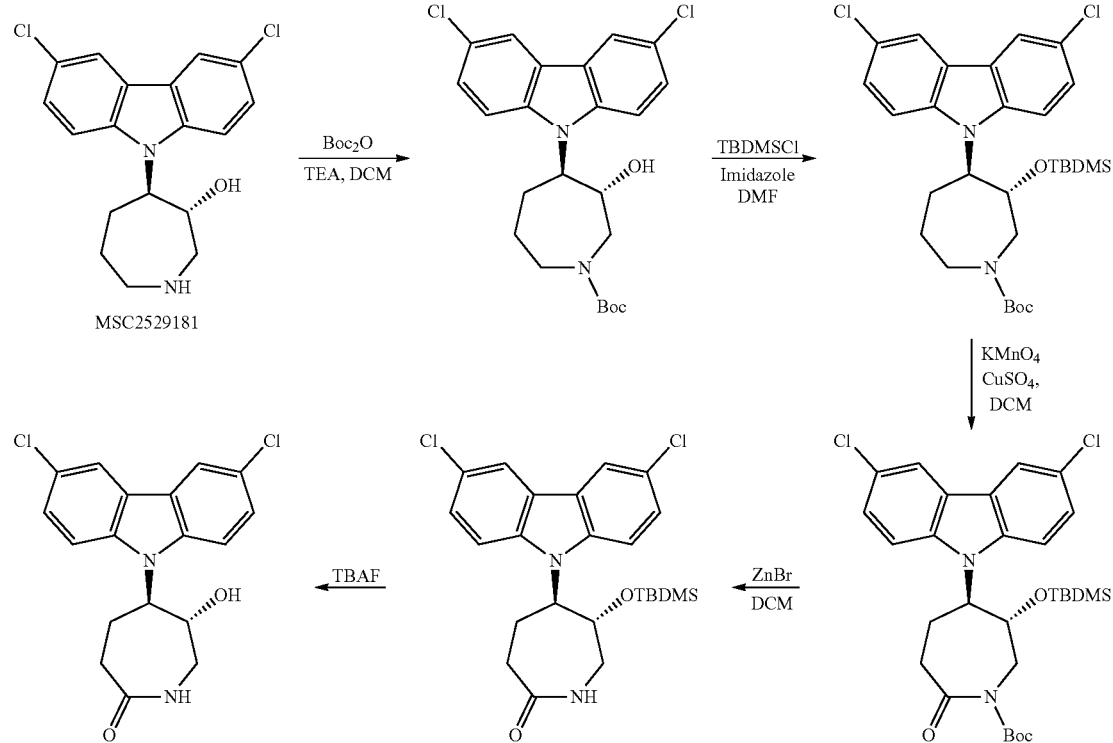

Step 1: (3S,4S)-4-(3,6-Dichloro-carbazol-9-yl)-azepan-3-ol (racemic) (1 g, 2.8 mmol) was taken in DCM (10 ml) and Triethylamine (0.724 g, 7.1 mmol) was added in to it and stirred the reaction mixture for 5 minutes then cooled the reaction mixture to 0° c. and boc anhydride (0.732 g, 3.3 mmol) was added in to it after addition attired the reaction mixture at RT for 2 h. The reaction mixture was diluted with DCM (50 ml) and washed with water (2×25 mL), dried (Na$_2$SO$_4$), then filtered and the solvent removed under reduced pressure. The crude product was purified by column chromatography using silica gel 230-400 mesh to get the desired product tert-butyl-(3R,4R-4-(3,6-dichloro-9H-carbazole-9yl)-3-hydroxyazepene-1-caroxylate obtained (1.1 g, 91.6%)

LCMS: (M+H) 349, RT. 4.07 min, 98.34% (Max).

Method A—0.1% HCOOH; B—ACN Flow=1.5 mL/min.

Column-ZORBAX XDB C18 (50×4.6 mm-5 μm) positive Mode

1H NMR: (400 MHz, DMSO-d6): δ 8.32-8.38 (m, 2H), 7.71 (d, J=8.80 Hz, 1H), 7.42-7.46 (m, 3H), 5.07 (d, J=5.60 Hz, 1H), 4.51 (q, J=10.00 Hz, 1H), 4.26-4.27 (m, 1H), 3.71-3.85 (m, 2H), 3.05-3.19 (m, 2H), 2.26-2.34 (m, 1H), 1.94-1.96 (m, 2H), 1.80-1.84 (m, 1H), 1.48 (s, 9H).

Step 2: tert-butyl(3R,4R)-4-(3,6-dichloro-9H-carbazole-9yl)-3-hydroxyazepene-1-caroxylate (1 g, 2.2 mmol). was taken in DCM (20 mL) and imidazole (0.224 g, 3.3 mmol) and was added in to it and cooled the reaction mixture to 0° c. and TBDMSCI was added in to it and stirred the reaction mixture at RT for 12 h. Reaction mixture was diluted with DCM (50 ml) and washed with water (2×25 mL), dried (Na$_2$SO$_4$), then filtered and the solvent removed under reduced pressure. The crude product was purified by column chromatography using silica gel 230-400 mesh to get the desired product tert-butyl(3R,4R)-3-(tertbutyldimethylsilyloxy)-4-(3,6-dichloro-9H-carbazole-9yl)-2-oxyazepene-1-caroxylate obtained (0.7 g, 20%)

Step 3: tert-butyl-(3R,4R)-6-(tertbutyldimethylsilyloxy)-5-(3,6-dichloro-9H-carbazole-9yl)-3-hydroxyazepene-1-caroxylate (0.7 g, 1.2 mmol). was taken in DCM (10 mL) and premixed powder of KMnO$_4$ (0.707 g, 4.4 mmol) and CuSO$_4$ was added in to it and stirred the reaction mixture at rt for 24 h in a sealed tube. Reaction mixture filtered through Celite® and washed with DCM and the filtrate was concentrated in vacuo, the crude obtained was directly purified by silica gel chromatography using ethyl acetate/petroleum ether to afford tert-butyl(5R,6R)-4-(3,6-dichloro-9H-carbazole-9yl)-3-oxyazepene-1-caroxylate (0.11 g, 15.3%)

UPLC: (M+H) 477, RT. 1.70 min, 97.68% (Max).

(Method): Acquity HSS T3 C18 (2.1×50 mm-1.8 μm)

Acq. Method3070FA.olp % B:0 min=30% 1.25-2.0 min=95% 2.5 min=30% 3.0 min=30%

$^1$H NMR (400 MHz, CDCl$_3$): δ 8.00 (s, 1H), 7.27-7.53 (m, 5H), 4.34-4.54 (m, 3H), 3.50-3.59 (m, 1H), 2.76-2.99 (m, 3H), 2.06-2.18 (m, 1H), 1.71 (s, 9H), 0.45 (s, 9H), (s, 3H), (s, 3H).

Step 4: tert-butyl-(5R,6R)-4-(3,6-dichloro-9H-carbazole-9yl)-3-oxyazepene-1-caroxylate (0.11 g, 0.019 mmol) was taken in DCM (3 mL) and zincbromide (0.214 g. 0.09 mmol) was added and stirred the reaction mixture at RT for 2 h. Reaction mixture was diluted with DCM (50 ml) and washed with water (2×25 mL), dried (Na$_2$SO$_4$), then filtered and the solvent removed under reduced pressure. The crude product was purified by column chromatography using silica gel 230-400 mesh to get the desired product the crude obtained was directly purified by silica gel chromatography using ethyl acetate/petroleum ether to afford rac-tert-butyl-(5R,6R)-4-(3,6-dichloro-9H-carbazole-9yl)-3-hydroxyazepene-1-caroxylate (0.016 g, 15.3%). UPLC: (M+H) 477, RT. 1.39 min, 94.84% (Max).

(Method): Acquity HSS T3 C18 (2.1×50 mm-1.8 μm)

Acq. Method3070FA.olp % B: 0 min=30% 1.25-2.0 min=95% 2.5 min=30% 3.0 min=30%

$^1$H NMR (400 MHz, MeOD): δ 8.08-8.13 (m, 2H), 7.64 (d, J=8.80 Hz, 2H), 7.42 (d, J=2.00 Hz, 2H), 4.77-4.88 (m, 1H), 4.39-4.44 (m, 1H), 3.59-3.65 (m, 1H), 3.28-3.32 (m, 1H), 3.00 (t, J=12.80 Hz, 1H), 2.75-2.79 (m, 1H), 2.46 (q, J=6.40 Hz, 1H), 2.13-2.15 (m, 1H), 0.43 (s, 9H), (s, 3H), (s, 3H).

Step 5: To a stirred solution of ( ) (0.0.16 g, 2.6 mmol) in dry CHCl3 (1 mL), was added 1M solution of TBAF (1.2 g, 4 mmol) under N2 atmosphere and the reaction mixture was stirred at RT for 24 h. Reaction mixture was diluted with DCM (50 ml) and washed with water (2×25 mL), dried (Na$_2$SO$_4$), then filtered and the solvent removed under reduced pressure. The crude product was purified by column chromatography using silica gel 230-400 mesh to get the desired compound 27 (0.003 g, 5.8%).

UPLC: 363 (M+H), RT. 1.36 min, 98.06% (Max).

(Method): Acquity HSS T3 C18 (2.1×50 mm-1.8 μm)

Acq. Method: 595FA.olp % B: 0 min=5% 2.0 min=95% 2.5 min=5% 3.0 min=5%

Example 35

Pharmakokinetic Properties of Selected Compounds of the Invention

Selected compounds of the invention were assayed for their anti-malarial activity using cultured *P. falciparum*, which may be done according to the following protocols:

Cultivation of *P. falciparum*:

*P. falciparum* strain NF54 was obtained from the Research and Reference Reagent Resource Center (MR4) (Manassas, Va.). The two strains were maintained in vitro by a modification of the method of Trager and Jensen. Cultures were maintained in A positive (A+) human erythrocytes suspended at 5% hematocrit in complete medium. 5 g albumax II (Gibco-Invitrogen, Cat No#11021037), 2.5 mg gentamicin (Sigma Aldrich), 25 mM HEPES (Invitrogen), 5 mg hypoxanthine (Sigma), and 1 L of RPMI 1640 (Invitrogen, Cat No#11875085). Cultures were grown in 100 mm petri-dishes (BD Falcon) at a volume of 15 mL and were kept in a standard gas environment of 4% CO$_2$ and 3% O$_2$ at temperature 37° C. in a tri-gas incubator (Cat#3131, Thermo Scientific Forma Series II Water Jacketed). Parasite growth and morphology were observed daily using thin smears at 100× (oil immersion) magnification following staining with Geimsa stain.

*P. falciparum* Growth Assay

This protocol or variations thereof may be used to assess the efficacy of selected compounds of the invention to inhibit growth of *P. falciparum* in vitro.

Parasite growth was detected in assay by the traditional [3H]hypoxanthine incorporation assay as previously described by Desjardins and colleagues (Antimicrob. Agents Chemother., 16(6), 710, 1979). To perform the [3H]hypoxanthine incorporation assay, the new antimalarial agents were serially diluted 1:1 into hypoxanthine-free complete medium to a final volume of 100 μL (final antimalarial agent concentration range, 10,000 nM to 4.8 nM may change in special case) in 96 well sterile cell culture plates. 100 μL of *P. falciparum* culture (0.3% p and 1.25% h-synchronized ring stage) is added per well, by addition, anti-malarial agents are diluted in such a way that the final DMSO concentration in the well does not exceed 0.1%. All cultures used in the study are albumax II adopted. The microtiter plates were incubated in chamber in a standard gas environment at 37° C. for 72 h. After 48 h of incubation and prior to addition of 50 μL (0.5 μCi/well) 3H-Hypoxanthine (specific activity, 20 Ci/mmol, Conc. 1.0 mCi/ml; American Radiolabeled Chemicals, Inc., St. Louis, Mo.), culture growth was assessed by making the smears that ensures the culture has grown and assay plate is further incubated for 24 h.

Following the incubation period, the plates were harvested with a FilterMate cell harvester (Perkin Elmer) onto unifilter-96 GF/B plates, washed with distilled water to remove excess radiochemical and plates were kept for drying 37° C. overnight or 60° C. for 1 h. 50 μL of Microscint scintillation cocktail (Microscint-High Efficiency LSC-Cocktail; Perkin Elmer) added in the unifilter-96 GF/B plates and kept for 15-20 min. The plates were counted in a Top Count NXT microplate scintillation and luminescence counter (Perkin Elmer). The mean values for [3H]hypoxanthine incorporation in parasitized control and non-parasitized control erythrocytes were calculated.

The resulting assay data is provided in Table 1.

TABLE 1

Anti-malarial activity of selected inventive compounds on *P. falciparum* NF54 expressed as the concentration in nM that inhibits by 50% (EC$_{50}$) the incorporation of [3H]-hypoxanthine at 72 h

| Compound | EC50 (nM) |
|---|---|
| 2 | 36.37 |
| 3 | 2.55 |
| 6 (racemic) | 45.93 |
| 8 (racemic) | 32.89 |
| 9 | 18.03 |
| 10 (racemic) | 21.01 |
| 10 (isomer 1) | 20.25 |
| 14 (i) | 16.59 |
| 14 (ii) | 26.88 |
| 17 | 12.8 |
| 18 | 5.4 |
| 19 | 24.0 |
| 20 | 13.1 |
| 21 | 41.7 |
| 22 | 46.1 |
| 23 | 11.2 |
| 24 | 2.3 |
| 27 | 28.18 |

In Vivo Assays

In vivo efficacy against *P falciparum* PF3D/0087/N9 for the compounds no. 2 and 3 as described in Examples 16 and 17.

The in vivo activity in a murine model of *P. falciparum*-malaria was adapted from the protocol as provided by Angulo-Barturen I, Jimènez-Diaz M B, Mulet T, Rullas J, Herreros E, et al. (2008) PLoS ONE 3(5): e2252. doi: 10.1371/journal.pone.0002252.

This study measures the therapeutic efficacy of compounds no. 2 and 3 against *Plasmodium falciparum* growing in peripheral blood of NODscidIL2Rynull mice engrafted with human erythrocytes. The antimalarial efficacy of compounds no. 2 and 3 were assessed using a "4-day test".

The parameters of efficacy estimated in the study are a) the dose of compounds no. 2 and 3 in mg·kg$^{-1}$ that reduces parasitemia at day 7 after infection by 90% with respect to vehicle-treated mice (parameter denoted as ED90)

The ED90 for compounds no. 2 and 3 were <10 mg·kg$^{-1}$ and <3 mg·kg$^{-1}$ respectively.

The invention claimed is:
1. A compound according to formula (i)

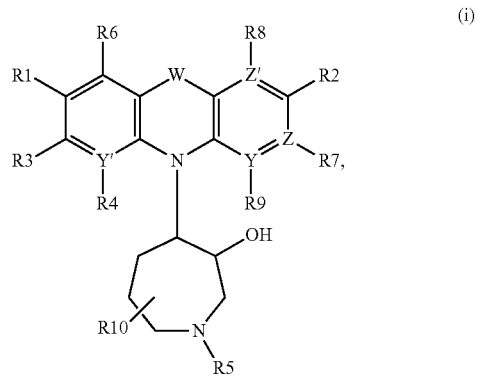

(i)

wherein
W is a C-Sp2-Sp2-C bond, O, SO$_2$, S, or N,
Z is C or N,
Z' is C or N,
Y' is C or N,
Y is C or N,
R1 denotes H, halogen, CF$_3$, Alk, Alkoxy, S-Ak, SO$_2$Alk, NO$_2$, or amino,
R2 denotes H, halogen, CF$_3$, Alkoxy, Alk, S-Ak, SO$_2$Alkyl, NO$_2$, or amino,
R3 denotes H, halogen, CF$_3$, SO$_2$, Alk, Alkoxy, S-Alkyl, SO$_2$Alk, NO$_2$, or amino,
R4 denotes H, halogen, CF$_3$, Alk, Alkoxy, S-Alkyl, SO$_2$Alk, NO$_2$, or amino,
R5 denotes H, alkyl, benzyl, sulfonamide, Alk, Alkoxy, NO$_2$, or amino,
R6 denotes H, alkyl, SO$_2$, Alk, Alkoxy, S-Alkyl, SO$_2$Alk, NO$_2$, or amino,
R7 denotes H, halogen, SO$_2$, SO$_2$Alk, or S-Alk, Alk, Alkoxy, or amino,
R8 denotes H, halogen, CF$_3$, alk, alkoxy, amino, SO$_2$, or S-Alk,
R9 denotes H, halogen, CF$_3$, Alk, Alkoxy, S-Alkyl, SO$_2$Alk, NO$_2$, amino, azepanyl, azepanyl-3-ol, or amino-azepanyl-3-ol,
R10 denotes H, halogen, CF$_3$, Alk, Alkoxy, S-Alkyl, SO$_2$Alk, NO$_2$, an oxygen double-bonded to a carbon in the azepanyl ring to form a keto group, aryl, hydroxyl, amino, or —CONH$_2$,
and
Alk is a branched or linear alkyl group having 1 to 8 carbon atoms or cycloalkyl having 3 to 6 carbon atoms, wherein 1 to 7 H-atoms may be independently replaced by Hal, OR, COOR, CN, NR$_2$, phenyl, linear or branched alkyl having 1, 2 or 3 C atoms, cycloalkyl having 3 to 6 carbon atoms and/or wherein 1 to 3 CH$_2$-groups may be replaced by O, —NRCO—, —CO—, —COO—, —CONR, —NR— or S, or cycloalkyl having 3 to 6 carbon atoms,
or a pharmaceutically acceptable salt, ester and/or N-oxide thereof, each in a racemic form or in an enantiomerically pure form or enriched mixture of the respective enantiomers in all ratios, and/or as a mixture of diastereoisomers in all ratios.
2. The compound according to claim 1, wherein R1 is H, halogen, CF$_3$, or NO$_2$.
3. The compound according to claim 1, wherein R2 is H, halogen, CF$_3$, or NO$_2$.

4. The compound according to claim 1, wherein R1, R2 are both H, Cl, F, $CF_3$, or $NO_2$.

5. The compound according to claim 1, wherein W is a C-Sp2-Sp2-C bond.

6. The compound according to claim 1, wherein W is O.

7. The compound according to claim 1, wherein W is $SO_2$.

8. The compound according to claim 1, wherein W is N.

9. The compound according to claim 1, wherein W is S.

10. The compound according to claim 1, wherein substituents R3, R4, R5, R7, R8, R9 and R10 are H.

11. The compound according to claim 1, wherein Y is C or N.

12. The compound according to claim 1, wherein Y' is C or N.

13. The compound according to claim 1, wherein Y' and Z' both are C.

14. The compound according to claim 1, wherein Z, Z' both are N.

15. The compound according to claim 1, wherein Y', Z' are both N.

16. The compound according to claim 1, wherein Z, Z' both are N and Y, Y' both are C.

17. The compound according to claim 1, wherein Z, Z' both are C and Y, Y' both are N.

18. The compound according to claim 1, wherein Z, Z' and Y, Y' are C.

19. The compound according to claim 1, wherein R8 is $SO_2Alk$.

20. The compound according to claim 1, wherein R8 is $NO_2$.

21. The compound according to claim 1, wherein R6 is alkoxy.

22. The compound according to claim 1, wherein R6 is selected from methoxy, ethoxy, propoxy, or tert-butoxy.

23. The compound according to claim 1, wherein R3 is alkoxy, $NO_2$, or amine ($NH_2$).

24. The compound according to claim 1, wherein R3 is methoxy, ethoxy, propoxy, or tert-butoxy.

25. The compound according to claim 1, wherein R4 is H, methoxy, ethoxy, or $NO_2$.

26. The compound according to claim 1, wherein R10 is $CF_3$ or an oxygen double-bonded to a carbon in the azepanyl ring to form a keto group.

27. The compound according to claim 1, wherein R9, R10 both are H.

28. A pharmaceutical composition comprising:
one or more compound selected from the group consisting of a compound according to claim 1, a pharmaceutically acceptable derivative thereof, a tautomer, a salt, a solvate, a stereoisomer thereof, and mixtures thereof in all ratios, and
optionally an excipient, an adjuvant, a carrier or combinations thereof.

29. The pharmaceutical composition according to claim 28, comprising at least one further pharmaceutically active compound.

30. The compound according to claim 1, selected from the group consisting of:
- (3R,4R)-4-[3,6-bis(trifluoromethyl)-9H-carbazol-9-yl]azepan-3-ol,
- (3S,4S)-4-[3,6-bis(trifluoromethyl)-9H-carbazol-9-yl]azepan-3-ol,
- (3R,4R)-4-(3,6-dichloro-2-methoxy-9-H-carbazol-9-yl)azepan-3-ol,
- (3S,4S)-4-(3,6-dichloro-2-methoxy-9-H-carbazol-9-yl)azepan-3-ol,
- (3R,4R)-4-[3,6-bis(trifluoromethyl)pyrido[2,3-b]indol-9-yl]azepan-3-ol,
- (3R,4R)-4-(7-methoxy-2,8-bis(trifluoromethyl)-5H-pyrido[3,2-b]indol-5-yl)azepan-3-ol, (
- 3S,4S)-4-(7-methoxy-2,8-bis(trifluoromethyl)-5H-pyrido[3,2-b]indol-5-yl)azepan-3-ol,
- (3S,4S)-4-(8-chloro-6-methoxy-2-(trifluoromethyl)-5H-pyrido[3,2-b]indol-5-yl)azepan-3-ol,
- (3R,4R)-4-(2,8-bis(trifluoromethyl)-5H-pyrrolo[2,3-b:4,5-b']dipyridin-5-yl)azepan-3-ol, and
- (3S,4S)-4-(2,8-bis(trifluoromethyl)-5H-pyrrolo[2,3-b:4,5-b']dipryridin-5-yl)azepan-3-ol.

* * * * *